US011203618B2

(12) United States Patent
Joens et al.

(10) Patent No.: US 11,203,618 B2
(45) Date of Patent: *Dec. 21, 2021

(54) CAMPYLOBACTER IMMUNOGENIC COMPOSITIONS AND USES THEREOF

(71) Applicant: ARIZONA BOARD OF REGENTS ON BEHALF OF THE UNIVERSITY OF ARIZONA, Tucson, AZ (US)

(72) Inventors: Lynn A. Joens, Tucson, AZ (US); Bibiana Law, Tucson, AZ (US); Alexandra Armstrong, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/893,667

(22) Filed: Jun. 5, 2020

(65) Prior Publication Data
US 2020/0317737 A1 Oct. 8, 2020

Related U.S. Application Data

(60) Continuation of application No. 16/027,575, filed on Jul. 5, 2018, now Pat. No. 10,683,330, which is a continuation of application No. 15/065,979, filed on Mar. 10, 2016, now Pat. No. 10,030,054, which is a division of application No. 14/375,365, filed as application No. PCT/US2013/024332 on Feb. 1, 2013, now Pat. No. 9,328,148.

(60) Provisional application No. 61/632,888, filed on Feb. 1, 2012, provisional application No. 61/689,078, filed on May 29, 2012.

(51) Int. Cl.
C07H 21/04 (2006.01)
C07K 14/205 (2006.01)
A61K 39/02 (2006.01)
C12N 15/74 (2006.01)
A61K 39/00 (2006.01)

(52) U.S. Cl.
CPC .......... *C07K 14/205* (2013.01); *A61K 39/105* (2013.01); *C12N 15/74* (2013.01); *A61K 2039/522* (2013.01); *A61K 2039/523* (2013.01); *A61K 2039/53* (2013.01)

(58) Field of Classification Search
CPC .................................................. C07K 14/205
See application file for complete search history.

(56) References Cited

U.S. PATENT DOCUMENTS

| 5,436,146 A | 7/1995 | Shenk et al. |
| 5,753,500 A | 5/1998 | Shenk et al. |
| 6,040,183 A | 3/2000 | Ferrari et al. |
| 6,093,570 A | 7/2000 | Ferrari et al. |
| 6,548,286 B1 | 4/2003 | Samulski et al. |
| 8,133,493 B2 | 3/2012 | Curtiss, III |
| 9,328,148 B2 | 5/2016 | Joens et al. |
| 10,030,054 B2 | 7/2018 | Joens et al. |
| 10,683,330 B2 * | 6/2020 | Joens .................. C07K 14/205 |
| 2001/0038844 A1 | 11/2001 | Nachamkin |
| 2002/0168342 A1 | 11/2002 | Wang et al. |

FOREIGN PATENT DOCUMENTS

| WO | 2005/049641 | 6/2005 |
| WO | 2008/008092 | 1/2008 |

OTHER PUBLICATIONS

International Search Report for PCT/US2013/024332, dated Jul. 8, 2013.
Nielsen, et al. (2012) "Identification of immunogenic and virulence-associated Campylobacter jejuni proteins," Clinical and Vaccine Immunology, 19(2): 113-119.
Buzby JC, Alios BM, Roberts T. The economic burden of Campylobacter-associated Guillain-Barre syndrome. Journal of Infectious Diseases. 1997;176:S192-S7.
Curtiss III, R., S-Y. Wanda, B. M. Gunn, X. Zhang, S. A. Tinge, V. Ananthnarayan, H. Mo, S. Wang, and W. Kong. 2009. *Salmonella* strains with regulated delayed attenuation in vivo. Infect. Immun. 77:1071-1082.
Kong, Q., Six, D.A., Roland, K.L., Liu, Q., Gu, L., Reynolds, C.M., Wang, X., Raetz, C.R., Curtiss, R., 3rd, 2011. *Salmonella* synthesizing 1-dephosphorylated [corrected] lipopolysaccharide exhibits low endotoxic activity while retaining its immunogenicity. J Immunol187, 412-423.
Li, Y., Wang, S., Scarpellini, G., Gunn, B., Xin, W., Wanda, S.Y., Roland, K.L., Curtiss, R., 3rd, 2009, Evaluation of new generation *Salmonella enterica* serovar Typhimurium vaccines with regulated delayed attenuation to induce immune responses against PspA. Proceedings of the National Academy of Sciences of the United States of America 106, 593-598.
Pope JE, Krizova A, Garg AX, Thiessen-Philbrook H, Ouimet JM. Campylobacter reactive arthritis: a systematic review. Semin Arthritis Rheum. 2007;37(1):48-55. Epub Mar. 16, 2007. doi: S0049-0 172(07)00005-4 [pii].
Scallan E, Hoekstra RM, Angulo FJ, Tauxe RV, Widdowson MA, Roy SL, et al. Foodborne illness acquired in the United States—major pathogens. Emerging infectious diseases. 2011;17(1):7-15.
Wyszynska, A., Raczko, A., Lis, M., Jagusztyn-Krynicka, E.K., 2004. Oral immunization of chickens with av irulent *Salmonella* vaccine strain carrying C. jejuni 72Dz/92 cjaA gene elicits specific humoral immune response associated with protection against challenge with wild-type Campylobacter. Vaccine 22, 1379-1389.
Curtiss et al., Crit Rev Immunol. 2010;30(3):255-70; 2010.
Strugnell et al., Infect. Immunol. 1992, 60:3994.

(Continued)

*Primary Examiner* — Albert M Navarro
(74) *Attorney, Agent, or Firm* — Carin R. Miller, Esq.; Johnson, Marcou, Issacs & Nix, LLC

(57) ABSTRACT

The present disclosure provides immunogenic compositions against *Campylobacter* and methods for using the immunogenic composition to generate an immune response against *Campylobacter* and/or reduce intestinal colonization by *Campylobacter*.

14 Claims, 1 Drawing Sheet
Specification includes a Sequence Listing.

(56) References Cited

OTHER PUBLICATIONS

Layton et al., Clinical and Vaccine Immunology Mar. 2011, 449-454.
Al-Ojali et al., Microbial Pathogenesis 52:326 (2012).
Parkhill, J. et al. "The genome sequence of the food-borne pathogen Campylobacter jejuni reveals hypervariable sequences" Nature (2000) vol. 403, pp. 665-668.
Qiu, et al., "Oral administration of attenuated *Salmonella typhimurium* containing a DNA vaccine against rabbit hemorrhagic disease", Journal of Virological Methods, vol. 188, pp. 108-113, Available online: Dec. 24, 2012.

* cited by examiner

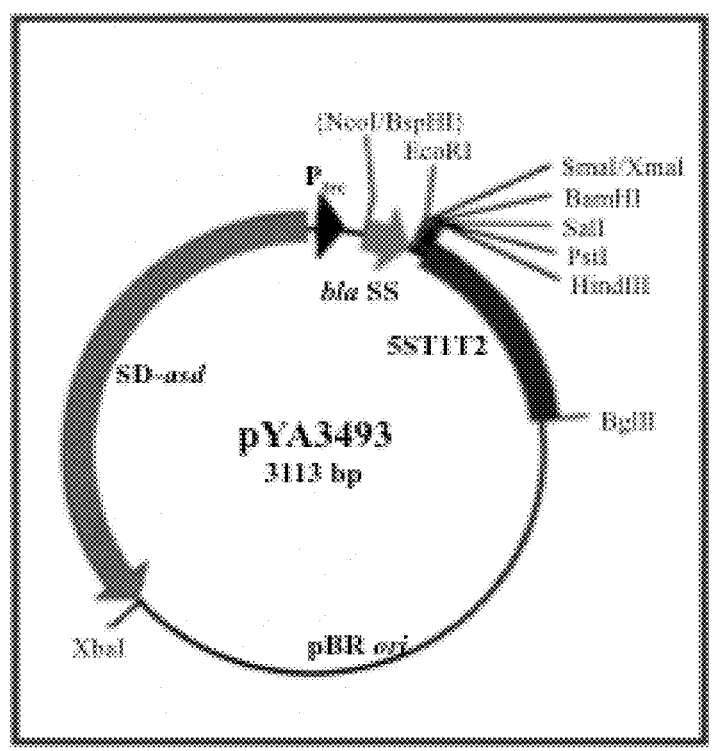

CAMPYLOBACTER IMMUNOGENIC COMPOSITIONS AND USES THEREOF

CROSS REFERENCE

This application is a continuation of U.S. application Ser. No. 16/027,575 filed Jul. 5, 2018, which is a continuation of U.S. application Ser. No. 15/065,979 filed Mar. 10, 2016, which is a divisional of U.S. application Ser. No. 14/375,365 filed Jul. 29, 2014, which is a US National Phase filing of PCT/US13/24332 filed Feb. 1, 2013, which claims priority to U.S. Provisional Patent Application Ser. Nos. 61/632,888 filed Feb. 1, 2012 and 61/689,078 filed May 29, 2012, all incorporated by reference herein in their entirety.

STATEMENT OF GOVERNMENT SUPPORT

This invention was made with government support under Grant No. NA/ARZT-1370170-R50-110, awarded by USDA/NIFA. The government has certain rights in the invention.

BACKGROUND

Campylobacteriosis is primarily a food-borne disease with the handling and consumption of poultry considered to be the most significant risk factor in transmission. Infection by *Campylobacter* spp. is one of the leading causes of bacterial gastroenteritis, causing an estimated 1.3 million cases annually in the U.S. (Scallan et al, 2011), resulting in health care costs of $0.8-5.6 billion per year (Buzby et al., 1997). Serious complications such as arthritis occur in an estimated 1-5% of cases (Pope et al., 2007)) and Guillain-Barre Syndrome, a form of neuromuscular paralysis, occurs at a rate of 1.0 per 1,000 patients (Altekruse and Tollefson, 2003). Due to the emergence and persistence of antibiotic resistance coupled with increasing regulatory restrictions on the industry, control strategies such as vaccination are urgently needed. To date, there is no intervention method or vaccine available to the producer to reduce numbers of *Campylobacter* in poultry going to processing.

Beginning Jul. 1, 2011, USDA-FSIS (Food Safety and Inspection Service) has implemented new performance standards for *Campylobacter* for young chicken chilled carcasses at slaughter establishments (FSIS NOTICE, 31-11, Jun. 30, 2011). These standards will allow no more than 8 positive *Campylobacter* samples out of a 51-sample set, with plans to initially warn the companies and fines to be imposed in 2013. A large baseline study was conducted in our laboratory (funded by the USDA) to quantify *Campylobacter* levels in slaughtering plants from 2007-2009. Our studies demonstrated 21.9% (213/972) of post-chilled carcass rinse samples were positive for *Campylobacter*, which amounts to 11.17 per 51-sample set. Clearly, this is over the allowable number of *Campylobacter* from chilled carcass samples and will precipitate the issuing of fines for both the producer and processing plant unless a reduction of *Campylobacter* in poultry can be obtained. Currently, there are no available intervention methods or vaccines available for producers to use to reduce the *Campylobacter* load in poultry.

SUMMARY OF THE INVENTION

In a first aspect, the present invention provides immunogenic compositions, comprising one or more expression vectors comprising:

(a) at least one polynucleotide encoding a protein selected from the group consisting of proteins comprising an amino acid sequence at least 80 percent identical to SEQ ID NO:2 (Cj0998c protein), SEQ ID NO:4 (Cj0588 protein), and SEQ ID NO:6 (Cj0248 protein), or antigenic portions thereof; and (b) a promoter operatively linked to the polynucleotide, wherein the promoter region is capable of directing expression of the encoded protein(s).

In a second aspect, the present invention provides immunogenic compositions, comprising (a) one or more isolated proteins selected from the group consisting of proteins comprising an amino acid sequence at least 80 percent identical to SEQ ID NO:2 (Cj0998c protein), SEQ ID NO:4 (Cj0588 protein), and SEQ ID NO:6 (Cj0248 protein), or antigenic portions thereof; and (b) a pharmaceutically acceptable carrier.

In a third aspect, the present invention provides methods for stimulating an immune response against *Campylobacter*, comprising administering to a subject an effective amount of the immunogenic composition according to any embodiment of the invention to generate an immune response against *Campylobacter*.

In a fourth aspect, the present invention provides methods for reducing *Campylobacter* intestinal colonization in a subject, comprising administering an amount effective of the immunogenic composition according to any embodiment of the invention to reduce *Campylobacter* intestinal colonization in the subject.

DESCRIPTION OF THE FIGURES

FIG. 1 is a schematic drawing of the pYA3493 plasmid.

DETAILED DESCRIPTION OF THE INVENTION

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

In a first aspect, the present invention provides immunogenic compositions, comprising one or more expression vectors comprising:

(i) at least one polynucleotide encoding a protein selected from the group consisting of proteins comprising an amino acid sequence at least 80 percent identical to SEQ ID NO:2 (Cj0998c protein), SEQ ID NO:4 (Cj0588 protein), and SEQ ID NO:6 (Cj0248 protein), or antigenic portions thereof; and (ii) a promoter operatively linked to the polynucleotide, wherein the promoter region is capable of directing expression of the encoded protein(s).

The inventors have identified three putative virulence genes (Cj0248, Cj0588, and Cj0998c) from *C. jejuni* encoding novel proteins from the outer-membrane of the bacterium. The inventors have further discovered that each of the Cj0998c protein, the Cj0588 protein, and the Cj0248 protein are potent immunogens for stimulating an effective immune response against *Campylobacter jejuni* ("*C. jejuni*"). For example, as disclosed in detail herein, two separate vaccination trials of chickens with a vector expressing the Cj0998c protein demonstrated reduced numbers of *C. jejuni* in birds after challenge an average of 2.5 logs CFU (geomean 3 logs) when compared to the cecal numbers of non-vaccinated control birds. Furthermore, vaccination trials demonstrated a significant reduction (1-4 logs) (1 log with heterologous strain and 4 logs with homologous strain) of *C. jejuni* in cecal contents of chickens vaccinated with vectors expressing the Cj0588 protein and challenged with *Campylobacter jejuni*. Each of the proteins was initially isolated from an outer-membrane (OMP) extraction of a *C. jejuni* biofilm.

Thus, the immunogenic compositions of the invention can be used, for example for stimulating an immune response in subjects at risk of *Campylobacter* infection and/or colonization, including but not limited to vertebrates such as chickens, turkeys, birds, cattle, sheep, pigs, dogs, cats, and humans.

In one embodiment, the one or more expression vectors encode one of the recited proteins, or antigenic fragments thereof. In another embodiment, the one or more expression vectors encode two proteins comprising an amino acid sequence at least 80 percent identical to the recited amino acid sequences (i.e.: SEQ ID NO:2 and SEQ ID NO:4; SEQ ID NO:2 and SEQ ID NO:6; or SEQ ID NO:6 and SEQ ID NO:8), or antigenic fragments thereof. In this embodiment, a single expression vector may encode both proteins, or antigenic fragments thereof, or the composition may comprise two expression vectors, with each expression vector encoding one of the recited proteins, or antigenic fragments thereof. In this embodiment, the expression vector used may be the same (other than the protein coding sequence) or different.

In a further embodiment, the one or more expression vectors encode all three of the proteins comprising an amino acid sequence at least 80 percent identical to the recited amino acid sequences (i.e.: SEQ ID NO:2, SEQ ID NO:4, and SEQ ID NO:6), or antigenic fragments thereof. In this embodiment, a single expression vector may encode all three proteins, or antigenic fragments thereof. Alternatively, the composition may comprise two expression vectors, with one expression vector encoding one of the recited proteins, or antigenic fragments thereof, and the other expression vector encoding two of the recited proteins, or antigenic fragments thereof. In a further alternative of this embodiment, the composition may comprise three expression vectors, with each expression vector encoding one of the recited proteins, or antigenic fragments thereof. In each of these alternative embodiments, the multiple expression vectors used may be the same or different. Non-limiting examples of expression vectors encoding the one or more recited proteins are provided herein. Based on the present disclosure, it is well within the level of those of skill in the art to prepare expression vectors according to all embodiments of the invention.

The Cj0998c, Cj0588, and Cj0248 proteins are present in highly conserved variants between different strains of *C. jejuni*, and thus the proteins encoded by the one or more expression vectors can be at least 80% identical or similar (residues with similar properties, i.e.: hydrophobic, hydrophilic, etc.) over the full length of the recited amino acid sequences, or antigenic fragments thereof. In various further embodiments, the proteins encoded by the one or more expression vectors are at least 81, 82, 83, 84, 85, 86, 87, 88, 89, 90, 91, 92, 93, 94, 95, 96, 97, 98, 99, or 100% percent identical over the full length of the recited amino acid sequence(s), or antigenic fragment thereof.

In one embodiment, the at least one polynucleotide encodes a protein selected from the group consisting of the following, or an antigenic fragment thereof:

(a) SEQ ID NO: 7 (Cj0998c genus)
MKK(I/V/F)(L/V)(V/A/L)S(V/I)(L/F)S(S/F)CLLASALSAVSF

KEDSLK(I/V)SFEGYKTKDM(I/V)G(T/V/I/A)(K/R)GEFKNVEY (K/N)FSK(N/S)(I/T)KD(L/F)ASYLKGAKATI(K/E)PS(N/D)AFM (G/S)EG(N/L)D(I/V)ITNNITKVFFPALLG(D/N)(T/A)DIKVVFQD (V/A/M)I(A/V)GE-X1ITMDKKSTI(V/I)PLTYTIKD(N/D)KFEAKG

Q(L/F)DLH(T/A)FKN(G/A)SKALKALSD(V/A)A(A/T/P)GHGGISW

PLVDISFNADL(A/T/V)E wherein X1 is absent or is
NKGVISAK (SEQ ID NO: 135);

(b) SEQ ID NO: 8: (Cj0588 genus)
X1-(L/M)(D/N/E)LL(S/R)EIY(V/I)SRAALKLK(K/N)FLEEN(D/

G/N)IE(I/V)(K/N)(H/Q/N)KNCLDIGSSTGGFVQILLEN(Q/K)ALK

IT(A/T)LDVG(S/N)NQLH(P/S/L)(S/N)LR(V/A/T)NE(K/I)(I/

V)IL(H/Y)EN(T/I)DLR(A/T/V)FKSEEKFE(L/F)(V/I)TCDVSFI

SL(I/V)NLLYY(I/V)(D/N)NLAL(K/R)EIILLFKPQFEVGKN(I/V)

KRDKKGVLKD(D/G)(K/R)(A/V)ILKA(R/K)MDFEK(A/E)CAKL(G/

S)W(L/F/I)LKNTQKS(S/C)IKGKEGNVEYFYYYIKN wherein X1 is absent or is
M(R/I)(F/-)(D/-)FF(V/I)SKRL(N/D)ISRNKALELIE(N/S)EE (I/V)LLNGK(S/N)FKAS(F/C)DVKN(F/L)LENLKK(T/A/K)QDLN (P/L/S)E(D/E)(I/V)(L/Y)L(A/T/S)(N/D/K)(E/G)L(K/N)

(SEQ ID NO: 136);
and (c) SEQ ID NO: 9 (Cj0248 genus)
(M/-)I(G/-)DMNELLLKSVEVLPPLPDTVSKLRKYVSEANSNIETMKV (A/V)EIISSDPLMTAKLLQLANSPYYGFTREITTI(N/S)QVITLLG (V/I)GNIINIV(M/T)ADSI(R/K)D(N/S)FKIDVSPYGL(N/D)T (Q/K)(N/V)FL(K/R)(T/N)CN(E/D)EATFI(A/V/T)NWLNDEDKKL

SHLLVPCAMLLRLGIVIFSNFLIQN(H/Y/F)(K/R)-X1 wherein X1 is absent, or is
(D/E)K(D/E)FL(A/T)FLN(-/E/K)(-/T)K(N/S/I))EN(L/I)AL

AENEFLGVDHISFLGFLL(H/Y)RWNFDD(V/I)LIESICFV(R/H)TPHA

ARE(K/E)VKKSAYALAITDHLF(A/T)PHDGSSPFN(A/V/T)KAAVALL (K/E)EAK-X2 (SEQ ID NO: 137 or 138);
and wherein X2 is absent or is selected from the group consisting of
TQGINFDL(N/D)NLLSKLP(N/S)KAKENL(N/D)(K/E)ED (SEQ ID NO: 139)
and

NSRN (SEQ ID NO: 140).

In various further embodiments, the at least one polynucleotide encodes a protein selected from the group consisting of SEQ ID NOS: 10-106, or an antigenic fragment thereof. SEQ ID NOS, 44-82 are each Cj0998c protein homologs from other *C. jejuni* strains; SEQ ID NOS, 83 to 106 are each Cj0588 protein homologs from other *C. jejuni* strains; and SEQ ID NOS, 10 to 43 are each Cj0248 protein homologs from other *C. jejuni* strains.

The expression vectors may encode "antigenic portions" of the recited protein. As used herein, and "antigenic portion" is any fragment of 10 or more contiguous amino acids in the recited amino acid sequence. In various further embodiments, the antigenic portion is any fragment of any of the embodiments of the invention is 15, 20, 25, 30, 40, 50, 75, 100, 125, 150, 175, 200, 225, 250, or 275 contiguous amino acids of the recited amino acid sequence.

The one or more isolated polynucleotides may be single or double stranded DNA, RNA, genomic DNA, or cDNA. The one or more isolated polynucleotides may be any nucleic acids encoding the recited one or more proteins, or antigenic fragments thereof. In one embodiment, the one or more isolated polynucleotides are one or more of SEQ ID NO:1 (Cj0998c gene), SEQ ID NO:3 (Cj0588 gene), and SEQ ID NO:5 (Cj0248 gene), or portions thereof encoding antigenic portions of the recited proteins. It will be apparent to those of skill in the art, based on the teachings herein, what polynucleotide sequences will encode the recited polypeptides or antigenic fragments thereof.

As used herein, "isolated polynucleotides" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, secretory signals, nuclear localization signals, and plasma membrane localization signals, as appropriate for a given use.

Any expression vector suitable for an intended use can be used in the immunogenic compositions of the present invention. Such expression vectors can be of any type known in the art, including but not limited to plasmid and viral-based expression vectors. The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors. Specifics of the expression vector will depend on the ultimate desired use. Designing appropriate expression vectors for an intended use is well within the level of those of skill in the art based on the teachings herein.

Any suitable promoter may be used that can direct expression (i.e.: is "operatively linked") of the encoded proteins. The term "promoter" includes any nucleic acid sequence sufficient to direct expression of the encoded protein(s), including inducible promoters, repressible promoters and constitutive promoters. If inducible, there are sequences present which mediate regulation of protein expression so that the polynucleotide is transcribed only when an inducer molecule is present. Such cis-active sequences for regulated expression of an associated polynucleotide in response to environmental signals are well known to the art. The expression vector may comprise any other control sequences as may be suitable for an intended use. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, enhancers, termination signals, and ribosome binding sites.

The immunogenic compositions of the present invention may further comprise any other suitable components as may be useful for a given purpose. In various non-limiting embodiments, the compositions may further comprise one or more expression vectors comprising at least one polynucleotide encoding a protein selected from the group consisting of proteins comprising an amino acid sequence at least 80 percent identical to an amino acid sequence of SEQ ID NO:142 (Cj1534c protein; encoded, for example, by SEQ ID NO:141), SEQ ID NO:108 (1656c protein; encoded, for example, by SEQ ID NO:107), SEQ ID NO:110 (0428 protein; encoded, for example, by SEQ ID NO:109), SEQ ID NO:112 (0168c protein; encoded, for example, by SEQ ID NO:111), SEQ ID NO:114 (0427 protein; encoded, for example, by SEQ ID NO:113), SEQ ID NO:116 (Cj0113 protein; encoded, for example, by SEQ ID NO:115), SEQ ID NO:118 (Cj0982c protein; encoded, for example, by SEQ ID NO:117), SEQ ID NO:120 (Cj0921c protein; encoded, for example, by SEQ ID NO:119), SEQ ID NO:122 (Cj1259 protein; encoded, for example, by SEQ ID NO:121), SEQ ID NO:124 (Cj1339c protein; encoded, for example, by SEQ ID NO:123), SEQ ID NO:126 (Cj0034c protein; encoded, for example, by SEQ ID NO:125), SEQ ID NO:128 (Cj0404 protein; encoded, for example, by SEQ ID NO:127), SEQ ID NO:130 (Cj0365c protein; encoded, for example, by SEQ ID NO:129), SEQ ID NO:132 (Cj0755 protein; encoded, for example, by SEQ ID NO:131), and SEQ ID NO:134 (Cj0420 protein; encoded, for example, by SEQ ID NO:133), or antigenic fragments thereof.

The one or more expression vectors may be the same or different one or more expression vectors that comprise the at least one polynucleotide encoding SEQ ID NO:2 (Cj0998c protein), SEQ ID NO:4 (Cj0588 protein), SEQ ID NO:6 (Cj0248 protein), or fragments thereof. All embodiments of the one or more expression vectors disclosed above apply equally for these additional components. By way of non-limiting example, the one or more expression vectors may be 1, 2, 3, or 4 additional vectors that encode SEQ ID NO:142 (Cj1534c protein), SEQ ID NO:108 (1656c protein), SEQ ID NO:110 (0428 protein), SEQ ID NO:112 (0168c protein), and SEQ ID NO:114 (0427 protein), or antigenic fragments thereof. Those of skill in the art will understand the variety of other combinations that can be employed in accordance with the methods of the invention. Based on the present disclosure, it is well within the level of those of skill in the art to prepare expression vectors according to all embodiments of the invention.

Similar to the immunogens recited above, the optional protein immunogens are present in highly conserved variants between different strains of *Campylobacter jejuni*, and thus the proteins encoded by the one or more expression vectors can be at least 80% identical over the full length of the recited amino acid sequences, or antigenic fragments thereof. In various further embodiments, the proteins encoded by the one or more expression vectors are at least 81, 82, 83, 84, 85, 86, 87, 88, 89, 90, 91, 92, 93, 94, 95, 96, 97, 98, 99, or 100% percent identical over the full length of the recited amino acid sequence(s), or antigenic fragment thereof.

The immunogenic compositions of the present invention may be used for inducing an immune response by administration as naked DNA using standard methods, such as by parenteral delivery. Alternatively, the expression vectors may comprise viral expression vectors, including but not limited to a recombinant adeno-associated virus (AAV) gene delivery vector. In this embodiment, the expression vector is bounded on the 5' and 3' end by functional AAV inverted terminal repeat (ITR) sequences. By "functional AAV ITR sequences" is meant that the ITR sequences function as intended for the rescue, replication and packaging of the AAV virion. Recombinant AAV (rAAV) virions encapsidating the expression vectors of the invention may be produced using standard methodology. In one embodiment, an AAV expression vector according to the invention is introduced into a producer cell, followed by introduction of an AAV helper construct, where the helper construct includes AAV coding regions capable of being expressed in the producer cell and which complement AAV helper functions absent in the AAV vector. This is followed by introduction of helper virus and/or additional vectors into the producer cell, wherein the helper virus and/or additional vectors provide accessory functions capable of supporting efficient rAAV virus production. The producer cells are then cultured to produce rAAV. These steps are carried out using standard methodology. Replication-defective AAV virions encapsulating the recombinant AAV vectors of the instant invention are made by standard techniques known in the art using AAV packaging cells and packaging technology. Examples of these methods may be found, for example, in U.S. Pat. Nos. 5,436,146; 5,753,500, 6,040,183, 6,093,570 and 6,548,286, expressly incorporated by reference herein in their entirety. Further compositions and methods for packaging are described in Wang et al. (US 2002/0168342), also incorporated by reference herein in its entirety. Any suitable method for producing viral particles for delivery can be used.

In another embodiment, the one or more expression vectors are present in a carrier cell, including but not limited to an avirulent, non-*Campylobacter* bacterial carrier cell. Live bacterial vaccine "vectors" (i.e.: bacterial cells comprising immunogenic compositions) have been used successfully to elicit effective immune responses in order to prevent infection. Recombinant attenuated bacterial cell delivered vaccines have been adapted to stably express protective antigens at high levels. They are capable of stimulating strong primary humoral, mucosal and lasting memory immune responses without significant tissue damage or other performance reducing effects. In various non-limiting embodiments, the bacterial carrier cell is an avirulent bacterial cell selected from the group consisting of attenuated *L. monocytogenes*, attenuated *Salmonella* spp., attenuated *V. cholerae*, attenuated *Shigella* spp., attenuated *M. bovis* BCG, attenuated *Y. enterocolitica*, attenuated *B. anthracis, S. gordonii, Lactobacillus* spp., and *Staphylococcus* spp. As used herein, "attenuated" means that the bacteria is reduced in causing disease symptoms in a host it is delivered to compared to a non-attenuated bacterial vector. Suitable attenuated bacteria can be any species or strain that is or can be sufficiently attenuated to allow for its non-pathological administration to humans and/or animals in live and/or dead form. In one embodiment, an attenuated *Salmonella* species is used. In exemplary embodiments, *Salmonella* that can be used include, but are not limited to *Salmonella enterica* strains selected from the group consisting of *S. typhimurium, S. enteriditis, S. heidelberg, S. gallinarum, S. hadar, S. agona, S. kentucky, S. typhi, S. paratyphi* and *S. infantis. S. typhimurium* is especially useful for vaccination purposes because the genome sequence is fully characterized and many animal studies confirm its safe medical use. Recombinant attenuated *Salmonella* vaccines (RASVs) have been constructed to deliver antigens from other pathogens to induce immunity to those pathogens in vaccinated hosts; see, for example, Curtiss et al., Crit Rev Immunol. 2010; 30(3):255-70; 2010; Qiu et al., J. Virological Methods 188:108; Strugnell et al., Infect. Immunol. 1992, 60:3994; Layton et al., Clinical and Vaccine Immunology march 2011, 449-454; Al-Ojali et al., Microbial Pathogenesis 52:326 (2012); and (Wyszynska et al., 2004) Wyszyńska et al. (2004). In one embodiment, the RASV comprises attenuating mutations in the pmi (mannose-6-phosphate isomerase), fur (ferric uptake regulator) and crp (cAMP regulatory protein) genes (see, for example, (Li et al., PNAS 106:592-597 2009, Curtiss et al., 2009) and U.S. Pat. No. 8,133,493. In another embodiment, the RASV comprises the χ9992 vector disclosed in U.S. Pat. No. 8,133,493. In another embodiment, the RASV is one that is commercially available, such as Megan®Vac1 (Lohman Animal Health, US).

Attenuated bacterial cells can be transfected with the one or more expression vectors using standard techniques in the art.

In a second aspect, the present invention provides an immunogenic composition, comprising (a) one or more isolated proteins selected from the group consisting of proteins comprising an amino acid sequence at least 80 percent identical to SEQ ID NO:2 (Cj0998c protein), SEQ ID NO:4 (Cj0588 protein), and SEQ ID NO:6 (Cj0248 protein), or antigenic portions thereof; and (b) a pharmaceutically acceptable carrier.

As disclosed above for the first aspect of the invention, the immunogenic compositions of the second aspect of the invention can be used, for example for stimulating an immune response in subjects at risk of *C. jejuni* infection or colonization, including but not limited to vertebrates such as chickens, turkeys, cattle, sheep, pigs, and humans.

In one embodiment, the immunogenic composition comprises one of the recited proteins, or antigenic fragments thereof. In another embodiment, the immunogenic composition comprises two of the proteins comprising an amino acid sequence at least 80 percent identical to the recited amino acid sequences (i.e.: SEQ ID NO:2 and SEQ ID NO:4; SEQ ID NO:2 and SEQ ID NO:6; or SEQ ID NO:6 and SEQ ID NO:8), or antigenic fragments thereof. In a further embodiment, the immunogenic composition comprises all three of the proteins comprising an amino acid sequence at least 80 percent identical to the recited amino acid sequences (i.e.: (i.e.: SEQ ID NO:2, SEQ ID NO:4, and SEQ ID NO:6), or antigenic fragments thereof.

The Cj0998c, Cj0588, and Cj0248 proteins are present in highly conserved variants between different strains of *C. jejuni*, and thus the proteins can be at least 80% identical over the full length of the recited amino acid sequences, or antigenic fragments thereof. In various further embodiments, the proteins are at least 81, 82, 83, 84, 85, 86, 87, 88, 89, 90, 91, 92, 93, 94, 95, 96, 97, 98, 99, or 100% percent identical over the full length of the recited amino acid sequence(s), or antigenic fragment thereof.

In one embodiment, the at least one protein is selected from the group consisting of the following, or an antigenic fragment thereof:

```
(a) SEQ ID NO: 7 (Cj0998c genus)
MKK(I/V/F)(LN)(V/A/L)S(V/I)(L/F)S(S/F)CLLASALSAVSFK

EDSLK(I/V)SFEGYKTKDM(I/V)G(T/V/I/A)(K/R)GEFKNVEY(K/

N)FSK(N/S)(I/T)KD(L/F)ASYLKGAKATI(K/E)PS(N/D)AFM(G/

S)EG(N/L)D(I/V)ITNNITKVFFPALLG(D/N)(T/A)DIKVVFQD(V/

A/M)I(A/V)GE-X1ITMDKKSTI(V/I)PLTYTIKD(N/D)KFEAKGQ (L/F)DLH(T/A)FKN(G/A)SKALKALSD(V/A)A(A/T/P)GHGGISWP

LVDISFNADL(A/T/V)E wherein X1 is absent or is
NKGVISAK (SEQ ID NO: 135);

(b) SEQ ID NO: 8: (00588 genus)
X1-(L/M)(D/N/E)LL(S/R)EIY(V/I)SRAALKLK(K/N)FLEEN(D/

G/N)IE(I/V)(K/N)(H/Q/N)KNCLDIGSSTGGFVQILLEN(Q/K)ALK

IT(A/T)LDVG(S/N)NQLH(P/S/L)(S/N)LR(V/A/T)NE(K/I)(I/

V)IL(H/Y)EN(T/I)DLR(A/T/V)FKSEEKFE(L/F)(V/I)TCDVSFI

SL(I/V)NLLYY(I/V)(D/N)NLAL(K/R)EIILLFKPQFEVGKN(I/V)

KRDKKGVLKD(D/G)(K/R)(A/V)ILKA(R/K)MDFEK(A/E)CAKL(G/

S)W(L/F/I)LKNTQKS(S/C)IKGKEGNVEYFYYYIKN wherein X1 is absent or is
M(R/I)(F/-)(D/-)FF(V/I)SKRL(N/D)ISRNKALELIE(N/S)EE (I/V)LLNGK(S/N)FKAS(F/C)DVKN(F/L)LENLKK(T/A/K)QDLN (P/L/S)E(D/E)(I/V)(L/Y)L(A/T/S)(N/D/K)(E/G)L(K/N)

(SEQ ID NO: 136);
and (c) SEQ ID NO: 9 (Cj0248 genus)
(M/-)I(G/-)DMNELLLKSVEVLPPLPDTVSKLRKYVSEANSNIETMKV (A/V)EIISSDPLMTAKLLQLANSPYYGFTREITTI(N/S)QVITLLG(V/

I)GNIINIV(M/T)ADSI(R/K)D(N/S)FKIDVSPYGL(N/D)T(Q/K)

(N/V)FL(K/R)(T/N)CN(E/D)EATFI(A/V/T)NWLNDEDKKLSHLLV

PCAMLLRLGIVIFSNFLIQN(H/Y/F)(K/R)-X1 wherein X1 is absent, or is
(D/E)K(D/E)FL(A/T)FLN(-/E/K)(-/T)K(N/S/I))EN(L/I)AL

AENEFLGVDHISFLGFLL(H/Y)RWNFDD(V/I)LIESICFV(R/H)TPHA

ARE(K/E)VKKSAYALAITDHLF(A/T)PHDGSSPFN(A/V/T)KAAVALL (K/E)EAK-X2 (SEQ ID NO: 137 or 138);
and wherein X2 is absent or is selected from the group
consisting of
TQGINFDL(N/D)NLLSKLP(N/S)KAKENL(N/D)(K/E)ED (SEQ ID NO: 139)
and

NSRN (SEQ ID NO: 140).
```

In various further embodiments, the at least one polynucleotide encodes a protein selected from the group consisting of SEQ ID NOS: 10-106, or an antigenic fragment thereof. SEQ ID NOS, 44-82 are each Cj0998c protein homologs from other *C. jejuni* strains; SEQ ID NOS, 83-106 are each Cj0588 protein homologs from other *C. jejuni* strains; and SEQ ID NOS, 10-43 are each Cj0248 protein homologs from other *C. jejuni* strains.

The immunogenic composition of any embodiment of this second aspect of the invention may comprise "antigenic portions" of the recited proteins. As used herein, and "antigenic portion" is any fragment of 10 or more contiguous amino acids in the recited amino acid sequence. In various further embodiments, the antigenic portion is any fragment of 15, 20, 25, 30, 40, 50, 75, 100, 125, 150, 175, 200, 225, 250, or 275 contiguous amino acids of the recited amino acid sequence.

The immunogenic compositions of the second aspect of the invention may comprise proteins modified in any suitable way. In one embodiment, the protein component(s) of the composition are treated to extend in vivo half-life by, for example, such as by PEGylation, HESylation, PASylation, or glycosylation. The proteins may also be glycosylated as deemed appropriate, using standard techniques in the art. In another embodiment, those protein components in the immunogenic compositions that possess N-glycosylation sequences (NXS or NXT) may be glycosylated, to help further stimulate the immune response.

The immunogenic compositions of the second aspect of the invention may further comprise any other suitable components as may be useful for a given purpose. In various non-limiting embodiments, the compositions may further comprise one or more additional proteins selected from the group consisting of proteins comprising an amino acid sequence at least 80% identical to SEQ ID NO:142 (Cj1534c protein), SEQ ID NO:108 (Cj1656c protein), SEQ ID NO:110 (Cj0428 protein), SEQ ID NO:112 (Cj0168c protein), SEQ ID NO:114 (Cj0427 protein), SEQ ID NO:116 (Cj0113 protein), SEQ ID NO:118 (Cj0982c protein), SEQ ID NO:120 (Cj0921c protein), SEQ ID NO:122 (Cj1259 protein), SEQ ID NO:124 (Cj1339c protein), SEQ ID NO:126 (Cj0034c protein), SEQ ID NO:128 (Cj0404 protein), SEQ ID NO:130 (Cj0365c protein), SEQ ID NO:132 (Cj0755 protein), and SEQ ID NO:134 (Cj0420 protein), or antigenic fragments thereof. Similar to the immunogens recited above, the optional protein immunogens are present in highly conserved variants between different strains of *Campylobacter jejuni*, and thus the proteins can be at least 80% identical over the full length of the recited amino acid sequences, or antigenic fragments thereof. In various further embodiments, the proteins encoded by the one or more expression vectors are at least 81, 82, 83, 84, 85, 86, 87, 88, 89, 90, 91, 92, 93, 94, 95, 96, 97, 98, 99, or 100% percent identical over the full length of the recited amino acid sequence(s), or antigenic fragment thereof.

In another embodiment, the immunogenic compositions of the second aspect of the invention may further comprise a *C. jejuni*pilus protein as described in WO 2008/008092, incorporated by reference herein in its entirety. The pilus protein described in WO 2008/008092 was shown to stimulate an immune response against *C. jejuni*, and thus it is suitable for inclusion in the immunogenic compositions of the second aspect of the present invention. Methods for isolating the *C. jejuni* pilus protein are described in WO 2008/008092.

The immunogenic compositions of the invention may comprise any suitable amount/dosage of the composition as determined most appropriate. In one embodiment, the immunogenic composition comprises about $10^6$-$10^{10}$ avirulent bacterial cells per dose. In another embodiment where the composition comprises immunogenic proteins, the composition may comprise about 0.1 ug/kg-100 mg/kg body weight of the proteins; alternatively, it may be 0.5 ug/kg to 50 mg/kg; 1 ug/kg to 25 mg/kg, or 5 ug/kg to 10 mg/kg body weight of the proteins.

The immunogenic compositions of the present invention (i.e.: any embodiment or combination of embodiments of the first and second aspects of the invention) can be formulated by any of the means known in the art. The immunogenic compositions are typically formulated as a pharmaceutical composition, such as those disclosed above, and can be formulated for administration via any suitable route, including orally, as injectables, parentally, by inhalation spray, intranasally, rectally, mucosally, topically, or for administration by oral gavage or ad libitum feeding, for example, in drinking water, either as liquid solutions or suspension, in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. Solid forms suitable for solution in, or suspension in, liquid prior to injection or other administration may also be prepared. The compositions may also, for example, be emulsified, or the encapsulated in liposomes or microparticles. The immunogenic compositions may also be present in and/or expressed by transgenic plants.

The immunogenic compositions according to the present invention may further comprise any suitable adjuvant. Immunological adjuvants in general comprise substances that boost the immune response of the host in a nonspecific manner. A number of different adjuvants are known in the art. Examples of adjuvants are Freunds Complete and Incomplete adjuvant, vitamin E, non-ionic block polymers and polyamines such as dextransulphate, carbopol and pyran, oligopeptide, emulsified paraffin-Emulsigen™ (MVP Labs, Ralston, Nebr.), L80 adjuvant containing aluminum hydroxide (Reheis, N.J.), Quil A™ (Superphos); surface active substances such as Span™, Tween™, hexadecylamine, lysolecitin, methoxyhexadecylglycerol and saponins; peptides such as muramyldipeptides, dimethylglycine, and tuftsin; immune-stimulating complexes (ISCOMS), mineral oil e.g. Bayol or Markol, vegetable oils or emulsions thereof, aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-s-n-glycero-3hydroxyphosphoryloxy)-ethylamine (CGP 19835A, referred to as MTP-PE); and RIBI, which contains three components extracted from bacteria: monophosphoryl lipid A, trehalose dimycolate and cell wall skeleton (MPL+TDM+CWS) in a 2% squalene/Tween 80 emulsion. In embodiments designed for mucosal administration, the immunogenic compositions may further comprise an adjuvant, including but not limited to such as the nontoxic cholera toxin B subunit (Sigma Chemical Company, St. Louis, Mo.) and organometallopolymers including linear, branched or cross-linked silicones which are bonded at the ends or along the length of the polymers to the particle or its core. Such polysiloxanes can vary in molecular weight from about 400 up to about 1,000,000 daltons; the preferred length range is from about 700 to about 60,000 daltons. Suitable functionalized silicones include (trialkoxysilyl) alkyl-terminated polydialkylsiloxanes and trialkoxysilyl terminated polydialkylsiloxanes, for example, 3-(triethyoxysilyl) propyl terminated polydimethylsiloxane. See U.S. Pat. No. 5,571,531, incorporated by reference herein. Phosphazene polyelectrolytes can also be incorporated into immunogenic compositions for mucosal administration (See e.g., U.S. Pat. No. 5,562,909).

The immunogenic compositions according to the present invention may also comprise preservatives such as sodium azide, thimersol, gentamicin, neomycin, and polymyxin.

The immunogenic compositions may be mixed with excipients or carriers which are pharmaceutically acceptable and compatible with the protein immunogen(s) to be used. Suitable excipients include, but are not limited to, water, saline, dextrose, glycerol, ethanol, or the like and combinations thereof. Such an immunogenic composition can easily be prepared by admixing the protein with a pharmaceutically acceptable carrier. A pharmaceutically acceptable carrier is understood to be a compound that does not adversely affect the health of the animal to be vaccinated, at least not to the extent that the adverse effect is worse than the effects seen when the animal is not vaccinated. A pharmaceutically acceptable carrier can be e.g. sterile water or a sterile physiological salt solution. In a more complex form, the carrier can e.g. be a buffer.

The immunogenic composition may further comprises stabilizers, e.g. to protect degradation-prone components from being degraded, to enhance the shelf-life of the composition, or to improve freeze-drying efficiency. Useful stabilizers include, without limitation, SPGA, skimmed milk, gelatin, bovine or other serum albumin, carbohydrates e.g. sorbitol, mannitol, trehalose, starch, sucrose, dextran or glucose, proteins such as albumin or casein or degradation products thereof, and buffers, such as alkali metal phosphates. Where an albumin is used, it is desirably from the same species as the animal (or human) to which the immunogenic composition containing it will be administered. Freeze-drying is an efficient method for conservation. Freeze-dried material can be stored stable for many years. Storage temperatures for freeze-dried material may well be above zero degrees, without being detrimental to the material. Freeze-drying can be done according to all well-known standard freeze-drying procedures. However, the immunogenic compositions of the invention may be stored in any suitable manner. For example, the immunogenic compositions could be lyophilized or otherwise stabilized and stored in food or water for delivery.

In an exemplary embodiment when the immunogenic compositions are designed for administration to a non-human subject, such as chickens, turkeys, birds, sheep, pigs, cattle, dogs, or cats, the immunogenic composition is formulated for mucosal administration, such as by admixing of the composition with drinking water or food, or admixing for use as a spray, to mist over the animals to uptake the immunogenic composition during grooming behavior. However, any suitable method of administration can be used for any subject. Thus, in various embodiments the immunogenic compositions are formulated for intraocular, intranasal, or transdermal administration.

In a third aspect, the present invention provides methods for stimulating an immune response against *Campylobacter*, comprising administering to a subject an effective amount of the immunogenic composition according to any embodiment or combination of embodiments of the first or second aspects of the present invention to generate an immune response against *Campylobacter.*

In a fourth aspect, the present invention provides methods for reducing *Campylobacter* intestinal colonization in a subject, comprising administering an amount effective of the immunogenic composition according to any embodiment or combination of embodiments of the first or second aspects of the present invention to reduce *Campylobacter* intestinal colonization in the subject.

As disclosed herein, the inventors have identified three novel putative virulence genes (Cj0248, Cj0588, and Cj0998c) from *C. jejuni* encoding novel proteins from the outer-membrane of the bacterium. The inventors have further discovered that each of the Cj0998c protein, the Cj0588 protein, and the Cj0248 protein are potent immunogens for stimulating an effective immune response against *Campylobacter jejuni* ("*C. jejuni*"). For example, as disclosed in detail herein, two separate vaccination trials of chickens with a vector expressing the Cj0988c protein demonstrated reduced numbers of *C. jejuni* in birds after challenge an average of 2.5 logs CFU (geomean 3 logs) when compared to the cecal numbers of non-vaccinated control birds. Furthermore, vaccination trials demonstrated a significant reduction (1-4 logs) (1 log with heterologous strain and 4 logs with homologous strain) of *C. jejuni* in cecal contents of chickens vaccinated with vectors expressing the Cj0588 protein and challenged. Each of the proteins was initially isolated from an outer-membrane (OMP) extraction of a *C. jejuni* biofilm.

Campylobacteriosis is a food-borne disease primarily generally caused by *C. jejuni*. The major risk factor in acquiring the disease is the handling and consumption of poultry. However, the epidemiology of poultry colonization with *Campylobacter* such as *C. jejuni* is extremely complex. Birds become colonized within 14 days of hatching, spreading the infection throughout the flock by the end of the grow-out period. Strain differences, based on subtyping and/or genotyping assays, exist between and within flocks. Although some flocks remain *Campylobacter*-free, most flocks have 50-100% of the birds colonized by grow-out. Nevertheless, broilers (i.e., chickens of either gender that will be slaughtered for meat at about 5 to 8 weeks old depending on weight) become contaminated with *Campylobacter*, such as *C. jejuni* and although this microorganism acts as normal flora in the chicken, undercooked chicken is a primary vehicle for transmission of *Campylobacter*, such as *C. jejuni* to humans and remains a significant public health concern.

The methods may be used on any suitable subject at risk of *Campylobacter* infection, including but not limited to vertebrates such as chickens, turkeys, birds, cattle, sheep, pigs, dogs, cats, and humans. In one non-limiting embodiment, a human subject may be anyone that consumes chicken, beef, turkey, or pork. In another embodiment, a human subject may be one that works with animals (i.e.: farm workers, workers at slaughterhouses and meat processing plants, etc.) such as chickens, turkeys, cattle, sheep, and pigs.

In another embodiment, the subject is a feed animal such as chickens, turkeys, cattle, sheep, and pigs. In a preferred embodiment, the subject is a chicken. In these embodiments, the feed animal may be of any suitable age. Birds become colonized with *C. jejuni* within 14 days of hatching, spreading the infection throughout the flock by the end of the grow-out period. Thus, in one embodiment, the methods are initially carried out by about 14 days after hatching. It will be understood by those of skill in the art that additional booster administrations may be desirable after the initial administration; such booster administrations can be carried out at any suitable time, such as by about 21 days after hatching.

In another non-limiting embodiment where the subject is a feed animal, the methods are carried out before slaughtering. However, it will be understood that the methods can be used on chickens or turkeys at any suitable time, as appropriate for a given use.

Campylobacteriosis is currently one of the most common bacterial food-borne diseases in humans in the U.S. and is responsible for causing an estimated 1.3 million cases annually in the U.S., often accompanied by acute gastroenteritis. The infectious dose in the development of the disease is variable and ranges from 500 to $10^6$ organisms. Variation in infectious dose is thought to be due to either individual susceptibility or to the relative virulence of the organism. The incubation period is one to seven days with clinical symptoms including fever, severe abdominal cramps, and a watery diarrhea or a dysentery-like syndrome typical of shigellosis. The disease is usually self-limiting, lasting from two to seven days but occasionally is fatal (120-360 deaths per year), mainly in infants and young adults. Serious complications such as arthritis occur in an estimated 1-5% of cases and Guillain-Barre Syndrome, a form of neuromuscular paralysis occurs at a rate of 1 per 1,000 patients.

Conversely, *Campylobacter*, such as *C. jejuni*, colonizes poultry as a commensal, that is, without producing any overt signs of disease. Similarly, *Campylobacter*, such as *C. jejuni* may colonize other feed animals as a commensal as well. However, infected cattle may suffer from diarrhea, weight loss, and suffer from fever and increased heart rate.

The methods of the third and fourth aspects of the invention may be used to stimulate an immune response against or to reduce intestinal colonization of any species of *Campylobacter*. In preferred embodiments, the methods of the third and fourth aspects of the invention are used to stimulate an immune response against or to reduce intestinal colonization of varied species of *Campylobacter* including but not limited to *C. jejuni*, *C. coli*, *C. lari* and/or *C. upsaliensis*.

As used herein, methods for "stimulating an immune response" result in one or more effects (e.g., maturation, proliferation, direct- or cross-presentation of antigen, gene expression profile) on cells of either the innate or adaptive immune system. For example, the immune response may involve, effect, or be detected in innate immune cells such as, for example, dendritic cells, monocytes, macrophages, natural killer cells, and/or granulocytes (e.g., neutrophils, basophils or eosinophils). The immune response may also involve, effect, or be detected in adaptive immune cells including, for example, lymphocytes (e.g., T cells and/or B cells). The immune response may be observed by detecting such involvement or effects including, for example, the presence, absence, or altered (e.g., increased or decreased) expression or activity of one or more immunomodulators. The immune response may stimulate a de novo or previously undetected antibody response, or enhance or suppress an existing response against the immunogen by, for example, causing an increased antibody response (e.g., amount of antibody, increased affinity/avidity) or an increased cellular response (e.g., increased number of activated T cells, and/or increased affinity/avidity of T cell receptors. In certain embodiments, the immune response may be protective, meaning that the immune response may be capable of preventing initiation or continued infection of or growth within a host and/or by eliminating *C. jejuni* from the host. In some instances, elimination of an agent from the host may mean that the method is therapeutic, in that the method is used to treat a subject already infected with *C. jejuni*. When the method is therapeutic, the method may comprise treating a *C. jejuni* infection, wherein "treating" means accomplishing one or more of the following: (a) reducing the severity of the infection; (b) limiting or preventing development of symptoms characteristic of the infection; (c) inhibiting worsening of symptoms characteristic of the infection; (d) limiting or preventing recurrence of the disorder(s) in subjects that have previously had the infection; and (e) limiting or preventing recurrence of symptoms in subjects that were previously symptomatic for the infection.

As used herein, "reducing *Campylobacter* intestinal colonization" means reducing a level of intestinal colonization that would be observed in the subject in the absence of administering the one or more immunogenic compositions of the invention. Any level of reduction is beneficial in reducing *Campylobacter* transmission, for example, from poultry to a human consuming the poultry. In one embodiment, the reduction comprises at least 10% reduction in intestinal colonization compared to intestinal colonization in the absence of treatment; in various further embodiments, the intestinal colonization is reduced by at least 20%, 25%, 50%, 75%, 80%, 85%, 90%, 95%, or more compared to intestinal colonization in the absence of treatment. Techniques for quantifying a level of *Campylobacter* intestinal colonization are well known in the art and include, but are not limited to, examining cecal or fecal levels of *Campylobacter*. Techniques for determining fecal contamination of *Campylobacter* in production to quantify the level of *Campylobacter* organisms from a carcass rinse of feed animals, such as poultry, at various points of processing, such as after chilling are also established.

In preferred embodiments of the third and fourth aspects of the invention, the one or more expression vectors are present in a carrier cell, including but not limited to a non-*Campylobacter* bacterial carrier cell. In various non-limiting embodiments, the bacterial carrier cell is an avirulent bacterial cell selected from the group consisting of attenuated *L. monocytogenes*, attenuated *Salmonella* spp., attenuated *V. cholerae*, attenuated *Shigella* spp., attenuated *M. bovis* BCG, attenuated *Y. enterocolitica*, attenuated *B. anthracis, S. gordonii, Lactobacillus* spp., and *Staphylococcus* spp. In one embodiment, an attenuated *Salmonella* species is used. In exemplary embodiments, *Salmonella* that can be used include, but are not limited to *Salmonella enterica* strains selected from the group consisting of *S. typhimurium, S. enteriditis, S. heidelberg, S. gallinarum, S. hadar, S. agona, S. kentucky, S. typhi, S. paratyphi* and *S. infantis. S. typhimurium* is especially useful for vaccination purposes because the genome sequence is fully characterized and many animal studies confirm its safe medical use. Recombinant attenuated *Salmonella* vaccines (RASVs) have been constructed to deliver antigens from other pathogens to induce immunity to those pathogens in vaccinated hosts; see, for example, Curtiss et al., Crit Rev Immunol. 2010; 30(3):255-70; 2010; Qiu et al., J. Virological Methods 188:108; Strugnell et al., Infect. Immunol. 1992, 60:3994; Layton et al., Clinical and Vaccine Immunology march 2011, 449-454; Al-Ojali et al., Microbial Pathogenesis 52:326 (2012); and Wyszyńska et al. (2004). In one embodiment, the RASV comprises attenuating mutations in the pmi, fur and crp genes and U.S. Pat. No. 8,133,493. In another embodiment, the RASV comprises the χ9992 vector disclosed in U.S. Pat. No. 8,133,493. In another embodiment, the RASV is one that is commercially available, such as Megan®Vac1 (Lohman Animal Health, US).

The immunogenic compositions can be administered via any suitable route, including orally, as injectables, parentally, by inhalation spray, intranasally, rectally, mucosally, topically, or for administration by oral gavage or ad libitum feeding, for example, in drinking water, either as liquid solutions or suspension, in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. Solid forms suitable for solution in, or suspension in, liquid prior to injection or other administration may also be prepared. The compositions may also, for example, be emulsified, or the encapsulated in liposomes.

In an exemplary embodiment when the subject is a non-human subject, such as chickens, turkeys, birds, sheep, pigs, cattle, dogs, or cats, the immunogenic composition are administered orally or mucosally, such as by admixing of the composition with drinking water or food, or admixing for use as a spray, to mist over the animals to uptake the immunogenic composition during grooming behavior. In exemplary embodiments where the subject is a human, the immunogenic compositions are administered orally or mucosally. However, any suitable method of administration can be used for any subject.

The immunogenic compositions are administered in a manner compatible with the dosage formulation, and in such amount and manner as will be prophylactically and/or therapeutically effective, according to what is known to the art. The quantity to be administered depends on the subject to be treated, the functional capacity of the subject's immune system, the degree of protection desired, and other factors. Precise amounts of the active ingredient required to be administered may depend on the judgment of the individual administering the immunogenic compositions and may be peculiar to each individual, but such a determination is within the level of those of skill in the art based on the teachings herein. In one embodiment, about $10^6$-$10^{10}$ avirulent bacterial cells per dose can be administered. In another embodiment where immunogenic proteins are administered, a suitable dosage range may, for instance, be 0.1 ug/kg-100 mg/kg body weight; alternatively, it may be 0.5 ug/kg to 50 mg/kg; 1 ug/kg to 25 mg/kg, or 5 ug/kg to 10 mg/kg body weight.

The immunogenic compositions may be administered in a single dose or in multiple dosages as determined most appropriate, such as a two dose schedule, for example two to eight weeks apart; or a multiple dose schedule or in combination with other vaccines. A multiple dose schedule is one in which a primary course of vaccination may include 1 to 10 or more separate doses, followed by other doses administered at subsequent time intervals as required to maintain and/or reinforce the immune response, e.g., at 1 to 4 months for a second dose, and if needed, a subsequent dose(s) after several months.

Example 1

Immunogenic Compositions Based on Cj0988c

The DNA and protein sequence of Cj0988c are provided in SEQ ID NO:1 and SEQ ID NO:2, respectively.

*Salmonella typhimurium* Vector χ9992:

The vector used was a *Salmonella typhimurium* vector χ9992 (Curtiss et al., 2009) which contains eight mutations, with three of the mutations attenuating: the pmi, fur, and crp genes.

1) Δpmi-2426-Eliminates phosphomannose isomerase which ceases LPS-O antigen synthesis in the absence of mannose;

2) ΔgmdfcI-Reduces biofilm formation and prevents the formation of colonic acid which aids in the survival of asdA mutants;

3) ΔasdA27-Deletion of a gene encoding an enzyme necessary for diaminopimelic acid (DAP). Strain requires supplemental DAP until the introduction of the plasmid. Eliminates need for antibiotic resistance markers;

4) $\Delta P_{fur77}$::TT araC $P_{BAD}$fur::TT araC $P_{BAD}$ c2 ΔPcrp527::TT araC $P_{BAD}$ crp—Allows fur and crp gene expression only in the presence of arabinose, producing pYA3493 (FIG. 1), a strain which is maximally invasive prior to display of attenuated phenotype following cell division;

5) ΔrelA198::araC$P_{BAD}$lacITT—eliminates relA gene to uncouple growth from protein synthesis and provides arabinose-dependent synthesis of the LacI repressor to confer regulated delayed in vivo synthesis of recombinant proteins, and 6) ΔaraE25 ΔaraBAD23—Eliminates the ability of *Salmonella* to metabolize arabinose. Allows retention of arabinose in the cytoplasm without use.

The vector plasmid pYA3493 contains the asd gene to compliment the chromosomal ΔasdA27 mutation and ensure that the plasmid will not be lost in vivo. The plasmid also fuses the expressed product to a β-lactamase signal sequence for periplasmic secretion of the protein. Finally, the plasmid has a strong promoter (−35 region of trp promoter/−10 lac) in $P_{trc}$ (FIG. 1). Use of this plasmid does not confer antibiotic resistance to the *Salmonella* vaccine.

The vector that we used for the amplification of the plasmid with the inserted *C. jejuni* gene is *E. coli* χ6212. This strain is Asd—allowing amplification of the plasmid, which is then extracted and electroporated into *Salmonella* χ9992.

Gene Cj0998c expresses a hypothetical protein that is part of the outer membrane of the bacterium. Gene Cj0998c was cloned individually into plasmid pYA3493 and expressed from the *Salmonella* vector χ9992.

A. Cloning of the Cj0998c Gene into the *Salmonella* Vector

The *Salmonella* strain (χ9992) used as the vector has three different mutations which results in its attenuation. The strain is safe and immunogenic and acts as a phenotypically wild-type strain at the time of immunization but becomes attenuated after colonization of host tissues. The plasmid contains the asd gene which provides a marker for laboratory differentiation using media not containing DAP to grow plasmid-containing strains. Since this gene is required for the survival of the vector without DAP, the plasmid is maintained in the vector during in vivo colonization. Gene Cj0998c was cloned into *Salmonella* χ9992. Essentially, primers to each gene were designed and the gene amplified using PCR. Each gene product was inserted into plasmid pYA3493 (asd+), cloned into *E. coli* χ6212 (asd−) and cultured for amplification. Following growth, the plasmid was extracted from the *E. coli* strain, cloned into the *Salmonella typhimurium* vector, and the transformants plated on LB media minus DAP, cultured at 37° C. on LB agar, harvested, and stored frozen at −80° C. Confirmation that the gene was present in the vector was accomplished through a plasmid extraction and sequence analysis of genes following PCR and gel electrophoresis.

B. *Salmonella* Growth In Vitro

The *Salmonella* vector expressing the Cj0998c protein and the *Salmonella* empty vector were grown in Luria Bertani (LB) broth supplemented with 0.1% glucose, 0.05% mannose, and 0.1% arabinose for 24 h at 37° C. with shaking. Following incubation, the overnight cultures were pelleted and re-suspended in PBS to a final concentration of $1\times10^{10}$ CFU/ml.

C. Vaccination of Poultry

Vaccination of chickens, twice, with the vector expressing the Cj0988c protein reduced cecal numbers of *C. jejuni* in birds an average of 2.5 logs CFU (geomean of 3.0 logs CFU) when compared to the cecal numbers of non-vaccinated control birds (Table 1). One outlier of 1.00E+07 (bold underlined cell, Table 3) was present in 31 birds examined. Cornish X Rock chickens were obtained from McMurray Hatchery (IA) and randomly assigned to isolated groups. The chickens were screened for the fecal presence of *C. jejuni* and/or *Salmonella*. The chickens were vaccinated orally, at days 10 and 16, with 1 ml of the *Salmonella* vector expressing the Cj0988 protein (~$10^{10}$ CFU/ml) or the *Salmonella* empty vector and challenged with $10^5$ CFU/ml of *C. jejuni* strain NCTC11168 10 days after the second vaccination. Prior to vaccination and challenge, chickens were fasted for 8 hours. Food was returned one hour post vaccination/challenge. Aside from this period, food and water were available ad libitum. The chickens were necropsied 10 days after challenge infection. Cecal contents were ten-fold diluted and direct plated onto modified Campy Cefex agar plates incubated for 48 h at 10% $CO_2$ microaerophilic conditions for enumeration of *Campylobacter*.

TABLE 1

Combined data of *C. jejuni* vaccination trials 1 & 2
*C. jejuni* NCTC11168 Challenge-Trials 1&2

| | Cj0998c | Control-EV | Controls |
|---|---|---|---|
| Average | 6.11E+05 | 6.75E+07 | 1.15E+08 |
| Geomean | 2.60E+04 | 4.41E+07 | 4.83E+07 |

TABLE 2

Vaccination Trial 1-Ten day old chickens vaccinated twice with the vector expressing gene Cj0998c, or the *Salmonella* empty vector only (Control-EV), or non-vaccinated controls
*C. jejuni* NCTC11168 Challenge-Trial 1

| | Cj0998c | Control-EV | Controls |
|---|---|---|---|
| | 1.0E+03 | 1.0E+07 | 3.0E+08 |
| | 7.0E+04 | 1.2E+07 | 6.0E+07 |
| | 7.4E+04 | 1.0E+08 | 1.0E+07 |
| | 8.2E+04 | 2.0E+08 | 1.0E+07 |
| | 1.0E+04 | 7.0E+07 | 2.0E+08 |
| | 2.0E+04 | 9.0E+07 | 2.0E+07 |
| | 3.0E+04 | 1.0E+08 | 4.0E+08 |
| | 2.0E+03 | 1.0E+08 | 1.2E+08 |
| | 6.0E+04 | 2.0E+07 | 1.0E+07 |
| | 3.0E+04 | 1.0E+07 | 2.0E+07 |
| Average | 3.79E+04 | 7.12E+07 | 1.15E+08 |
| Geomean | 1.98E+04 | 4.45E+07 | 4.83E+07 |

TABLE 3

Vaccination Trial 2-Ten day old chickens vaccinated twice with the vector expressing gene Cj0998c (two groups), or the *Salmonella* empty vector only (Control-EV)
*C. jejuni* NCTC11168 Challenge-Trial 2

| Cj0998c | Cj0998c | Control-EV |
|---|---|---|
| 1.40E+04 | 2.00E+05 | 5.00E+07 |
| 3.20E+03 | 1.70E+05 | 3.00E+07 |
| 7.00E+04 | 3.00E+04 | 2.00E+07 |

TABLE 3-continued

Vaccination Trial 2-Ten day old chickens vaccinated
twice with the vector expressing gene Cj0998c (two groups),
or the *Salmonella* empty vector only (Control-EV)
C. *jejuni* NCTC11168 Challenge-Trial 2

|  | Cj0998c | Cj0998c | Control-EV |
|---|---|---|---|
|  | 1.00E+02 | 2.70E+05 | 1.70E+08 |
|  | 7.00E+04 | 3.00E+05 | 3.00E+07 |
|  | 9.00E+03 | 2.40E+04 |  |
|  | 1.05E+04 | 1.50E+04 |  |
|  | 1.00E+00 | 5.00E+06 |  |
|  | 6.00E+03 | 2.30E+06 |  |
|  | 3.00E+03 | 1.00E+07 |  |
|  | 6.00E+04 |  |  |
| Average | 2.23E+04 | 1.83E+06 | 6.00E+07 |
| Geomean | 3.78E+03 | 2.84E+05 | 4.33E+07 |

Example 2

Immunogenic Compositions Based on Cj0588 and Cj0248

1. The DNA and protein sequence of Cj0588 are provided in SEQ ID NO:3 and SEQ ID NO:4, respectively.
2. The DNA and protein sequence of Cj0248 are provided in SEQ ID NO:5 and SEQ ID NO:6, respectively.
3. Mutation of *C. jejuni* Genes Genes Cj0588 and Cj0248 were cloned and mutated in *C. jejuni* by insertion of a chloramphenicol cassette in the center of each gene. Essentially, two sets of primers were designed for each gene to yield fragments consisting of the initial and terminal 15 bases of the gene and their associated flanking regions. These fragments were cloned into a suicide vector and positioned around the chloramphenicol acetyltransferase (CAT) gene, such that the antibiotic cassette was between the initial and terminal regions of the gene, taking up ~255 bases of each gene. The vector containing the CAT gene and the flanking bases of each gene was then introduced by electroporation into *C. jejuni* strain M129 (Cj0588) or strain NCTC11168 (Cj0248), and the mutation transferred into the genome via a double crossover. Following electroporation the mutant strain was plated on Mueller Hinton agar containing chloramphenicol. Colonies that grew on the selective media were then confirmed by PCR to contain the cassette in the chromosome in the proper direction. Colonies were then harvested and stored at −78° C.

4. Effects of the Cj0588 Mutation on Broiler Colonization.

The ΔCj0588 mutant and M129 *C. jejuni* parent strain were each examined for colonization traits in poultry. Four separate studies were conducted. The detection limit is less than 10 organisms. There was a significant reduction in the colonization of birds inoculated with the M129::tlyA mutant, demonstrating that the *C. jejuni* Cj0588 gene is important in the colonization of poultry.

Study 1:

Chickens were obtained and housed as above. At 12 days, chickens were orally inoculated with 1.0 ml of approximately 1.0×10$^5$ per ml of viable *C. jejuni* M129 and the M129::tlyA mutant. At day 22 the birds were necropsied, and *Campylobacter* was enumerated as above. There was a significant reduction in the colonization of birds inoculated with the M129::tlyA mutant.

TABLE 4

Colonization of chickens with a *C. jejuni*
parent M129 and M129::tlyA strain.

| M129::tlyA | M129::tlyA | M129 | M129 |
|---|---|---|---|
| 52 | ND | 73 | 1.00E+02 |
| 53 | ND | 74 | ND |
| 54 | ND | 75 | 2.00E+02 |
| 55 | ND | 76 | ND |
| 56 | ND | 77 | 4.20E+03 |
| 57 | ND | 78 | ND |
| 58 | ND | 79 | ND |
| 59 | ND | 80 | ND |
| 60 | ND | 81 | 1.20E+04 |
| 61 | ND | 82 | 1.00E+04 |
| TOTAL | ND | Average | 5.30E+03 |

Study 2:

Chickens were obtained and housed as above. At 14 days, birds were orally inoculated with 1.0 ml of approximately 1.0×10$^6$ per ml of viable *C. jejuni* M129 and the M129::tlyA mutant. At day 28, the birds were necropsied, and *Campylobacter* was enumerated as above. There was a significant reduction in the colonization of birds inoculated with the M129::tlyA mutant.

TABLE 5

Colonization of chickens with a *C. jejuni*
parent M129 and M129::tlyA strain.

| M129::tlyA | M129::tlyA | M129 | M129 |
|---|---|---|---|
| 1 | ND | 1 | 2.30E+05 |
| 2 | ND | 2 | 1.40E+05 |
| 3 | ND | 3 | 1.50E+03 |
| 4 | ND | 4 | ND |
| 5 | ND | 5 | ND |
| 6 | ND | 6 | 1.30E+06 |
| 7 | ND | 7 | ND |
| 8 | ND | 8 | 1.90E+03 |
| 9 | ND | 9 | 1.80E+03 |
| 10 | ND | 10 | ND |
| 11 | ND | 11 | 8.70E+03 |
| 12 | ND | 12 | ND |
| 13 | ND | 13 | 1.70E+03 |
| 14 | ND | 14 | 1.70E+03 |
| 15 | ND | 15 | ND |
| 16 | ND | 16 | 3.60E+03 |
| 17 | ND | 17 | 3.10E+03 |
| TOTAL | ND | Average | 1.54E+05 |

Study 3:

Chickens were obtained and housed as above. At 14 days, birds were orally inoculated with 1.0 ml of approximately $1.0\times10^8$ per ml of viable *C. jejuni* M129 and the M129::tlyA mutant. At day 28, the birds were necropsied, and *Campylobacter* was enumerated as above. There was a significant reduction in the colonization of birds inoculated with the M129::tlyA mutant.

TABLE 6

Colonization of chickens with a *C. jejuni* parent M129 and M129::tlyA strain.

| M129::tlyA | M129::tlyA | M129 | M129 |
|---|---|---|---|
| 1 | ND | 1 | 9.40E+04 |
| 2 | ND | 2 | 2.10E+03 |
| 3 | ND | 3 | 2.10E+03 |
| 4 | ND | 4 | 1.00E+02 |
| 5 | ND | 5 | 4.70E+03 |
| 6 | ND | 6 | 2.60E+07 |
| 7 | ND | 7 | 3.70E+03 |
| 8 | ND | 8 | 1.10E+03 |
| 9 | ND | 9 | 4.00E+03 |
| 10 | ND | 10 | 2.70E+03 |
| 11 | ND | 11 | 2.80E+03 |
| 12 | ND | 12 | 1.50E+04 |
| 13 | ND | 13 | 2.10E+03 |
| 14 | ND | 14 | 1.10E+03 |
| 15 | ND | 15 | 1.50E+05 |
| 16 | ND | 16 | 5.10E+03 |
|  |  | 17 | 2.00E+02 |
| TOTAL | ND | Average | 1.55E+06 |

Study 4

Chickens were obtained and housed as above. At 14 days, birds were orally inoculated with 1.0 ml of approximately $1.0\times10^8$ per ml of viable *C. jejuni* M129 and the M129::tlyA mutant. At day 28, the birds were necropsied, and *Campylobacter* was enumerated as above. There was a significant reduction in the colonization of birds inoculated with the M129::tlyA mutant.

TABLE 7

Colonization of chickens with a *C. jejuni* parent M129 and M129::tlyA strain.

| M129::tlyA | M129::tlyA | M129 | M129 |
|---|---|---|---|
| 1 | ND | 1 | 1.10E+03 |
| 2 | ND | 2 | 2.00E+04 |
| 3 | ND | 3 | ND |
| 4 | ND | 4 | 1.00E+02 |
| 5 | ND | 5 | 4.30E+03 |
| 6 | ND | 6 | 2.30E+03 |
| 7 | ND | 7 | 1.00E+02 |
| 8 | ND | 8 | 3.00E+02 |
| 9 | ND | 9 | 1.00E+02 |
| 10 | ND | 10 | ND |
| 11 | ND | 11 | 2.30E+03 |
| 12 | ND | 12 | 2.80E+03 |
| 13 | ND | 13 | 1.70E+06 |
| 14 | ND | 14 | 1.10E+03 |
| 15 | ND | 15 | 1.50E+03 |
| 16 | ND | 16 | 2.80E+03 |
| 17 | ND | 17 | 1.10E+04 |
| 18 | ND | 18 | 1.10E+03 |
| 19 | ND | 19 | 7.00E+02 |
| 20 | ND | 20 | 2.50E+05 |
| 21 | ND | 21 | 1.10E+06 |
| 22 | ND | 22 | ND |
| 23 | ND | 23 | 4.80E+03 |
| TOTAL | ND | Average | 1.35E+05 |

5. Effects of the ΔCj0248 Mutation on Broiler Colonization.

The ΔCj0248 mutant and NCTC11168 *C. jejuni* parent strain were examined for colonization traits in poultry. Chickens were obtained and housed as above. At day 14, the birds were orally inoculated with 0.5 ml of approximately $1.0\times10^5$ per ml of viable *C. jejuni* strain NCTC11168 (n=31), the ΔCj0248 mutant strain (n=30), or served as negative controls. At day 24, the birds were necropsied, and *Campylobacter* was enumerated as above. There was a significant reduction in the colonization of birds inoculated with the ΔCj0248 mutant strain. All the birds inoculated with the wild-type strain NCTC11168 were colonized at an average of 7.42E+07 CFU/g, whereas, 3 of 30 birds (<10 CFUs) were colonized at an average of 7.33E+01 CFU/g with the *C. jejuni* mutant strain ΔCj0248 (Table 8).

TABLE 8

Colonization of Broilers with *C. jejuni* NCTC11168 Wild-type and Mutant

|  | NCTC11168 Wild Type | | | NCTC11168 Mutant Cj0248 | | |
|---|---|---|---|---|---|---|
| Controls | Group 1 | Group 2 | Group 3 | Group 1 | Group 2 | Group 3 |
| ND | 3.30E+07 | 2.30E+08 | 4.60E+05 | ND | ND | 2.00E+02 |
| ND | 4.10E+08 | 3.20E+07 | 8.00E+03 | ND | ND | ND |
| ND | 1.60E+07 | 4.20E+05 | 1.00E+04 | ND | 1.90E+03 | ND |
| ND | 2.40E+07 | 7.10E+07 | 1.20E+04 | ND | ND | ND |
| ND | 9.30E+05 | 8.20E+04 | 3.40E+07 | ND | ND | 1.00E+02 |
| ND | 2.00E+06 | 9.50E+07 | 3.30E+05 | ND | ND | ND |
| ND | 1.40E+07 | 5.00E+06 | 3.10E+07 | ND | ND | ND |
| ND | 9.50E+08 | 5.30E+07 | 1.50E+06 | ND | ND | ND |
| ND | 5.90E+07 | 8.30E+07 | 1.00E+02 | ND | ND | ND |
| ND | 2.40E+07 | 2.30E+04 | 3.10E+03 | ND | ND |  |
| — | 1.30E+08 |  |  | ND |  |  |
| Average | 1.51E+08 | 5.70E+07 | 6.73E+06 | ND | 1.90E+02 | 3.33E+01 |

Average: Wild type = 7.42E+07; Mutant = 7.33E+01; ND = not detected, <10CFU

6. *Salmonella typhimurium* Vector χ9992:

The vector used is a *Salmonella typhimurium* vector χ9992, as described above.

7. Cloning and Expressing *C. jejuni* Genes into the *Salmonella* Vector.

Both genes Cj0588 and Cj0248 were cloned into the vector plasmid pYA3493 and expressed from the attenuated *Salmonella typhimurium* vector χ9992, as described above.

8. Vaccination of Chickens with the Attenuated *Salmonella* Vector Expressing Cj0588 from Plasmid pYA3493.

Chickens were obtained, housed, and vaccinated as above. Trial 1 chickens were orally challenged with 1.0 ml of the homologous *C. jejuni* strain M129 (~1×10$^7$ CFU/ml) and trial 2 chickens were orally challenged with 1.0 ml of a heterologous strain *C. jejuni* NCTC11168 (~1×10$^5$ CFU/ml) at 10 days after the final vaccination. Ten days post challenge, the chickens were necropsied, and *Campylobacter* enumerated as above.

In trial 1, a 4-log reduction of *C. jejuni* in cecal contents of chickens vaccinated with the vector expressing Cj0588 protein following challenge with the homologous M129 strain was observed, as compared to chickens receiving the empty vector (EV) vaccine. A 2-log reduction in *C. jejuni* was observed when the Cj0588 vaccinates were compared to the normal controls. In trial 2, an overall 1-log reduction of *C. jejuni* in cecal contents of chickens vaccinated with the Cj0588 protein was observed following challenge with a heterologous strain NCTC11168, as compared to chickens receiving the EV vaccine. These trials demonstrated a significant reduction of *C. jejuni* in cecal contents of chickens vaccinated with the vector expressing the Cj0588 protein and challenged with the homologous strain. In addition, a 1-log reduction was seen in chickens challenged with a heterologous strain. A greater reduction would have occurred in trial 2 if not for three outliers (bold underlined boxes) (Table 9).

vaccine, 1 ml per antigen, at each vaccination. Chickens were orally challenged with 1.0 ml of the homologous *C. jejuni* strain NCTC11168 (~1×10$^5$ CFU/ml) at 10 days after the final vaccination. Ten days post challenge the chickens were necropsied, and *Campylobacter* enumerated as above. One vaccinate group showed a near total ~7 log reduction in *Campylobacter* colonization, while colonization was reduced by ~1 log in the other group, as compared to empty vector and positive control groups.

Example 4

Water Vaccination Using Cj0998c

Chickens were obtained and housed as above, with the exception that no fasting period was observed prior to vaccination and that water was removed for two hours prior to vaccination. On days 10 and 16, ~1×10$^{10}$ cfu of *Salmonella* expressing Cj0998c (prepared as above) was added to ~2 L of water in commercially available fountain waterers. Water was returned when all vaccine had been consumed (8-12 hours). Controls received ~1×10^10 cfu empty vector *Salmonella* or no vaccine orally. Chickens were orally challenged with 1.0 ml of the homologous *C. jejuni* strain NCTC11168 (~1×10$^5$ CFU/ml) at 10 days after the final vaccination. At day 36, the chickens were necropsied and *Campylobacter* enumerated as above. *Campylobacter* colonization was reduced in vaccinate groups by approximately 2.5 logs as compared to empty vector and positive control groups.

REFERENCES

Kong, Q., Six, D. A., Roland, K. L., Liu, Q., Gu, L., Reynolds, C. M., Wang, X., Raetz, C. R., Curtiss, R., 3rd, 2011. *Salmonella* synthesizing 1-dephosphorylated [corrected] lipopolysaccharide exhibits low endotoxic activity while retaining its immunogenicity. J Immunol 187, 412-423.

Wyszynska, A., Raczko, A., Lis, M., Jagusztyn-Krynicka, E. K., 2004. Oral immunization of chickens with avirulent *Salmonella* vaccine strain carrying *C. jejuni* 72Dz/92

TABLE 9

Cecal numbers of C. jejuni in vaccinated (Cj0588) and control chickens

| C. jejuni M129 Challenge-Trial 1 | | | | C. jejuni NCTC11168 Challenge-Trial 2 | | | |
|---|---|---|---|---|---|---|---|
| Cj0588 | Control-EV | Controls | | Cj0588 | Cj0588 | Cj0588 | Control-EV |
| 6.00E+03 | 1.00E+04 | 2.00E+04 | | 1.10E+03 | 5.00E+03 | 1.20E+05 | 5.00E+07 |
| 7.00E+02 | 2.00E+04 | 7.00E+04 | | 1.50E+03 | 9.00E+04 | 1.00E+00 | 3.00E+07 |
| 7.00E+03 | 1.00E+04 | 1.00E+05 | | 1.00E+02 | 3.00E+03 | 1.20E+04 | 2.00E+07 |
| 3.30E+03 | 1.00E+05 | 3.00E+04 | | 1.00E+02 | 1.00E+00 | 6.00E+04 | 1.70E+08 |
| 2.00E+02 | 3.00E+04 | 3.00E+04 | | 5.00E+03 | 4.00E+01 | 1.00E+02 | 3.00E+07 |
| 7.00E+02 | 3.00E+04 | 7.00E+04 | | 1.00E+03 | 3.00E+07 | 4.00E+07 | |
| 8.00E+03 | 1.00E+04 | 1.00E+04 | | 2.00E+03 | 5.00E+01 | 2.70E+04 | |
| 3.00E+03 | 3.00E+04 | 1.00E+06 | | 7.00E+02 | 1.70E+04 | 6.00E+02 | |
| 3.00E+03 | 3.00E+04 | 1.00E+04 | | 2.00E+01 | 5.00E+07 | 7.00E+04 | |
| 3.20E+03 | 5.00E+04 | 1.00E+04 | | 5.00E+04 | 2.00E+02 | 1.20E+05 | |
| 1.00E+03 | 2.30E+04 | 3.50E+05 | | 7.00E+01 | 1.00E+00 | 2.00E+04 | |
| 4.00E+03 | 1.00E+04 | 7.00E+04 | | 5.60E+03 | 1.00E+00 | 2.00E+04 | |
| 6.80E+03 | 1.00E+04 | 2.10E+06 | Average | 5.60E+03 | 6.68E+06 | 3.37E+06 | 6.00E+07 |
| 2.30E+03 | 3.00E+08 | 7.00E+04 | Geomean | 7.73E+02 | 1.24E+03 | 1.28E+04 | 4.33E+07 |
| 1.40E+03 | 1.00E+04 | 3.00E+05 | | | | | |
| 7.00E+03 | | 6.00E+05 | | | | | |
| Average 3.60E+03 | 2.00E+07 | 3.03E+05 | Average | 3.35E+06 | | 6.00E+07 | |
| Geomean 2.47E+03 | 3.83E+04 | 8.36E+04 | Geomean | 2.31E+03 | | 4.33E+07 | |

Example 3

Dual Vaccination Using Cj0998c and Cj0588

Chickens were obtained, housed, and vaccinated as above, with the exception that each chicken received 2 ml of cjaA gene elicits specific humoral immune response associated with protection against challenge with wild-type *Campylobacter*. Vaccine 22, 1379-1389.

Scallan E, Hoekstra R M, Angulo F J, Tauxe R V, Widdowson M A, Roy S L, et al. Foodborne illness acquired in the United States—major pathogens. Emerging infectious diseases. 2011; 17(1):7-15. Epub 2011 Jan. 5. doi: 10.3201/eid/1701.091101p1. PubMed PMID: 21192848.

Buzby J C, Allos B M, Roberts T. The economic burden of *Campylobacter*-associated Guillain-Barre syndrome. Journal of Infectious Diseases. 1997; 176:S192-S7. PubMed PMID: ISI:A1997YH50600023.

Pope J E, Krizova A, Garg A X, Thiessen-Philbrook H, Ouimet J M. *Campylobacter* reactive arthritis: a systematic review. Semin Arthritis Rheum. 2007; 37(1):48-55. Epub 2007 Mar. 16. doi: S0049-0172(07)00005-4 [pii]

Li, Y., Wang, S., Scarpellini, G., Gunn, B., Xin, W., Wanda, S. Y., Roland, K. L., Curtiss, R., 3rd, 2009, Evaluation of new generation *Salmonella enterica* serovar *typhimurium* vaccines with regulated delayed attenuation to induce immune responses against PspA. Proceedings of the National Academy of Sciences of the United States of America 106, 593-598.

Curtiss III, R., S-Y. Wanda, B. M. Gunn, X. Zhang, S. A. Tinge, V. Ananthnarayan, H. Mo, S. Wang, and W. Kong. 2009. *Salmonella* strains with regulated delayed attenuation in vivo. Infect. Immun. 77:1071-1082.

---

We claim:

1. An immunogenic composition, comprising
   (a) one or more polynucleotide encoding two or more proteins including
      (i) a protein comprising an amino acid sequence at least 80 percent identical to SEQ ID NO:6 (Cj0248 protein), or antigenic portions thereof, and
      (ii) one or more proteins comprising an amino acid sequence at least 80 percent identical to a protein selected from the group consisting of SEQ ID NO:2 (Cj0988c protein), SEQ ID NO:142 (Cj1534c protein), SEQ ID NO:108 (Cj1656c protein), SEQ ID NO:110 (Cj0428 protein), SEQ ID NO:112 (Cj0168c protein), SEQ ID NO:114 (Cj0427 protein), SEQ ID NO:116 (Cj0113 protein), SEQ ID NO:118 (Cj0982c protein), SEQ ID NO:120 (Cj0921c protein), SEQ ID NO:122 (Cj1259 protein), SEQ ID NO:124 (Cj1339c protein), SEQ ID NO:126 (Cj0034c protein), SEQ ID NO:128 (Cj0404 protein), SEQ ID NO:130 (Cj0365c protein), SEQ ID NO:132 (Cj0755 protein), and SEQ ID NO:134 (Cj0420 protein), or antigenic portions thereof; and
   (b) a promoter operatively linked to each of the one or more polynucleotide, wherein the promoter region is capable of directing expression of the encoded protein(s).

2. The immunogenic composition of claim 1, wherein the composition comprises one or more polynucleotide encoding three or more of the recited proteins, or antigenic portions thereof.

3. The immunogenic composition of claim 1, wherein the composition further comprises a polynucleotide encoding a protein comprising an amino acid sequence at least 80 percent identical to SEQ ID NO:116 (Cj0113 protein), or an antigenic portion thereof.

4. The immunogenic composition of claim 1, wherein the one or more polynucleotide encodes two or more proteins including
   (i) a protein comprising the amino acid sequence of SEQ ID NO:6 (Cj0248 protein), or antigenic portions thereof, and
   (ii) one or more proteins comprising the amino acid sequence of a protein elected from the group consisting of SEQ ID NO:4 (Cj0588 protein), SEQ ID NO:2 (Cj0988c protein), SEQ ID NO:142 (Cj1534c protein), SEQ ID NO:108 (Cj1656c protein), SEQ ID NO:110 (Cj0428 protein), SEQ ID NO:112 (Cj0168c protein), SEQ ID NO:114 (Cj0427 protein), SEQ ID NO:116 (Cj0113 protein), SEQ ID NO:118 (Cj0982c protein), SEQ ID NO:120 (Cj0921c protein), SEQ ID NO:122 (Cj1259 protein), SEQ ID NO:124 (Cj1339c protein), SEQ ID NO:126 (Cj0034c protein), SEQ ID NO:128 (Cj0404 protein), SEQ ID NO:130 (Cj0365c protein), SEQ ID NO:132 (Cj0755 protein), and SEQ ID NO:134 (Cj0420 protein), or antigenic portions thereof.

5. The immunogenic composition of claim 1, wherein the immunogenic composition is present in an avirulent, non-*Campylobacter* bacterial carrier cell.

6. The immunogenic composition of claim 5, wherein the avirulent, non-*Campylobacter* bacterial carrier cell is selected from the group consisting of attenuated *L. monocytogenes*, attenuated *Salmonella*, attenuated *V. cholerae*, attenuated *Shigella* spp., attenuated *M. bovis* BCG, attenuated *Y. enterocolitica*, attenuated *B. anthracis, S. gordonii, Lactobacillus* spp., and *Staphylococcus* spp.

7. The immunogenic composition of claim 5, wherein the avirulent, non-*Campylobacter* bacterial carrier cell is an attenuated *Salmonella*.

8. The immunogenic composition of claim 4, wherein the immunogenic composition is present in an avirulent, non-*Campylobacter* bacterial carrier cell.

9. The immunogenic composition of claim 8, wherein the avirulent, non-*Campylobacter* bacterial carrier cell is selected from the group consisting of attenuated *L. monocytogenes*, attenuated *Salmonella*, attenuated *V. cholerae*, attenuated *Shigella* spp., attenuated *M. bovis* BCG, attenuated *Y. enterocolitica*, attenuated *B. anthracis, S. gordonii, Lactobacillus* spp., and *Staphylococcus* spp.

10. The immunogenic composition of claim 8, wherein the avirulent, non-*Campylobacter* bacterial carrier cell is an attenuated *Salmonella*.

11. The immunogenic composition of claim 1, wherein the immunogenic composition is formulated for oral delivery or mucosal delivery.

12. The immunogenic composition of claim 1, further comprising an adjuvant.

13. The immunogenic composition of claim 4, wherein the immunogenic composition is formulated for oral delivery or mucosal delivery.

14. The immunogenic composition of claim 4, further comprising an adjuvant.

* * * * *

SEQUENCE LISTING

```
<160> NUMBER OF SEQ ID NOS: 142

<210> SEQ ID NO 1
<211> LENGTH: 573
<212> TYPE: DNA
<213> ORGANISM: Campylobacter jejuni

<400> SEQUENCE: 1
atgaaaaaaa ttcttgtaag tgttttaagt tcttgcttgt tagcttcggc tttaagtgct    60
gtatctttta aagaagatag tttaaagatt tcttttgaag gatataaaac taaagatatg   120
ataggaacaa aaggtgaatt taaaaatgta gaatataaat tttctaaaaa tataaaggat   180
ttggcaagtt atcttaaagg cgctaaagct accataaagc caagcaatgc ttttatgggt   240
gaaggcaatg atattataac caataatatc acaaaagtat ttttccctgc tttattggga   300
gatacggata ttaaagttgt ttttcaagat gtgattgcgg gtgaaaataa aggcgttatt   360
tcagcaaaaa ttactatgga taaaaaaagt actattgtac ctttaactta taccatcaaa   420
gataataaat ttgaagctaa aggacaactt gatttgcata cttttaaaaa tggttctaaa   480
gcattaaaag cattaagcga tgttgctgca ggacatggtg gaatttcttg gcctttagtg   540
gatatcagtt ttaatgctga tttagcagaa taa                                573

<210> SEQ ID NO 2
<211> LENGTH: 190
<212> TYPE: PRT
<213> ORGANISM: Campylobacter jejuni

<400> SEQUENCE: 2

Met Lys Lys Ile Leu Val Ser Val Leu Ser Cys Leu Leu Ala Ser
1               5                   10                  15

Ala Leu Ser Ala Val Ser Phe Lys Glu Asp Ser Leu Lys Ile Ser Phe
                20                  25                  30

Glu Gly Tyr Lys Thr Lys Asp Met Ile Gly Thr Lys Gly Glu Phe Lys
            35                  40                  45

Asn Val Glu Tyr Lys Phe Ser Lys Asn Ile Lys Asp Leu Ala Ser Tyr
        50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
            100                 105                 110

Ala Gly Glu Asn Lys Gly Val Ile Ser Ala Lys Ile Thr Met Asp Lys
        115                 120                 125
```

```
Lys Ser Thr Ile Val Pro Leu Thr Tyr Thr Ile Lys Asp Asn Lys Phe
    130                 135                 140
Glu Ala Lys Gly Gln Leu Asp Leu His Thr Phe Lys Asn Gly Ser Lys
145                 150                 155                 160
Ala Leu Lys Ala Leu Ser Asp Val Ala Ala Gly His Gly Gly Ile Ser
                165                 170                 175
Trp Pro Leu Val Asp Ile Ser Phe Asn Ala Asp Leu Ala Glu
                180                 185                 190
```

<210> SEQ ID NO 3
<211> LENGTH: 762
<212> TYPE: DNA
<213> ORGANISM: Campylobacter jejuni

<400> SEQUENCE: 3

```
atgagatttg attttttgt ttcaaagcgt ttaaatatca gtagaaataa agccttagag      60
cttatagaaa atgaagagat tttacttaat ggtaagagtt ttaaagcttc ttttgatgtg     120
aaaaatttt tagaaaattt aaaaaaaacg caagatttaa atcctgaaga tatactttta      180
gccaatgagt taaaattgga tcttttaagt gaaatttatg tttcaagagc agctttgaaa     240
ttaaaaaaat ttttagaaga aaatgatatt gaaataaaac ataaaaattg tcttgatata     300
ggatctagta cgggcggttt tgttcaaatt ttacttgaaa atcaggcttt aaaaatcact     360
gctcttgatg tgggtagtaa tcaactccat ccaagtttaa gagtaaatga aaaaattatc     420
ttgcatgaaa atacagatct tagagccttt aaaagtgaag aaaaatttga acttgttact     480
tgtgatgtga gttttatttc tcttattaat ttactttatt atattgataa tttagcttta     540
aaggaaatta ttttactttt taaacctcag tttgaagtgg gaaaaaatat caaaagagat     600
aaaaaaggtg ttttaaaaga tgataaggca atcttaaagg caagaatgga ttttgaaaaa     660
gcatgtgcta aattgggttg gcttttaaaa aatacgcaaa aatcaagcat taaggaaag     720
gaaggtaatg ttgaatattt ttactactat atcaaaaatt aa                       762
```

<210> SEQ ID NO 4
<211> LENGTH: 253
<212> TYPE: PRT
<213> ORGANISM: Campylobacter jejuni

<400> SEQUENCE: 4

```
Met Arg Phe Asp Phe Phe Val Ser Lys Arg Leu Asn Ile Ser Arg Asn
1               5                   10                  15
Lys Ala Leu Glu Leu Ile Glu Asn Glu Ile Leu Leu Asn Gly Lys
            20                  25                  30
Ser Phe Lys Ala Ser Phe Asp Val Lys Asn Phe Leu Glu Asn Leu Lys
            35                  40                  45
Lys Thr Gln Asp Leu Asn Pro Glu Asp Ile Leu Leu Ala Asn Glu Leu
        50                  55                  60
Lys Leu Asp Leu Leu Ser Glu Ile Tyr Val Ser Arg Ala Ala Leu Lys
65                  70                  75                  80
Leu Lys Lys Phe Leu Glu Glu Asn Asp Ile Glu Ile Lys His Lys Asn
                85                  90                  95
Cys Leu Asp Ile Gly Ser Ser Thr Gly Gly Phe Val Gln Ile Leu Leu
            100                 105                 110
Glu Asn Gln Ala Leu Lys Ile Thr Ala Leu Asp Val Gly Ser Asn Gln
            115                 120                 125
```

Leu His Pro Ser Leu Arg Val Asn Glu Lys Ile Ile Leu His Glu Asn
    130                 135                 140
Thr Asp Leu Arg Ala Phe Lys Ser Glu Lys Phe Glu Leu Val Thr
145                 150                 155                 160
Cys Asp Val Ser Phe Ile Ser Leu Ile Asn Leu Leu Tyr Tyr Ile Asp
                165                 170                 175
Asn Leu Ala Leu Lys Glu Ile Ile Leu Leu Phe Lys Pro Gln Phe Glu
                180                 185                 190
Val Gly Lys Asn Ile Lys Arg Asp Lys Gly Val Leu Lys Asp Asp
                195                 200                 205
Lys Ala Ile Leu Lys Ala Arg Met Asp Phe Glu Lys Ala Cys Ala Lys
210                 215                 220
Leu Gly Trp Leu Leu Lys Asn Thr Gln Lys Ser Ser Ile Lys Gly Lys
225                 230                 235                 240
Glu Gly Asn Val Glu Tyr Phe Tyr Tyr Tyr Ile Lys Asn
                245                 250

<210> SEQ ID NO 5
<211> LENGTH: 858
<212> TYPE: DNA
<213> ORGANISM: Campylobacter jejuni

<400> SEQUENCE: 5
atgattggag atatgaatga cttttatta aaaagcgttg aagtattgcc acctttacct     60
gatactgtaa gtaagttaag aaaatatgtg agcgaggcta attcaaatat agaaactatg    120
aaagttgctg aaatcatttc aagcgatccg ttgatgacgg ctaagctttt gcaattagca    180
aattctcctt attatggttt tacaagagaa attacaacca taaatcaagt gattactta    240
ttaggcgttg gtaatatcat caatatagtt atggctgact ccattagaga taattttaaa    300
atagacgttt caccttatgg tttaaatact caaaattttt taaaaacgtg caatgaagag    360
gcaactttta tcgcaaattg gcttaatgat gaagataaaa actttctca tcttttagtt    420
ccttgtgcaa tgcttttaag gcttggtatt gttattttt caaatttcct tatacaaaat    480
cataaggata aggattttt agcttttta aataaaaatg aaaatcttgc tttagcggag    540
aatgaatttt taggcgtaga tcatatttct ttcttgggat ttttgttaca tcgttggaat    600
tttgatgatg ttttgattga agtatatgt tttgttcgca ctcctcatgc tgctcgcgaa    660
aaagtgaaaa aatccgctta tgcttagca ataacagatc atcttttgc tccgcatgat    720
ggttcttctc catttaacgc aaagctgca gttgctttac ttaaagaggc aaaaactcaa    780
ggaattaatt ttgatttaaa caatctttta tctaagcttc ctaacaaagc taaggaaaat    840
ttaaacaaag aagattaa                                                  858

<210> SEQ ID NO 6
<211> LENGTH: 285
<212> TYPE: PRT
<213> ORGANISM: Campylobacter jejuni

<400> SEQUENCE: 6

Met Ile Gly Asp Met Asn Glu Leu Leu Leu Lys Ser Val Glu Val Leu
1               5                   10                  15
Pro Pro Leu Pro Asp Thr Val Ser Lys Leu Arg Lys Tyr Val Ser Glu
                20                  25                  30
Ala Asn Ser Asn Ile Glu Thr Met Lys Val Ala Glu Ile Ile Ser Ser
            35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Met Ala Asp Ser Ile Arg
                85                  90                  95

Asp Asn Phe Lys Ile Asp Val Ser Pro Tyr Gly Leu Asn Thr Gln Asn
                100                 105                 110

Phe Leu Lys Thr Cys Asn Glu Ala Thr Phe Ile Ala Asn Trp Leu
            115                 120                 125

Asn Asp Glu Asp Lys Lys Leu Ser His Leu Leu Val Pro Cys Ala Met
    130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
                180                 185                 190

Gly Phe Leu Leu His Arg Trp Asn Phe Asp Asp Val Leu Ile Glu Ser
            195                 200                 205

Ile Cys Phe Val Arg Thr Pro His Ala Ala Arg Glu Lys Val Lys Lys
210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Val Ala Leu Leu Lys Glu
            245                 250                 255

Ala Lys Thr Gln Gly Ile Asn Phe Asp Leu Asn Asn Leu Leu Ser Lys
            260                 265                 270

Leu Pro Asn Lys Ala Lys Glu Asn Leu Asn Lys Glu Asp
            275                 280                 285

```
<210> SEQ ID NO 7
<211> LENGTH: 190
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X is I, V, or F
<220> FEATURE:
<221> NAME/KEY: MISC_FEATURE
<222> LOCATION: (5)..(5)
<223> OTHER INFORMATION: X is V or F
<220> FEATURE:
<221> NAME/KEY: MISC_FEATURE
<222> LOCATION: (6)..(6)
<223> OTHER INFORMATION: X is V, A, or L
<220> FEATURE:
<221> NAME/KEY: MISC_FEATURE
<222> LOCATION: (8)..(8)
<223> OTHER INFORMATION: X is V or I
<220> FEATURE:
<221> NAME/KEY: MISC_FEATURE
<222> LOCATION: (9)..(9)
<223> OTHER INFORMATION: X is L or F
<220> FEATURE:
<221> NAME/KEY: MISC_FEATURE
<222> LOCATION: (11)..(11)
<223> OTHER INFORMATION: X is S or F
<220> FEATURE:
<221> NAME/KEY: MISC_FEATURE
<222> LOCATION: (30)..(30)
```

```
<223> OTHER INFORMATION: X is I or V
<220> FEATURE:
<221> NAME/KEY: MISC_FEATURE
<222> LOCATION: (41)..(41)
<223> OTHER INFORMATION: X is I or V
<220> FEATURE:
<221> NAME/KEY: MISC_FEATURE
<222> LOCATION: (43)..(43)
<223> OTHER INFORMATION: X is T, V, I or A
<220> FEATURE:
<221> NAME/KEY: MISC_FEATURE
<222> LOCATION: (44)..(44)
<223> OTHER INFORMATION: X is K or R
<220> FEATURE:
<221> NAME/KEY: MISC_FEATURE
<222> LOCATION: (53)..(53)
<223> OTHER INFORMATION: X is K or N
<220> FEATURE:
<221> NAME/KEY: MISC_FEATURE
<222> LOCATION: (57)..(57)
<223> OTHER INFORMATION: X is N or S
<220> FEATURE:
<221> NAME/KEY: MISC_FEATURE
<222> LOCATION: (58)..(58)
<223> OTHER INFORMATION: X is I or T
<220> FEATURE:
<221> NAME/KEY: MISC_FEATURE
<222> LOCATION: (61)..(61)
<223> OTHER INFORMATION: X is L or F
<220> FEATURE:
<221> NAME/KEY: MISC_FEATURE
<222> LOCATION: (73)..(73)
<223> OTHER INFORMATION: X is K or E
<220> FEATURE:
<221> NAME/KEY: MISC_FEATURE
<222> LOCATION: (76)..(76)
<223> OTHER INFORMATION: X is N or D
<220> FEATURE:
<221> NAME/KEY: MISC_FEATURE
<222> LOCATION: (80)..(80)
<223> OTHER INFORMATION: X is G or S
<220> FEATURE:
<221> NAME/KEY: MISC_FEATURE
<222> LOCATION: (83)..(83)
<223> OTHER INFORMATION: X is N or L
<220> FEATURE:
<221> NAME/KEY: MISC_FEATURE
<222> LOCATION: (85)..(85)
<223> OTHER INFORMATION: X is I or V
<220> FEATURE:
<221> NAME/KEY: MISC_FEATURE
<222> LOCATION: (101)..(101)
<223> OTHER INFORMATION: X is D or N
<220> FEATURE:
<221> NAME/KEY: MISC_FEATURE
<222> LOCATION: (102)..(102)
<223> OTHER INFORMATION: X is T or A
<220> FEATURE:
<221> NAME/KEY: MISC_FEATURE
<222> LOCATION: (111)..(111)
<223> OTHER INFORMATION: X is V, A or M
<220> FEATURE:
<221> NAME/KEY: MISC_FEATURE
<222> LOCATION: (113)..(113)
<223> OTHER INFORMATION: X is V or  A
<220> FEATURE:
<221> NAME/KEY: MISC_FEATURE
<222> LOCATION: (116)..(123)
<223> OTHER INFORMATION: Amino Acid is optionally absent
<220> FEATURE:
<221> NAME/KEY: MISC_FEATURE
<222> LOCATION: (133)..(133)
<223> OTHER INFORMATION: X is V or I
<220> FEATURE:
<221> NAME/KEY: MISC_FEATURE
<222> LOCATION: (142)..(142)
<223> OTHER INFORMATION: X is N or D
<220> FEATURE:
<221> NAME/KEY: MISC_FEATURE
```

<222> LOCATION: (150)..(150)
<223> OTHER INFORMATION: X is L or F
<220> FEATURE:
<221> NAME/KEY: MISC_FEATURE
<222> LOCATION: (154)..(154)
<223> OTHER INFORMATION: X is T or A
<220> FEATURE:
<221> NAME/KEY: MISC_FEATURE
<222> LOCATION: (158)..(158)
<223> OTHER INFORMATION: X is G or A
<220> FEATURE:
<221> NAME/KEY: MISC_FEATURE
<222> LOCATION: (168)..(168)
<223> OTHER INFORMATION: X is V or A
<220> FEATURE:
<221> NAME/KEY: MISC_FEATURE
<222> LOCATION: (170)..(170)
<223> OTHER INFORMATION: X is A, T or P
<220> FEATURE:
<221> NAME/KEY: MISC_FEATURE
<222> LOCATION: (189)..(189)
<223> OTHER INFORMATION: X is A, T or V

<400> SEQUENCE: 7

Met Lys Lys Xaa Xaa Xaa Ser Xaa Xaa Ser Xaa Cys Leu Leu Ala Ser
1               5                   10                  15

Ala Leu Ser Ala Val Ser Phe Lys Glu Asp Ser Leu Lys Xaa Ser Phe
            20                  25                  30

Glu Gly Tyr Lys Thr Lys Asp Met Xaa Gly Xaa Xaa Gly Glu Phe Lys
        35                  40                  45

Asn Val Glu Tyr Xaa Phe Ser Lys Xaa Xaa Lys Asp Xaa Ala Ser Tyr
    50                  55                  60

Leu Lys Gly Ala Lys Ala Thr Ile Xaa Pro Ser Xaa Ala Phe Met Xaa
65                  70                  75                  80

Glu Gly Xaa Asp Xaa Ile Thr Asn Asn Ile Thr Lys Val Phe Phe Pro
                85                  90                  95

Ala Leu Leu Gly Xaa Xaa Asp Ile Lys Val Val Phe Gln Asp Xaa Ile
            100                 105                 110

Xaa Gly Glu Asn Lys Gly Val Ile Ser Ala Lys Ile Thr Met Asp Lys
        115                 120                 125

Lys Ser Thr Ile Xaa Pro Leu Thr Tyr Thr Ile Lys Asp Xaa Lys Phe
130                 135                 140

Glu Ala Lys Gly Gln Xaa Asp Leu His Xaa Phe Lys Asn Xaa Ser Lys
145                 150                 155                 160

Ala Leu Lys Ala Leu Ser Asp Xaa Ala Xaa Gly His Gly Gly Ile Ser
            165                 170                 175

Trp Pro Leu Val Asp Ile Ser Phe Asn Ala Asp Leu Xaa Glu
        180                 185                 190

<210> SEQ ID NO 8
<211> LENGTH: 253
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(65)
<223> OTHER INFORMATION: Amino Acids are optionally absent
<220> FEATURE:
<221> NAME/KEY: MISC_FEATURE
<222> LOCATION: (2)..(2)
<223> OTHER INFORMATION: X is R or I
<220> FEATURE:
<221> NAME/KEY: MISC_FEATURE
<222> LOCATION: (3)..(3)

```
<223> OTHER INFORMATION: X is F or absent
<220> FEATURE:
<221> NAME/KEY: MISC_FEATURE
<222> LOCATION: (4)..(4)
<223> OTHER INFORMATION: X is D or absent
<220> FEATURE:
<221> NAME/KEY: MISC_FEATURE
<222> LOCATION: (7)..(7)
<223> OTHER INFORMATION: X is V or I
<220> FEATURE:
<221> NAME/KEY: MISC_FEATURE
<222> LOCATION: (12)..(12)
<223> OTHER INFORMATION: X is N or D
<220> FEATURE:
<221> NAME/KEY: MISC_FEATURE
<222> LOCATION: (24)..(24)
<223> OTHER INFORMATION: X is N or S
<220> FEATURE:
<221> NAME/KEY: MISC_FEATURE
<222> LOCATION: (27)..(27)
<223> OTHER INFORMATION: X is I or V
<220> FEATURE:
<221> NAME/KEY: MISC_FEATURE
<222> LOCATION: (33)..(33)
<223> OTHER INFORMATION: X is S or N
<220> FEATURE:
<221> NAME/KEY: MISC_FEATURE
<222> LOCATION: (38)..(38)
<223> OTHER INFORMATION: X is F or C
<220> FEATURE:
<221> NAME/KEY: MISC_FEATURE
<222> LOCATION: (43)..(43)
<223> OTHER INFORMATION: X is F or L
<220> FEATURE:
<221> NAME/KEY: MISC_FEATURE
<222> LOCATION: (50)..(50)
<223> OTHER INFORMATION: X is T, A or K
<220> FEATURE:
<221> NAME/KEY: MISC_FEATURE
<222> LOCATION: (55)..(55)
<223> OTHER INFORMATION: X is P, L or S
<220> FEATURE:
<221> NAME/KEY: MISC_FEATURE
<222> LOCATION: (57)..(57)
<223> OTHER INFORMATION: X is D or E
<220> FEATURE:
<221> NAME/KEY: MISC_FEATURE
<222> LOCATION: (58)..(58)
<223> OTHER INFORMATION: X is I or V
<220> FEATURE:
<221> NAME/KEY: MISC_FEATURE
<222> LOCATION: (59)..(59)
<223> OTHER INFORMATION: X is L or Y
<220> FEATURE:
<221> NAME/KEY: MISC_FEATURE
<222> LOCATION: (61)..(61)
<223> OTHER INFORMATION: X is A, T or S
<220> FEATURE:
<221> NAME/KEY: MISC_FEATURE
<222> LOCATION: (62)..(62)
<223> OTHER INFORMATION: X is N, D or K
<220> FEATURE:
<221> NAME/KEY: MISC_FEATURE
<222> LOCATION: (63)..(63)
<223> OTHER INFORMATION: X is E or G
<220> FEATURE:
<221> NAME/KEY: MISC_FEATURE
<222> LOCATION: (65)..(65)
<223> OTHER INFORMATION: X is K or N
<220> FEATURE:
<221> NAME/KEY: MISC_FEATURE
<222> LOCATION: (66)..(66)
<223> OTHER INFORMATION: X is L or M
<220> FEATURE:
<221> NAME/KEY: MISC_FEATURE
<222> LOCATION: (67)..(67)
<223> OTHER INFORMATION: X is D, N or E
<220> FEATURE:
<221> NAME/KEY: MISC_FEATURE
```

```
<222> LOCATION: (70)..(70)
<223> OTHER INFORMATION: X is S or R
<220> FEATURE:
<221> NAME/KEY: MISC_FEATURE
<222> LOCATION: (74)..(74)
<223> OTHER INFORMATION: X is V or I
<220> FEATURE:
<221> NAME/KEY: MISC_FEATURE
<222> LOCATION: (83)..(83)
<223> OTHER INFORMATION: X is K or N
<220> FEATURE:
<221> NAME/KEY: MISC_FEATURE
<222> LOCATION: (89)..(89)
<223> OTHER INFORMATION: X is D, G or N
<220> FEATURE:
<221> NAME/KEY: MISC_FEATURE
<222> LOCATION: (92)..(92)
<223> OTHER INFORMATION: X is I or V
<220> FEATURE:
<221> NAME/KEY: MISC_FEATURE
<222> LOCATION: (93)..(93)
<223> OTHER INFORMATION: X is K or N
<220> FEATURE:
<221> NAME/KEY: MISC_FEATURE
<222> LOCATION: (94)..(94)
<223> OTHER INFORMATION: X is H, Q or N
<220> FEATURE:
<221> NAME/KEY: MISC_FEATURE
<222> LOCATION: (115)..(115)
<223> OTHER INFORMATION: X is Q or K
<220> FEATURE:
<221> NAME/KEY: MISC_FEATURE
<222> LOCATION: (121)..(121)
<223> OTHER INFORMATION: X is A or T
<220> FEATURE:
<221> NAME/KEY: MISC_FEATURE
<222> LOCATION: (126)..(126)
<223> OTHER INFORMATION: X is S or N
<220> FEATURE:
<221> NAME/KEY: MISC_FEATURE
<222> LOCATION: (131)..(131)
<223> OTHER INFORMATION: X is P, S or L
<220> FEATURE:
<221> NAME/KEY: MISC_FEATURE
<222> LOCATION: (132)..(132)
<223> OTHER INFORMATION: X is S or N
<220> FEATURE:
<221> NAME/KEY: MISC_FEATURE
<222> LOCATION: (135)..(135)
<223> OTHER INFORMATION: X is V, A or T
<220> FEATURE:
<221> NAME/KEY: MISC_FEATURE
<222> LOCATION: (138)..(138)
<223> OTHER INFORMATION: X is K or I
<220> FEATURE:
<221> NAME/KEY: MISC_FEATURE
<222> LOCATION: (139)..(139)
<223> OTHER INFORMATION: X is V or I
<220> FEATURE:
<221> NAME/KEY: MISC_FEATURE
<222> LOCATION: (142)..(142)
<223> OTHER INFORMATION: X is H or Y
<220> FEATURE:
<221> NAME/KEY: MISC_FEATURE
<222> LOCATION: (145)..(145)
<223> OTHER INFORMATION: X is T or I
<220> FEATURE:
<221> NAME/KEY: MISC_FEATURE
<222> LOCATION: (149)..(149)
<223> OTHER INFORMATION: X is A, T or V
<220> FEATURE:
<221> NAME/KEY: MISC_FEATURE
<222> LOCATION: (158)..(158)
<223> OTHER INFORMATION: X is L or F
<220> FEATURE:
<221> NAME/KEY: MISC_FEATURE
<222> LOCATION: (159)..(159)
<223> OTHER INFORMATION: X is V or I
<220> FEATURE:
```

```
<221> NAME/KEY: MISC_FEATURE
<222> LOCATION: (169)..(169)
<223> OTHER INFORMATION: X is V or I
<220> FEATURE:
<221> NAME/KEY: MISC_FEATURE
<222> LOCATION: (175)..(175)
<223> OTHER INFORMATION: X is V or I
<220> FEATURE:
<221> NAME/KEY: MISC_FEATURE
<222> LOCATION: (176)..(176)
<223> OTHER INFORMATION: X is D or N
<220> FEATURE:
<221> NAME/KEY: MISC_FEATURE
<222> LOCATION: (181)..(181)
<223> OTHER INFORMATION: X is K or R
<220> FEATURE:
<221> NAME/KEY: MISC_FEATURE
<222> LOCATION: (197)..(197)
<223> OTHER INFORMATION: X is I or V
<220> FEATURE:
<221> NAME/KEY: MISC_FEATURE
<222> LOCATION: (208)..(208)
<223> OTHER INFORMATION: X is D or G
<220> FEATURE:
<221> NAME/KEY: MISC_FEATURE
<222> LOCATION: (209)..(209)
<223> OTHER INFORMATION: X is K or R
<220> FEATURE:
<221> NAME/KEY: MISC_FEATURE
<222> LOCATION: (210)..(210)
<223> OTHER INFORMATION: X is A or V
<220> FEATURE:
<221> NAME/KEY: MISC_FEATURE
<222> LOCATION: (215)..(215)
<223> OTHER INFORMATION: X is K or R
<220> FEATURE:
<221> NAME/KEY: MISC_FEATURE
<222> LOCATION: (221)..(221)
<223> OTHER INFORMATION: X is A or E
<220> FEATURE:
<221> NAME/KEY: MISC_FEATURE
<222> LOCATION: (226)..(226)
<223> OTHER INFORMATION: X is G or S
<220> FEATURE:
<221> NAME/KEY: MISC_FEATURE
<222> LOCATION: (228)..(228)
<223> OTHER INFORMATION: X is L, F or I
<220> FEATURE:
<221> NAME/KEY: MISC_FEATURE
<222> LOCATION: (236)..(236)
<223> OTHER INFORMATION: X is S or C

<400> SEQUENCE: 8

Met Xaa Xaa Xaa Phe Phe Xaa Ser Lys Arg Leu Xaa Ile Ser Arg Asn
1               5                   10                  15

Lys Ala Leu Glu Leu Ile Glu Xaa Glu Glu Xaa Leu Leu Asn Gly Lys
            20                  25                  30

Xaa Phe Lys Ala Ser Xaa Asp Val Lys Asn Xaa Leu Glu Asn Leu Lys
        35                  40                  45

Lys Xaa Gln Asp Leu Asn Xaa Glu Xaa Xaa Xaa Leu Xaa Xaa Xaa Leu
    50                  55                  60

Xaa Xaa Xaa Leu Leu Xaa Glu Ile Tyr Xaa Ser Arg Ala Ala Leu Lys
65                  70                  75                  80

Leu Lys Xaa Phe Leu Glu Glu Asn Xaa Ile Glu Xaa Xaa Xaa Lys Asn
                85                  90                  95

Cys Leu Asp Ile Gly Ser Ser Thr Gly Gly Phe Val Gln Ile Leu Leu
            100                 105                 110

Glu Asn Xaa Ala Leu Lys Ile Thr Xaa Leu Asp Val Gly Xaa Asn Gln
        115                 120                 125

Leu His Xaa Xaa Leu Arg Xaa Asn Glu Xaa Xaa Ile Leu Xaa Glu Asn
```

-continued

```
                    130                 135                 140
Xaa Asp Leu Arg Xaa Phe Lys Ser Glu Glu Lys Phe Glu Xaa Xaa Thr
145                 150                 155                 160

Cys Asp Val Ser Phe Ile Ser Leu Xaa Asn Leu Leu Tyr Tyr Xaa Xaa
                165                 170                 175

Asn Leu Ala Leu Xaa Glu Ile Ile Leu Phe Lys Pro Gln Phe Glu
            180                 185                 190

Val Gly Lys Asn Xaa Lys Arg Asp Lys Lys Gly Val Leu Lys Asp Xaa
        195                 200                 205

Xaa Xaa Ile Leu Lys Ala Xaa Met Asp Phe Glu Lys Xaa Cys Ala Lys
        210                 215                 220

Leu Xaa Trp Xaa Leu Lys Asn Thr Gln Lys Ser Xaa Ile Lys Gly Lys
225                 230                 235                 240

Glu Gly Asn Val Glu Tyr Phe Tyr Tyr Tyr Ile Lys Asn
                245                 250

<210> SEQ ID NO 9
<211> LENGTH: 287
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is M or absent
<220> FEATURE:
<221> NAME/KEY: MISC_FEATURE
<222> LOCATION: (3)..(3)
<223> OTHER INFORMATION: X is G or absent
<220> FEATURE:
<221> NAME/KEY: MISC_FEATURE
<222> LOCATION: (43)..(43)
<223> OTHER INFORMATION: X is A or V
<220> FEATURE:
<221> NAME/KEY: MISC_FEATURE
<222> LOCATION: (75)..(75)
<223> OTHER INFORMATION: X is N or S
<220> FEATURE:
<221> NAME/KEY: MISC_FEATURE
<222> LOCATION: (83)..(83)
<223> OTHER INFORMATION: X is V or I
<220> FEATURE:
<221> NAME/KEY: MISC_FEATURE
<222> LOCATION: (91)..(91)
<223> OTHER INFORMATION: X is M or T
<220> FEATURE:
<221> NAME/KEY: MISC_FEATURE
<222> LOCATION: (96)..(96)
<223> OTHER INFORMATION: X is K or R
<220> FEATURE:
<221> NAME/KEY: MISC_FEATURE
<222> LOCATION: (98)..(98)
<223> OTHER INFORMATION: X is N or S
<220> FEATURE:
<221> NAME/KEY: MISC_FEATURE
<222> LOCATION: (109)..(109)
<223> OTHER INFORMATION: X is N or D
<220> FEATURE:
<221> NAME/KEY: MISC_FEATURE
<222> LOCATION: (111)..(111)
<223> OTHER INFORMATION: X is Q or K
<220> FEATURE:
<221> NAME/KEY: MISC_FEATURE
<222> LOCATION: (112)..(112)
<223> OTHER INFORMATION: X is N or V
<220> FEATURE:
<221> NAME/KEY: MISC_FEATURE
<222> LOCATION: (115)..(115)
<223> OTHER INFORMATION: X is K or R
<220> FEATURE:
```

```
<221> NAME/KEY: MISC_FEATURE
<222> LOCATION: (116)..(116)
<223> OTHER INFORMATION: X is T or N
<220> FEATURE:
<221> NAME/KEY: MISC_FEATURE
<222> LOCATION: (119)..(119)
<223> OTHER INFORMATION: X is E or D
<220> FEATURE:
<221> NAME/KEY: MISC_FEATURE
<222> LOCATION: (125)..(125)
<223> OTHER INFORMATION: X is A, V or T
<220> FEATURE:
<221> NAME/KEY: MISC_FEATURE
<222> LOCATION: (161)..(161)
<223> OTHER INFORMATION: X is H, Y or F
<220> FEATURE:
<221> NAME/KEY: MISC_FEATURE
<222> LOCATION: (162)..(162)
<223> OTHER INFORMATION: X is K or R
<220> FEATURE:
<221> NAME/KEY: MISC_FEATURE
<222> LOCATION: (163)..(163)
<223> OTHER INFORMATION: X is D or E
<220> FEATURE:
<221> NAME/KEY: MISC_FEATURE
<222> LOCATION: (163)..(260)
<223> OTHER INFORMATION: amino acids are optionally absent
<220> FEATURE:
<221> NAME/KEY: MISC_FEATURE
<222> LOCATION: (165)..(165)
<223> OTHER INFORMATION: X is D or E
<220> FEATURE:
<221> NAME/KEY: MISC_FEATURE
<222> LOCATION: (168)..(168)
<223> OTHER INFORMATION: X is A or T
<220> FEATURE:
<221> NAME/KEY: MISC_FEATURE
<222> LOCATION: (172)..(172)
<223> OTHER INFORMATION: X is E, K or absent
<220> FEATURE:
<221> NAME/KEY: MISC_FEATURE
<222> LOCATION: (173)..(173)
<223> OTHER INFORMATION: X is T or absent
<220> FEATURE:
<221> NAME/KEY: MISC_FEATURE
<222> LOCATION: (175)..(175)
<223> OTHER INFORMATION: X is N, S or I
<220> FEATURE:
<221> NAME/KEY: MISC_FEATURE
<222> LOCATION: (178)..(178)
<223> OTHER INFORMATION: X is L or I
<220> FEATURE:
<221> NAME/KEY: MISC_FEATURE
<222> LOCATION: (199)..(199)
<223> OTHER INFORMATION: X is H or Y
<220> FEATURE:
<221> NAME/KEY: MISC_FEATURE
<222> LOCATION: (206)..(206)
<223> OTHER INFORMATION: X is V or I
<220> FEATURE:
<221> NAME/KEY: MISC_FEATURE
<222> LOCATION: (215)..(215)
<223> OTHER INFORMATION: X is R or H
<220> FEATURE:
<221> NAME/KEY: MISC_FEATURE
<222> LOCATION: (223)..(223)
<223> OTHER INFORMATION: X is K or E
<220> FEATURE:
<221> NAME/KEY: MISC_FEATURE
<222> LOCATION: (239)..(239)
<223> OTHER INFORMATION: X is A or T
<220> FEATURE:
<221> NAME/KEY: MISC_FEATURE
<222> LOCATION: (249)..(249)
<223> OTHER INFORMATION: X is A, V or T
<220> FEATURE:
<221> NAME/KEY: MISC_FEATURE
<222> LOCATION: (257)..(257)
<223> OTHER INFORMATION: X is K or E
```

```
<220> FEATURE:
<221> NAME/KEY: MISC_FEATURE
<222> LOCATION: (261)..(287)
<223> OTHER INFORMATION: Amino acids are optionally absent
<220> FEATURE:
<221> NAME/KEY: MISC_FEATURE
<222> LOCATION: (261)..(287)
<223> OTHER INFORMATION: amino acids are optionally NSRN with the rest
      absent
<220> FEATURE:
<221> NAME/KEY: MISC_FEATURE
<222> LOCATION: (269)..(269)
<223> OTHER INFORMATION: X is N or D
<220> FEATURE:
<221> NAME/KEY: MISC_FEATURE
<222> LOCATION: (277)..(277)
<223> OTHER INFORMATION: X is N or D
<220> FEATURE:
<221> NAME/KEY: MISC_FEATURE
<222> LOCATION: (277)..(277)
<223> OTHER INFORMATION: X is N or S
<220> FEATURE:
<221> NAME/KEY: MISC_FEATURE
<222> LOCATION: (284)..(284)
<223> OTHER INFORMATION: X is N or D
<220> FEATURE:
<221> NAME/KEY: MISC_FEATURE
<222> LOCATION: (285)..(285)
<223> OTHER INFORMATION: X is K or E

<400> SEQUENCE: 9

Xaa Ile Xaa Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Xaa Glu Ile Ile Ser Ser
        35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Xaa Gln Val Ile Thr Leu
65                  70                  75                  80

Leu Gly Xaa Gly Asn Ile Ile Asn Ile Val Xaa Ala Asp Ser Ile Xaa
                85                  90                  95

Asp Xaa Phe Lys Ile Asp Val Ser Pro Tyr Gly Leu Xaa Thr Xaa Xaa
            100                 105                 110

Phe Leu Xaa Xaa Cys Asn Xaa Glu Ala Thr Phe Ile Xaa Asn Trp Leu
        115                 120                 125

Asn Asp Glu Asp Lys Lys Leu Ser His Leu Leu Val Pro Cys Ala Met
    130                 135                 140

Leu Leu Arg Leu Gly Ile Val Ile Phe Ser Asn Phe Leu Ile Gln Asn
145                 150                 155                 160

Xaa Xaa Xaa Lys Xaa Phe Leu Xaa Phe Leu Asn Xaa Xaa Lys Xaa Glu
                165                 170                 175

Asn Xaa Ala Leu Ala Glu Asn Glu Phe Leu Gly Val Asp His Ile Ser
        180                 185                 190

Phe Leu Gly Phe Leu Leu Xaa Arg Trp Asn Phe Asp Asp Xaa Leu Ile
    195                 200                 205

Glu Ser Ile Cys Phe Val Xaa Thr Pro His Ala Arg Glu Xaa Val
210                 215                 220

Lys Lys Ser Ala Tyr Ala Leu Ala Ile Thr Asp His Leu Phe Xaa Pro
225                 230                 235                 240

His Asp Gly Ser Ser Pro Phe Asn Xaa Lys Ala Ala Val Ala Leu Leu
                245                 250                 255
```

Xaa Glu Ala Lys Thr Gln Gly Ile Asn Phe Asp Leu Xaa Asn Leu Leu
        260                 265                 270

Ser Lys Leu Pro Xaa Lys Ala Lys Glu Asn Leu Xaa Xaa Glu Asp
            275                 280                 285

<210> SEQ ID NO 10
<211> LENGTH: 298
<212> TYPE: PRT
<213> ORGANISM: Campylobacter jejuni

<400> SEQUENCE: 10

Met Gln Ile Ile Ile Ile Leu Ile Lys Asp Lys Leu Asn Met Ile Gly
1               5                   10                  15

Asp Met Asn Glu Leu Leu Leu Lys Ser Val Glu Val Leu Pro Pro Leu
            20                  25                  30

Pro Asp Thr Val Ser Lys Leu Arg Lys Tyr Val Ser Glu Ala Asn Ser
        35                  40                  45

Asn Ile Glu Thr Met Lys Val Ala Glu Ile Ile Ser Ser Asp Pro Leu
    50                  55                  60

Met Thr Ala Lys Leu Leu Gln Leu Ala Asn Ser Pro Tyr Tyr Gly Phe
65                  70                  75                  80

Thr Arg Glu Ile Thr Thr Ile Asn Gln Val Ile Thr Leu Leu Gly Val
                85                  90                  95

Gly Asn Ile Ile Asn Ile Val Met Ala Asp Ser Ile Arg Asp Asn Phe
            100                 105                 110

Lys Ile Asp Val Ser Pro Tyr Gly Leu Asn Thr Gln Asn Phe Leu Lys
        115                 120                 125

Thr Cys Asn Glu Glu Ala Thr Phe Ile Ala Asn Trp Leu Asn Asp Glu
    130                 135                 140

Asp Lys Lys Leu Ser His Leu Leu Val Pro Cys Ala Met Leu Leu Arg
145                 150                 155                 160

Leu Gly Ile Val Ile Phe Ser Asn Phe Leu Ile Gln Asn His Lys Asp
                165                 170                 175

Lys Asp Phe Leu Ala Phe Leu Asn Lys Asn Glu Asn Leu Ala Leu Ala
            180                 185                 190

Glu Asn Glu Phe Leu Gly Val Asp His Ile Ser Phe Leu Gly Phe Leu
        195                 200                 205

Leu His Arg Trp Asn Phe Asp Asp Val Leu Ile Glu Ser Ile Cys Phe
    210                 215                 220

Val Arg Thr Pro His Ala Ala Arg Glu Lys Val Lys Lys Ser Ala Tyr
225                 230                 235                 240

Ala Leu Ala Ile Thr Asp His Leu Phe Ala Pro His Asp Gly Ser Ser
                245                 250                 255

Pro Phe Asn Ala Lys Ala Ala Val Ala Leu Leu Lys Glu Ala Lys Thr
            260                 265                 270

Gln Gly Ile Asn Phe Asp Leu Asn Asn Leu Leu Ser Lys Leu Pro Asn
        275                 280                 285

Lys Ala Lys Glu Asn Leu Asn Lys Glu Asp
    290                 295

<210> SEQ ID NO 11
<211> LENGTH: 285
<212> TYPE: PRT
<213> ORGANISM: Campylobacter jejuni

<400> SEQUENCE: 11

```
Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
            35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Met Ala Asp Ser Ile Arg
                85                  90                  95

Asp Asn Phe Lys Ile Asp Val Ser Pro Tyr Gly Leu Asn Thr Gln Asn
                100                 105                 110

Phe Leu Lys Thr Cys Asn Glu Glu Ala Thr Phe Ile Ala Asn Trp Leu
            115                 120                 125

Asn Asp Glu Asp Lys Lys Leu Ser His Leu Leu Val Pro Cys Ala Met
    130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
                180                 185                 190

Gly Phe Leu Leu His Arg Trp Asn Phe Asp Asp Val Leu Ile Glu Ser
            195                 200                 205

Ile Cys Phe Val Arg Thr Pro His Ala Ala Arg Glu Lys Val Lys Lys
    210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Ala Val Ala Leu Leu Lys Glu
                245                 250                 255

Ala Lys Thr Gln Gly Ile Asn Phe Asp Leu Asn Leu Leu Ser Lys
                260                 265                 270

Leu Pro Asn Lys Ala Lys Glu Asn Leu Asn Lys Glu Asp
            275                 280                 285

<210> SEQ ID NO 12
<211> LENGTH: 285
<212> TYPE: PRT
<213> ORGANISM: Campylobacter jejuni

<400> SEQUENCE: 12

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
            35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Met Ala Asp Ser Ile Arg
```

```
                85                  90                  95
Asp Asn Phe Lys Ile Asp Val Ser Pro Tyr Gly Leu Asn Thr Gln Asn
                100                 105                 110

Phe Leu Lys Thr Cys Asn Glu Glu Ala Thr Phe Ile Ala Asn Trp Leu
            115                 120                 125

Asn Asp Glu Asp Lys Lys Leu Ser His Leu Leu Val Pro Cys Ala Met
        130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Ser Glu Asn Leu
                165                 170                 175

Ala Leu Ala Glu Asn Glu Phe Leu Gly Val Asp His Ile Ser Phe Leu
                180                 185                 190

Gly Phe Leu Leu His Arg Trp Asn Phe Asp Val Leu Ile Glu Ser
                195                 200                 205

Ile Cys Phe Val Arg Thr Pro His Ala Ala Arg Glu Lys Val Lys Lys
            210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Val Ala Leu Leu Lys Glu
                245                 250                 255

Ala Lys Thr Gln Gly Ile Asn Phe Asp Leu Asn Asn Leu Leu Ser Lys
            260                 265                 270

Leu Pro Asn Lys Ala Lys Glu Asn Leu Asn Lys Glu Asp
            275                 280                 285

<210> SEQ ID NO 13
<211> LENGTH: 285
<212> TYPE: PRT
<213> ORGANISM: Campylobacter jejuni

<400> SEQUENCE: 13

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
        35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Met Ala Asp Ser Ile Arg
                85                  90                  95

Asp Asn Phe Lys Ile Asp Val Ser Pro Tyr Gly Leu Asn Thr Gln Asn
                100                 105                 110

Phe Leu Lys Thr Cys Asn Asp Glu Ala Thr Phe Ile Ala Asn Trp Leu
            115                 120                 125

Asn Asp Glu Asp Lys Lys Leu Ser His Leu Leu Val Pro Cys Ala Met
        130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175
```

```
Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
            195                 200                 205

Ile Cys Phe Val Arg Thr Pro His Ala Ala Arg Glu Lys Val Lys Lys
210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Val Ala Leu Leu Lys Glu
            245                 250                 255

Ala Lys Thr Gln Gly Ile Asn Phe Asp Leu Asn Asn Leu Leu Ser Lys
            260                 265                 270

Leu Pro Asn Lys Ala Lys Glu Asn Leu Asn Lys Glu Asp
            275                 280                 285

<210> SEQ ID NO 14
<211> LENGTH: 285
<212> TYPE: PRT
<213> ORGANISM: Campylobacter jejuni

<400> SEQUENCE: 14

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
            35                  40                  45

Asp Pro Leu Met Thr Ala Lys Leu Leu Gln Leu Ala Asn Ser Pro Tyr
50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Met Ala Asp Ser Ile Arg
            85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Ala Asn Trp Leu
            115                 120                 125

Asn Asp Glu Asp Lys Lys Leu Ser His Leu Leu Val Pro Cys Ala Met
130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
            165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
            195                 200                 205

Ile Cys Phe Val Arg Thr Pro His Ala Ala Arg Glu Lys Val Lys Lys
210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Val Ala Leu Leu Glu Glu
            245                 250                 255

Ala Lys Thr Gln Gly Ile Asn Phe Asp Leu Asn Asn Leu Leu Ser Lys
            260                 265                 270
```

Leu Pro Asn Lys Ala Lys Glu Asn Leu Asn Lys Glu Asp
        275                 280                 285

<210> SEQ ID NO 15
<211> LENGTH: 285
<212> TYPE: PRT
<213> ORGANISM: Campylobacter jejuni

<400> SEQUENCE: 15

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
        35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Met Ala Asp Ser Ile Arg
                85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Ala Asn Trp Leu
        115                 120                 125

Asn Asp Glu Asp Lys Lys Leu Ser His Leu Leu Val Pro Cys Ala Met
130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Lys Val Lys Lys
    210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Val Ala Leu Leu Lys Glu
                245                 250                 255

Ala Lys Thr Gln Gly Ile Asn Phe Asp Leu Asn Asn Leu Leu Ser Lys
            260                 265                 270

Leu Pro Asn Lys Ala Lys Glu Asn Leu Asn Lys Lys Asp
        275                 280                 285

<210> SEQ ID NO 16
<211> LENGTH: 285
<212> TYPE: PRT
<213> ORGANISM: Campylobacter jejuni

<400> SEQUENCE: 16

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
        35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Met Ala Asp Ser Ile Arg
                85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Ala Asn Trp Leu
        115                 120                 125

Asn Asp Glu Asp Lys Lys Leu Ser His Leu Leu Val Pro Cys Ala Met
    130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205

Ile Cys Phe Val His Thr Pro His Ala Ala Arg Glu Lys Val Lys Lys
    210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Val Ala Leu Leu Lys Glu
                245                 250                 255

Ala Lys Thr Gln Gly Ile Asn Phe Asp Leu Asn Asn Leu Leu Ser Lys
            260                 265                 270

Leu Pro Asn Lys Ala Lys Glu Asn Leu Asn Lys Glu Asp
        275                 280                 285

<210> SEQ ID NO 17
<211> LENGTH: 285
<212> TYPE: PRT
<213> ORGANISM: Campylobacter jejuni

<400> SEQUENCE: 17

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
        35                  40                  45

Asp Pro Leu Met Met Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Met Ala Asp Ser Ile Arg
                85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Ala Asn Trp Leu

```
            115                 120                 125
Asn Asp Glu Asp Lys Lys Leu Ser His Leu Leu Val Pro Cys Ala Met
130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Ser Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Lys Val Lys Lys
210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Ala Val Ala Leu Leu Lys Glu
                245                 250                 255

Ala Lys Thr Gln Gly Ile Asn Phe Asp Leu Asn Asn Leu Leu Ser Lys
            260                 265                 270

Leu Pro Asn Lys Ala Lys Glu Asn Leu Asn Lys Glu Asp
        275                 280                 285

<210> SEQ ID NO 18
<211> LENGTH: 285
<212> TYPE: PRT
<213> ORGANISM: Campylobacter jejuni

<400> SEQUENCE: 18

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
                20                  25                  30

Ala Asn Ser Asn Ile Glu Thr Met Lys Val Ala Glu Ile Ile Ser Ser
            35                  40                  45

Asp Pro Leu Met Met Ala Lys Leu Leu Gln Leu Ala Asn Ser Pro Tyr
50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Met Ala Asp Ser Ile Arg
                85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Ala Asn Trp Leu
        115                 120                 125

Asn Asp Glu Asp Lys Lys Leu Ser His Leu Leu Val Pro Cys Ala Met
130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205
```

-continued

```
Ile Cys Phe Val Arg Thr Pro His Ala Ala Arg Glu Lys Val Lys Lys
    210                 215                 220
Ser Ala Tyr Ala Leu Ala Ile Thr Asp His Leu Phe Ala Pro His Asp
225                 230                 235                 240
Gly Ser Ser Pro Phe Asn Ala Lys Ala Val Ala Leu Leu Lys Glu
                245                 250                 255
Ala Lys Thr Gln Gly Ile Asn Phe Asp Leu Asn Asn Leu Leu Ser Lys
            260                 265                 270
Leu Pro Ser Lys Ala Lys Glu Asn Leu Asn Lys Glu Asp
            275                 280                 285

<210> SEQ ID NO 19
<211> LENGTH: 285
<212> TYPE: PRT
<213> ORGANISM: Campylobacter jejuni

<400> SEQUENCE: 19

Met Ile Gly Asp Met Asn Glu Leu Leu Lys Ser Val Glu Val Leu
1               5                   10                  15
Pro Pro Leu Pro Asp Thr Val Ser Lys Leu Arg Lys Tyr Val Ser Glu
            20                  25                  30
Ala Asn Ser Asn Ile Glu Thr Met Lys Val Ala Glu Ile Ile Ser Ser
        35                  40                  45
Asp Pro Leu Met Met Ala Lys Leu Leu Gln Leu Ala Asn Ser Pro Tyr
    50                  55                  60
Tyr Gly Phe Thr Arg Glu Ile Thr Thr Ile Asn Gln Val Ile Thr Leu
65                  70                  75                  80
Leu Gly Val Gly Asn Ile Ile Asn Ile Val Met Ala Asp Ser Ile Arg
                85                  90                  95
Asp Asn Phe Lys Ile Asp Val Ser Pro Tyr Gly Leu Asn Thr Gln Asn
            100                 105                 110
Phe Leu Lys Thr Cys Asn Glu Glu Ala Thr Phe Ile Val Asn Trp Leu
        115                 120                 125
Asn Asp Glu Asp Lys Lys Leu Ser His Leu Leu Val Pro Cys Ala Met
    130                 135                 140
Leu Leu Arg Leu Gly Ile Val Ile Phe Ser Asn Phe Leu Ile Gln Asn
145                 150                 155                 160
His Lys Asp Lys Asp Phe Leu Ala Phe Leu Asn Lys Asn Glu Asn Leu
                165                 170                 175
Ala Leu Ala Glu Asn Glu Phe Leu Gly Val Asp His Ile Ser Phe Leu
            180                 185                 190
Gly Phe Leu Leu His Arg Trp Asn Phe Asp Asp Val Leu Ile Glu Ser
        195                 200                 205
Ile Cys Phe Val Arg Thr Pro His Ala Ala Arg Glu Lys Val Lys Lys
    210                 215                 220
Ser Ala Tyr Ala Leu Ala Ile Thr Asp His Leu Phe Ala Pro His Asp
225                 230                 235                 240
Gly Ser Ser Pro Phe Asn Ala Lys Ala Val Ala Leu Leu Lys Glu
                245                 250                 255
Ala Lys Thr Gln Gly Ile Asn Phe Asp Leu Asn Asn Leu Leu Ser Lys
            260                 265                 270
Leu Pro Asn Lys Ala Lys Glu Asn Leu Asn Lys Glu Asp
            275                 280                 285

<210> SEQ ID NO 20
```

```
<211> LENGTH: 285
<212> TYPE: PRT
<213> ORGANISM: Campylobacter jejuni

<400> SEQUENCE: 20

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
        35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Thr Ala Asp Ser Ile Arg
                85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Thr Asn Trp Leu
        115                 120                 125

Asn Asp Glu Asp Lys Lys Leu Ser His Leu Leu Val Pro Cys Ala Met
130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Ser Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Glu Val Lys Lys
    210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Ala Val Ala Leu Leu Lys Glu
                245                 250                 255

Ala Lys Thr Gln Gly Ile Asn Phe Asp Leu Asn Asn Leu Leu Ser Lys
            260                 265                 270

Leu Pro Asn Lys Ala Lys Glu Asn Leu Asn Lys Glu Asp
        275                 280                 285

<210> SEQ ID NO 21
<211> LENGTH: 285
<212> TYPE: PRT
<213> ORGANISM: Campylobacter jejuni

<400> SEQUENCE: 21

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
        35                  40                  45

Asp Pro Leu Met Thr Ala Lys Leu Leu Gln Leu Ala Asn Ser Pro Tyr
    50                  55                  60
```

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Thr Ala Asp Ser Ile Arg
                85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Thr Asn Trp Leu
        115                 120                 125

Asn Asp Glu Asp Lys Lys Leu Ser His Leu Leu Val Pro Cys Ala Met
    130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Glu Val Lys Lys
210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Ala Val Ala Leu Leu Glu Glu
                245                 250                 255

Ala Lys Thr Gln Gly Ile Asn Phe Asp Leu Asn Asn Leu Leu Ser Lys
            260                 265                 270

Leu Pro Ser Lys Ala Lys Glu Asn Leu Asn Lys Glu Asp
        275                 280                 285

<210> SEQ ID NO 22
<211> LENGTH: 285
<212> TYPE: PRT
<213> ORGANISM: Campylobacter jejuni

<400> SEQUENCE: 22

Met Met Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
                20                  25                  30

Ala Asn Ser Asn Ile Glu Thr Met Lys Val Ala Glu Ile Ile Ser Ser
            35                  40                  45

Asp Pro Leu Met Thr Ala Lys Leu Leu Gln Leu Ala Asn Ser Pro Tyr
        50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Thr Ala Asp Ser Ile Arg
                85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Thr Asn Trp Leu
        115                 120                 125

Asn Asp Glu Asp Lys Lys Leu Ser His Leu Leu Val Pro Cys Ala Met
    130                 135                 140

Leu Leu Arg Leu Gly Ile Val Ile Phe Ser Asn Phe Leu Ile Gln Asn

```
            145                 150                 155                 160
His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
                195                 200                 205

Ile Cys Phe Val Arg Thr Pro His Ala Ala Arg Glu Glu Val Lys Lys
210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Val Ala Leu Leu Glu Glu
                245                 250                 255

Ala Lys Thr Gln Gly Ile Asn Phe Asp Leu Asn Asn Leu Leu Ser Lys
                260                 265                 270

Leu Pro Ser Lys Ala Lys Glu Asn Leu Asn Lys Glu Asp
                275                 280                 285

<210> SEQ ID NO 23
<211> LENGTH: 285
<212> TYPE: PRT
<213> ORGANISM: Campylobacter jejuni

<400> SEQUENCE: 23

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
                20                  25                  30

Ala Asn Ser Asn Ile Glu Thr Met Lys Val Ala Glu Ile Ile Ser Ser
            35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Thr Ala Asp Ser Ile Arg
                85                  90                  95

Asp Asn Phe Lys Ile Asp Val Ser Pro Tyr Gly Leu Asn Thr Gln Asn
                100                 105                 110

Phe Leu Lys Thr Cys Asn Glu Glu Ala Thr Phe Ile Thr Asn Trp Leu
            115                 120                 125

Asn Asp Glu Asp Lys Lys Leu Ser His Leu Leu Val Pro Cys Ala Met
130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
                195                 200                 205

Ile Cys Phe Val Arg Thr Pro His Ala Ala Arg Glu Glu Val Lys Lys
210                 215                 220

Ser Ala Tyr Ala Leu Ala Ile Thr Asp His Leu Phe Ala Pro His Asp
225                 230                 235                 240
```

```
Gly Ser Ser Pro Phe Asn Ala Lys Ala Ala Val Ala Leu Leu Glu Glu
                245                 250                 255

Ala Lys Thr Gln Gly Ile Asn Phe Asp Leu Asn Asn Leu Leu Ser Lys
            260                 265                 270

Leu Pro Ser Lys Ala Lys Glu Asn Leu Asn Glu Glu Asp
        275                 280                 285
```

<210> SEQ ID NO 24
<211> LENGTH: 285
<212> TYPE: PRT
<213> ORGANISM: Campylobacter jejuni

<400> SEQUENCE: 24

```
Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Leu Asn Ile Glu Thr Met Lys Val Ala Glu Ile Ile Ser Ser
        35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Ile Asn Gln Val Ile Thr Leu
65                  70                  75                  80

Leu Gly Val Gly Asn Ile Ile Asn Ile Val Thr Ala Asp Ser Ile Arg
                85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Ala Asn Trp Leu
        115                 120                 125

Asn Asp Glu Asp Lys Lys Leu Ser His Leu Leu Val Pro Cys Ala Met
    130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Glu Val Lys Lys
    210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Ala Val Ala Leu Leu Glu Glu
                245                 250                 255

Ala Lys Thr Gln Gly Ile Asn Phe Asp Leu Asn Asn Leu Leu Ser Lys
            260                 265                 270

Leu Pro Ser Lys Ala Lys Glu Asn Leu Asn Lys Glu Asp
        275                 280                 285
```

<210> SEQ ID NO 25
<211> LENGTH: 285
<212> TYPE: PRT
<213> ORGANISM: Campylobacter jejuni

<400> SEQUENCE: 25

-continued

```
Met Ile Gly Asp Met Asn Glu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Leu Asn Ile Glu Thr Met Lys Val Ala Glu Ile Ile Ser Ser
        35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Thr Ala Asp Ser Ile Arg
                85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Thr Asn Trp Leu
        115                 120                 125

Asn Asp Glu Asp Lys Lys Leu Ser His Leu Leu Val Pro Cys Ala Met
    130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Glu Val Lys Lys
    210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Val Ala Leu Leu Glu Glu
                245                 250                 255

Ala Lys Thr Gln Gly Ile Asn Phe Asp Leu Asn Asn Leu Leu Ser Lys
            260                 265                 270

Leu Pro Ser Lys Ala Lys Glu Asn Leu Asn Lys Glu Asp
        275                 280                 285

<210> SEQ ID NO 26
<211> LENGTH: 285
<212> TYPE: PRT
<213> ORGANISM: Campylobacter jejuni

<400> SEQUENCE: 26

Met Ile Gly Asp Met Asn Glu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
        35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Thr Ala Asp Ser Ile Arg
                85                  90                  95
```

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Thr Asn Trp Leu
        115                 120                 125

Asn Asp Glu Asp Lys Lys Leu Ser His Leu Leu Val Pro Cys Ala Met
130                 135                 140

Leu Leu Arg Leu Gly Ile Val Ile Phe Ser Asn Phe Leu Ile Gln Asn
145                 150                 155                 160

Tyr Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Glu Val Lys Lys
210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Ala Val Ala Leu Leu Glu Glu
                245                 250                 255

Ala Lys Thr Gln Gly Ile Asn Phe Asp Leu Asn Asn Leu Leu Ser Lys
            260                 265                 270

Leu Pro Ser Lys Ala Lys Glu Asn Leu Asn Glu Glu Asp
        275                 280                 285

<210> SEQ ID NO 27
<211> LENGTH: 285
<212> TYPE: PRT
<213> ORGANISM: Campylobacter jejuni

<400> SEQUENCE: 27

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
        35                  40                  45

Asp Pro Leu Met Thr Ala Lys Leu Leu Gln Leu Ala Asn Ser Pro Tyr
50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Thr Ala Asp Ser Ile Arg
                85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Thr Asn Trp Leu
        115                 120                 125

Asn Asp Glu Asp Lys Lys Leu Ser His Leu Leu Val Pro Cys Ala Met
130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu

```
            180                 185                 190
Gly Phe Leu Leu His Arg Trp Asn Phe Asp Asp Val Leu Ile Glu Ser
        195                 200                 205

Ile Cys Phe Val Arg Thr Pro His Ala Ala Arg Glu Glu Val Lys Lys
        210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Ala Val Ala Leu Leu Glu Glu
                245                 250                 255

Ala Lys Thr Gln Gly Ile Asn Phe Asp Leu Asn Leu Leu Ser Lys
                260                 265                 270

Leu Pro Ser Lys Ala Lys Glu Asn Leu Asp Lys Glu Asp
                275                 280                 285

<210> SEQ ID NO 28
<211> LENGTH: 285
<212> TYPE: PRT
<213> ORGANISM: Campylobacter jejuni

<400> SEQUENCE: 28

Met Ile Gly Asp Met Asn Glu Leu Leu Lys Ser Val Glu Val Leu
1               5                   10                  15

Pro Pro Leu Pro Asp Thr Val Ser Lys Leu Arg Lys Tyr Val Ser Glu
                20                  25                  30

Ala Asn Ser Asn Ile Glu Thr Met Lys Val Ala Glu Ile Ile Ser Ser
            35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Ile Gly Asn Ile Ile Asn Ile Val Thr Ala Asp Ser Ile Arg
                85                  90                  95

Asp Ser Phe Lys Ile Asp Val Ser Pro Tyr Gly Leu Asp Thr Gln Asn
            100                 105                 110

Phe Leu Lys Thr Cys Asn Glu Glu Ala Thr Phe Ile Thr Asn Trp Leu
        115                 120                 125

Asn Asp Glu Asp Lys Lys Leu Ser His Leu Leu Val Pro Cys Ala Met
130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Glu Val Lys Lys
        210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Ala Val Ala Leu Leu Glu Glu
                245                 250                 255

Ala Lys Thr Gln Gly Ile Asn Phe Asp Leu Asn Leu Leu Ser Lys
                260                 265                 270
```

Leu Pro Ser Lys Ala Lys Glu Asn Leu Asn Lys Glu Asp
            275                 280                 285

<210> SEQ ID NO 29
<211> LENGTH: 285
<212> TYPE: PRT
<213> ORGANISM: Campylobacter jejuni

<400> SEQUENCE: 29

Met Ile Gly Asp Met Asn Glu Leu Leu Lys Ser Val Glu Val Leu
 1               5                  10                  15

Pro Pro Leu Pro Asp Thr Val Ser Lys Leu Arg Lys Tyr Val Ser Glu
                20                  25                  30

Ala Asn Ser Asn Ile Glu Thr Met Lys Val Ala Glu Ile Ile Ser Ser
            35                  40                  45

Asp Pro Leu Met Thr Ala Lys Leu Leu Gln Leu Ala Asn Ser Pro Tyr
        50                  55                  60

Tyr Gly Phe Thr Arg Glu Ile Thr Thr Ile Asn Gln Val Ile Thr Leu
 65                 70                  75                  80

Leu Gly Ile Gly Asn Ile Ile Asn Ile Val Thr Ala Asp Ser Ile Arg
                85                  90                  95

Asp Ser Phe Lys Ile Asp Val Ser Pro Tyr Gly Leu Asn Thr Gln Asn
                100                 105                 110

Phe Leu Lys Thr Cys Asn Glu Glu Ala Thr Phe Ile Thr Asn Trp Leu
            115                 120                 125

Asn Asp Glu Asp Lys Lys Leu Ser His Leu Leu Val Pro Cys Ala Met
        130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
                180                 185                 190

Gly Phe Leu Leu His Arg Trp Asn Phe Asp Asp Val Leu Ile Glu Ser
            195                 200                 205

Ile Cys Phe Val Arg Thr Pro His Ala Ala Arg Glu Glu Val Lys Lys
        210                 215                 220

Ser Ala Tyr Ala Leu Ala Ile Thr Asp His Leu Phe Ala Pro His Asp
225                 230                 235                 240

Gly Ser Ser Pro Phe Asn Val Lys Ala Ala Val Ala Leu Leu Glu Glu
                245                 250                 255

Ala Lys Thr Gln Gly Ile Asn Phe Asp Leu Asn Asn Leu Leu Ser Lys
            260                 265                 270

Leu Pro Ser Lys Ala Lys Glu Asn Leu Asn Lys Glu Asp
            275                 280                 285

<210> SEQ ID NO 30
<211> LENGTH: 283
<212> TYPE: PRT
<213> ORGANISM: Campylobacter jejuni

<400> SEQUENCE: 30

Met Asp Met Asn Glu Leu Leu Leu Lys Ser Val Glu Val Leu Pro Pro
 1               5                  10                  15

Leu Pro Asp Thr Val Ser Lys Leu Arg Lys Tyr Val Ser Glu Ala Asn
                20                  25                  30

Ser Asn Ile Glu Thr Met Lys Val Ala Glu Ile Ile Ser Asp Pro
 35                  40                  45

Leu Met Thr Ala Lys Leu Leu Gln Leu Ala Asn Ser Pro Tyr Tyr Gly
 50                  55                  60

Phe Thr Arg Glu Ile Thr Thr Ile Asn Gln Val Ile Thr Leu Leu Gly
 65                  70                  75                  80

Val Gly Asn Ile Ile Asn Ile Val Thr Ala Asp Ser Ile Arg Asp Asn
                 85                  90                  95

Phe Lys Ile Asp Val Ser Pro Tyr Gly Leu Asn Thr Gln Asn Phe Leu
             100                 105                 110

Lys Thr Cys Asn Glu Glu Ala Thr Phe Ile Thr Asn Trp Leu Asn Asp
         115                 120                 125

Glu Asp Lys Lys Leu Ser His Leu Leu Val Pro Cys Ala Met Leu Leu
     130                 135                 140

Arg Leu Gly Ile Val Ile Phe Ser Asn Phe Leu Ile Gln Asn His Lys
145                 150                 155                 160

Asp Lys Asp Phe Leu Ala Phe Leu Asn Lys Asn Glu Asn Leu Ala Leu
                165                 170                 175

Ala Glu Asn Glu Phe Leu Gly Val Asp His Ile Ser Phe Leu Gly Phe
            180                 185                 190

Leu Leu His Arg Trp Asn Phe Asp Asp Val Leu Ile Glu Ser Ile Cys
        195                 200                 205

Phe Val Arg Thr Pro His Ala Ala Arg Glu Glu Val Lys Lys Ser Ala
    210                 215                 220

Tyr Ala Leu Ala Ile Thr Asp His Leu Phe Ala Pro His Asp Gly Ser
225                 230                 235                 240

Ser Pro Phe Asn Ala Lys Ala Ala Val Ala Leu Leu Glu Glu Ala Lys
                245                 250                 255

Thr Gln Gly Ile Asn Phe Asp Leu Asn Asn Leu Leu Ser Lys Leu Pro
            260                 265                 270

Ser Lys Ala Lys Glu Asn Leu Asn Lys Glu Asp
        275                 280

```
<210> SEQ ID NO 31
<211> LENGTH: 297
<212> TYPE: PRT
<213> ORGANISM: Campylobacter jejuni
<220> FEATURE:
<221> NAME/KEY: MISC_FEATURE
<222> LOCATION: (1)..(1)
<223> OTHER INFORMATION: X can be any amino acid
<220> FEATURE:
<221> NAME/KEY: MISC_FEATURE
<222> LOCATION: (13)..(13)
<223> OTHER INFORMATION: X can be any amino acid
<220> FEATURE:
<221> NAME/KEY: MISC_FEATURE
<222> LOCATION: (17)..(17)
<223> OTHER INFORMATION: X can be any amino acid
<220> FEATURE:
<221> NAME/KEY: MISC_FEATURE
<222> LOCATION: (52)..(52)
<223> OTHER INFORMATION: X can be any amino acid
<220> FEATURE:
<221> NAME/KEY: MISC_FEATURE
<222> LOCATION: (64)..(64)
<223> OTHER INFORMATION: X can be any amino acid
<220> FEATURE:
<221> NAME/KEY: MISC_FEATURE
<222> LOCATION: (103)..(103)
<223> OTHER INFORMATION: X can be any amino acid
<220> FEATURE:
<221> NAME/KEY: MISC_FEATURE
```

<222> LOCATION: (156)..(156)
<223> OTHER INFORMATION: X can be any amino acid

<400> SEQUENCE: 31

Xaa Gly Ser Asp Lys Ile His His His His His Xaa Ile Gly Asp
1               5                   10                  15

Xaa Asn Glu Leu Leu Leu Lys Ser Val Glu Val Leu Pro Pro Leu Pro
            20                  25                  30

Asp Thr Val Ser Lys Leu Arg Lys Tyr Val Ser Glu Ala Asn Ser Asn
        35                  40                  45

Ile Glu Thr Xaa Lys Val Ala Glu Ile Ile Ser Ser Asp Pro Leu Xaa
    50                  55                  60

Thr Ala Lys Leu Leu Gln Leu Ala Asn Ser Pro Tyr Tyr Gly Phe Thr
65                  70                  75                  80

Arg Glu Ile Thr Thr Ile Asn Gln Val Ile Thr Leu Leu Gly Val Gly
                85                  90                  95

Asn Ile Ile Asn Ile Val Xaa Ala Asp Ser Ile Arg Asp Asn Phe Lys
            100                 105                 110

Ile Asp Val Ser Pro Tyr Gly Leu Asn Thr Gln Asn Phe Leu Lys Thr
        115                 120                 125

Cys Asn Glu Glu Ala Thr Phe Ile Ala Asn Trp Leu Asn Asp Glu Asp
130                 135                 140

Lys Lys Leu Ser His Leu Leu Val Pro Cys Ala Xaa Leu Leu Arg Leu
145                 150                 155                 160

Gly Ile Val Ile Phe Ser Asn Phe Leu Ile Gln Asn His Lys Asp Lys
                165                 170                 175

Asp Phe Leu Ala Phe Leu Asn Lys Asn Glu Asn Leu Ala Leu Ala Glu
            180                 185                 190

Asn Glu Phe Leu Gly Val Asp His Ile Ser Phe Leu Gly Phe Leu Leu
        195                 200                 205

His Arg Trp Asn Phe Asp Asp Val Leu Ile Glu Ser Ile Cys Phe Val
210                 215                 220

Arg Thr Pro His Ala Ala Arg Glu Lys Val Lys Lys Ser Ala Tyr Ala
225                 230                 235                 240

Leu Ala Ile Thr Asp His Leu Phe Ala Pro His Asp Gly Ser Ser Pro
                245                 250                 255

Phe Asn Ala Lys Ala Ala Val Ala Leu Leu Lys Glu Ala Lys Thr Gln
            260                 265                 270

Gly Ile Asn Phe Asp Leu Asn Asn Leu Leu Ser Lys Leu Pro Asn Lys
        275                 280                 285

Ala Lys Glu Asn Leu Asn Lys Glu Asp
290                 295

<210> SEQ ID NO 32
<211> LENGTH: 285
<212> TYPE: PRT
<213> ORGANISM: Campylobacter jejuni

<400> SEQUENCE: 32

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
        35                  40                  45

```
Asp Pro Leu Met Thr Ala Lys Leu Leu Gln Leu Ala Asn Ser Pro Tyr
        50                  55                  60

Tyr Gly Phe Thr Arg Glu Ile Thr Thr Ile Asn Gln Val Ile Thr Leu
 65                  70                  75                  80

Leu Gly Val Ser Asn Ile Ile Asn Ile Val Thr Ala Asp Ser Ile Arg
                 85                  90                  95

Asp Ser Phe Lys Ile Asp Val Ser Pro Tyr Gly Leu Asp Thr Gln Val
            100                 105                 110

Phe Leu Arg Asn Cys Asn Glu Glu Ala Thr Phe Ile Thr Asn Trp Leu
            115                 120                 125

Asn Asp Glu Asp Lys Lys Leu Ser His Leu Leu Val Pro Cys Ala Met
130                 135                 140

Leu Leu Arg Phe Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
            165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
            195                 200                 205

Ile Cys Phe Val Arg Thr Pro His Ala Ala Arg Glu Glu Val Lys Lys
            210                 215                 220

Ser Ala Tyr Ala Leu Ala Ile Thr Asp His Leu Phe Thr Pro His Asp
225                 230                 235                 240

Gly Ser Ser Pro Phe Asn Ala Lys Ala Ala Val Ala Leu Leu Glu Glu
            245                 250                 255

Ala Lys Thr Gln Gly Ile Asn Phe Asp Leu Asn Asn Leu Leu Ser Lys
            260                 265                 270

Leu Pro Ser Lys Ala Lys Glu Asn Leu Asp Lys Glu Asp
            275                 280                 285

<210> SEQ ID NO 33
<211> LENGTH: 287
<212> TYPE: PRT
<213> ORGANISM: Campylobacter jejuni

<400> SEQUENCE: 33

Met Ile Gly Asp Met Asn Glu Leu Leu Lys Ser Val Glu Val Leu
 1               5                  10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
            35                  40                  45

Asp Pro Leu Met Thr Ala Lys Leu Leu Gln Leu Ala Asn Ser Pro Tyr
        50                  55                  60

Tyr Gly Phe Thr Arg Glu Ile Thr Thr Ile Asn Gln Val Ile Thr Leu
 65                  70                  75                  80

Leu Gly Val Gly Asn Ile Ile Asn Ile Val Thr Ala Asp Ser Ile Lys
                 85                  90                  95

Asp Ser Phe Lys Ile Asp Val Ser Pro Tyr Gly Leu Asp Thr Gln Val
            100                 105                 110

Phe Leu Arg Asn Cys Asn Glu Glu Ala Thr Phe Ile Thr Asn Trp Leu
            115                 120                 125

Asn Asp Glu Asp Lys Lys Leu Ser His Leu Leu Val Pro Cys Ala Met
130                 135                 140
```

Leu Leu Arg Leu Gly Ile Val Ile Phe Ser Asn Phe Leu Ile Gln Asn
145                 150                 155                 160

His Arg Glu Lys Glu Phe Leu Thr Phe Leu Asn Glu Thr Lys Ile Glu
                165                 170                 175

Asn Ile Ala Leu Ala Glu Asn Glu Phe Leu Gly Val Asp His Ile Ser
            180                 185                 190

Phe Leu Gly Phe Leu His Arg Trp Asn Phe Asp Asp Val Leu Ile
        195                 200                 205

Glu Ser Ile Cys Phe Val Arg Thr Pro His Ala Ala Arg Glu Glu Val
    210                 215                 220

Lys Lys Ser Ala Tyr Ala Leu Ala Ile Thr Asp His Leu Phe Ala Pro
225                 230                 235                 240

His Asp Gly Ser Ser Pro Phe Asn Ala Lys Ala Val Ala Leu Leu
                245                 250                 255

Glu Glu Ala Lys Thr Gln Gly Ile Asn Phe Asp Leu Asn Asn Leu Leu
            260                 265                 270

Ser Lys Leu Pro Ser Lys Ala Lys Glu Asn Leu Asn Lys Glu Asp
        275                 280                 285

<210> SEQ ID NO 34
<211> LENGTH: 287
<212> TYPE: PRT
<213> ORGANISM: Campylobacter jejuni

<400> SEQUENCE: 34

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Val Glu Ile Ile Ser Ser
        35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Ser Gln Val Ile Thr Leu
65                  70                  75                  80

Leu Gly Ile Gly Asn Ile Ile Asn Ile Val Thr Ala Asp Ser Ile Arg
                85                  90                  95

Asp Asn Phe Lys Ile Asp Val Ser Pro Tyr Gly Leu Asp Thr Lys Asn
            100                 105                 110

Phe Leu Lys Thr Cys Asn Glu Glu Ala Thr Phe Ile Thr Asn Trp Leu
        115                 120                 125

Asn Asp Glu Asp Lys Lys Leu Ser Phe Leu Val Pro Cys Ala Met
    130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Thr Lys Asn Glu
                165                 170                 175

Asn Ile Ala Leu Ala Glu Asn Glu Phe Leu Gly Val Asp His Ile Ser
            180                 185                 190

Phe Leu Gly Phe Leu Leu Tyr His Trp Asn Phe Asp Asp Ile Leu Ile
        195                 200                 205

Glu Ser Ile Cys Phe Val Arg Thr Pro His Ala Ala Arg Glu Glu Val
    210                 215                 220

Lys Lys Ser Ala Tyr Ala Leu Ala Ile Thr Asp His Leu Phe Ala Pro

His Asp Gly Ser Ser Pro Phe Asn Thr Lys Ala Ala Ile Ala Leu Leu
            225                 230                 235                 240

Glu Glu Ala Lys Thr Gln Gly Ile Asn Phe Asp Leu Asn Asn Leu Leu
            245                 250                 255

Ser Lys Leu Pro Ser Lys Ala Lys Glu Asn Leu Asp Lys Glu Asp
        260                 265                 270

275                 280                 285

<210> SEQ ID NO 35
<211> LENGTH: 264
<212> TYPE: PRT
<213> ORGANISM: Campylobacter jejuni

<400> SEQUENCE: 35

Met Ile Gly Asp Met Asn Glu Leu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ile Ser Ser
        35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Thr Ala Asp Ser Ile Lys
                85                  90                  95

Asp Ser Phe Lys Ile Asp Val Ser Pro Tyr Gly Leu Asp Thr Gln Val
            100                 105                 110

Phe Leu Arg Asn Cys Asn Glu Glu Ala Thr Phe Ile Thr Asn Trp Leu
        115                 120                 125

Asn Asp Glu Asp Lys Lys Leu Ser His Leu Leu Val Pro Cys Ala Met
130                 135                 140

Leu Leu Arg Leu Gly Ile Val Ile Phe Ser Asn Phe Leu Ile Gln Asn
145                 150                 155                 160

His Arg Glu Lys Glu Phe Leu Thr Phe Leu Asn Glu Thr Lys Ile Glu
                165                 170                 175

Asn Ile Ala Leu Ala Glu Asn Glu Phe Leu Gly Val Asp His Ile Ser
            180                 185                 190

Phe Leu Gly Phe Leu Leu His Arg Trp Asn Phe Asp Asp Val Leu Ile
        195                 200                 205

Glu Ser Ile Cys Phe Val Arg Thr Pro His Ala Ala Arg Glu Glu Val
    210                 215                 220

Lys Lys Ser Ala Tyr Ala Leu Ala Ile Thr Asp His Leu Phe Ala Pro
225                 230                 235                 240

His Asp Gly Ser Ser Pro Phe Asn Ala Lys Ala Ala Val Ala Leu Leu
                245                 250                 255

Glu Glu Ala Lys Asn Ser Arg Asn
            260

<210> SEQ ID NO 36
<211> LENGTH: 162
<212> TYPE: PRT
<213> ORGANISM: Campylobacter jejuni

<400> SEQUENCE: 36

Met Ile Gly Asp Met Asn Glu Leu Leu Leu Lys Ser Val Glu Val Leu

```
            1               5                  10                 15
    Pro Pro Leu Pro Asp Thr Val Ser Lys Leu Arg Lys Tyr Val Ser Glu
                    20                  25                 30

Ala Asn Ser Asn Ile Glu Thr Met Lys Val Ala Glu Ile Ile Ser Ser
                    35                  40                 45

Asp Pro Leu Met Thr Ala Lys Leu Leu Gln Leu Ala Asn Ser Pro Tyr
                50                  55                 60

Tyr Gly Phe Thr Arg Glu Ile Thr Thr Ile Asn Gln Val Ile Thr Leu
    65                  70                  75                 80

Leu Gly Val Gly Asn Ile Ile Asn Ile Val Met Ala Asp Ser Ile Arg
                    85                  90                 95

Asp Asn Phe Lys Ile Asp Val Ser Pro Tyr Gly Leu Asn Thr Gln Asn
                    100                 105                110

Phe Leu Lys Thr Cys Asn Glu Glu Ala Thr Phe Ile Ala Asn Trp Leu
                    115                 120                125

Asn Asp Glu Asp Lys Lys Leu Ser His Leu Leu Val Pro Cys Ala Met
                    130                 135                140

Leu Leu Arg Leu Gly Ile Val Ile Phe Ser Asn Phe Leu Ile Gln Asn
    145                 150                 155                160

Phe Lys

<210> SEQ ID NO 37
<211> LENGTH: 298
<212> TYPE: PRT
<213> ORGANISM: Campylobacter jejuni

<400> SEQUENCE: 37

Met Asn Asn Leu Leu Glu Lys Asn Ile Asn Glu Ile Asn Glu Met Leu
    1               5                  10                 15

Ile Lys Ser Leu Asp Asp Leu Pro Pro Leu Pro Glu Thr Ile Gln Lys
                    20                  25                 30

Leu Gln Glu Tyr Ile Ala Thr His Gly Ser Asn Ile Val Ile Asp Glu
                    35                  40                 45

Val Ala Asp Ile Ile Ser Thr Asp Pro Leu Ile Thr Ala Asn Leu Leu
                50                  55                 60

His Leu Thr Asn Ser Ala Tyr Tyr Gly Phe Ser Lys Glu Ile Lys Thr
    65                  70                  75                 80

Val Asn Gln Ala Leu Val Leu Gly Val Ser Asn Val Lys Asn Met
                    85                  90                 95

Ile Ile Ala Asp Tyr Ala Lys Ser Ser Phe Val Ile Asn Leu Ser Pro
                    100                 105                110

Tyr Gly Ile Glu Thr Asp Arg Phe Leu Thr Leu Ile His Glu Gln Thr
                    115                 120                125

Asn Phe Ile Ser Thr Trp Leu Ile Glu Glu Asp Arg Ile Leu Cys Tyr
                    130                 135                140

Asn Leu Ile Pro Cys Val Met Met Leu Arg Leu Gly Ile Met Val Phe
    145                 150                 155                160

Ser Asn Phe Leu Ile Gln Asn Asn Ile Asp Lys Lys Phe Leu Leu His
                    165                 170                175

Leu Ser Lys Asn Asn Phe Asn Asn Ile Leu Arg Leu Glu Arg Glu Phe
                    180                 185                190

Leu Gly Val Asp His Ile Ser Phe Leu Ser Asn Leu Phe Lys Val Trp
                    195                 200                205

Asn Leu Asp Glu Asp Leu Ile Glu Ile Ile Ser Ser Leu Asp Tyr Leu
```

```
                210                 215                 220
Gly Ser Thr Ser Ala Lys Val Lys Glu Thr Tyr Ala Leu Ala Ala
225                 230                 235                 240

Ile Glu Ala Leu Phe Ser Pro Glu Lys Asn Ala Tyr Asp Asp Phe Cys
                245                 250                 255

Val Gln Lys Ala Tyr Gln Ile Leu Lys Asp Gly Lys Ala Asn Gly Val
                260                 265                 270

Asp Phe Asn Leu Glu Asn Phe Leu Asn Lys Leu Pro Glu Lys Phe Ile
                275                 280                 285

Glu Ile Leu Ser Lys Ser Lys Glu Gln Leu
                290                 295

<210> SEQ ID NO 38
<211> LENGTH: 127
<212> TYPE: PRT
<213> ORGANISM: Campylobacter jejuni

<400> SEQUENCE: 38

Met Leu Phe Phe Gln Ile Phe Leu Tyr Lys Ile Leu Asn Lys Asn Glu
1               5                   10                  15

Asn Leu Ala Leu Ala Glu Asn Glu Phe Leu Gly Val Asp His Ile Ser
                20                  25                  30

Phe Leu Gly Phe Leu Leu His Arg Trp Asn Phe Asp Asp Val Leu Ile
            35                  40                  45

Glu Ser Ile Cys Phe Val Arg Thr Pro His Ala Ala Arg Glu Lys Val
        50                  55                  60

Lys Lys Ser Ala Tyr Ala Leu Ala Ile Thr Asp His Leu Phe Ala Pro
65                  70                  75                  80

His Asp Gly Ser Ser Pro Phe Asn Ala Lys Ala Val Ala Leu Leu
                85                  90                  95

Lys Glu Ala Lys Thr Gln Gly Ile Asn Phe Asp Leu Asn Asn Leu Leu
                100                 105                 110

Ser Lys Leu Pro Asn Lys Ala Lys Glu Asn Leu Asn Lys Glu Asp
            115                 120                 125

<210> SEQ ID NO 39
<211> LENGTH: 202
<212> TYPE: PRT
<213> ORGANISM: Campylobacter jejuni

<400> SEQUENCE: 39

Met Asn Asn Leu Leu Glu Lys Asn Ile Asn Glu Val Asn Glu Met Leu
1               5                   10                  15

Ile Lys Ser Leu Asp Asp Leu Pro Pro Leu Pro Glu Thr Ile Gln Lys
                20                  25                  30

Leu Gln Glu Tyr Ile Ala Thr His Gly Ser Asn Ile Ala Ile Asp Glu
            35                  40                  45

Val Ala Asp Ile Ile Ser Thr Asp Pro Leu Ile Thr Ala Asn Leu Leu
        50                  55                  60

His Leu Thr Asn Ser Ala Tyr Tyr Gly Phe Ser Lys Glu Ile Lys Thr
65                  70                  75                  80

Val Asn Gln Ala Leu Val Leu Leu Gly Val Asn Asn Val Lys Asn Met
                85                  90                  95

Ile Ile Ala Asp Tyr Ala Lys Ser Ser Phe Val Ile Asn Leu Ser Pro
            100                 105                 110

Tyr Gly Ile Glu Thr Asp Arg Phe Leu Ala Leu Ile His Glu Gln Thr
```

```
            115                 120                 125
Asp Phe Ile Ser Thr Trp Leu Met Lys Glu Asp Lys Met Leu Cys Leu
        130                 135                 140

Asn Leu Ile Pro Cys Val Met Met Leu Arg Leu Gly Ile Met Val Phe
145                 150                 155                 160

Ser Asn Phe Leu Ile Gln Asn Lys Ile Asp Lys Lys Phe Leu Leu His
                165                 170                 175

Leu Ser Lys Asn Asn Phe Asn Asn Ile Leu Arg Leu Glu Arg Glu Phe
            180                 185                 190

Leu Gly Ile Glu Val Val Trp Ala Arg Asn
        195                 200

<210> SEQ ID NO 40
<211> LENGTH: 368
<212> TYPE: PRT
<213> ORGANISM: Campylobacter jejuni

<400> SEQUENCE: 40

Met Lys Glu Gln Ile Leu Glu Lys Leu Lys Thr Val Lys Tyr Pro Gly
1               5                   10                  15

Phe Glu Lys Asp Ile Val Ser Phe Asn Phe Val Lys Asp Ile Lys Ile
            20                  25                  30

Gln Asp Asp Gly Val Phe Ile Asp Ile Glu Ile Val Ser Ala Asn Pro
        35                  40                  45

Glu Val Val Asn Glu Ile Arg Lys Asn Val Thr Glu Ala Leu Ser Ser
50                  55                  60

Leu Ala Leu Lys Asn Ile Glu Leu Asn Ile Ile Thr Pro Lys Ile Pro
65                  70                  75                  80

Glu Glu Lys Ser Asn Ser Arg Ser Gly Lys Asn Ile Ala Pro Gln Val
                85                  90                  95

Lys Asn Phe Ile Met Val Ser Ser Gly Lys Gly Val Gly Lys Ser
            100                 105                 110

Thr Thr Thr Val Asn Leu Ala Ile Ser Met Ala Lys Met Gly Lys Arg
        115                 120                 125

Val Gly Ile Leu Asp Ala Asp Ile Tyr Gly Pro Asn Ile Pro Arg Met
    130                 135                 140

Leu Gly Glu Thr Lys Thr Gln Pro Glu Val Val Gly Gln Arg Leu Lys
145                 150                 155                 160

Pro Ile Leu Thr His Gly Val Tyr Met Met Ser Met Gly Val Leu Ile
                165                 170                 175

Glu Glu Gly Gln Gly Leu Met Trp Arg Gly Ala Met Ile Met Lys Ala
            180                 185                 190

Ile Glu Gln Leu Leu Ala Asp Val Ile Trp Pro Glu Leu Asp Val Leu
        195                 200                 205

Phe Leu Asp Met Pro Pro Gly Thr Gly Asp Ala Gln Ile Thr Ser Ala
    210                 215                 220

Gln Ser Ile Pro Ile Thr Ala Gly Val Cys Val Ser Thr Pro Gln Thr
225                 230                 235                 240

Val Ser Leu Asp Asp Ser Lys Arg Ala Leu Asp Met Phe Asn Lys Leu
                245                 250                 255

His Ile Pro Ile Ala Gly Val Ile Glu Asn Met Ser Gly Phe Leu Cys
            260                 265                 270

Pro Asp Asn Gly Lys Glu Tyr Asp Ile Phe Gly Lys Gly Thr Ala Glu
        275                 280                 285
```

```
Asp Met Ala Lys Ala Tyr Lys Ser Glu Val Leu Ala Gln Ile Pro Ile
    290                 295                 300

Glu Met Ile Val Arg Glu Gly Asp Glu Gly Lys Pro Val Ser Phe
305                 310                 315                 320

Tyr His Pro Glu Ser Val Ser Ser Lys Arg Tyr Leu Thr Ala Ala Glu
                325                 330                 335

Lys Ile Trp Ser Phe Ile Glu Lys Ile Asn Asn Glu Gly Gly Ala Asp
                340                 345                 350

Asn Ser Ala Ile Gln Pro Val Met Asn Gly Lys Ser Ala Cys Ser His
                355                 360                 365
```

<210> SEQ ID NO 41
<211> LENGTH: 368
<212> TYPE: PRT
<213> ORGANISM: Campylobacter jejuni

<400> SEQUENCE: 41

```
Met Lys Glu Gln Ile Leu Glu Lys Leu Lys Thr Val Lys Tyr Pro Gly
1               5                   10                  15

Phe Glu Lys Asp Ile Val Ser Phe Asn Phe Val Lys Asp Ile Lys Ile
                20                  25                  30

Gln Asp Asp Gly Val Phe Ile Asp Ile Glu Ile Val Ser Ala Asn Pro
            35                  40                  45

Glu Val Val Asn Glu Ile Arg Lys Asn Val Thr Glu Ala Leu Ser Ser
    50                  55                  60

Leu Ala Leu Lys Asn Ile Glu Leu Asn Ile Ile Thr Pro Lys Ile Pro
65                  70                  75                  80

Glu Glu Lys Ser Asn Ser Arg Ser Gly Lys Asn Ile Ala Pro Gln Val
                85                  90                  95

Lys Asn Phe Ile Met Val Ser Ser Gly Lys Gly Val Gly Lys Ser
                100                 105                 110

Thr Thr Thr Val Asn Leu Ala Ile Ser Met Ala Lys Met Gly Lys Arg
                115                 120                 125

Val Gly Ile Leu Asp Ala Asp Ile Tyr Gly Pro Asn Ile Pro Arg Met
    130                 135                 140

Leu Gly Glu Thr Lys Thr Gln Pro Glu Val Val Gly Gln Arg Leu Lys
145                 150                 155                 160

Pro Ile Leu Thr His Gly Val Tyr Met Met Ser Met Gly Val Leu Ile
                165                 170                 175

Glu Glu Gly Gln Gly Leu Met Trp Arg Gly Ala Met Ile Met Lys Ala
                180                 185                 190

Ile Glu Gln Leu Leu Ala Asp Val Ile Trp Pro Glu Leu Asp Val Leu
            195                 200                 205

Phe Leu Asp Met Pro Pro Gly Thr Gly Asp Ala Gln Ile Thr Ser Ala
    210                 215                 220

Gln Ser Ile Pro Ile Thr Ala Gly Val Cys Val Ser Thr Pro Gln Thr
225                 230                 235                 240

Val Ser Leu Asp Asp Ser Lys Arg Ala Leu Asp Met Phe Asn Lys Leu
                245                 250                 255

His Ile Pro Ile Ala Gly Val Ile Glu Asn Met Ser Gly Phe Leu Cys
                260                 265                 270

Pro Asp Asn Gly Lys Glu Tyr Asp Ile Phe Gly Lys Gly Thr Ala Glu
            275                 280                 285

Asp Met Ala Lys Ala Tyr Lys Ser Glu Val Leu Ala Gln Ile Pro Ile
    290                 295                 300
```

Glu Met Ile Val Arg Glu Gly Asp Glu Gly Lys Pro Val Ser Phe
305                 310                 315                 320

Tyr His Pro Glu Ser Val Ser Lys Arg Tyr Leu Met Ala Ala Glu
                325                 330                 335

Lys Ile Trp Ser Phe Ile Glu Lys Ile Asn Asn Glu Gly Gly Ala Asp
            340                 345                 350

Asn Ser Ala Ile Gln Pro Val Met Asn Gly Lys Ser Ala Cys Ser His
            355                 360                 365

<210> SEQ ID NO 42
<211> LENGTH: 402
<212> TYPE: PRT
<213> ORGANISM: Campylobacter jejuni

<400> SEQUENCE: 42

Met Asn Leu Lys Gly Ile Phe Arg Lys Ser Phe Arg Glu Ser Lys Lys
1               5                   10                  15

Gly Tyr Leu His Leu Ile Leu Leu His Met Ile Leu Ile Tyr Leu Met
            20                  25                  30

Gln Lys Lys Ser Arg His Tyr Ile Phe Leu Lys Leu Cys Ser Tyr Leu
        35                  40                  45

Ser Lys Val Asn Met Lys Thr Val Phe Tyr Tyr Gln Ala Glu Phe Tyr
50                  55                  60

Phe Phe Tyr Ala Glu Tyr Lys Lys Ala Leu Asn Tyr Ile Asp Leu Phe
65                  70                  75                  80

Leu Glu Lys Tyr Pro Leu Asn Ile Asp Gly Lys Leu Leu Lys Ile Gln
                85                  90                  95

Leu Leu Tyr Leu Leu Gly Asp Lys Thr Lys Ala Leu Tyr Glu Leu Glu
            100                 105                 110

Lys Ile Gln Gln Glu Ser Asn Arg Leu Lys Ile Trp Met Leu Met Ser
        115                 120                 125

Lys Leu Val Asn Thr Lys Ile Asp Leu Lys Asn Met Glu Lys Leu Tyr
130                 135                 140

Leu Lys Tyr Ile Glu Lys Lys Arg Asn Ile Ser Thr Lys Ile Glu Ile
145                 150                 155                 160

Gln Lys Tyr Ile Ser Ser Ala Ala Ala Ser Ile Glu Ala Tyr Asp Ile
                165                 170                 175

Ala Glu Tyr Tyr Leu Lys Asn Ser Leu Lys Leu His Glu Lys Phe Ser
            180                 185                 190

Leu Lys Asn Thr Lys Lys Tyr Phe Ser Lys Tyr Asp Ala Leu Ile
        195                 200                 205

Ala Leu Glu Asp Leu Ser Ser Val Phe Asn Ser Leu Asn Ile Lys Phe
210                 215                 220

Phe Leu Val Ser Gly Thr Phe Leu Gly Cys Ile Arg Glu Asn Asn Phe
225                 230                 235                 240

Ile Ser Asn Asp Tyr Asp Ile Asp Val Gly Val Trp Glu Glu Asp Phe
                245                 250                 255

Ser Asn Glu Leu Lys Ile Ala Leu Glu Gln Tyr Gly Thr Phe Tyr Ile
            260                 265                 270

His Asp Pro Lys Trp Lys Gly Gly Ile Lys Leu Lys His Ile Asn Gly
        275                 280                 285

Ile Leu Ile Asp Ile Phe Ile His Tyr Lys Asp Gly Cys Lys His Tyr
290                 295                 300

His Leu Gly Ser Ala Val Lys Trp Tyr Asn Ser Thr Phe Asp Leu Ile

```
            305                 310                 315                 320
Lys Tyr Asp Phe Leu Gly Lys Glu Tyr Phe Gly Phe Lys Glu Tyr Asp
                325                 330                 335

Arg Tyr Leu Ser Glu Asn Tyr Gly Asp Trp Arg Ile Pro Lys Lys Asn
                340                 345                 350

Phe Asp Asn Ile Leu Asp Thr Pro Asn Ala Val Ile Phe Asn Glu Asn
                355                 360                 365

Asn Phe Ile Leu His Leu Tyr Ser Leu Leu Met Lys Gln Tyr Ala Ile
                370                 375                 380

Asp Tyr Lys Asn Thr Ile Leu Asp Leu Lys Lys Tyr Lys Phe Arg
385                 390                 395                 400

Glu Asp

<210> SEQ ID NO 43
<211> LENGTH: 402
<212> TYPE: PRT
<213> ORGANISM: Campylobacter jejuni

<400> SEQUENCE: 43

Met Asn Leu Lys Gly Ile Phe Arg Lys Ser Phe Arg Glu Thr Lys Lys
1               5                   10                  15

Trp Tyr Leu His Met Ile Leu His Met Ile Leu Ile Tyr Leu Met
                20                  25                  30

Gln Lys Lys Ser Arg His Tyr Ile Phe Leu Lys Leu Cys Ile Tyr Leu
                35                  40                  45

Ser Lys Val Asn Met Lys Thr Val Phe Tyr Tyr Gln Ala Glu Phe Tyr
                50                  55                  60

Phe Phe Tyr Ala Glu Tyr Lys Lys Ala Leu Asn Tyr Ile Asp Leu Phe
65                  70                  75                  80

Leu Glu Lys Tyr Pro Leu Asn Ile Asp Gly Lys Leu Leu Lys Ile Gln
                85                  90                  95

Leu Leu Tyr Leu Leu Gly Asp Lys Thr Lys Ala Leu Tyr Glu Leu Glu
                100                 105                 110

Lys Ile Gln Gln Glu Ser Asn Arg Leu Lys Ile Trp Met Leu Met Ser
                115                 120                 125

Lys Leu Val Asn Thr Lys Ile Asp Leu Lys Asn Met Glu Lys Leu Tyr
                130                 135                 140

Leu Lys Tyr Ile Glu Lys Lys Arg Asn Ile Ser Thr Lys Ile Glu Ile
145                 150                 155                 160

Gln Lys Tyr Ile Ser Ser Ala Ala Ala Ser Ile Glu Ala Tyr Asp Ile
                165                 170                 175

Ala Glu Tyr Tyr Leu Lys Asn Ser Leu Lys Leu His Glu Lys Phe Ser
                180                 185                 190

Leu Lys Asn Thr Lys Lys Lys Tyr Phe Ser Lys Tyr Asp Ala Leu Ile
                195                 200                 205

Ala Leu Glu Asp Leu Ser Ser Val Phe Asn Ser Leu Asn Ile Lys Phe
                210                 215                 220

Phe Leu Val Ser Gly Thr Phe Leu Gly Cys Ile Arg Glu Asn Asn Phe
225                 230                 235                 240

Ile Ser Asn Asp Tyr Asp Ile Asp Val Gly Val Trp Glu Glu Asp Phe
                245                 250                 255

Ser Asn Glu Leu Lys Ile Ala Leu Glu Gln Tyr Gly Thr Phe Tyr Ile
                260                 265                 270

His Asp Pro Lys Trp Lys Gly Gly Ile Lys Leu Lys His Ile Asn Gly
```

```
                    275                 280                 285
Ile Leu Ile Asp Ile Phe Ile His Tyr Lys Asp Gly Cys Lys His Tyr
        290                 295                 300

His Leu Gly Ser Ala Val Lys Trp Tyr Asn Ser Thr Phe Asp Leu Ile
305                 310                 315                 320

Lys Tyr Asp Phe Leu Gly Lys Glu Tyr Phe Gly Phe Lys Glu Tyr Asp
                325                 330                 335

Arg Tyr Leu Ser Glu Asn Tyr Gly Asp Trp Arg Ile Pro Lys Lys Asn
                340                 345                 350

Phe Asp Asn Ile Leu Asp Thr Pro Asn Ala Val Ile Phe Asn Lys Asn
                355                 360                 365

Asn Phe Ile Leu His Leu Tyr Ser Leu Leu Met Lys Gln Tyr Ala Ile
        370                 375                 380

Asp Tyr Lys Asn Thr Ile Leu Asp Leu Lys Lys Tyr Lys Phe Arg
385                 390                 395                 400

Glu Asp

<210> SEQ ID NO 44
<211> LENGTH: 190
<212> TYPE: PRT
<213> ORGANISM: Campylobacter jejuni

<400> SEQUENCE: 44

Met Lys Lys Ile Leu Val Ser Val Leu Ser Ser Cys Leu Leu Ala Ser
1               5                   10                  15

Ala Leu Ser Ala Val Ser Phe Lys Glu Asp Ser Leu Lys Ile Ser Phe
            20                  25                  30

Glu Gly Tyr Lys Thr Lys Asp Met Ile Gly Thr Lys Gly Glu Phe Lys
        35                  40                  45

Asn Val Glu Tyr Lys Phe Ser Lys Asn Ile Lys Asp Leu Ala Ser Tyr
    50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
            100                 105                 110

Ala Gly Glu Asn Lys Gly Val Ile Ser Ala Lys Ile Thr Met Asp Lys
        115                 120                 125

Lys Ser Thr Ile Val Pro Leu Thr Tyr Thr Ile Lys Asp Asn Lys Phe
    130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Ile Ser
                165                 170                 175

Trp Pro Leu Val Asp Ile Ser Phe Asn Ala Asp Leu Ala Glu
            180                 185                 190

<210> SEQ ID NO 45
<211> LENGTH: 190
<212> TYPE: PRT
<213> ORGANISM: Campylobacter jejuni

<400> SEQUENCE: 45

Met Lys Lys Ile Leu Val Ser Val Leu Ser Ser Cys Leu Leu Ala Ser
1               5                   10                  15
```

Ala Leu Ser Ala Val Ser Phe Lys Glu Asp Ser Leu Lys Val Ser Phe
            20                  25                  30

Glu Gly Tyr Lys Thr Lys Asp Met Ile Gly Thr Lys Gly Glu Phe Lys
        35                  40                  45

Asn Val Glu Tyr Lys Phe Ser Lys Asn Ile Lys Asp Leu Ala Ser Tyr
    50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
                100                 105                 110

Ala Gly Glu Asn Lys Gly Val Ile Ser Ala Lys Ile Thr Met Asp Lys
            115                 120                 125

Lys Ser Thr Ile Val Pro Leu Thr Tyr Thr Ile Lys Asp Asn Lys Phe
130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
                165                 170                 175

Trp Pro Leu Val Asp Ile Ser Phe Asn Ala Asp Leu Ala Glu
                180                 185                 190

<210> SEQ ID NO 46
<211> LENGTH: 190
<212> TYPE: PRT
<213> ORGANISM: Campylobacter jejuni

<400> SEQUENCE: 46

Met Lys Lys Ile Leu Val Ser Val Leu Ser Ser Cys Leu Leu Ala Ser
1               5                   10                  15

Ala Leu Ser Ala Val Ser Phe Lys Glu Asp Ser Leu Lys Val Ser Phe
            20                  25                  30

Glu Gly Tyr Lys Thr Lys Asp Met Ile Gly Thr Arg Gly Glu Phe Lys
        35                  40                  45

Asn Val Glu Tyr Lys Phe Ser Lys Asn Ile Lys Asp Leu Ala Ser Tyr
    50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
                100                 105                 110

Ala Gly Glu Asn Lys Gly Val Ile Ser Ala Lys Ile Thr Met Asp Lys
            115                 120                 125

Lys Ser Thr Ile Val Pro Leu Thr Tyr Thr Ile Lys Asp Asn Lys Phe
130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
                165                 170                 175

Trp Pro Leu Val Asp Ile Ser Phe Asn Ala Asp Leu Ala Glu
                180                 185                 190

<210> SEQ ID NO 47
<211> LENGTH: 190
<212> TYPE: PRT
<213> ORGANISM: Campylobacter jejuni

<400> SEQUENCE: 47

```
Met Lys Lys Ile Leu Val Ser Val Leu Ser Ser Cys Leu Leu Ala Ser
1               5                   10                  15

Ala Leu Ser Ala Val Ser Phe Lys Glu Asp Ser Leu Lys Val Ser Phe
            20                  25                  30

Glu Gly Tyr Lys Thr Lys Asp Met Ile Gly Thr Lys Gly Glu Phe Lys
        35                  40                  45

Asn Val Glu Tyr Lys Phe Ser Lys Asn Thr Lys Asp Leu Ala Ser Tyr
    50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Ile Thr Lys Val Phe Phe Pro
                85                  90                  95

Ala Leu Leu Gly Asp Thr Asp Ile Lys Val Val Phe Gln Asp Val Ile
            100                 105                 110

Ala Gly Glu Asn Lys Gly Val Ile Ser Ala Lys Ile Thr Met Asp Lys
        115                 120                 125

Lys Ser Thr Ile Val Pro Leu Thr Tyr Thr Ile Lys Asp Asn Lys Phe
    130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
                165                 170                 175

Trp Pro Leu Val Asp Ile Ser Phe Asn Ala Asp Leu Ala Glu
                180                 185                 190
```

<210> SEQ ID NO 48
<211> LENGTH: 190
<212> TYPE: PRT
<213> ORGANISM: Campylobacter jejuni

<400> SEQUENCE: 48

```
Met Lys Lys Ile Leu Val Ser Val Leu Ser Ser Cys Leu Leu Ala Ser
1               5                   10                  15

Ala Leu Ser Ala Val Ser Phe Lys Glu Asp Ser Leu Lys Val Ser Phe
            20                  25                  30

Glu Gly Tyr Lys Thr Lys Asp Met Ile Gly Thr Lys Gly Glu Phe Lys
        35                  40                  45

Asn Val Glu Tyr Lys Phe Ser Lys Asn Ile Lys Asp Leu Ala Ser Tyr
    50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
            100                 105                 110

Ala Gly Glu Asn Lys Gly Val Ile Ser Ala Lys Ile Thr Met Asp Lys
        115                 120                 125

Lys Ser Thr Ile Val Pro Leu Thr Tyr Thr Ile Lys Asp Asn Lys Phe
    130                 135                 140

Glu Ala Lys Gly Gln Leu Asp Leu His Thr Phe Lys Asn Gly Ser Lys
```

```
                    145                 150                 155                 160
Ala Leu Lys Ala Leu Ser Asp Val Ala Ala Gly His Gly Gly Ile Ser
                165                 170                 175

Trp Pro Leu Val Asp Ile Ser Phe Asn Ala Asn Leu Ala Glu
            180                 185                 190

<210> SEQ ID NO 49
<211> LENGTH: 190
<212> TYPE: PRT
<213> ORGANISM: Campylobacter jejuni

<400> SEQUENCE: 49

Met Lys Lys Ile Leu Val Ser Val Leu Ser Ser Cys Leu Leu Ala Ser
1               5                   10                  15

Ala Leu Ser Ala Val Ser Phe Lys Glu Asp Ser Leu Lys Val Ser Phe
            20                  25                  30

Glu Gly Tyr Lys Thr Lys Asp Met Ile Gly Thr Lys Gly Glu Phe Lys
        35                  40                  45

Asn Val Glu Tyr Lys Phe Ser Lys Asn Ile Lys Asp Leu Ala Ser Tyr
    50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
            100                 105                 110

Ala Gly Glu Asn Lys Gly Val Ile Ser Ala Lys Ile Thr Met Asp Lys
        115                 120                 125

Lys Ser Thr Ile Val Pro Leu Thr Tyr Thr Ile Lys Asp Asn Lys Phe
    130                 135                 140

Glu Ala Lys Gly Gln Phe Asp Leu His Thr Phe Lys Asn Gly Ser Lys
145                 150                 155                 160

Ala Leu Lys Ala Leu Ser Asp Val Ala Ala Gly His Gly Gly Ile Ser
                165                 170                 175

Trp Pro Leu Val Asp Ile Ser Phe Asn Ala Asp Leu Ala Glu
            180                 185                 190

<210> SEQ ID NO 50
<211> LENGTH: 190
<212> TYPE: PRT
<213> ORGANISM: Campylobacter jejuni

<400> SEQUENCE: 50

Met Lys Lys Ile Leu Ala Ser Val Leu Ser Ser Cys Leu Leu Ala Ser
1               5                   10                  15

Ala Leu Ser Ala Val Ser Phe Lys Glu Asp Ser Leu Lys Val Ser Phe
            20                  25                  30

Glu Gly Tyr Lys Thr Lys Asp Met Ile Gly Thr Lys Gly Glu Phe Lys
        35                  40                  45

Asn Val Glu Tyr Lys Phe Ser Lys Asn Ile Lys Asp Leu Ala Ser Tyr
    50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
```

```
                    100                 105                 110
Ala Gly Glu Asn Lys Gly Val Ile Ser Ala Lys Ile Thr Met Asp Lys
                115                 120                 125

Lys Ser Thr Ile Val Pro Leu Thr Tyr Thr Ile Lys Asp Asn Lys Phe
            130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
                165                 170                 175

Trp Pro Leu Val Asp Ile Ser Phe Asn Ala Asp Leu Ala Glu
            180                 185                 190

<210> SEQ ID NO 51
<211> LENGTH: 190
<212> TYPE: PRT
<213> ORGANISM: Campylobacter jejuni

<400> SEQUENCE: 51

Met Lys Lys Ile Leu Val Ser Val Leu Ser Ser Cys Leu Leu Ala Ser
1               5                   10                  15

Ala Leu Ser Ala Val Ser Phe Lys Glu Asp Ser Leu Lys Val Ser Phe
                20                  25                  30

Glu Gly Tyr Lys Thr Lys Asp Met Ile Gly Thr Lys Gly Glu Phe Lys
            35                  40                  45

Asn Val Glu Tyr Lys Phe Ser Lys Ser Ile Lys Asp Leu Ala Ser Tyr
        50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
                100                 105                 110

Ala Gly Glu Asn Lys Gly Val Ile Ser Ala Lys Ile Thr Met Asp Lys
                115                 120                 125

Lys Ser Thr Ile Val Pro Leu Thr Tyr Thr Ile Lys Asp Asn Lys Phe
            130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
                165                 170                 175

Trp Pro Leu Val Asp Ile Ser Phe Asn Ala Asp Leu Ala Glu
            180                 185                 190

<210> SEQ ID NO 52
<211> LENGTH: 190
<212> TYPE: PRT
<213> ORGANISM: Campylobacter jejuni

<400> SEQUENCE: 52

Met Lys Lys Val Leu Val Ser Val Leu Ser Ser Cys Leu Leu Ala Ser
1               5                   10                  15

Ala Leu Ser Ala Val Ser Phe Lys Glu Asp Ser Leu Lys Val Ser Phe
                20                  25                  30

Glu Gly Tyr Lys Thr Lys Asp Met Ile Gly Thr Lys Gly Glu Phe Lys
            35                  40                  45

Asn Val Glu Tyr Lys Phe Ser Lys Asn Ile Lys Asp Leu Ala Ser Tyr
```

```
                    50                  55                  60
Leu Lys Gly Ala Lys Ala Thr Ile Lys Pro Ser Asn Ala Phe Met Gly
 65                  70                  75                  80

Glu Gly Asn Asp Ile Ile Thr Asn Asn Ile Thr Lys Val Phe Phe Pro
                 85                  90                  95

Ala Leu Leu Gly Asp Thr Asp Ile Lys Val Val Phe Gln Asp Val Ile
                100                 105                 110

Ala Gly Glu Asn Lys Gly Val Ile Ser Ala Lys Ile Thr Met Asp Lys
            115                 120                 125

Lys Ser Thr Ile Val Pro Leu Thr Tyr Thr Ile Lys Asp Asn Lys Phe
130                 135                 140

Glu Ala Lys Gly Gln Phe Asp Leu His Thr Phe Lys Asn Gly Ser Lys
145                 150                 155                 160

Ala Leu Lys Ala Leu Ser Asp Val Ala Ala Gly His Gly Gly Ile Ser
                165                 170                 175

Trp Pro Leu Val Asp Ile Ser Phe Asn Ala Asp Leu Ala Glu
                180                 185                 190
```

<210> SEQ ID NO 53
<211> LENGTH: 190
<212> TYPE: PRT
<213> ORGANISM: Campylobacter jejuni

<400> SEQUENCE: 53

```
Met Lys Lys Ile Leu Ala Ser Val Leu Ser Ser Cys Leu Leu Ala Ser
  1               5                  10                  15

Ala Leu Ser Ala Val Ser Phe Lys Glu Asp Ser Leu Lys Val Ser Phe
                 20                  25                  30

Glu Gly Tyr Lys Thr Lys Asp Met Ile Gly Thr Lys Gly Glu Phe Lys
             35                  40                  45

Asn Val Glu Tyr Lys Phe Ser Lys Asn Ile Lys Asp Leu Ala Ser Tyr
 50                  55                  60

Leu Lys Gly Ala Lys Ala Thr Ile Glu Pro Ser Asn Ala Phe Met Gly
 65                  70                  75                  80

Glu Gly Asn Asp Ile Ile Thr Asn Asn Ile Thr Lys Val Phe Phe Pro
                 85                  90                  95

Ala Leu Leu Gly Asp Thr Asp Ile Lys Val Val Phe Gln Asp Val Ile
                100                 105                 110

Ala Gly Glu Asn Lys Gly Val Ile Ser Ala Lys Ile Thr Met Asp Lys
            115                 120                 125

Lys Ser Thr Ile Val Pro Leu Thr Tyr Thr Ile Lys Asp Asn Lys Phe
130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
                165                 170                 175

Trp Pro Leu Val Asp Ile Ser Phe Asn Ala Asp Leu Ala Glu
                180                 185                 190
```

<210> SEQ ID NO 54
<211> LENGTH: 190
<212> TYPE: PRT
<213> ORGANISM: Campylobacter jejuni

<400> SEQUENCE: 54

Met Lys Lys Ile Leu Ala Ser Val Leu Ser Ser Cys Leu Leu Ala Ser

```
1               5                   10                  15
Ala Leu Ser Ala Val Ser Phe Lys Glu Asp Ser Leu Lys Val Ser Phe
            20                  25                  30

Glu Gly Tyr Lys Thr Lys Asp Met Ile Gly Thr Lys Gly Glu Phe Lys
            35                  40                  45

Asn Val Glu Tyr Lys Phe Ser Lys Asn Ile Lys Asp Leu Ala Ser Tyr
    50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Ala Ile
            100                 105                 110

Ala Gly Glu Asn Lys Gly Val Ile Ser Ala Lys Ile Thr Met Asp Lys
            115                 120                 125

Lys Ser Thr Ile Val Pro Leu Thr Tyr Thr Ile Lys Asp Asn Lys Phe
    130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
                165                 170                 175

Trp Pro Leu Val Asp Ile Ser Phe Asn Ala Asp Leu Ala Glu
            180                 185                 190

<210> SEQ ID NO 55
<211> LENGTH: 190
<212> TYPE: PRT
<213> ORGANISM: Campylobacter jejuni

<400> SEQUENCE: 55

Met Lys Lys Ile Leu Val Ser Val Leu Ser Ser Cys Leu Leu Ala Ser
1               5                   10                  15

Ala Leu Ser Ala Val Ser Phe Lys Glu Asp Ser Leu Lys Val Ser Phe
            20                  25                  30

Glu Gly Tyr Lys Thr Lys Asp Met Ile Gly Thr Lys Gly Glu Phe Lys
            35                  40                  45

Asn Val Glu Tyr Asn Phe Ser Lys Asn Ile Lys Asp Leu Ala Ser Tyr
    50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
            100                 105                 110

Ala Gly Glu Asn Lys Gly Val Ile Ser Ala Lys Ile Thr Met Asp Lys
            115                 120                 125

Lys Ser Thr Ile Val Pro Leu Thr Tyr Thr Ile Lys Asp Asn Lys Phe
    130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
                165                 170                 175

Trp Pro Leu Val Asp Ile Ser Phe Asn Ala Asn Leu Ala Glu
            180                 185                 190
```

<210> SEQ ID NO 56
<211> LENGTH: 190
<212> TYPE: PRT
<213> ORGANISM: Campylobacter jejuni

<400> SEQUENCE: 56

Met Lys Lys Ile Leu Val Ser Val Leu Ser Ser Cys Leu Leu Ala Ser
1               5                   10                  15

Ala Leu Ser Ala Val Ser Phe Lys Glu Asp Ser Leu Lys Val Ser Phe
            20                  25                  30

Glu Gly Tyr Lys Thr Lys Asp Met Ile Gly Ile Lys Gly Glu Phe Lys
        35                  40                  45

Asn Val Glu Tyr Lys Phe Ser Lys Asn Thr Lys Asp Leu Ala Ser Tyr
    50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
            100                 105                 110

Ala Gly Glu Asn Lys Gly Val Ile Ser Ala Lys Ile Thr Met Asp Lys
        115                 120                 125

Lys Ser Thr Ile Val Pro Leu Thr Tyr Thr Ile Lys Asp Asn Lys Phe
    130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
                165                 170                 175

Trp Pro Leu Val Asp Ile Ser Phe Asn Ala Asp Leu Ala Glu
            180                 185                 190

<210> SEQ ID NO 57
<211> LENGTH: 190
<212> TYPE: PRT
<213> ORGANISM: Campylobacter jejuni

<400> SEQUENCE: 57

Met Lys Lys Ile Leu Val Ser Val Leu Ser Ser Cys Leu Leu Ala Ser
1               5                   10                  15

Ala Leu Ser Ala Val Ser Phe Lys Glu Asp Ser Leu Lys Val Ser Phe
            20                  25                  30

Glu Gly Tyr Lys Thr Lys Asp Met Ile Gly Val Lys Gly Glu Phe Lys
        35                  40                  45

Asn Val Glu Tyr Lys Phe Ser Lys Asn Ile Lys Asp Leu Ala Ser Tyr
    50                  55                  60

Leu Lys Gly Ala Lys Ala Ile Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Met Ile
            100                 105                 110

Ala Gly Glu Asn Lys Gly Val Ile Ser Ala Lys Ile Thr Met Asp Lys
        115                 120                 125

Lys Ser Thr Ile Val Pro Leu Thr Tyr Thr Ile Lys Asp Asn Lys Phe
    130                 135                 140

```
Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
                165                 170                 175

Trp Pro Leu Val Asp Ile Ser Phe Asn Ala Asp Leu Ala Glu
            180                 185                 190
```

<210> SEQ ID NO 58
<211> LENGTH: 190
<212> TYPE: PRT
<213> ORGANISM: Campylobacter jejuni

<400> SEQUENCE: 58

```
Met Lys Lys Ile Leu Val Ser Val Leu Ser Ser Cys Leu Leu Val Ser
1               5                   10                  15

Ala Leu Ser Ala Val Ser Phe Lys Glu Asp Ser Leu Lys Val Ser Phe
                20                  25                  30

Glu Gly Tyr Lys Thr Lys Asp Met Ile Gly Ala Lys Gly Glu Phe Lys
            35                  40                  45

Asn Val Glu Tyr Lys Phe Ser Lys Asn Thr Lys Asp Leu Ala Ser Tyr
    50                  55                  60

Leu Lys Gly Ala Lys Ala Thr Ile Lys Pro Ser Asn Ala Phe Met Ser
65                  70                  75                  80

Glu Gly Asn Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
            100                 105                 110

Ala Gly Glu Asn Lys Gly Val Ile Ser Ala Lys Ile Thr Met Asp Lys
        115                 120                 125

Lys Ser Thr Ile Val Pro Leu Thr Tyr Thr Ile Lys Asp Asn Lys Phe
130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
                165                 170                 175

Trp Pro Leu Val Asp Ile Ser Phe Asn Ala Asp Leu Ala Glu
            180                 185                 190
```

<210> SEQ ID NO 59
<211> LENGTH: 190
<212> TYPE: PRT
<213> ORGANISM: Campylobacter jejuni

<400> SEQUENCE: 59

```
Met Lys Lys Ile Leu Ala Ser Val Leu Ser Ser Cys Leu Leu Ala Ser
1               5                   10                  15

Ala Leu Ser Ala Val Ser Phe Lys Glu Asp Ser Leu Lys Val Ser Phe
                20                  25                  30

Glu Gly Tyr Lys Thr Lys Asp Met Ile Gly Thr Lys Gly Glu Phe Lys
            35                  40                  45

Asn Val Glu Tyr Lys Phe Ser Lys Asn Thr Lys Asp Leu Ala Ser Tyr
    50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
                85                  90                  95
```

```
Ala Leu Leu Gly Asp Thr Asp Ile Lys Val Val Phe Gln Asp Val Ile
            100                 105                 110

Val Gly Glu Asn Lys Gly Val Ile Ser Ala Lys Ile Thr Met Asp Lys
        115                 120                 125

Lys Ser Thr Ile Val Pro Leu Thr Tyr Thr Ile Lys Asp Asn Lys Phe
    130                 135                 140

Glu Ala Lys Gly Gln Phe Asp Leu His Ala Phe Lys Asn Gly Ser Lys
145                 150                 155                 160

Ala Leu Lys Ala Leu Ser Asp Val Ala Thr Gly His Gly Gly Ile Ser
                165                 170                 175

Trp Pro Leu Val Asp Ile Ser Phe Asn Ala Asp Leu Thr Glu
            180                 185                 190
```

<210> SEQ ID NO 60
<211> LENGTH: 190
<212> TYPE: PRT
<213> ORGANISM: Campylobacter jejuni

<400> SEQUENCE: 60

```
Met Lys Lys Ile Val Leu Ser Ile Leu Ser Ser Cys Leu Leu Ala Ser
1               5                   10                  15

Ala Leu Ser Ala Val Ser Phe Lys Glu Asp Ser Leu Lys Ile Ser Phe
                20                  25                  30

Glu Gly Tyr Lys Thr Lys Asp Met Val Gly Val Glu Gly Glu Phe Lys
            35                  40                  45

Asn Val Glu Tyr Lys Phe Ser Lys Asn Thr Lys Asp Phe Ala Ser Tyr
        50                  55                  60

Leu Lys Gly Ala Lys Ala Thr Ile Lys Pro Ser Asn Ala Phe Met Gly
65                  70                  75                  80

Glu Gly Asn Asp Val Ile Thr Asn Asn Ile Thr Lys Val Phe Phe Pro
                85                  90                  95

Ala Leu Leu Gly Asn Ala Asp Ile Lys Val Val Phe Gln Asp Val Ile
            100                 105                 110

Val Gly Glu Asn Lys Gly Val Ile Ser Ala Lys Ile Thr Met Asp Lys
        115                 120                 125

Lys Ser Thr Ile Val Pro Leu Thr Tyr Thr Ile Lys Asp Asn Lys Phe
    130                 135                 140

Glu Ala Lys Gly Gln Leu Asp Leu His Thr Phe Lys Asn Gly Ser Lys
145                 150                 155                 160

Ala Leu Lys Ala Leu Ser Asp Ala Ala Pro Gly His Gly Gly Ile Ser
                165                 170                 175

Trp Pro Leu Val Asp Ile Ser Phe Asn Ala Asp Leu Ala Glu
            180                 185                 190
```

<210> SEQ ID NO 61
<211> LENGTH: 190
<212> TYPE: PRT
<213> ORGANISM: Campylobacter jejuni

<400> SEQUENCE: 61

```
Met Lys Lys Ile Val Leu Ser Ile Leu Ser Ser Cys Leu Leu Ala Ser
1               5                   10                  15

Ala Leu Ser Ala Val Ser Phe Lys Glu Asp Ser Leu Lys Ile Ser Phe
                20                  25                  30

Glu Gly Tyr Lys Thr Lys Asp Met Val Gly Val Glu Gly Glu Phe Lys
            35                  40                  45
```

```
Asn Val Glu Tyr Lys Phe Ser Lys Asn Thr Lys Asp Phe Ala Ser Tyr
    50                  55                  60

Leu Lys Gly Ala Lys Ala Thr Ile Lys Pro Ser Asn Ala Phe Met Gly
65                  70                  75                  80

Glu Gly Asn Asp Val Ile Thr Asn Asn Ile Thr Lys Val Phe Phe Pro
                85                  90                  95

Ala Leu Leu Gly Asn Ala Asp Ile Lys Val Val Phe Gln Asp Val Ile
                100                 105                 110

Val Gly Glu Asn Lys Gly Val Ile Ser Ala Lys Ile Thr Met Asp Lys
                115                 120                 125

Lys Ser Thr Ile Ile Pro Leu Thr Tyr Thr Ile Lys Asp Asn Lys Phe
130                 135                 140

Glu Ala Lys Gly Gln Leu Asp Leu His Thr Phe Lys Asn Gly Ser Lys
145                 150                 155                 160

Ala Leu Lys Ala Leu Ser Asp Ala Ala Pro Gly His Gly Gly Ile Ser
                165                 170                 175

Trp Pro Leu Val Asp Ile Ser Phe Asn Ala Asp Leu Ala Glu
                180                 185                 190

<210> SEQ ID NO 62
<211> LENGTH: 190
<212> TYPE: PRT
<213> ORGANISM: Campylobacter jejuni

<400> SEQUENCE: 62

Met Lys Lys Phe Leu Val Ser Val Phe Ser Phe Cys Leu Leu Ala Ser
1               5                   10                  15

Ala Leu Ser Ala Val Ser Phe Lys Glu Asp Ser Leu Lys Ile Ser Phe
                20                  25                  30

Glu Gly Tyr Lys Thr Lys Asp Met Ile Gly Thr Lys Gly Glu Phe Lys
            35                  40                  45

Asn Val Glu Tyr Lys Phe Ser Lys Asn Thr Lys Asp Leu Ala Ser Tyr
    50                  55                  60

Leu Lys Gly Ala Lys Ala Thr Ile Lys Pro Ser Asp Ala Phe Met Gly
65                  70                  75                  80

Glu Gly Leu Asp Ile Ile Thr Asn Asn Ile Thr Lys Val Phe Phe Pro
                85                  90                  95

Ala Leu Leu Gly Asp Thr Asp Ile Lys Val Val Phe Gln Asp Val Ile
                100                 105                 110

Val Gly Glu Asn Lys Gly Val Ile Ser Ala Lys Ile Thr Met Asp Lys
                115                 120                 125

Lys Ser Thr Ile Val Pro Leu Thr Tyr Thr Ile Lys Asp Asp Lys Phe
130                 135                 140

Glu Ala Lys Gly Gln Leu Asp Leu His Thr Phe Lys Asn Ala Ser Lys
145                 150                 155                 160

Ala Leu Lys Ala Leu Ser Asp Val Ala Pro Gly His Gly Gly Ile Ser
                165                 170                 175

Trp Pro Leu Val Asp Ile Ser Phe Asn Ala Asp Leu Val Glu
                180                 185                 190

<210> SEQ ID NO 63
<211> LENGTH: 719
<212> TYPE: PRT
<213> ORGANISM: Campylobacter jejuni

<400> SEQUENCE: 63
```

```
Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
                20                  25                  30

Asp Asn Pro Lys Glu Ala Leu Ala Gln Ala Leu Lys Gln Asn Leu Gly
            35                  40                  45

Leu Ser Lys Asp Ala Ser Ser Glu Glu Ile Leu Ala Lys Phe Val Gln
        50                  55                  60

Asn Glu Thr Gly Thr Lys Leu Lys Glu Leu Val Asn Lys Leu Leu Asp
65                  70                  75                  80

Gln Ile Asn Ala Gln Lys Asn Pro Asp Ser Pro Val Leu Lys Gln Gly
                85                  90                  95

Lys Asn Leu Asn Leu Ala Pro Asn Phe Ala Asn Glu Leu Lys Ile Leu
            100                 105                 110

Ser Thr Glu Leu Ala Lys Ser Asp Thr Phe Thr Gln Val Leu Asp Arg
        115                 120                 125

Leu Asn Gln Ile Leu Lys Pro Ala Ser Glu Ile Lys Asn Asn Asn Leu
    130                 135                 140

Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
                165                 170                 175

Ser Thr Ile Lys Gly Leu Ser Ser Glu Lys Leu Ser Val Gln Ile Ala
            180                 185                 190

Gln Leu Ala Asn Thr Asn Leu Ser Pro Lys Asp Thr Leu Lys Glu Leu
        195                 200                 205

Lys Asn Ile Ile Asn Ser Ser Lys Asn Glu Asn Lys Gln Ile Leu Asn
    210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser His Ala Gln Glu Lys Ile
                245                 250                 255

Thr Pro Ile Ala Asn Lys Ile Leu Lys Glu Leu Asn Ser Ile Lys Asn
            260                 265                 270

Asp Phe Phe Lys Ala Leu Asn Lys Pro Glu Asn Leu Met Ile Lys Asp
        275                 280                 285

Pro Asn Ile Leu Lys Gln Thr Ala Thr Ala Phe Glu Lys Leu Glu Asn
    290                 295                 300

Thr Leu Lys Asn Ile Leu Gly Asn Gln Ala Ser Lys Ile Gln Asp Lys
305                 310                 315                 320

Glu Asn Ile Leu Glu Asn Leu Leu Ser Asn Lys Glu Asn Met Lys Glu
                325                 330                 335

Glu Lys Leu Asn His Asn Thr Lys Asn Gln Asp Glu Lys His Ile
            340                 345                 350

Lys Ala Ser Lys Glu Asp Glu Asn Leu Asp Ser Gly Ile Lys Thr His
        355                 360                 365

Glu Glu Asp Thr Gln Thr Lys Asn Asp Ile Gln Asn Asn Glu Thr
    370                 375                 380

Glu Asn Lys Pro Asp Asn Asp Ile Lys Asn Ser Thr Pro Asn Gln Glu
385                 390                 395                 400

Lys Ile Lys Asp Glu Lys Gln Glu Lys Ser Lys Glu Asn Ile Lys Glu
                405                 410                 415

Asn Pro Lys Phe Tyr Glu Thr Lys Thr Glu Asn Lys Thr Ser Ile Asn
```

```
                420            425             430
Thr Asn Thr Asn Thr Ser Asn Pro Asn Thr Asn Asn Thr Gln Asn Leu
            435             440             445
Asn Asn Thr Gln Asn Ile Gln Ser Asn Asn Gln Thr Met Gln Asn
450             455             460
Ile Phe Lys Asn Gln Glu Phe Ile Lys Gln Asn Ile Val Lys Asn Leu
465             470             475             480
Ala Phe Asn Val Glu Asn Leu Asp Leu Glu Gln Val Gln Asp Leu Ser
            485             490             495
Lys Asn Leu Ser Asn Leu Ser Arg Arg Leu Asn Glu Ser Leu Lys Glu
            500             505             510
Leu Glu Pro Tyr Thr Gln Asn Ala Lys Leu Asn Gln Ala Glu Leu Lys
            515             520             525
Asn Leu Glu His Lys Leu Asn Leu Ser Ile Lys Asp Leu Ala Gln Ile
            530             535             540
Lys Pro Lys Thr Glu Gln Asp Ile Ala Glu Ser Leu His His Asp Ala
545             550             555             560
Lys Ser Thr Leu Leu Gln Ile Ser Asn Leu Ala Lys Asn Glu Gly Asn
            565             570             575
Glu Ala Val Tyr Asn Gln Ala Asn Arg Leu Leu Ala Gln Ile Glu Ile
            580             585             590
Asn Gln Leu Met Ser Leu Ala Asn Asp Ser Ile Asn Thr Tyr Leu Pro
            595             600             605
Phe Ser Trp Asp Asp Leu Asn Asp Ser Lys Ile Met Phe Arg Arg Gly
            610             615             620
Lys Lys Asp Lys Phe Phe Ala Gln Ile Lys Leu Glu Phe Ala Lys Leu
625             630             635             640
Gly Asp Leu Glu Ile Leu Ile Ser Leu Asn Asn Glu Lys Tyr Ile Asp
            645             650             655
Ile Asn Ile Met Ala Glu Asn Ile Glu Phe Arg Lys Thr Ile Tyr Glu
            660             665             670
Asn Ala His Glu Leu Lys Arg Asn Ile Asn Lys Ala Gly Leu Leu Ser
            675             680             685
Ala Asn Phe Phe Val Gly Asp Ile Ile Arg Ser Lys Phe Asp Thr Arg
            690             695             700
Asn Met Lys Asn Leu Asp Leu Glu Met Gly Met Asp Lys Lys Val
705             710             715

<210> SEQ ID NO 64
<211> LENGTH: 703
<212> TYPE: PRT
<213> ORGANISM: Campylobacter jejuni

<400> SEQUENCE: 64

Met Ile Asn Thr Gln Leu Ala Ser Gln Ile Ala Asn Thr Gln Lys Asn
1               5               10              15
Asp Leu Lys Val Asp Asn Ser Thr Ser Lys Asp Lys Thr Asn Leu Lys
            20              25              30
Asp Asn Pro Lys Glu Ala Leu Ala Gln Ala Leu Lys Gln Asn Leu Gly
            35              40              45
Leu Ser Lys Asp Ala Ser Ser Glu Glu Ile Leu Ala Lys Phe Val Gln
            50              55              60
Asn Glu Thr Gly Thr Lys Leu Lys Glu Leu Val Asn Lys Leu Leu Asp
65              70              75              80
```

-continued

```
Gln Ile Asn Ala Gln Lys Asn Pro Asp Ser Pro Val Leu Lys Gln Gly
                 85                  90                  95
Lys Asn Leu Asn Leu Ala Pro Asn Phe Ala Asn Glu Leu Lys Thr Leu
            100                 105                 110
Ser Thr Glu Leu Ala Lys Ser Asp Thr Phe Thr Gln Val Leu Asp Arg
        115                 120                 125
Leu Asn Gln Ile Leu Lys Pro Ala Ser Glu Ile Lys Asn Asn Asn Leu
    130                 135                 140
Ala Pro Leu Phe Lys Asn Ser Gly Val Phe Leu Glu Ala Lys Leu Lys
145                 150                 155                 160
Asp Ala Leu Asn Glu Glu Leu Leu Pro Lys Ser Phe His Ser Leu Leu
                165                 170                 175
Ser Thr Ile Lys Gly Leu Ser Ser Glu Lys Leu Ser Val Gln Ile Ala
            180                 185                 190
Gln Leu Ala Asn Thr Asn Leu Asn Pro Lys Asn Thr Leu Lys Glu Leu
        195                 200                 205
Lys Asn Ile Ile Asn Ser Lys Asn Glu Asn Lys Gln Ile Leu Asn
    210                 215                 220
Gln Ser Ser Phe Lys Ala Leu Leu Asn Leu Ser Ser Lys Leu Glu Asn
225                 230                 235                 240
Phe Lys Asn Tyr Ile Ser Lys Asn Pro Ser His Ala Gln Glu Lys Ile
                245                 250                 255
Thr Pro Ile Ala Asn Lys Ile Leu Lys Glu Leu Asn Ser Ile Lys Asn
            260                 265                 270
Asp Phe Phe Lys Ala Leu Asn Lys Pro Glu Asn Leu Met Ile Lys Asp
        275                 280                 285
Pro Asn Ile Leu Lys Gln Thr Ala Thr Ala Phe Glu Lys Leu Glu Asn
    290                 295                 300
Thr Leu Lys Asn Ile Leu Gly Asn Gln Ala Ser Lys Ile Gln Asp Lys
305                 310                 315                 320
Glu Asn Ile Leu Glu Asn Leu Leu Ser Asn Lys Glu Asn Ile Lys Glu
                325                 330                 335
Glu Gln Leu Asn His Asn Thr Lys Asn Gln Asp Glu Glu Lys His Ile
            340                 345                 350
Lys Val Ser Lys Glu Glu Thr Leu Ala Asp Asp Ala Lys Thr Asp Ile
        355                 360                 365
Lys Gln Asp Val Lys Asn Glu Glu Asn Leu Pro Lys Lys Glu Val Asn
    370                 375                 380
Ala Asn Leu Asp Ser Ser Thr Lys Thr His Glu Glu Asn Ile Lys Glu
385                 390                 395                 400
Asn Pro Lys Phe Tyr Glu Thr Lys Thr Glu Asn Lys Thr Ser Ile Asn
                405                 410                 415
Thr Asn Thr Asn Thr Ser Asn Pro Asn Thr Asn Asn Thr Gln Asn Leu
            420                 425                 430
Asn Asn Thr Gln Asn Ile Gln Ser Asn Asn Gln Thr Met Gln Asn
    435                 440                 445
Ile Phe Lys Asn Gln Glu Phe Ile Lys Gln Asn Ile Val Lys Asn Leu
    450                 455                 460
Ala Phe Asn Val Glu Asn Leu Asp Leu Glu Gln Val Gln Asp Leu Ser
465                 470                 475                 480
Lys Asn Leu Ser Asn Leu Ser Arg Arg Leu Asn Glu Ser Leu Lys Glu
                485                 490                 495
Leu Glu Pro Tyr Thr Gln Asn Ala Lys Leu Asn Gln Ala Glu Leu Lys
```

```
            500                 505                 510
Asn Leu Glu His Lys Leu Asn Leu Ser Ile Lys Asp Leu Ala Gln Ile
            515                 520                 525

Lys Pro Lys Thr Glu Gln Asp Ile Ala Glu Ser Leu His His Asp Val
        530                 535                 540

Lys Ser Thr Leu Leu Gln Ile Ser Asn Leu Ala Lys Asn Glu Gly Asn
545                 550                 555                 560

Glu Ala Val Tyr Asn Gln Ala Asn Arg Leu Leu Ala Gln Ile Glu Ile
                565                 570                 575

Asn Gln Leu Met Ser Leu Ala Asn Asp Ser Ile Asn Thr Tyr Leu Pro
            580                 585                 590

Phe Ser Trp Asp Asp Leu Asn Asp Ser Lys Ile Met Phe Arg Arg Gly
        595                 600                 605

Lys Lys Asp Lys Phe Phe Ala Gln Ile Lys Leu Glu Phe Ala Lys Leu
    610                 615                 620

Gly Asp Leu Glu Ile Leu Ile Ser Leu Asn Asn Glu Lys Tyr Ile Asp
625                 630                 635                 640

Ile Asn Ile Met Ala Glu Asn Ile Glu Phe Arg Lys Thr Ile Tyr Glu
                645                 650                 655

Asn Ala His Glu Leu Lys Arg Asn Ile Asn Lys Ala Gly Leu Leu Ser
            660                 665                 670

Ala Asn Phe Phe Val Gly Asp Ile Ile Arg Ser Lys Phe Asp Thr Arg
        675                 680                 685

Asn Met Lys Asn Leu Asp Leu Glu Met Gly Met Asp Lys Lys Val
    690                 695                 700

<210> SEQ ID NO 65
<211> LENGTH: 720
<212> TYPE: PRT
<213> ORGANISM: Campylobacter jejuni

<400> SEQUENCE: 65

Met Met Ile Asn Thr Gln Leu Ala Ser Gln Ile Ala Asn Thr Gln Lys
1               5                   10                  15

Asn Asp Leu Lys Val Asp Asn Ser Ala Ser Lys Asp Lys Thr Asn Leu
            20                  25                  30

Lys Asp Asn Pro Lys Glu Ala Leu Ala Gln Ala Leu Lys Gln Asn Leu
        35                  40                  45

Gly Leu Ser Lys Asp Ala Ser Ser Glu Glu Ile Leu Ala Lys Phe Val
    50                  55                  60

Gln Asn Glu Thr Gly Thr Lys Leu Lys Glu Leu Val Asn Lys Leu Leu
65                  70                  75                  80

Asp Gln Ile Asn Ala Gln Lys Asn Pro Asp Ser Pro Val Leu Lys Gln
                85                  90                  95

Gly Lys Asn Leu Asn Leu Ala Pro Asn Phe Ala Asn Glu Leu Lys Ile
            100                 105                 110

Leu Ser Thr Glu Leu Ala Lys Ser Asp Thr Phe Thr Gln Val Leu Asp
        115                 120                 125

Arg Leu Asn Gln Ile Leu Lys Pro Ala Ser Glu Ile Lys Asn Asn Asn
    130                 135                 140

Leu Ala Pro Leu Phe Lys Asn Ser Gly Val Phe Leu Glu Ala Lys Leu
145                 150                 155                 160

Lys Asp Ala Leu Asn Glu Glu Leu Leu Pro Lys Ser Phe His Ser Leu
                165                 170                 175
```

```
Leu Ser Thr Ile Lys Gly Leu Ser Ser Glu Lys Leu Ser Val Gln Ile
                180                 185                 190

Ala Gln Leu Ala Asn Thr Asn Leu Ser Pro Lys Asp Thr Leu Lys Glu
        195                 200                 205

Leu Lys Asn Ile Ile Asn Ser Ser Lys Asn Glu Asn Lys Gln Ile Leu
    210                 215                 220

Asn Gln Ser Ser Phe Lys Ala Leu Leu Asn Leu Ser Ser Lys Leu Glu
225                 230                 235                 240

Asn Phe Lys Asn Tyr Ile Ser Lys Asn Pro Ser His Ala Gln Glu Lys
                245                 250                 255

Ile Thr Pro Ile Ala Asn Lys Ile Leu Lys Glu Leu Asn Ser Ile Lys
                260                 265                 270

Asn Asp Phe Phe Lys Ala Leu Asn Lys Pro Glu Asn Leu Met Ile Lys
            275                 280                 285

Asp Pro Asn Ile Leu Lys Gln Thr Ala Thr Ala Phe Glu Lys Leu Glu
        290                 295                 300

Asn Thr Leu Lys Asn Ile Leu Gly Asn Gln Ala Ser Lys Ile Gln Asp
305                 310                 315                 320

Lys Glu Asn Ile Leu Glu Asn Leu Leu Ser Asn Lys Glu Asn Ile Lys
                325                 330                 335

Glu Glu Lys Leu Asn His Asn Thr Lys Asn Gln Asp Glu Glu Lys His
                340                 345                 350

Ile Lys Ala Ser Lys Glu Asp Glu Asn Leu Asp Ser Gly Ile Lys Thr
            355                 360                 365

His Glu Glu Asp Thr Gln Asp Thr Lys Asn Asp Ile Gln Asn Asn Glu
    370                 375                 380

Thr Glu Asn Lys Pro Asp Asn Asp Ile Lys Asn Ser Thr Pro Asn Gln
385                 390                 395                 400

Glu Lys Ile Lys Asp Glu Lys Gln Glu Lys Ser Lys Glu Asn Ile Lys
                405                 410                 415

Glu Asn Pro Lys Phe Tyr Glu Thr Lys Thr Glu Asn Lys Thr Ser Ile
                420                 425                 430

Asn Thr Asn Thr Asn Thr Ser Asn Pro Asn Thr Asn Thr Gln Asn
            435                 440                 445

Leu Asn Asn Thr Gln Asn Ile Gln Ser Asn Asn Gln Thr Met Gln
    450                 455                 460

Asn Ile Phe Lys Asn Gln Glu Phe Ile Lys Gln Asn Ile Val Lys Asn
465                 470                 475                 480

Leu Ala Phe Asn Val Glu Asn Leu Asp Leu Glu Gln Val Gln Asp Leu
                485                 490                 495

Ser Lys Lys Leu Ser Asn Leu Ser Arg Arg Leu Asn Glu Ser Leu Lys
            500                 505                 510

Glu Leu Glu Pro Tyr Thr Gln Asn Ala Lys Leu Asn Gln Ala Glu Leu
        515                 520                 525

Lys Asn Leu Glu His Lys Leu Asn Leu Ser Ile Lys Asp Leu Ala Gln
530                 535                 540

Ile Lys Pro Lys Thr Glu Gln Asp Ile Ala Glu Ser Leu His His Asp
545                 550                 555                 560

Val Lys Ser Thr Leu Leu Gln Ile Ser Asn Leu Ala Lys Asn Glu Gly
                565                 570                 575

Asn Glu Ala Val Tyr Asn Gln Ala Asn Arg Leu Leu Ala Gln Ile Glu
            580                 585                 590

Ile Asn Gln Leu Met Ser Leu Ala Asn Asp Ser Ile Asn Thr Tyr Leu
```

```
                595                 600                 605
Pro Phe Ser Trp Asp Asp Leu Asn Asp Ser Lys Ile Met Phe Arg Arg
610                 615                 620

Gly Lys Lys Asp Lys Phe Phe Ala Gln Ile Lys Leu Glu Phe Ala Lys
625                 630                 635                 640

Leu Gly Asp Leu Glu Ile Leu Ile Ser Leu Asn Asn Glu Lys Tyr Ile
                645                 650                 655

Asp Ile Asn Ile Met Ala Glu Asn Ile Glu Phe Arg Lys Thr Ile Tyr
                660                 665                 670

Glu Asn Ala His Glu Leu Lys Arg Asn Ile Asn Lys Ala Gly Leu Leu
                675                 680                 685

Ser Ala Asn Phe Phe Val Gly Asp Ile Ile Arg Ser Lys Phe Asp Thr
690                 695                 700

Arg Asn Met Lys Asn Leu Asp Leu Glu Met Gly Met Asp Lys Lys Val
705                 710                 715                 720

<210> SEQ ID NO 66
<211> LENGTH: 703
<212> TYPE: PRT
<213> ORGANISM: Campylobacter jejuni

<400> SEQUENCE: 66

Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
                20                  25                  30

Asp Asn Pro Lys Glu Ala Leu Ala Gln Ala Leu Lys Gln Asn Leu Gly
            35                  40                  45

Leu Ser Lys Asp Ala Ser Ser Glu Glu Ile Leu Ala Lys Phe Val Gln
50                  55                  60

Asn Glu Thr Gly Thr Lys Leu Lys Glu Leu Val Asn Lys Leu Leu Asp
65                  70                  75                  80

Gln Ile Asn Ala Gln Lys Asn Pro Asp Ser Pro Val Leu Lys Gln Gly
                85                  90                  95

Lys Asn Leu Asn Leu Ala Pro Asn Phe Ala Asn Glu Leu Lys Thr Leu
            100                 105                 110

Ser Thr Glu Leu Ala Lys Ser Asp Thr Phe Thr Gln Val Leu Asp Arg
        115                 120                 125

Leu Asn Gln Ile Leu Lys Pro Ala Ser Glu Ile Lys Asn Asn Asn Leu
130                 135                 140

Ala Pro Leu Phe Lys Asn Ser Gly Val Phe Leu Glu Ala Lys Leu Lys
145                 150                 155                 160

Asp Ala Leu Asn Glu Glu Leu Pro Lys Ser Phe His Ser Leu Leu
                165                 170                 175

Ser Thr Ile Lys Gly Leu Ser Ser Glu Lys Leu Ser Val Gln Ile Ala
            180                 185                 190

Gln Leu Ala Asn Thr Asn Leu Asn Pro Lys Asn Thr Leu Lys Glu Leu
        195                 200                 205

Lys Asn Ile Ile Asn Ser Ser Lys Asn Glu Asn Lys Gln Ile Leu Asn
210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser His Ala Gln Glu Lys Ile
                245                 250                 255
```

```
Thr Pro Ile Ala Asn Lys Ile Leu Lys Glu Leu Asn Ser Ile Lys Asn
            260                 265                 270

Asp Phe Phe Lys Ala Leu Asn Lys Pro Glu Asn Leu Met Ile Lys Asp
            275                 280                 285

Pro Asn Ile Leu Lys Gln Thr Ala Thr Ala Phe Glu Lys Leu Glu Asn
            290                 295                 300

Thr Leu Lys Asn Ile Leu Gly Asn Gln Ala Ser Lys Ile Gln Asp Lys
305                 310                 315                 320

Glu Asn Ile Leu Glu Asn Leu Leu Ser Asn Lys Glu Asn Ile Lys Glu
                325                 330                 335

Glu Gln Leu Asn His Asn Thr Lys Asn Gln Asp Glu Glu Lys His Ile
            340                 345                 350

Lys Val Ser Lys Glu Glu Thr Leu Ala Asp Asp Ala Lys Thr Asp Ile
            355                 360                 365

Lys Gln Asp Val Lys Asn Glu Glu Asn Leu Pro Lys Lys Glu Val Asn
            370                 375                 380

Ala Asn Leu Asp Ser Ser Thr Lys Thr His Glu Glu Asn Ile Lys Glu
385                 390                 395                 400

Asn Pro Lys Phe Tyr Glu Thr Lys Thr Glu Asn Lys Thr Ser Ile Asn
                405                 410                 415

Thr Asn Thr Asn Thr Ser Asn Pro Asn Thr Asn Asn Thr Gln Asn Leu
            420                 425                 430

Asn Asn Thr Gln Asn Ile Gln Ser Asn Asn Gln Thr Met Gln Asn
            435                 440                 445

Ile Phe Lys Asn Gln Glu Phe Ile Lys Gln Asn Ile Val Lys Asn Leu
450                 455                 460

Ala Phe Asn Val Glu Asn Leu Asp Leu Glu Gln Val Gln Asp Leu Ser
465                 470                 475                 480

Lys Asn Leu Ser Asn Leu Ser Arg Arg Leu Asn Glu Ser Leu Lys Glu
                485                 490                 495

Leu Glu Pro Tyr Thr Gln Asn Ala Lys Leu Asn Gln Ala Glu Leu Lys
            500                 505                 510

Asn Leu Glu His Lys Leu Asn Leu Ser Ile Lys Asp Leu Ala Gln Ile
            515                 520                 525

Lys Pro Lys Thr Glu Gln Asp Ile Ala Glu Ser Leu His His Asp Val
            530                 535                 540

Lys Ser Thr Leu Leu Gln Ile Ser Asn Leu Ala Lys Asn Glu Gly Asn
545                 550                 555                 560

Glu Ala Val Tyr Asn Gln Ala Asn Arg Leu Leu Ala Gln Ile Glu Ile
                565                 570                 575

Asn Gln Leu Met Ser Leu Ala Asn Asp Ser Ile Asn Thr Tyr Leu Pro
            580                 585                 590

Phe Ser Trp Asp Asp Leu Asn Asp Ser Lys Ile Met Phe Arg Arg Gly
            595                 600                 605

Lys Lys Asp Lys Phe Phe Ala Gln Ile Lys Leu Glu Phe Ala Lys Leu
            610                 615                 620

Gly Asp Leu Glu Ile Leu Ile Ser Leu Asn Asn Glu Lys Tyr Ile Asp
625                 630                 635                 640

Ile Asn Ile Met Ala Glu Asn Ile Glu Phe Arg Lys Thr Ile Tyr Glu
                645                 650                 655

Asn Ala His Glu Leu Lys Arg Asn Ile Asn Lys Ala Gly Leu Leu Ser
            660                 665                 670

Ala Asn Phe Phe Val Gly Asp Ile Ile Arg Ser Lys Phe Asp Thr Arg
```

675                 680                 685
Asn Met Lys Asn Leu Asp Leu Glu Met Gly Met Asp Lys Lys Val
    690                 695                 700

<210> SEQ ID NO 67
<211> LENGTH: 703
<212> TYPE: PRT
<213> ORGANISM: Campylobacter jejuni

<400> SEQUENCE: 67

Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
            20                  25                  30

Asp Asn Pro Lys Glu Ala Leu Ala Gln Ala Leu Lys Gln Asn Leu Gly
        35                  40                  45

Leu Ser Lys Asp Ala Ser Ser Glu Ile Leu Ala Lys Phe Val Gln
    50                  55                  60

Asn Glu Thr Gly Thr Lys Leu Lys Glu Leu Val Asn Lys Leu Leu Asp
65              70                  75                  80

Gln Ile Asn Ala Gln Lys Asn Pro Asp Ser Pro Val Leu Lys Gln Gly
            85                  90                  95

Lys Asn Leu Asn Leu Ala Pro Asn Phe Ala Asn Glu Leu Lys Ile Leu
        100                 105                 110

Ser Thr Glu Leu Ala Lys Ser Asp Thr Phe Thr Gln Val Leu Asp Arg
    115                 120                 125

Leu Asn Gln Ile Leu Lys Pro Ala Ser Glu Ile Lys Asn Asn Asn Leu
130                 135                 140

Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
            165                 170                 175

Ser Thr Ile Lys Gly Leu Ser Ser Glu Lys Leu Ser Val Gln Ile Ala
        180                 185                 190

Gln Leu Ala Asn Thr Asn Leu Ser Pro Lys Asp Thr Leu Lys Glu Leu
    195                 200                 205

Lys Asn Ile Ile Asn Ser Ser Lys Asn Glu Asn Lys Gln Ile Leu Asn
210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser His Ala Gln Glu Lys Ile
            245                 250                 255

Thr Pro Ile Ala Asn Lys Ile Leu Lys Glu Leu Asn Ser Ile Lys Asn
        260                 265                 270

Asp Phe Phe Lys Ala Leu Asn Lys Pro Glu Asn Leu Met Ile Lys Asp
    275                 280                 285

Pro Asn Ile Leu Lys Gln Thr Ala Thr Ala Phe Glu Lys Leu Glu Asn
290                 295                 300

Thr Leu Lys Asn Ile Leu Gly Asn Gln Ala Ser Lys Ile Gln Asp Lys
305                 310                 315                 320

Glu Asn Ile Leu Glu Asn Leu Leu Ser Asn Lys Glu Asn Ile Lys Glu
            325                 330                 335

Glu Lys Leu Asn His Asn Thr Lys Asn Gln Asp Glu Glu Lys Tyr Ile
        340                 345                 350

-continued

```
Lys Val Ser Lys Glu Glu Thr Leu Ala Asp Asp Ala Lys Thr Asp Ile
            355                 360                 365

Lys Gln Asp Val Lys Asn Glu Glu Asn Leu Pro Lys Lys Glu Val Asn
        370                 375                 380

Ala Asn Leu Asp Ser Ser Thr Lys Thr His Glu Glu Asn Ile Lys Glu
385                 390                 395                 400

Asn Pro Lys Phe Tyr Glu Thr Lys Thr Glu Asn Lys Thr Ser Ile Asn
                405                 410                 415

Thr Asn Thr Asn Thr Ser Asn Pro Asn Thr Asn Thr Gln Asn Leu
            420                 425                 430

Asn Asn Thr Gln Asn Ile Gln Ser Asn Asn Gln Thr Met Gln Asn
        435                 440                 445

Ile Phe Lys Asn Gln Glu Phe Ile Lys Gln Asn Ile Val Lys Asn Leu
    450                 455                 460

Ala Phe Asn Val Glu Asn Leu Asp Leu Glu Gln Val Gln Asp Leu Ser
465                 470                 475                 480

Lys Asn Leu Ser Asn Leu Ser Arg Arg Leu Asn Glu Ser Leu Lys Glu
                485                 490                 495

Leu Glu Pro Tyr Thr Gln Asn Ala Lys Leu Asn Gln Ala Glu Leu Lys
            500                 505                 510

Asn Leu Glu His Lys Leu Asn Leu Ser Ile Lys Asp Leu Ala Gln Ile
        515                 520                 525

Lys Pro Lys Thr Glu Gln Asp Ile Ala Glu Ser Leu His His Asp Val
530                 535                 540

Lys Ser Thr Leu Leu Gln Ile Ser Asn Leu Ala Lys Asn Glu Gly Asn
545                 550                 555                 560

Glu Ala Val Tyr Asn Gln Ala Asn Arg Leu Leu Ala Gln Ile Glu Ile
                565                 570                 575

Asn Gln Leu Met Ser Leu Ala Asn Asp Ser Ile Asn Thr Tyr Leu Pro
            580                 585                 590

Phe Ser Trp Asp Asp Leu Asn Asp Ser Lys Ile Met Phe Arg Arg Gly
        595                 600                 605

Lys Lys Asp Lys Phe Phe Ala Gln Ile Lys Leu Glu Phe Ala Lys Leu
610                 615                 620

Gly Asp Leu Glu Ile Leu Ile Ser Leu Asn Asn Glu Lys Tyr Ile Asp
625                 630                 635                 640

Ile Asn Ile Met Ala Glu Asn Ile Glu Phe Arg Lys Thr Ile Tyr Glu
                645                 650                 655

Asn Ala His Glu Leu Lys Arg Asn Ile Asn Lys Ala Gly Leu Leu Ser
            660                 665                 670

Ala Asn Phe Phe Val Gly Asp Ile Ile Arg Ser Lys Phe Asp Thr Arg
        675                 680                 685

Asn Met Lys Asn Leu Asp Leu Glu Met Gly Met Asp Lys Lys Val
690                 695                 700

<210> SEQ ID NO 68
<211> LENGTH: 719
<212> TYPE: PRT
<213> ORGANISM: Campylobacter jejuni

<400> SEQUENCE: 68

Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
            20                  25                  30
```

```
Asp Asn Pro Lys Glu Ala Leu Ala Gln Ala Leu Lys Gln Asn Leu Gly
        35                  40                  45

Leu Ser Lys Asp Ala Ser Ser Glu Glu Ile Leu Ala Lys Phe Val Gln
50                  55                  60

Asn Glu Thr Gly Thr Lys Leu Lys Glu Leu Val Asn Lys Leu Leu Asp
65                  70                  75                  80

Gln Ile Asn Ala Gln Lys Asn Pro Asp Ser Pro Val Leu Lys Gln Gly
                85                  90                  95

Lys Asn Leu Asn Leu Ala Pro Asn Phe Ala Asn Glu Leu Lys Ile Leu
                100                 105                 110

Ser Thr Glu Leu Ala Lys Ser Asp Thr Phe Thr Gln Val Leu Asp Arg
                115                 120                 125

Leu Asn Gln Ile Leu Lys Pro Ala Ser Glu Ile Lys Asn Asn Asn Leu
130                 135                 140

Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
                165                 170                 175

Ser Thr Ile Lys Gly Leu Ser Ser Glu Lys Leu Ser Val Gln Ile Ala
                180                 185                 190

Gln Leu Ala Asn Thr Asn Leu Ser Pro Lys Asp Thr Leu Lys Glu Leu
                195                 200                 205

Lys Asn Ile Ile Asn Ser Ser Lys Asn Glu Asn Lys Gln Ile Leu Asn
                210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser His Ala Gln Glu Lys Ile
                245                 250                 255

Thr Pro Ile Ala Asn Lys Ile Leu Lys Glu Leu Asn Ser Ile Lys Asn
                260                 265                 270

Asp Phe Phe Lys Ala Leu Asn Lys Pro Glu Asn Leu Met Ile Lys Asp
                275                 280                 285

Pro Asn Ile Leu Lys Gln Thr Ala Thr Ala Phe Glu Lys Leu Glu Asn
                290                 295                 300

Thr Leu Lys Asn Ile Leu Gly Asn Gln Ala Ser Lys Ile Gln Asp Lys
305                 310                 315                 320

Glu Asn Ile Leu Glu Asn Leu Leu Ser Asn Lys Glu Asn Ile Lys Glu
                325                 330                 335

Glu Lys Leu Asn His Asn Thr Lys Asn Gln Asp Glu Glu Lys His Ile
                340                 345                 350

Lys Ala Ser Lys Glu Asp Glu Asn Leu Asn Ser Gly Ile Lys Thr His
                355                 360                 365

Glu Glu Asp Thr Gln Asp Thr Lys Asn Asp Ile Gln Asn Asn Glu Thr
370                 375                 380

Glu Asn Lys Pro Asp Asn Asp Ile Lys Asn Ser Thr Pro Asn Gln Glu
385                 390                 395                 400

Lys Ile Lys Asp Glu Lys Gln Glu Lys Ser Lys Glu Asn Ile Lys Glu
                405                 410                 415

Asn Pro Lys Phe Tyr Glu Thr Lys Thr Glu Asn Lys Thr Ser Ile Asn
                420                 425                 430

Thr Asn Thr Asn Thr Ser Asn Pro Asn Thr Asn Thr Gln Asn Leu
                435                 440                 445
```

```
Asn Asn Thr Gln Asn Ile Gln Ser Asn Asn Asn Gln Thr Met Gln Asn
        450                 455                 460
Ile Phe Lys Asn Gln Glu Phe Ile Lys Gln Asn Ile Val Lys Asn Leu
465                 470                 475                 480
Ala Phe Asn Val Glu Asn Leu Asp Leu Glu Gln Val Gln Asp Leu Ser
                485                 490                 495
Lys Asn Leu Ser Asn Leu Ser Arg Arg Leu Asn Glu Ser Leu Lys Glu
            500                 505                 510
Leu Glu Pro Tyr Thr Gln Asn Ala Lys Leu Asn Gln Ala Glu Leu Lys
                515                 520                 525
Asn Leu Glu His Lys Leu Asn Leu Ser Ile Lys Asp Leu Ala Gln Ile
530                 535                 540
Lys Pro Lys Thr Glu Gln Asp Ile Ala Glu Ser Leu His His Asp Val
545                 550                 555                 560
Lys Ser Thr Leu Leu Gln Ile Ser Asn Leu Ala Lys Asn Glu Gly Asn
                565                 570                 575
Glu Ala Val Tyr Asn Gln Ala Asn Arg Leu Leu Ala Gln Ile Glu Ile
                580                 585                 590
Asn Gln Leu Met Ser Leu Ala Asn Asp Ser Ile Asn Thr Tyr Leu Pro
                595                 600                 605
Phe Ser Trp Asp Asp Leu Asn Asp Ser Lys Ile Met Phe Arg Arg Gly
610                 615                 620
Lys Lys Asp Lys Phe Phe Ala Gln Ile Lys Leu Glu Phe Ala Lys Leu
625                 630                 635                 640
Gly Asp Leu Glu Ile Leu Ile Ser Leu Asn Asn Glu Lys Tyr Ile Asp
                645                 650                 655
Ile Asn Ile Met Ala Glu Asn Ile Glu Phe Arg Lys Thr Ile Tyr Glu
                660                 665                 670
Asn Ala His Glu Leu Lys Arg Asn Ile Asn Lys Ala Gly Leu Leu Ser
                675                 680                 685
Ala Asn Phe Phe Val Gly Asp Ile Ile Arg Ser Lys Phe Asp Thr Arg
            690                 695                 700
Asn Met Lys Asn Leu Asp Leu Glu Met Gly Met Asp Lys Lys Val
705                 710                 715

<210> SEQ ID NO 69
<211> LENGTH: 719
<212> TYPE: PRT
<213> ORGANISM: Campylobacter jejuni

<400> SEQUENCE: 69

Met Ile Asn Thr Gln Leu Ala Ser Gln Ile Ala Asn Thr Gln Lys Asn
1               5                   10                  15
Asp Leu Lys Val Asp Asn Ser Ala Ser Lys Asp Lys Thr Asn Leu Lys
                20                  25                  30
Asp Asn Pro Lys Glu Ala Leu Ala Gln Ala Leu Lys Gln Asn Leu Gly
            35                  40                  45
Leu Ser Lys Asp Ala Ser Ser Glu Glu Ile Leu Ala Lys Phe Val Gln
        50                  55                  60
Asn Glu Thr Gly Thr Lys Leu Lys Glu Leu Val Asn Lys Leu Leu Asp
65                  70                  75                  80
Gln Ile Asn Ala Gln Lys Asn Pro Asp Ser Pro Val Leu Lys Gln Gly
                85                  90                  95
Lys Asn Leu Asn Leu Ala Pro Asn Phe Ala Asn Glu Leu Lys Ile Leu
            100                 105                 110
```

-continued

```
Ser Thr Glu Leu Ala Lys Ser Asp Thr Phe Thr Gln Val Leu Asp Arg
        115                 120                 125
Leu Asn Gln Ile Leu Lys Pro Ala Ser Glu Ile Lys Asn Asn Asn Leu
    130                 135                 140
Ala Pro Leu Phe Lys Asn Ser Gly Val Phe Leu Glu Ala Lys Leu Lys
145                 150                 155                 160
Asp Ala Leu Asn Glu Glu Leu Leu Pro Lys Ser Phe His Ser Leu Leu
                165                 170                 175
Ser Thr Ile Lys Gly Leu Ser Ser Glu Lys Leu Ser Val Gln Ile Ala
                180                 185                 190
Gln Leu Ala Asn Thr Asn Leu Ser Pro Lys Asp Thr Leu Lys Glu Leu
            195                 200                 205
Lys Asn Ile Ile Asn Ser Ser Lys Asn Glu Asn Lys Gln Ile Leu Asn
210                 215                 220
Gln Ser Ser Phe Lys Ala Leu Leu Asn Leu Ser Ser Lys Leu Glu Asn
225                 230                 235                 240
Phe Lys Asn Tyr Ile Ser Lys Asn Pro Ser His Ala Gln Glu Lys Ile
                245                 250                 255
Thr Pro Ile Ala Asn Lys Ile Leu Lys Glu Leu Asn Ser Ile Lys Asn
            260                 265                 270
Asp Phe Phe Lys Ala Leu Asn Lys Pro Glu Asn Leu Met Ile Lys Asp
    275                 280                 285
Pro Asn Ile Leu Lys Gln Thr Ala Thr Ala Phe Glu Lys Leu Glu Asn
290                 295                 300
Thr Leu Lys Asn Ile Leu Gly Asn Gln Ala Ser Lys Ile Gln Asp Lys
305                 310                 315                 320
Glu Asn Ile Leu Glu Asn Leu Leu Ser Asn Lys Glu Asn Ile Lys Glu
                325                 330                 335
Glu Lys Leu Asn His Asn Thr Lys Asn Gln Asp Glu Lys His Ile
            340                 345                 350
Lys Ala Ser Lys Glu Asp Glu Asn Leu Asp Ser Gly Ile Lys Thr His
    355                 360                 365
Glu Glu Asp Thr Gln Asp Thr Lys Asn Asp Ile Gln Asn Asn Glu Thr
    370                 375                 380
Glu Asn Lys Pro Asp Asn Asp Ile Lys Asn Ser Thr Pro Asn Gln Glu
385                 390                 395                 400
Lys Ile Lys Asp Glu Lys Gln Glu Lys Ser Lys Glu Asn Ile Lys Glu
                405                 410                 415
Asn Pro Lys Phe Tyr Glu Thr Lys Thr Glu Asn Lys Thr Ser Ile Asn
            420                 425                 430
Thr Asn Thr Asn Thr Ser Asn Pro Asn Thr Asn Thr Gln Asn Leu
    435                 440                 445
Asn Asn Thr Gln Asn Ile Gln Ser Asn Asn Gln Thr Met Gln Asn
450                 455                 460
Ile Phe Lys Asn Gln Glu Phe Ile Lys Gln Asn Ile Val Lys Asn Leu
465                 470                 475                 480
Ala Phe Asn Val Glu Asn Leu Asp Leu Glu Gln Val Gln Asp Leu Ser
                485                 490                 495
Lys Asn Leu Ser Asn Leu Ser Arg Arg Leu Asn Glu Ser Leu Lys Glu
            500                 505                 510
Leu Glu Pro Tyr Thr Gln Asn Ala Lys Leu Asn Gln Ala Glu Leu Lys
        515                 520                 525
```

```
Asn Leu Glu His Lys Leu Asn Leu Ser Ile Lys Asp Leu Ala Gln Ile
    530                 535                 540

Lys Pro Lys Thr Glu Gln Asp Ile Ala Glu Ser Leu His His Asp Val
545                 550                 555                 560

Lys Ser Thr Leu Leu Gln Ile Ser Asn Leu Ala Lys Asn Glu Gly Asn
                565                 570                 575

Glu Ala Val Tyr Asn Gln Ala Asn Arg Leu Leu Ala Gln Ile Glu Ile
            580                 585                 590

Asn Gln Leu Met Ser Leu Ala Asn Asp Ser Ile Asn Thr Tyr Leu Pro
        595                 600                 605

Phe Ser Trp Asp Asp Leu Asn Asp Ser Lys Ile Met Phe Arg Arg Gly
610                 615                 620

Lys Lys Asp Lys Phe Phe Ala Gln Ile Lys Leu Glu Phe Ala Lys Leu
625                 630                 635                 640

Gly Asp Leu Glu Ile Leu Ile Ser Leu Asn Asn Glu Lys Tyr Ile Asp
                645                 650                 655

Ile Asn Ile Met Ala Glu Asn Ile Glu Phe Arg Lys Thr Ile Tyr Glu
            660                 665                 670

Asn Ala His Glu Leu Lys Arg Asn Ile Asn Lys Ala Gly Leu Leu Ser
        675                 680                 685

Ala Asn Phe Phe Val Gly Asp Ile Ile Arg Ser Lys Phe Asp Thr Arg
690                 695                 700

Asn Met Lys Asn Leu Asp Leu Glu Met Gly Met Asp Lys Lys Val
705                 710                 715

<210> SEQ ID NO 70
<211> LENGTH: 719
<212> TYPE: PRT
<213> ORGANISM: Campylobacter jejuni

<400> SEQUENCE: 70

Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
            20                  25                  30

Asp Asn Pro Lys Glu Ala Leu Ala Gln Ala Leu Lys Gln Asn Leu Gly
        35                  40                  45

Leu Ser Lys Asp Ala Ser Ser Glu Glu Ile Leu Ala Lys Phe Val Gln
    50                  55                  60

Asn Glu Thr Gly Thr Lys Leu Lys Glu Leu Val Asn Lys Leu Leu Asp
65                  70                  75                  80

Gln Ile Asn Ala Gln Lys Asn Pro Asp Ser Pro Val Leu Lys Gln Gly
                85                  90                  95

Lys Asn Leu Asn Leu Ala Pro Asn Phe Ala Asn Glu Leu Lys Ile Leu
            100                 105                 110

Ser Thr Glu Leu Ala Lys Ser Asp Thr Phe Thr Gln Val Leu Asp Arg
        115                 120                 125

Leu Asn Gln Ile Leu Lys Pro Ala Ser Glu Ile Lys Asn Asn Asn Leu
    130                 135                 140

Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
                165                 170                 175

Ser Thr Ile Lys Gly Leu Ser Ser Glu Lys Leu Ser Val Gln Ile Ala
            180                 185                 190
```

```
Gln Leu Ala Asn Thr Asn Leu Ser Pro Lys Asp Thr Leu Lys Glu Leu
            195                 200                 205

Lys Asn Ile Ile Asn Ser Ser Lys Asn Glu Asn Lys Gln Ile Leu Asn
        210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser His Ala Gln Glu Lys Ile
                245                 250                 255

Thr Pro Ile Ala Asn Lys Ile Leu Lys Glu Leu Asn Ser Ile Lys Asn
                260                 265                 270

Asp Phe Phe Lys Ala Leu Asn Lys Pro Glu Asn Leu Met Ile Lys Asp
                275                 280                 285

Pro Asn Ile Leu Lys Gln Thr Ala Thr Ala Phe Glu Lys Leu Glu Asn
            290                 295                 300

Thr Leu Lys Asn Ile Leu Gly Asn Gln Ala Ser Lys Ile Gln Asp Lys
305                 310                 315                 320

Glu Asn Ile Leu Glu Asn Leu Leu Ser Asn Lys Glu Asn Met Lys Glu
                325                 330                 335

Glu Lys Leu Asn His Asn Thr Lys Asn Gln Asp Glu Glu Lys His Ile
            340                 345                 350

Lys Ala Ser Lys Glu Asp Glu Asn Leu Asp Ser Gly Ile Lys Thr His
                355                 360                 365

Glu Glu Asp Thr Gln Asp Thr Lys Asn Asp Ile Gln Asn Asn Glu Thr
            370                 375                 380

Glu Asn Lys Pro Asp Asn Asp Ile Lys Asn Ser Thr Pro Asn Gln Glu
385                 390                 395                 400

Lys Ile Lys Asp Glu Lys Gln Glu Lys Ser Lys Glu Asn Ile Lys Glu
                405                 410                 415

Asn Pro Lys Phe Tyr Glu Thr Lys Thr Glu Asn Lys Thr Ser Ile Asn
            420                 425                 430

Thr Asn Thr Asn Thr Ser Asn Pro Asn Thr Asn Asn Thr Gln Asn Leu
        435                 440                 445

Asn Asn Thr Gln Asn Ile Gln Ser Asn Asn Gln Thr Met Gln Asn
        450                 455                 460

Ile Phe Lys Asn Gln Glu Phe Ile Lys Gln Asn Ile Val Lys Asn Leu
465                 470                 475                 480

Ala Phe Asn Val Glu Asn Leu Asp Leu Glu Gln Val Gln Asp Leu Ser
                485                 490                 495

Lys Asn Leu Ser Asn Leu Ser Arg Arg Leu Asn Glu Ser Leu Lys Glu
            500                 505                 510

Leu Glu Pro Tyr Thr Gln Asn Ala Lys Leu Asn Gln Ala Glu Leu Lys
            515                 520                 525

Asn Leu Glu His Lys Leu Asn Leu Ser Ile Lys Asp Leu Ala Gln Ile
        530                 535                 540

Lys Pro Lys Thr Glu Gln Asp Ile Ala Glu Ser Leu His His Asp Val
545                 550                 555                 560

Lys Ser Thr Leu Leu Gln Ile Ser Asn Leu Ala Lys Asn Glu Gly Asn
                565                 570                 575

Glu Ala Val Tyr Asn Gln Ala Asn Arg Leu Leu Ala Gln Ile Glu Ile
                580                 585                 590

Asn Gln Leu Met Ser Leu Ala Asn Asp Ser Ile Asn Thr Tyr Leu Pro
            595                 600                 605
```

```
Phe Ser Trp Asp Asp Leu Asn Asp Ser Lys Ile Met Phe Arg Arg Gly
    610                 615                 620

Lys Lys Asp Lys Phe Phe Ala Gln Ile Lys Leu Glu Phe Ala Lys Leu
625                 630                 635                 640

Gly Asp Leu Glu Ile Leu Ile Ser Leu Asn Asn Glu Lys Tyr Ile Asp
                645                 650                 655

Ile Asn Ile Met Ala Glu Asn Ile Glu Phe Arg Lys Thr Ile Tyr Glu
                660                 665                 670

Asn Ala His Glu Leu Lys Arg Asn Ile Asn Lys Ala Gly Leu Leu Ser
            675                 680                 685

Ala Asn Phe Phe Val Gly Asp Ile Ile Arg Ser Lys Phe Asp Thr Arg
690                 695                 700

Asn Met Lys Asn Leu Asp Leu Glu Met Gly Met Asp Lys Lys Val
705                 710                 715
```

<210> SEQ ID NO 71
<211> LENGTH: 749
<212> TYPE: PRT
<213> ORGANISM: Campylobacter jejuni

<400> SEQUENCE: 71

```
Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
                20                  25                  30

Asp Asn Pro Lys Glu Ala Leu Ala Gln Ala Leu Lys Gln Asn Leu Gly
            35                  40                  45

Leu Ser Lys Asp Ala Ser Ser Glu Glu Ile Leu Ala Lys Phe Val Gln
50                  55                  60

Asn Glu Thr Gly Val Lys Leu Lys Glu Leu Val Asn Lys Leu Leu Asp
65                  70                  75                  80

Gln Ile Asn Ala Gln Lys Asn Pro Asp Ser Pro Val Leu Lys Gln Gly
                85                  90                  95

Lys Asn Leu Asn Leu Ala Pro Asn Phe Ala Asn Glu Leu Lys Thr Leu
            100                 105                 110

Ser Thr Glu Leu Ala Lys Ser Asp Thr Phe Thr Gln Val Leu Asp Arg
            115                 120                 125

Leu Asn Gln Ile Leu Lys Pro Ala Ser Glu Ile Lys Asn Asn Asn Leu
    130                 135                 140

Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
                165                 170                 175

Ser Thr Ile Lys Gly Leu Ser Ser Glu Lys Leu Ser Val Gln Ile Ala
            180                 185                 190

Gln Leu Ala Asn Thr Asn Leu Ser Pro Lys Asp Thr Leu Lys Glu Leu
            195                 200                 205

Lys Asn Ile Ile Asn Ser Ser Lys Asn Glu Asn Lys Gln Ile Leu Asn
    210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser His Ala Gln Glu Lys Ile
                245                 250                 255

Thr Pro Ile Ala Asn Lys Ile Leu Lys Glu Leu Asn Ser Ile Lys Asn
            260                 265                 270
```

-continued

```
Asp Phe Phe Lys Ala Leu Asn Lys Pro Glu Asn Leu Met Ile Lys Asp
        275                 280                 285
Pro Asn Ile Leu Lys Gln Thr Ala Thr Ala Phe Glu Lys Leu Glu Asn
    290                 295                 300
Thr Leu Lys Asn Ile Leu Gly Asn Gln Ala Ser Lys Ile Gln Asp Lys
305                 310                 315                 320
Glu Asn Ile Leu Glu Asn Leu Leu Ser Asn Lys Glu Asn Met Lys Glu
                325                 330                 335
Glu Lys Leu Asn His Asn Thr Lys Asn Gln Asp Glu Lys His Ile
                340                 345                 350
Lys Ala Ser Lys Glu Glu Thr Leu Thr Asp Asp Thr Lys Thr Asp Ile
            355                 360                 365
Lys Gln Asp Ser Lys Asn Glu Glu Asn Ser His Ala Lys Glu Thr Asp
        370                 375                 380
Ile Lys Glu Asp Glu Asn Leu Asp Ser Asp Ile Lys Thr His Glu Glu
385                 390                 395                 400
Asp Thr Gln Asp Thr Lys Asn Asp Ile Gln Asn Asn Glu Thr Glu Asn
                405                 410                 415
Lys Pro Asp Asn Asp Ile Lys Asn Ser Thr Pro Asn Gln Glu Lys Ile
            420                 425                 430
Lys Asp Glu Lys Gln Glu Lys Ser Lys Glu Asn Ile Lys Glu Asn Pro
        435                 440                 445
Lys Phe Tyr Glu Thr Lys Thr Glu Asn Lys Thr Ser Val Asn Thr Asn
    450                 455                 460
Thr Asn Thr Ser Asn Pro Asn Thr Asn Asn Thr Gln Asn Leu Asn Asn
465                 470                 475                 480
Ser Gln Asn Ile Gln Ser Asn Asn Asn Gln Thr Met Gln Asn Ile Phe
                485                 490                 495
Lys Asn Gln Glu Phe Ile Lys Gln Asn Ile Val Lys Asn Leu Ala Phe
            500                 505                 510
Asn Val Glu Asn Leu Asp Leu Glu Gln Val Gln Asp Leu Ser Lys Asn
        515                 520                 525
Leu Ser Asn Leu Ser Arg Arg Leu Asn Glu Ser Leu Lys Glu Leu Glu
    530                 535                 540
Pro Tyr Thr Gln Asn Ala Lys Leu Asn Gln Ala Glu Leu Lys Asn Leu
545                 550                 555                 560
Glu His Lys Leu Asn Leu Ser Ile Lys Asp Leu Ala Gln Ile Lys Pro
                565                 570                 575
Lys Thr Glu Gln Asp Ile Ala Glu Ser Leu His His Asp Val Lys Ser
            580                 585                 590
Thr Leu Leu Gln Ile Ser Asn Leu Ala Lys Asn Glu Gly Asn Glu Ala
        595                 600                 605
Val Tyr Asn Gln Ala Asn Arg Leu Leu Ala Gln Ile Glu Ile Asn Gln
    610                 615                 620
Leu Met Ser Leu Ala Asn Asp Ser Ile Asn Thr Tyr Leu Pro Phe Ser
625                 630                 635                 640
Trp Asp Asp Leu Asn Asp Ser Lys Ile Met Phe Arg Arg Gly Lys Lys
                645                 650                 655
Asp Lys Phe Phe Ala Gln Ile Lys Leu Glu Phe Ala Lys Leu Gly Asp
            660                 665                 670
Leu Glu Ile Leu Ile Ser Leu Asn Asn Glu Lys Tyr Ile Asp Ile Asn
        675                 680                 685
```

```
Ile Met Ala Glu Asn Ile Glu Phe Arg Lys Thr Ile Tyr Glu Asn Ala
        690                 695                 700

His Glu Leu Lys Arg Asn Ile Asn Lys Ala Gly Leu Leu Ser Ala Asn
705                 710                 715                 720

Phe Phe Val Gly Asp Ile Ile Arg Ser Lys Phe Asp Thr Arg Asn Met
                725                 730                 735

Lys Asn Leu Asp Leu Glu Met Gly Met Asp Lys Lys Val
            740                 745

<210> SEQ ID NO 72
<211> LENGTH: 719
<212> TYPE: PRT
<213> ORGANISM: Campylobacter jejuni

<400> SEQUENCE: 72

Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
            20                  25                  30

Asp Asn Pro Lys Glu Ala Leu Ala Gln Ala Leu Lys Gln Asn Leu Gly
        35                  40                  45

Leu Ser Lys Asp Ala Ser Ser Glu Glu Ile Leu Ala Lys Phe Val Gln
    50                  55                  60

Asn Glu Thr Gly Thr Lys Leu Lys Glu Leu Val Asn Lys Leu Leu Asp
65                  70                  75                  80

Gln Ile Asn Ala Gln Lys Asn Pro Asp Ser Pro Val Phe Lys Gln Gly
                85                  90                  95

Lys Asn Leu Asn Leu Ala Pro Asn Phe Ala Asn Glu Leu Lys Ile Leu
            100                 105                 110

Ser Thr Glu Leu Ala Lys Ser Asp Thr Phe Thr Gln Val Leu Asp Arg
        115                 120                 125

Leu Asn Gln Ile Leu Lys Pro Ala Ser Glu Ile Lys Asn Asn Asn Leu
    130                 135                 140

Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
                165                 170                 175

Ser Thr Ile Lys Gly Leu Ser Ser Glu Lys Leu Ser Val Gln Ile Ala
            180                 185                 190

Gln Leu Ala Asn Thr Asn Leu Ser Pro Lys Asp Thr Leu Lys Glu Leu
        195                 200                 205

Lys Asn Ile Ile Asn Ser Ser Lys Asn Glu Asn Lys Gln Ile Leu Asn
    210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser His Ala Gln Glu Lys Ile
                245                 250                 255

Thr Pro Ile Ala Asn Lys Ile Leu Lys Glu Leu Asn Ser Ile Lys Asn
            260                 265                 270

Asp Phe Phe Lys Ala Leu Asn Lys Pro Glu Asn Leu Met Ile Lys Asp
        275                 280                 285

Pro Asn Ile Leu Lys Gln Thr Ala Thr Ala Phe Glu Lys Leu Glu Asn
    290                 295                 300

Thr Leu Lys Asn Ile Leu Gly Asn Gln Ala Ser Lys Ile Gln Asp Lys
305                 310                 315                 320
```

Glu Asn Ile Leu Glu Asn Leu Leu Ser Asn Lys Glu Asn Met Lys Glu
                325                 330                 335

Glu Lys Leu Asn His Asn Thr Lys Asn Gln Asp Glu Glu Lys His Ile
            340                 345                 350

Lys Ala Ser Lys Glu Asp Glu Asn Leu Asp Ser Gly Ile Lys Thr His
        355                 360                 365

Glu Glu Asp Thr Gln Asp Thr Lys Asn Asp Ile Gln Asn Asn Glu Thr
    370                 375                 380

Glu Asn Lys Pro Asp Asn Asp Ile Lys Asn Ser Thr Pro Asn Gln Glu
385                 390                 395                 400

Lys Ile Lys Asp Glu Lys Gln Glu Lys Ser Lys Glu Asn Ile Lys Glu
                405                 410                 415

Asn Pro Lys Phe Tyr Glu Thr Lys Thr Glu Asn Lys Thr Ser Ile Asn
            420                 425                 430

Thr Asn Thr Asn Thr Ser Asn Pro Asn Thr Asn Asn Thr Gln Asn Leu
        435                 440                 445

Asn Asn Thr Gln Asn Ile Gln Ser Asn Asn Asn Gln Thr Met Gln Asn
    450                 455                 460

Ile Phe Lys Asn Gln Glu Phe Ile Lys Gln Asn Ile Val Lys Asn Leu
465                 470                 475                 480

Ala Phe Asn Val Glu Asn Leu Asp Leu Glu Gln Val Gln Asp Leu Ser
                485                 490                 495

Lys Asn Leu Ser Asn Leu Ser Arg Arg Leu Asn Glu Ser Leu Lys Glu
            500                 505                 510

Leu Glu Pro Tyr Thr Gln Asn Ala Lys Leu Asn Gln Ala Glu Leu Lys
        515                 520                 525

Asn Leu Glu His Lys Leu Asn Leu Ser Ile Lys Asp Leu Ala Gln Ile
    530                 535                 540

Lys Pro Lys Thr Glu Gln Asp Ile Ala Glu Ser Leu His His Asp Val
545                 550                 555                 560

Lys Ser Thr Leu Leu Gln Ile Ser Asn Leu Ala Lys Asn Glu Gly Asn
                565                 570                 575

Glu Ala Val Tyr Asn Gln Ala Asn Arg Leu Leu Ala Gln Ile Glu Ile
            580                 585                 590

Asn Gln Leu Met Ser Leu Ala Asn Asp Ser Ile Asn Thr Tyr Leu Pro
        595                 600                 605

Phe Ser Trp Asp Asp Leu Asn Asp Ser Lys Ile Met Phe Arg Arg Gly
    610                 615                 620

Lys Lys Asp Lys Phe Phe Ala Gln Ile Lys Leu Glu Phe Ala Lys Leu
625                 630                 635                 640

Gly Asp Leu Glu Ile Leu Ile Ser Leu Asn Asn Glu Lys Tyr Ile Asp
                645                 650                 655

Ile Asn Ile Met Ala Glu Asn Ile Glu Phe Arg Lys Thr Ile Tyr Glu
            660                 665                 670

Asn Ala His Glu Leu Lys Arg Asn Ile Asn Lys Ala Gly Leu Leu Ser
        675                 680                 685

Ala Asn Phe Phe Val Gly Asp Ile Ile Arg Ser Lys Phe Asp Thr Arg
    690                 695                 700

Asn Met Lys Asn Leu Asp Leu Glu Met Gly Met Asp Lys Lys Val
705                 710                 715

<210> SEQ ID NO 73
<211> LENGTH: 719

<212> TYPE: PRT
<213> ORGANISM: Campylobacter jejuni

<400> SEQUENCE: 73

```
Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
            20                  25                  30

Asp Asn Pro Lys Glu Ala Leu Ala Gln Ala Leu Lys Gln Asn Leu Gly
        35                  40                  45

Leu Ser Lys Asp Ala Ser Ser Glu Glu Ile Leu Ala Lys Phe Val Gln
    50                  55                  60

Asn Glu Thr Gly Thr Lys Leu Lys Glu Leu Val Asn Lys Leu Leu Asp
65                  70                  75                  80

Gln Ile Asn Ala Gln Lys Asn Pro Asp Ser Pro Val Leu Lys Gln Gly
                85                  90                  95

Lys Asn Leu Asn Leu Ala Pro Asn Phe Ala Asn Glu Leu Lys Ile Leu
            100                 105                 110

Ser Thr Glu Leu Ala Lys Ser Asp Thr Phe Thr Gln Val Leu Asp Arg
        115                 120                 125

Leu Asn Gln Ile Leu Lys Pro Ala Ser Glu Ile Lys Asn Asn Asn Leu
    130                 135                 140

Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
                165                 170                 175

Ser Thr Ile Lys Gly Leu Ser Ser Glu Lys Leu Ser Val Gln Ile Ala
            180                 185                 190

Gln Leu Ala Asn Thr Asn Leu Ser Pro Lys Asp Thr Leu Lys Glu Leu
        195                 200                 205

Lys Asn Ile Ile Asn Ser Ser Lys Asn Glu Asn Lys Gln Ile Leu Asn
    210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser Tyr Ala Gln Glu Lys Ile
                245                 250                 255

Thr Pro Ile Ala Asn Lys Ile Leu Lys Glu Leu Asn Ser Ile Lys Asn
            260                 265                 270

Asp Phe Phe Lys Ala Leu Asn Lys Pro Glu Asn Leu Met Thr Lys Asp
        275                 280                 285

Pro Asn Ile Leu Lys Gln Thr Ala Thr Ala Phe Glu Lys Leu Glu Asn
    290                 295                 300

Thr Leu Lys Asn Ile Leu Gly Asn Gln Ala Ser Lys Ile Gln Asp Lys
305                 310                 315                 320

Glu Asn Ile Leu Glu Asn Leu Leu Ser Asn Lys Glu Asn Ile Lys Glu
                325                 330                 335

Glu Lys Leu Asn His Asn Thr Lys Asn Gln Asp Glu Lys His Ile
            340                 345                 350

Lys Ala Ser Lys Glu Asp Glu Asn Leu Asp Ser Gly Ile Lys Thr His
        355                 360                 365

Glu Glu Asp Thr Gln Asp Thr Lys Asn Asp Ile Gln Asn Asn Glu Thr
    370                 375                 380

Glu Asn Lys Pro Asp Asn Asp Ile Lys Asn Ser Thr Pro Asn Gln Glu
385                 390                 395                 400
```

```
Lys Ile Lys Asp Glu Lys Gln Glu Lys Ser Lys Glu Asn Ile Lys Glu
            405                 410                 415

Asn Pro Lys Phe Tyr Glu Thr Lys Thr Glu Asn Lys Thr Ser Ile Asn
            420                 425                 430

Thr Asn Thr Asn Thr Ser Asn Pro Asn Thr Asn Thr Gln Asn Leu
            435                 440                 445

Asn Asn Thr Gln Asn Ile Gln Ser Asn Asn Gln Thr Met Gln Asn
450                 455                 460

Ile Phe Lys Asn Gln Glu Phe Ile Lys Gln Asn Ile Val Lys Asn Leu
465                 470                 475                 480

Ala Phe Asn Val Glu Asn Leu Asp Leu Glu Gln Val Gln Asp Leu Ser
            485                 490                 495

Lys Asn Leu Ser Asn Leu Ser Arg Arg Leu Asn Glu Ser Leu Lys Glu
            500                 505                 510

Leu Glu Pro Tyr Thr Gln Asn Ala Lys Leu Asn Gln Ala Glu Leu Lys
            515                 520                 525

Asn Leu Glu His Lys Leu Asn Leu Ser Ile Lys Asp Leu Ala Gln Ile
            530                 535                 540

Lys Pro Lys Thr Glu Gln Asp Ile Ala Glu Ser Leu His His Asp Val
545                 550                 555                 560

Lys Ser Thr Leu Leu Gln Ile Ser Asn Leu Ala Lys Asn Glu Gly Asn
            565                 570                 575

Glu Ala Val Tyr Asn Gln Ala Asn Arg Leu Leu Ala Gln Ile Glu Ile
            580                 585                 590

Asn Gln Leu Met Ser Leu Ala Asn Asp Ser Ile Asn Thr Tyr Leu Pro
            595                 600                 605

Phe Ser Trp Asp Asp Leu Asn Asp Ser Lys Ile Met Phe Arg Arg Gly
            610                 615                 620

Lys Lys Asp Lys Phe Phe Ala Gln Ile Lys Leu Glu Phe Ala Lys Leu
625                 630                 635                 640

Gly Asp Leu Glu Ile Leu Ile Ser Leu Asn Asn Glu Lys Tyr Ile Asp
            645                 650                 655

Ile Asn Ile Met Ala Glu Asn Ile Glu Phe Arg Lys Thr Ile Tyr Glu
            660                 665                 670

Asn Ala His Glu Leu Lys Arg Asn Ile Asn Lys Ala Gly Leu Leu Ser
            675                 680                 685

Ala Asn Phe Phe Val Gly Asp Ile Ile Arg Ser Lys Phe Asp Thr Arg
            690                 695                 700

Asn Met Lys Asn Leu Asp Leu Glu Met Gly Met Asp Lys Lys Val
705                 710                 715

<210> SEQ ID NO 74
<211> LENGTH: 323
<212> TYPE: PRT
<213> ORGANISM: Campylobacter jejuni

<400> SEQUENCE: 74

Met Lys Lys Tyr Ile Ser Ser Cys Leu Ala Ile Cys Cys Leu Ser Ser
1               5                   10                  15

Ala Ile Tyr Ala Asn Asp Val Lys Tyr Asp Ala Gln Lys Ile Ala Asp
            20                  25                  30

Ile Phe Tyr Gln Leu Asn Ala Asp Pro Lys Asn Pro Lys Val Lys Val
            35                  40                  45

Asn His Ala Lys Gly Phe Cys Ala Met Gly Thr Phe Glu Pro Ala Gln
```

```
            50                  55                  60
Ser Ile Asn Lys Glu Ile Asp Val Pro Leu Leu Thr Tyr Lys Ser Leu
 65                  70                  75                  80

Pro Ile Gln Val Arg Tyr Ser Leu Gly Gly Ala Phe Lys Asp Asp Lys
                 85                  90                  95

Ser Lys Thr Arg Gly Met Ala Ile Arg Ile Thr Asp Pro Gln Asp Ser
            100                 105                 110

Ala Ser Trp Thr Met Val Met Leu Asn Thr Glu Ile Asn Phe Ala Lys
            115                 120                 125

Asn Leu Lys Glu Phe Gly Gln Phe Phe Glu Met Arg Leu Pro Val Asn
130                 135                 140

Gly Lys Val Asp Gln Glu Lys Ile Ser Lys Met Met Gln Glu Val Asp
145                 150                 155                 160

Ser Tyr Arg Asn Phe Ala Ala Tyr Thr Asp Lys Ile Gly Ile Ser Lys
                165                 170                 175

Ser Val Ala Asn Thr Pro Phe Phe Ser Ile His Thr Phe Tyr Phe Lys
            180                 185                 190

Gln Thr Gly Ser Glu Asn Tyr Leu Pro Ala Arg Trp Lys Leu Val Pro
        195                 200                 205

Ser Glu Gly Val Ala Tyr Leu Asn Glu Ala Gln Met Lys Ser Ala Ser
210                 215                 220

Ser Asp Phe Leu Lys Glu Asp Phe Glu Asp Arg Val Lys Thr Asn Lys
225                 230                 235                 240

Pro Val Glu Tyr Lys Met Tyr Leu Val Tyr Ala Asn Lys Asn Asp Ile
                245                 250                 255

Ile Asn Glu Thr Thr Ala Leu Trp Glu Gly Lys His Lys Glu Ser Leu
            260                 265                 270

Val Gly Thr Phe Lys Val Asn Ala Leu Ser Glu Glu Asp Cys Asn Phe
        275                 280                 285

Asn Val Tyr Phe Pro Ser Asp Ile Pro Gln Gly Val Asn Pro Pro Gln
290                 295                 300

Asp Pro Leu Phe Asp Val Arg Asn Glu Thr Tyr Ala Ile Thr Phe Gly
305                 310                 315                 320

Met Arg Gln

<210> SEQ ID NO 75
<211> LENGTH: 495
<212> TYPE: PRT
<213> ORGANISM: Campylobacter jejuni

<400> SEQUENCE: 75

Gln Ser Ser Phe Lys Ala Leu Leu Asn Leu Ser Ser Lys Leu Glu Asn
  1               5                  10                  15

Phe Lys Asn Tyr Ile Ser Lys Asn Pro Ser His Ala Gln Glu Lys Ile
             20                  25                  30

Thr Pro Ile Ala Asn Lys Ile Leu Lys Glu Leu Asn Ser Ile Lys Asn
        35                  40                  45

Asp Phe Phe Lys Ala Leu Asn Lys Pro Glu Asn Leu Met Ile Lys Asp
     50                  55                  60

Pro Asn Ile Leu Lys Gln Thr Ala Thr Ala Phe Glu Lys Leu Glu Asn
 65                  70                  75                  80

Thr Leu Lys Asn Ile Leu Gly Asn Gln Ala Ser Lys Ile Gln Asp Lys
                 85                  90                  95

Glu Asn Ile Leu Glu Asn Leu Leu Ser Asn Lys Glu Asn Met Lys Glu
```

```
            100                 105                 110
Glu Lys Leu Asn His Asn Thr Lys Asn Gln Asp Glu Glu Lys His Ile
        115                 120                 125

Lys Ala Ser Lys Glu Asp Glu Asn Leu Asp Ser Gly Ile Lys Thr His
    130                 135                 140

Glu Glu Asp Thr Gln Asp Thr Lys Asn Asp Ile Gln Asn Asn Glu Thr
145                 150                 155                 160

Glu Asn Lys Pro Asp Asn Asp Ile Lys Asn Ser Thr Pro Asn Gln Glu
                165                 170                 175

Lys Ile Lys Asp Glu Lys Gln Glu Lys Ser Lys Glu Asn Ile Lys Glu
            180                 185                 190

Asn Pro Lys Phe Tyr Glu Thr Lys Thr Glu Asn Lys Thr Ser Ile Asn
        195                 200                 205

Thr Asn Thr Asn Thr Ser Asn Pro Asn Thr Asn Thr Gln Asn Leu
    210                 215                 220

Asn Asn Thr Gln Asn Ile Gln Ser Asn Asn Gln Thr Met Gln Asn
225                 230                 235                 240

Ile Phe Lys Asn Gln Glu Phe Ile Lys Gln Asn Ile Val Lys Asn Leu
                245                 250                 255

Ala Phe Asn Val Glu Asn Leu Asp Leu Glu Gln Val Gln Asp Leu Ser
            260                 265                 270

Lys Asn Leu Ser Asn Leu Ser Arg Arg Leu Asn Glu Ser Leu Lys Glu
        275                 280                 285

Leu Glu Pro Tyr Thr Gln Asn Ala Lys Leu Asn Gln Ala Glu Leu Lys
    290                 295                 300

Asn Leu Glu His Lys Leu Asn Leu Ser Ile Lys Asp Leu Ala Gln Ile
305                 310                 315                 320

Lys Pro Lys Thr Glu Gln Asp Ile Ala Glu Ser Leu His His Asp Val
                325                 330                 335

Lys Ser Thr Leu Leu Gln Ile Ser Asn Leu Ala Lys Asn Glu Gly Asn
            340                 345                 350

Glu Ala Val Tyr Asn Gln Ala Asn Arg Leu Leu Ala Gln Ile Glu Ile
        355                 360                 365

Asn Gln Leu Met Ser Leu Ala Asn Asp Ser Ile Asn Thr Tyr Leu Pro
    370                 375                 380

Phe Ser Trp Asp Asp Leu Asn Asp Ser Lys Ile Met Phe Arg Arg Gly
385                 390                 395                 400

Lys Lys Asp Lys Phe Phe Ala Gln Ile Lys Leu Glu Phe Ala Lys Leu
                405                 410                 415

Gly Asp Leu Glu Ile Leu Ile Ser Leu Asn Asn Gly Lys Tyr Ile Asp
            420                 425                 430

Ile Asn Ile Met Ala Glu Asn Ile Glu Phe Arg Lys Thr Ile Tyr Glu
        435                 440                 445

Asn Ala His Glu Leu Lys Arg Asn Ile Asn Lys Ala Gly Leu Leu Ser
    450                 455                 460

Ala Asn Phe Phe Val Gly Asp Ile Ile Arg Ser Lys Phe Asp Thr Arg
465                 470                 475                 480

Asn Met Lys Asn Leu Asp Leu Glu Met Gly Met Asp Lys Lys Val
                485                 490                 495

<210> SEQ ID NO 76
<211> LENGTH: 749
<212> TYPE: PRT
<213> ORGANISM: Campylobacter jejuni
```

<400> SEQUENCE: 76

Met Ile Asn Thr Gln Leu Ala Ser Gln Ile Ala Asn Thr Gln Lys Asn
1               5                   10                  15

Asp Leu Lys Val Asp Asn Ser Thr Ser Lys Asp Lys Thr Asn Leu Lys
            20                  25                  30

Asp Asn Pro Lys Glu Ala Leu Ala Gln Ala Leu Lys Gln Asn Leu Gly
        35                  40                  45

Leu Ser Lys Asp Ala Ser Ser Glu Glu Ile Leu Ala Lys Phe Val Gln
    50                  55                  60

Asn Glu Thr Gly Ile Lys Leu Lys Glu Leu Val Asn Lys Leu Leu Asp
65                  70                  75                  80

Gln Ile Asn Ala Gln Lys Asn Pro Asp Ser Pro Val Leu Lys Gln Gly
                85                  90                  95

Lys Asn Leu Asn Leu Ala Pro Asn Phe Ala Asn Glu Leu Lys Ile Leu
            100                 105                 110

Ser Thr Glu Leu Ala Lys Ser Asp Thr Phe Thr Gln Val Leu Asp Arg
        115                 120                 125

Leu Asn Gln Ile Leu Lys Pro Ala Ser Glu Ile Lys Asn Asn Asn Leu
    130                 135                 140

Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
                165                 170                 175

Ser Thr Ile Lys Gly Leu Ser Ser Glu Lys Leu Ser Val Gln Ile Ala
            180                 185                 190

Gln Leu Ala Asn Thr Asn Leu Ser Pro Lys Asp Thr Leu Lys Glu Leu
    195                 200                 205

Lys Asn Ile Ile Asn Ser Ser Lys Ile Glu Asn Lys Gln Ile Leu Asn
210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser His Ala Gln Glu Lys Ile
                245                 250                 255

Thr Pro Ile Ala Asn Lys Ile Leu Lys Glu Leu Asn Ser Ile Lys Asn
            260                 265                 270

Asp Phe Phe Lys Ala Leu Asn Lys Pro Glu Asn Leu Met Ile Lys Asp
    275                 280                 285

Pro Asn Ile Leu Lys Gln Thr Ala Thr Ala Phe Glu Lys Leu Glu Asn
290                 295                 300

Thr Leu Lys Asn Ile Leu Gly Asn Gln Ala Ser Lys Ile Gln Asp Lys
305                 310                 315                 320

Glu Asn Ile Leu Glu Asn Leu Leu Ser Asn Lys Glu Asn Met Lys Glu
                325                 330                 335

Glu Lys Leu Asn His Asn Thr Lys Asn Gln Asp Glu Glu Lys His Ile
            340                 345                 350

Lys Ala Ser Lys Glu Glu Thr Leu Thr Asp Asp Thr Lys Thr Asp Ile
    355                 360                 365

Lys Gln Asp Ser Lys Asn Glu Glu Asn Ser His Ala Lys Glu Thr Asp
370                 375                 380

Ile Lys Glu Asp Glu Asn Leu Asp Ser Asp Ile Lys Thr His Glu Glu
385                 390                 395                 400

Asp Thr Gln Asp Thr Lys Asn Asp Ile Gln Asn Asn Glu Thr Glu Asn

```
                405                 410                 415
Lys Pro Asp Asn Asp Ile Lys Asn Ser Thr Pro Asn Gln Glu Lys Ile
            420                 425                 430
Lys Asp Gly Lys Gln Glu Lys Ser Lys Glu Asn Ile Lys Glu Asn Pro
        435                 440                 445
Lys Phe Tyr Glu Thr Lys Thr Glu Asn Lys Thr Ser Ile Asn Thr Asn
    450                 455                 460
Thr Asn Thr Ser Asn Pro Asn Thr Asn Thr Gln Asn Leu Asn Asn
465                 470                 475                 480
Ser Gln Asn Ile Gln Ser Asn Asn Gln Thr Met Gln Asn Ile Phe
            485                 490                 495
Lys Asn Gln Glu Phe Ile Lys Gln Asn Ile Val Lys Asn Leu Ala Phe
        500                 505                 510
Asn Val Glu Asn Leu Asp Leu Glu Gln Val Gln Asp Leu Ser Lys Asn
    515                 520                 525
Leu Ser Asn Leu Ser Arg Arg Leu Asn Glu Ser Leu Lys Glu Leu Glu
530                 535                 540
Pro Tyr Thr Gln Asn Ala Lys Leu Asn Gln Ala Glu Leu Lys Asn Leu
545                 550                 555                 560
Glu His Lys Leu Asn Leu Ser Thr Lys Asp Leu Ala Gln Ile Lys Pro
            565                 570                 575
Lys Thr Glu Gln Asp Ile Ala Glu Ser Leu His His Asp Val Lys Ser
        580                 585                 590
Thr Leu Leu Gln Ile Ser Asn Leu Ala Lys Asn Glu Gly Asn Glu Ala
    595                 600                 605
Ile Tyr Asn Gln Ala Asn Arg Leu Leu Ala Gln Ile Glu Ile Asn Gln
    610                 615                 620
Leu Met Ser Leu Ala Asn Asp Ser Ile Asn Thr Tyr Leu Pro Phe Ser
625                 630                 635                 640
Trp Asp Asp Leu Asn Asp Ser Lys Ile Met Phe Arg Arg Gly Lys Lys
            645                 650                 655
Asp Lys Phe Phe Ala Gln Ile Lys Leu Glu Phe Ala Lys Leu Gly Asp
        660                 665                 670
Leu Glu Ile Leu Ile Ser Leu Asn Asn Glu Lys Tyr Ile Asp Ile Asn
    675                 680                 685
Ile Met Ala Glu Asn Ile Glu Phe Arg Lys Thr Ile Tyr Glu Asn Ala
    690                 695                 700
His Glu Leu Lys Arg Asn Ile Asn Lys Ala Gly Leu Leu Ser Ala Asn
705                 710                 715                 720
Phe Phe Val Gly Asp Ile Ile Arg Ser Lys Phe Asp Thr Arg Asn Met
            725                 730                 735
Lys Asn Leu Asp Leu Glu Met Gly Met Asp Lys Lys Val
            740                 745

<210> SEQ ID NO 77
<211> LENGTH: 749
<212> TYPE: PRT
<213> ORGANISM: Campylobacter jejuni

<400> SEQUENCE: 77

Met Ile Asn Thr Gln Leu Ala Ser Gln Ile Ala Asn Thr Gln Lys Asn
1               5                   10                  15
Asp Leu Lys Val Asp Asn Ser Ala Ser Lys Asp Lys Thr Asn Leu Lys
            20                  25                  30
```

-continued

```
Asp Asn Pro Lys Glu Ala Leu Ala Gln Ala Leu Lys Gln Asn Leu Gly
         35                  40                  45
Leu Ser Lys Asp Ala Ser Ser Glu Glu Ile Leu Ala Lys Phe Val Gln
 50                  55                  60
Asn Glu Thr Gly Thr Lys Leu Lys Glu Leu Val Asn Lys Leu Leu Asp
 65                  70                  75                  80
Gln Ile Asn Ala Gln Lys Asn Pro Asp Ser Pro Val Leu Lys Gln Gly
                 85                  90                  95
Lys Asn Leu Asn Leu Ala Pro Asn Phe Ala Asn Glu Leu Lys Thr Leu
                100                 105                 110
Ser Thr Glu Leu Ala Lys Ser Asp Thr Phe Thr Gln Val Leu Asp Arg
                115                 120                 125
Leu Asn Gln Ile Leu Lys Pro Ala Ser Glu Ile Lys Asn Asn Asn Leu
        130                 135                 140
Ala Pro Leu Phe Lys Asn Ser Gly Val Phe Leu Glu Ala Lys Leu Lys
145                 150                 155                 160
Asp Ala Leu Asn Glu Glu Leu Leu Pro Lys Ser Phe His Ser Leu Leu
                165                 170                 175
Ser Thr Ile Lys Gly Leu Ser Ser Glu Lys Leu Ser Val Gln Ile Ala
                180                 185                 190
Gln Leu Ala Asn Thr Asn Leu Ser Pro Lys Asp Thr Leu Lys Glu Leu
        195                 200                 205
Lys Asn Ile Ile Asn Ser Ser Lys Ile Glu Asn Lys Gln Ile Leu Asn
        210                 215                 220
Gln Ser Ser Phe Lys Ala Leu Leu Asn Leu Ser Ser Lys Leu Glu Asn
225                 230                 235                 240
Phe Lys Asn Tyr Ile Ser Lys Asn Pro Ser His Ala Gln Glu Lys Ile
                245                 250                 255
Thr Pro Ile Ala Asn Lys Ile Leu Lys Glu Leu Asn Ser Ile Lys Asn
                260                 265                 270
Asp Phe Phe Lys Ala Leu Asn Lys Pro Glu Asn Leu Met Ile Lys Asp
        275                 280                 285
Pro Asn Ile Leu Lys Gln Thr Ala Thr Ala Phe Glu Lys Leu Glu Asn
290                 295                 300
Thr Leu Lys Asn Ile Leu Gly Asn Gln Ala Ser Lys Ile Gln Asp Lys
305                 310                 315                 320
Glu Asn Ile Leu Glu Asn Leu Leu Ser Asn Lys Glu Asn Met Lys Glu
                325                 330                 335
Glu Lys Leu Asn His Asn Thr Lys Asn Gln Asp Glu Glu Lys His Ile
                340                 345                 350
Lys Ala Ser Lys Glu Glu Thr Leu Thr Asp Asp Thr Lys Thr Asp Ile
                355                 360                 365
Lys Gln Asp Leu Lys Asn Glu Glu Asn Ser His Ala Lys Glu Thr Asp
        370                 375                 380
Ile Lys Glu Asp Glu Asn Leu Asp Ser Asp Ile Lys Thr His Glu Glu
385                 390                 395                 400
Asp Thr Gln Asp Thr Lys Asn Asp Ile Gln Asn Asn Glu Thr Glu Asn
                405                 410                 415
Lys Pro Asp Asn Asp Ile Lys Asn Phe Thr Pro Asn Gln Glu Lys Ile
                420                 425                 430
Lys Asp Glu Lys Gln Glu Lys Ser Lys Glu Asn Ile Lys Glu Asn Pro
        435                 440                 445
Lys Phe Tyr Glu Thr Lys Thr Glu Asn Lys Thr Ser Ile Asn Thr Asn
```

```
                450                 455                 460
Thr Asn Thr Ser Asn Pro Asn Thr Asn Thr Gln Asn Leu Asn Asn
465                 470                 475                 480

Ser Gln Asn Ile Gln Ser Asn Asn Gln Thr Met Gln Asn Ile Phe
            485                 490                 495

Lys Asn Gln Glu Phe Ile Lys Gln Asn Ile Ile Lys Asn Leu Ala Phe
            500                 505                 510

Asn Val Glu Asn Leu Asp Leu Glu Gln Val Gln Asp Leu Ser Lys Asn
            515                 520                 525

Leu Ser Asn Leu Ser Arg Arg Leu Asn Glu Ser Leu Lys Glu Leu Glu
            530                 535                 540

Pro Tyr Thr Gln Asn Ala Lys Leu Asn Gln Ala Glu Leu Lys Asn Leu
545                 550                 555                 560

Glu His Lys Leu Asn Leu Ser Thr Lys Asp Leu Ala Gln Ile Lys Pro
                565                 570                 575

Lys Thr Glu Gln Asp Ile Ala Glu Ser Leu His His Asp Val Lys Ser
            580                 585                 590

Thr Leu Leu Gln Ile Ser Asn Leu Ala Lys Asn Glu Gly Asn Glu Ala
            595                 600                 605

Ile Tyr Asn Gln Ala Asn Arg Leu Leu Ala Gln Ile Glu Ile Asn Gln
            610                 615                 620

Leu Met Ser Leu Ala Asn Asp Ser Ile Asn Thr Tyr Leu Pro Phe Ser
625                 630                 635                 640

Trp Asp Asp Leu Asn Asp Ser Lys Ile Met Phe Arg Arg Gly Lys Lys
                645                 650                 655

Asp Lys Phe Phe Ala Gln Ile Lys Leu Glu Phe Ala Lys Leu Gly Asp
            660                 665                 670

Leu Glu Ile Leu Ile Ser Leu Asn Asn Glu Lys Tyr Val Asp Ile Asn
            675                 680                 685

Ile Met Ala Glu Asn Ile Glu Phe Arg Lys Thr Ile Tyr Glu Asn Ala
            690                 695                 700

His Glu Leu Lys Arg Asn Ile Asn Lys Ala Gly Leu Leu Ser Ala Asn
705                 710                 715                 720

Phe Phe Val Gly Asp Ile Ile Arg Ser Lys Phe Asp Thr Arg Asn Met
                725                 730                 735

Lys Asn Leu Asp Leu Glu Met Gly Met Asp Lys Lys Val
            740                 745

<210> SEQ ID NO 78
<211> LENGTH: 749
<212> TYPE: PRT
<213> ORGANISM: Campylobacter jejuni

<400> SEQUENCE: 78

Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
            20                  25                  30

Asp Asn Pro Lys Glu Ala Leu Ala Gln Ala Leu Lys Gln Asn Leu Gly
        35                  40                  45

Leu Ser Lys Asp Ala Ser Ser Glu Glu Ile Leu Ala Lys Phe Val Gln
    50                  55                  60

Asn Glu Thr Gly Thr Lys Leu Lys Glu Leu Val Asn Lys Leu Leu Asp
65                  70                  75                  80
```

-continued

Gln Ile Asn Ala Gln Lys Asn Pro Asp Ser Pro Val Leu Lys Gln Gly
                     85                  90                  95

Lys Asn Leu Asn Leu Ala Pro Asn Phe Ala Asn Glu Leu Lys Thr Leu
                100                 105                 110

Ser Thr Glu Leu Ala Lys Ser Asp Thr Phe Thr Gln Val Leu Asp Arg
                115                 120                 125

Leu Asn Gln Ile Leu Lys Pro Ala Ser Glu Ile Lys Asn Asn Asn Leu
                130                 135                 140

Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
                165                 170                 175

Ser Thr Ile Lys Gly Leu Ser Ser Glu Lys Leu Ser Val Gln Ile Ala
                180                 185                 190

Gln Leu Ala Asn Thr Asn Leu Ser Pro Lys Asp Thr Leu Lys Glu Leu
                195                 200                 205

Lys Asn Ile Ile Asn Ser Ser Lys Ile Glu Asn Lys Gln Ile Leu Asn
                210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser His Ala Gln Glu Lys Ile
                245                 250                 255

Thr Pro Ile Ala Asn Lys Ile Leu Lys Glu Leu Asn Ser Ile Lys Asn
                260                 265                 270

Asp Phe Phe Lys Ala Leu Asn Lys Pro Glu Asn Leu Met Ile Lys Asp
                275                 280                 285

Pro Asn Ile Leu Lys Gln Thr Ala Thr Ala Phe Glu Lys Leu Glu Asn
290                 295                 300

Thr Leu Lys Asn Ile Leu Gly Asn Gln Ala Ser Lys Ile Gln Asp Lys
305                 310                 315                 320

Glu Asn Ile Leu Glu Asn Leu Leu Ser Asn Lys Glu Asn Met Lys Glu
                325                 330                 335

Glu Lys Leu Asn His Asn Thr Lys Asn Gln Asp Glu Glu Lys His Ile
                340                 345                 350

Lys Ala Ser Lys Glu Glu Thr Leu Thr Asp Asp Thr Lys Thr Asp Ile
                355                 360                 365

Lys Gln Asp Leu Lys Asn Glu Glu Asn Ser His Ala Lys Glu Thr Asp
                370                 375                 380

Ile Lys Glu Asp Glu Asn Leu Asp Ser Asp Ile Lys Thr His Glu Glu
385                 390                 395                 400

Asp Thr Gln Asp Thr Lys Asn Asp Ile Gln Asn Asn Glu Thr Glu Asn
                405                 410                 415

Lys Pro Asp Asn Asp Ile Lys Asn Phe Ala Pro Asn Gln Glu Lys Ile
                420                 425                 430

Lys Asp Glu Lys Gln Glu Lys Ser Lys Glu Asn Ile Lys Glu Asn Pro
                435                 440                 445

Lys Phe Tyr Glu Thr Lys Thr Glu Asn Lys Thr Ser Ile Asn Thr Asn
                450                 455                 460

Thr Asn Thr Ser Asn Pro Asn Thr Asn Thr Gln Asn Leu Asn Asn
465                 470                 475                 480

Ser Gln Asn Ile Gln Ser Asn Asn Gln Thr Met Gln Asn Ile Phe
                485                 490                 495

Lys Asn Gln Glu Phe Ile Lys Gln Asn Ile Ile Lys Asn Leu Ala Phe 500                 505                 510
Asn Val Glu Asn Leu Asp Leu Glu Gln Val Gln Asp Leu Ser Lys Asn
            515                 520                 525

Leu Ser Asn Leu Ser Arg Arg Leu Asn Glu Ser Leu Lys Glu Leu Glu
        530                 535                 540

Pro Tyr Thr Gln Asn Ala Lys Leu Asn Gln Ala Glu Leu Lys Asn Leu
545                 550                 555                 560

Glu His Lys Leu Asn Leu Ser Thr Lys Asp Leu Ala Gln Ile Lys Pro
                565                 570                 575

Lys Thr Glu Gln Asp Ile Ala Glu Ser Leu His His Asp Val Lys Ser
            580                 585                 590

Thr Leu Leu Gln Ile Ser Asn Leu Ala Lys Asn Glu Gly Asn Glu Ala
        595                 600                 605

Ile Tyr Asn Gln Ala Asn Arg Leu Leu Ala Gln Ile Glu Ile Asn Gln
610                 615                 620

Leu Met Ser Leu Ala Asn Asp Ser Ile Asn Thr Tyr Leu Pro Phe Ser
625                 630                 635                 640

Trp Asp Asp Leu Asn Asp Ser Lys Ile Met Phe Arg Arg Gly Lys Lys
                645                 650                 655

Asp Lys Phe Phe Ala Gln Ile Lys Leu Glu Phe Ala Lys Leu Gly Asp
            660                 665                 670

Leu Glu Ile Leu Ile Ser Leu Asn Asn Glu Lys Tyr Val Asp Ile Asn
        675                 680                 685

Ile Met Ala Glu Asn Ile Glu Phe Arg Lys Thr Ile Tyr Glu Asn Ala
690                 695                 700

His Glu Leu Lys Arg Asn Ile Asn Lys Ala Gly Leu Leu Ser Ala Asn
705                 710                 715                 720

Phe Phe Val Gly Asp Ile Ile Arg Ser Lys Phe Asp Thr Arg Asn Met
                725                 730                 735

Lys Asn Leu Asp Leu Glu Met Gly Met Asp Lys Lys Val
            740                 745

<210> SEQ ID NO 79
<211> LENGTH: 749
<212> TYPE: PRT
<213> ORGANISM: Campylobacter jejuni

<400> SEQUENCE: 79

Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
            20                  25                  30

Asp Asn Pro Lys Glu Ala Leu Ala Gln Ala Leu Lys Gln Asn Leu Gly
        35                  40                  45

Leu Ser Lys Asp Ala Ser Ser Glu Glu Ile Leu Ala Lys Phe Val Gln
    50                  55                  60

Asn Glu Thr Gly Thr Lys Leu Lys Glu Leu Val Asn Lys Leu Leu Asp
65                  70                  75                  80

Gln Ile Asn Ala Gln Lys Asn Pro Asp Ser Pro Val Leu Lys Gln Gly
                85                  90                  95

Lys Asn Leu Asn Leu Ala Pro Asn Phe Ala Asn Glu Leu Lys Thr Leu
            100                 105                 110

Ser Thr Glu Leu Ala Lys Ser Asp Thr Phe Thr Gln Val Leu Asp Arg
        115                 120                 125

```
Leu Asn Gln Ile Leu Lys Pro Ala Ser Glu Ile Lys Asn Asn Asn Leu
    130                 135                 140

Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
                165                 170                 175

Ser Thr Ile Lys Gly Leu Ser Ser Glu Lys Leu Ser Val Gln Ile Ala
                180                 185                 190

Gln Leu Ala Asn Thr Asn Leu Ser Pro Lys Asp Thr Leu Lys Glu Leu
            195                 200                 205

Lys Asn Ile Ile Asn Ser Ser Lys Ile Glu Asn Lys Gln Ile Leu Asn
    210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser His Ala Gln Glu Lys Ile
                245                 250                 255

Thr Pro Ile Ala Asn Lys Ile Leu Lys Glu Leu Asn Ser Ile Lys Asn
                260                 265                 270

Asp Phe Phe Lys Ala Leu Asn Lys Pro Glu Asn Leu Met Ile Lys Asp
            275                 280                 285

Pro Asn Ile Leu Lys Gln Thr Ala Thr Ala Phe Glu Lys Leu Glu Asn
290                 295                 300

Thr Leu Lys Asn Ile Leu Gly Asn Gln Ala Ser Lys Ile Gln Asp Lys
305                 310                 315                 320

Glu Asn Ile Leu Glu Asn Leu Leu Ser Asn Lys Glu Asn Met Lys Glu
                325                 330                 335

Glu Lys Leu Asn His Asn Thr Lys Asn Gln Asp Glu Lys His Ile
            340                 345                 350

Lys Ala Ser Lys Glu Glu Thr Leu Thr Asp Asp Thr Lys Thr Asp Ile
            355                 360                 365

Lys Gln Asp Leu Lys Asn Glu Glu Asn Ser His Ala Lys Glu Thr Asp
    370                 375                 380

Ile Lys Glu Asp Glu Asn Leu Asp Ser Asp Ile Lys Thr His Glu Glu
385                 390                 395                 400

Asp Thr Gln Asp Thr Lys Asn Asp Ile Gln Asn Asn Glu Thr Glu Asn
                405                 410                 415

Lys Pro Asp Asn Asp Ile Lys Asn Phe Thr Pro Asn Gln Glu Lys Ile
                420                 425                 430

Lys Asp Glu Lys Gln Glu Lys Ser Lys Glu Asn Ile Lys Glu Asn Pro
            435                 440                 445

Lys Phe Tyr Glu Thr Lys Thr Glu Asn Lys Thr Ser Ile Asn Thr Asn
    450                 455                 460

Thr Asn Thr Ser Asn Pro Asn Thr Asn Asn Thr Gln Asn Leu Asn Asn
465                 470                 475                 480

Ser Gln Asn Ile Gln Ser Asn Asn Gln Thr Met Gln Asn Ile Phe
            485                 490                 495

Lys Asn Gln Glu Phe Ile Lys Gln Asn Ile Ile Lys Asn Leu Ala Phe
                500                 505                 510

Asn Val Glu Asn Leu Asp Leu Glu Gln Val Gln Asp Leu Ser Lys Asn
            515                 520                 525

Leu Ser Asn Leu Ser Arg Arg Leu Asn Glu Ser Leu Lys Glu Leu Glu
530                 535                 540

Pro Tyr Thr Gln Asn Ala Lys Leu Asn Gln Ala Glu Leu Lys Asn Leu
```

-continued

```
            545                 550                 555                 560
        Glu His Lys Leu Asn Leu Ser Thr Lys Asp Leu Ala Gln Ile Lys Pro
                        565                 570                 575
        Lys Thr Glu Gln Asp Ile Ala Glu Ser Leu His His Asp Val Lys Ser
                        580                 585                 590
        Thr Leu Leu Gln Ile Ser Asn Leu Ala Lys Asn Glu Gly Asn Glu Ala
                        595                 600                 605
        Ile Tyr Asn Gln Ala Asn Arg Leu Leu Ala Gln Ile Glu Ile Asn Gln
                        610                 615                 620
        Leu Met Ser Leu Ala Asn Asp Ser Ile Asn Thr Tyr Leu Pro Phe Ser
        625                 630                 635                 640
        Trp Asp Asp Leu Asn Asp Ser Lys Ile Met Phe Arg Arg Gly Lys Lys
                            645                 650                 655
        Asp Lys Phe Phe Ala Gln Ile Lys Leu Glu Phe Ala Lys Leu Gly Asp
                        660                 665                 670
        Leu Glu Ile Leu Ile Ser Leu Asn Asn Glu Lys Tyr Ile Asp Ile Asn
                        675                 680                 685
        Ile Met Ala Glu Asn Ile Glu Phe Arg Lys Thr Ile Tyr Glu Asn Ala
                        690                 695                 700
        His Glu Leu Lys Arg Asn Ile Asn Lys Ala Gly Leu Leu Ser Ala Asn
        705                 710                 715                 720
        Phe Phe Val Gly Asp Ile Ile Arg Ser Lys Phe Asp Thr Arg Asn Met
                            725                 730                 735
        Lys Asn Leu Asp Leu Glu Met Gly Met Asp Lys Lys Val
                        740                 745
```

<210> SEQ ID NO 80
<211> LENGTH: 749
<212> TYPE: PRT
<213> ORGANISM: Campylobacter jejuni

<400> SEQUENCE: 80

```
        Met Ile Asn Thr Gln Leu Ala Ser Gln Ile Ala Asn Thr Gln Lys Asn
        1                   5                   10                  15
        Asp Leu Lys Val Asp Asn Ser Thr Ser Lys Asp Lys Thr Asn Leu Lys
                        20                  25                  30
        Asp Asn Pro Lys Glu Ala Leu Ala Gln Ala Leu Lys Gln Asn Leu Gly
                        35                  40                  45
        Leu Ser Lys Asp Ala Ser Ser Glu Ile Leu Ala Lys Phe Ile Gln
                50                  55                  60
        Asn Glu Thr Gly Thr Lys Leu Lys Glu Leu Val Asn Lys Leu Leu Asp
        65                  70                  75                  80
        Gln Ile Asn Ala Gln Lys Asn Pro Asp Ser Pro Ile Leu Lys Gln Gly
                        85                  90                  95
        Lys Asn Leu Asn Leu Ala Pro Asn Phe Ala Asn Glu Leu Lys Thr Leu
                        100                 105                 110
        Ser Thr Glu Leu Ala Lys Ser Asp Thr Phe Thr Gln Val Leu Asp Arg
                        115                 120                 125
        Leu Asn Gln Ile Leu Lys Pro Ala Ser Glu Ile Lys Asn Asn Asn Leu
                        130                 135                 140
        Ala Pro Leu Phe Lys Asn Ser Gly Val Phe Leu Glu Ala Lys Leu Lys
        145                 150                 155                 160
        Asp Ala Leu Asn Glu Glu Leu Leu Pro Lys Ser Phe His Ser Leu Leu
                        165                 170                 175
```

```
Ser Thr Ile Lys Gly Leu Ser Ser Glu Lys Leu Ser Val Gln Ile Ala
            180                 185                 190

Gln Leu Ala Asn Thr Asn Leu Ser Pro Lys Asp Thr Leu Lys Glu Leu
        195                 200                 205

Lys Asn Ile Ile Asn Ser Ser Lys Asn Glu Asn Lys Gln Ile Leu Asn
    210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser His Ala Gln Glu Lys Ile
            245                 250                 255

Thr Pro Ile Ala Asn Lys Ile Leu Lys Glu Leu Asn Ser Ile Lys Asn
            260                 265                 270

Asp Phe Phe Lys Ala Leu Asn Lys Pro Glu Asn Leu Met Ile Lys Asp
            275                 280                 285

Pro Asn Ile Leu Lys Gln Thr Ala Thr Ala Phe Glu Lys Leu Glu Asn
            290                 295                 300

Thr Leu Lys Asn Ile Leu Gly Asn Gln Ala Ser Lys Ile Gln Asp Lys
305                 310                 315                 320

Glu Asn Ile Leu Glu Asn Leu Leu Ser Asn Lys Glu Asn Met Lys Glu
            325                 330                 335

Glu Lys Leu Asn His Asn Thr Lys Asn Gln Asp Glu Lys His Ile
            340                 345                 350

Lys Ala Ser Lys Glu Glu Thr Leu Thr Asp Asp Thr Lys Thr Asp Ile
            355                 360                 365

Lys Gln Asp Ser Lys Asn Glu Glu Asn Ser His Ala Lys Glu Thr Asp
            370                 375                 380

Ile Lys Glu Asp Glu Asn Leu Asp Ser Asp Ile Lys Thr His Glu Glu
385                 390                 395                 400

Asp Thr Gln Asp Thr Lys Asn Asp Ile Gln Asn Asn Glu Thr Glu Asn
            405                 410                 415

Lys Pro Asp Asn Asp Ile Lys Asn Ser Thr Pro Asn Gln Glu Lys Ile
            420                 425                 430

Lys Asp Gly Lys Gln Glu Lys Ser Lys Glu Asn Ile Lys Glu Asn Pro
            435                 440                 445

Lys Phe Tyr Glu Thr Lys Thr Glu Asn Lys Thr Ser Ile Asn Thr Asn
            450                 455                 460

Thr Asn Thr Ser Asn Pro Asn Thr Asn Asn Thr Gln Asn Leu Asn Asn
465                 470                 475                 480

Ser Gln Asn Ile Gln Ser Asn Asn Gln Thr Met Gln Asn Ile Phe
            485                 490                 495

Lys Asn Gln Glu Phe Ile Lys Gln Asn Ile Val Lys Asn Leu Ala Phe
            500                 505                 510

Asn Val Glu Asn Leu Asp Leu Glu Gln Val Gln Asp Leu Ser Lys Asn
            515                 520                 525

Leu Ser Asn Leu Ser Arg Arg Leu Asn Glu Ser Leu Lys Glu Leu Glu
            530                 535                 540

Pro Tyr Thr Gln Asn Ala Lys Leu Asn Gln Ala Glu Leu Lys Asn Leu
545                 550                 555                 560

Glu His Lys Leu Asn Leu Ser Thr Lys Asp Leu Ala Gln Ile Lys Pro
            565                 570                 575

Lys Thr Glu Gln Asp Ile Ala Glu Ser Leu His His Asp Val Lys Ser
            580                 585                 590

Thr Leu Leu Gln Ile Ser Asn Leu Ala Lys Asn Glu Gly Asn Glu Ala
```

```
            595                 600                 605
Ile Tyr Asn Gln Ala Asn Arg Leu Leu Ala Gln Ile Glu Ile Asn Gln
    610                 615                 620

Leu Met Ser Leu Ala Asn Asp Ser Ile Asn Thr Tyr Leu Pro Phe Ser
625                 630                 635                 640

Trp Asp Asp Leu Asn Asp Ser Lys Ile Met Phe Arg Arg Gly Lys Lys
                645                 650                 655

Asp Lys Phe Phe Ala Gln Ile Lys Leu Lys Phe Ala Lys Leu Gly Asp
            660                 665                 670

Leu Glu Ile Leu Ile Ser Leu Asn Asn Glu Lys Tyr Ile Asp Ile Asn
        675                 680                 685

Ile Met Ala Glu Asn Ile Glu Phe Arg Lys Thr Ile Tyr Glu Asn Ala
    690                 695                 700

His Glu Leu Lys Arg Asn Ile Asn Lys Ala Gly Leu Leu Ser Ala Asn
705                 710                 715                 720

Phe Phe Val Gly Asp Ile Ile Arg Ser Lys Phe Asp Thr Arg Asn Met
                725                 730                 735

Lys Asn Leu Asp Leu Glu Met Gly Met Asp Lys Lys Val
            740                 745

<210> SEQ ID NO 81
<211> LENGTH: 698
<212> TYPE: PRT
<213> ORGANISM: Campylobacter jejuni

<400> SEQUENCE: 81

Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
            20                  25                  30

Asp Asn Pro Lys Glu Ala Leu Ala Gln Ala Leu Lys Gln Asn Leu Gly
        35                  40                  45

Leu Ser Lys Asp Thr Ser Ser Glu Glu Ile Leu Ala Lys Phe Val Gln
    50                  55                  60

Asn Glu Thr Gly Ala Lys Leu Lys Glu Leu Val Asn Lys Leu Leu Asp
65                  70                  75                  80

Gln Ile Asn Ala Gln Lys Asn Pro Asp Ser Pro Val Leu Lys Gln Gly
                85                  90                  95

Lys Asn Leu Asn Leu Ala Pro Asn Phe Ala Asn Glu Leu Lys Thr Leu
            100                 105                 110

Ser Thr Glu Leu Ala Lys Ser Asp Thr Phe Thr Gln Val Leu Asp Arg
        115                 120                 125

Leu Asn Gln Ile Leu Lys Pro Ala Ser Glu Ile Lys Asn Asn Asn Leu
    130                 135                 140

Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
                165                 170                 175

Ser Thr Ile Lys Gly Leu Ser Ser Glu Lys Leu Ser Val Gln Ile Ala
            180                 185                 190

Gln Leu Ala Asn Thr Asn Leu Ser Pro Lys Asp Thr Leu Lys Glu Leu
        195                 200                 205

Lys Asn Ile Ile Asn Ser Ser Lys Asn Glu Asn Lys Gln Ile Leu Asn
    210                 215                 220
```

```
Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser His Ala Gln Glu Lys Ile
            245                 250                 255

Thr Pro Ile Ala Asn Lys Ile Leu Lys Glu Leu Asn Ser Val Lys Asn
                260                 265                 270

Asp Phe Phe Lys Ala Leu Asn Lys Pro Glu Asn Leu Met Ile Lys Asp
            275                 280                 285

Pro Asn Ile Leu Lys Gln Thr Ala Thr Ala Phe Glu Lys Leu Glu Asn
290                 295                 300

Thr Leu Lys Asn Ile Leu Gly Asn Gln Ala Ser Lys Ile Gln Asp Lys
305                 310                 315                 320

Glu Asn Ile Leu Glu Asn Leu Leu Ser Asn Lys Glu Asn Ile Lys Glu
                325                 330                 335

Glu Lys Leu Asn His Asn Thr Lys Asn Gln Asp Glu Glu Lys His Ile
                340                 345                 350

Lys Val Ser Lys Glu Glu Thr Leu Ala Asp Asp Ala Lys Thr Asn Ile
            355                 360                 365

Lys Gln Asp Val Lys Asn Glu Glu Asn Leu Pro Lys Lys Glu Val Asn
370                 375                 380

Ala Asn Leu Asp Ser Ser Thr Lys Thr His Glu Glu Ser Ile Lys Glu
385                 390                 395                 400

Asn Pro Lys Phe Tyr Glu Thr Lys Thr Glu Ser Lys Thr Ser Ile Asn
                405                 410                 415

Thr Asn Thr Asn Thr Asn Asn Thr Gln Asn Leu Asn Asn Ser Gln Asn
                420                 425                 430

Ile Gln Ser Asn Asn Asn Gln Thr Met Gln Asn Ile Phe Lys Asn Gln
            435                 440                 445

Glu Phe Ile Lys Gln Asn Ile Val Lys Asn Leu Ala Phe Asn Val Glu
    450                 455                 460

Asn Leu Asp Leu Glu Gln Val Gln Asp Leu Ser Lys Asn Leu Ser Asn
465                 470                 475                 480

Leu Ser Arg Arg Leu Asn Glu Ser Leu Lys Glu Leu Glu Pro Tyr Thr
                485                 490                 495

Gln Asn Ala Lys Leu Asn Gln Ala Glu Leu Lys Asn Leu Glu His Lys
                500                 505                 510

Leu Asn Leu Ser Ile Lys Asp Leu Val Gln Ile Lys Pro Lys Thr Glu
            515                 520                 525

Gln Asp Ile Ala Glu Ser Leu His His Asp Val Lys Ser Thr Leu Leu
530                 535                 540

Gln Ile Ser Asn Leu Ala Lys Asn Glu Gly Asn Glu Ala Val Tyr Asn
545                 550                 555                 560

Gln Ala Asn Arg Leu Leu Ala Gln Ile Glu Ile Asn Gln Leu Met Ser
                565                 570                 575

Leu Ala Asn Asp Ser Ile Asn Thr Tyr Leu Pro Phe Ser Trp Asp Asp
                580                 585                 590

Leu Asn Asp Ser Lys Ile Met Phe Arg Arg Gly Lys Lys Asp Lys Phe
                595                 600                 605

Phe Ala Gln Ile Lys Leu Glu Phe Ala Lys Leu Gly Asp Leu Glu Ile
                610                 615                 620

Leu Ile Ser Leu Asn Asn Glu Lys Tyr Ile Asp Ile Asn Ile Met Ala
625                 630                 635                 640

Glu Asn Ile Glu Phe Arg Lys Thr Ile Tyr Glu Asn Ala His Glu Leu
```

```
                    645                 650                 655
Lys Arg Asn Ile Asn Lys Ala Gly Leu Leu Ser Ala Asn Phe Phe Val
                660                 665                 670

Gly Asp Ile Ile Arg Ser Lys Phe Asp Thr Arg Asn Met Lys Asn Leu
                675                 680                 685

Asp Leu Glu Met Gly Met Asp Lys Lys Val
                690                 695

<210> SEQ ID NO 82
<211> LENGTH: 698
<212> TYPE: PRT
<213> ORGANISM: Campylobacter jejuni

<400> SEQUENCE: 82

Met Ile Asn Thr Gln Leu Ala Ser Gln Ile Ala Asn Thr Gln Lys Asn
1               5                   10                  15

Asp Leu Lys Val Asp Asn Ser Ala Ser Lys Asp Lys Thr Asn Leu Lys
                20                  25                  30

Asp Asn Pro Lys Glu Ala Leu Ala Gln Ala Leu Lys Gln Asn Leu Gly
            35                  40                  45

Leu Ser Lys Asp Ala Ser Ser Glu Glu Ile Leu Ala Lys Phe Val Gln
    50                  55                  60

Asn Glu Thr Gly Thr Lys Leu Lys Glu Leu Val Asn Lys Leu Leu Asp
65                  70                  75                  80

Gln Ile Asn Ala Gln Lys Asn Pro Asp Ser Pro Val Leu Lys Gln Gly
                85                  90                  95

Lys Asn Leu Asn Leu Ala Pro Asn Phe Ala Asn Glu Leu Lys Ile Leu
            100                 105                 110

Ser Thr Glu Leu Ala Lys Ser Asp Thr Phe Thr Gln Val Leu Asp Arg
        115                 120                 125

Leu Asn Gln Ile Leu Lys Pro Ala Ser Glu Ile Lys Asn Asn Asn Leu
    130                 135                 140

Ala Pro Leu Phe Lys Asn Ser Gly Val Phe Leu Glu Ala Lys Leu Lys
145                 150                 155                 160

Asp Ala Leu Asn Glu Glu Leu Leu Pro Lys Ser Phe His Ser Leu Leu
                165                 170                 175

Ser Thr Ile Lys Gly Leu Ser Ser Glu Lys Leu Ser Val Gln Ile Ala
            180                 185                 190

Gln Leu Ala Asn Thr Ile Leu Ser Pro Lys Asp Thr Leu Lys Glu Leu
        195                 200                 205

Lys Asn Ile Ile Asn Ser Ser Lys Asn Glu Asn Lys Gln Ile Leu Asn
    210                 215                 220

Gln Ser Ser Phe Lys Ala Leu Leu Asn Leu Ser Ser Lys Leu Glu Asn
225                 230                 235                 240

Phe Lys Asn Tyr Ile Ser Lys Asn Pro Ser His Ala Gln Glu Lys Ile
                245                 250                 255

Thr Pro Ile Ala Asn Lys Ile Leu Glu Leu Asn Ser Ile Lys Asn
            260                 265                 270

Asp Phe Phe Lys Ala Leu Asn Lys Pro Glu Asn Leu Met Ile Lys Asp
        275                 280                 285

Pro Asn Ile Leu Lys Gln Thr Ala Thr Ala Phe Glu Lys Leu Glu Asn
    290                 295                 300

Thr Leu Lys Asn Ile Leu Gly Asn Gln Ala Ser Lys Ile Gln Asp Lys
305                 310                 315                 320
```

```
Glu Asn Ile Leu Glu Asn Leu Leu Ser Asn Lys Glu Asn Ile Lys Glu
                325                 330                 335

Glu Lys Leu Asn His Asn Thr Lys Asn Gln Asp Glu Glu Lys Tyr Ile
            340                 345                 350

Lys Val Ser Lys Glu Glu Thr Leu Ala Asp Asp Ala Lys Thr Asn Ile
        355                 360                 365

Lys Gln Asp Val Lys Asn Glu Glu Asn Leu Pro Lys Lys Glu Val Asn
    370                 375                 380

Ala Asn Leu Asp Ser Ser Thr Lys Thr His Glu Glu Asn Ile Lys Glu
385                 390                 395                 400

Asn Pro Lys Phe Tyr Glu Thr Lys Thr Glu Ser Lys Thr Ser Ile Asn
                405                 410                 415

Thr Asn Thr Asn Thr Asn Asn Thr Gln Asn Leu Asn Asn Ser Gln Asn
            420                 425                 430

Ile Gln Ser Asn Asn Asn Gln Thr Met Gln Asn Ile Phe Lys Asn Gln
        435                 440                 445

Glu Phe Ile Lys Gln Asn Ile Val Lys Asn Leu Ala Phe Asn Val Glu
    450                 455                 460

Asn Leu Asp Leu Glu Gln Val Gln Asp Leu Ser Lys Asn Leu Ser Asn
465                 470                 475                 480

Leu Ser Arg Arg Leu Asn Glu Ser Leu Lys Glu Leu Glu Pro Tyr Thr
                485                 490                 495

Gln Asn Ala Lys Leu Asn Ala Glu Leu Lys Asn Leu Glu His Lys
            500                 505                 510

Leu Asn Leu Ser Ile Lys Asp Leu Val Gln Ile Lys Pro Lys Thr Glu
        515                 520                 525

Gln Asp Ile Ala Glu Ser Leu His His Asp Val Lys Ser Thr Leu Leu
    530                 535                 540

Gln Ile Ser Asn Leu Ala Lys Asn Glu Gly Asn Glu Ala Val Tyr Asn
545                 550                 555                 560

Gln Ala Asn Arg Leu Leu Ala Gln Ile Glu Ile Asn Gln Leu Met Ser
                565                 570                 575

Leu Ala Asn Asp Ser Ile Asn Thr Tyr Leu Pro Phe Ser Trp Asp Asp
            580                 585                 590

Leu Asn Asp Ser Lys Ile Met Phe Arg Arg Gly Lys Lys Asp Lys Phe
        595                 600                 605

Phe Ala Gln Ile Lys Leu Glu Phe Ala Lys Leu Gly Asp Leu Glu Ile
    610                 615                 620

Leu Ile Ser Leu Asn Asn Glu Lys Tyr Ile Asp Ile Asn Ile Met Ala
625                 630                 635                 640

Glu Asn Ile Glu Phe Arg Lys Thr Ile Tyr Glu Asn Ala His Glu Leu
                645                 650                 655

Lys Arg Asn Ile Asn Lys Ala Gly Leu Leu Ser Ala Asn Phe Phe Val
            660                 665                 670

Gly Asp Ile Ile Arg Ser Lys Phe Asp Thr Arg Asn Met Lys Asn Leu
        675                 680                 685

Asp Leu Glu Met Gly Met Asp Lys Lys Val
    690                 695
```

<210> SEQ ID NO 83
<211> LENGTH: 253
<212> TYPE: PRT
<213> ORGANISM: Campylobacter jejuni

<400> SEQUENCE: 83

Met Arg Phe Asp Phe Val Ser Lys Arg Leu Asn Ile Ser Arg Asn
1               5                   10                  15

Lys Ala Leu Glu Leu Ile Glu Asn Glu Ile Leu Leu Asn Gly Lys
            20                  25                  30

Ser Phe Lys Ala Ser Phe Asp Val Lys Asn Phe Leu Glu Asn Leu Lys
        35                  40                  45

Lys Thr Gln Asp Leu Asn Pro Glu Asp Ile Leu Leu Ala Asn Glu Leu
50                  55                  60

Lys Leu Asp Leu Leu Ser Glu Ile Tyr Val Ser Arg Ala Ala Leu Lys
65                  70                  75                  80

Leu Lys Lys Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
        115                 120                 125

Leu His Pro Ser Leu Arg Val Asn Glu Lys Ile Ile Leu His Glu Asn
        130                 135                 140

Thr Asp Leu Arg Ala Phe Lys Ser Glu Glu Lys Phe Glu Leu Val Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Gly Val Leu Lys Asp Asp
        195                 200                 205

Lys Ala Ile Leu Lys Ala Arg Met Asp Phe Lys Ala Cys Ala Lys
210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
            245                 250

<210> SEQ ID NO 84
<211> LENGTH: 253
<212> TYPE: PRT
<213> ORGANISM: Campylobacter jejuni

<400> SEQUENCE: 84

Met Arg Phe Asp Phe Val Ser Lys Arg Leu Asn Ile Ser Arg Asn
1               5                   10                  15

Lys Ala Leu Glu Leu Ile Glu Asn Glu Ile Leu Leu Asn Gly Lys
            20                  25                  30

Ser Phe Lys Ala Ser Phe Asp Val Lys Asn Phe Leu Glu Asn Leu Lys
        35                  40                  45

Lys Thr Gln Asp Leu Asn Pro Glu Asp Ile Leu Leu Ala Asn Glu Leu
50                  55                  60

Lys Leu Asp Leu Leu Ser Glu Ile Tyr Val Ser Arg Ala Ala Leu Lys
65                  70                  75                  80

Leu Lys Lys Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln

```
                115                 120                 125
Leu His Pro Ser Leu Arg Val Asn Glu Lys Ile Ile Leu His Glu Asn
        130                 135                 140

Thr Asp Leu Arg Ala Phe Lys Ser Glu Glu Lys Phe Glu Leu Val Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Ala Cys Ala Lys
    210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Phe Lys Asn
                245                 250
```

<210> SEQ ID NO 85
<211> LENGTH: 253
<212> TYPE: PRT
<213> ORGANISM: Campylobacter jejuni

<400> SEQUENCE: 85

```
Met Arg Phe Asp Phe Phe Val Ser Lys Arg Leu Asn Ile Ser Arg Asn
1               5                   10                  15

Lys Ala Leu Glu Leu Ile Glu Asn Glu Ile Leu Leu Asn Gly Lys
            20                  25                  30

Ser Phe Lys Ala Ser Phe Asp Val Lys Asn Phe Leu Glu Asn Leu Lys
        35                  40                  45

Lys Thr Gln Asp Leu Asn Pro Glu Asp Ile Leu Leu Ala Asn Glu Leu
    50                  55                  60

Lys Leu Asp Leu Leu Ser Glu Ile Tyr Val Ser Arg Ala Ala Leu Lys
65                  70                  75                  80

Leu Lys Lys Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
        115                 120                 125

Leu His Pro Ser Leu Arg Ala Asn Glu Lys Ile Ile Leu His Glu Asn
    130                 135                 140

Thr Asp Leu Arg Ala Phe Lys Ser Glu Glu Lys Phe Glu Leu Val Thr
145                 150                 155                 160

Cys Asp Val Ser Phe Ile Ser Leu Ile Asn Leu Leu Tyr Tyr Val Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Glu Cys Ala Lys
    210                 215                 220

Leu Gly Trp Leu Leu Lys Asn Thr Gln Lys Ser Ser Ile Lys Gly Lys
225                 230                 235                 240
```

Glu Gly Asn Val Glu Tyr Phe Tyr Tyr Tyr Ile Lys Asn
            245                 250

<210> SEQ ID NO 86
<211> LENGTH: 253
<212> TYPE: PRT
<213> ORGANISM: Campylobacter jejuni

<400> SEQUENCE: 86

Met Arg Phe Asp Phe Phe Val Ser Lys Arg Leu Asn Ile Ser Arg Asn
1               5                   10                  15

Lys Ala Leu Glu Leu Ile Glu Asn Glu Glu Ile Leu Leu Asn Gly Lys
            20                  25                  30

Ser Phe Lys Ala Ser Phe Asp Val Lys Asn Phe Leu Glu Asn Leu Lys
        35                  40                  45

Lys Thr Gln Asp Leu Asn Pro Glu Asp Ile Leu Leu Ala Asn Glu Leu
    50                  55                  60

Lys Leu Asp Leu Leu Ser Glu Ile Tyr Val Ser Arg Ala Ala Leu Lys
65                  70                  75                  80

Leu Lys Lys Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
        115                 120                 125

Leu His Pro Ser Leu Arg Ala Asn Glu Lys Ile Ile Leu His Glu Asn
    130                 135                 140

Thr Asp Leu Arg Ala Phe Lys Ser Lys Glu Lys Phe Glu Leu Val Thr
145                 150                 155                 160

Cys Asp Val Ser Phe Ile Ser Leu Ile Asn Leu Leu Tyr Tyr Val Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Glu Cys Ala Lys
    210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
            245                 250

<210> SEQ ID NO 87
<211> LENGTH: 253
<212> TYPE: PRT
<213> ORGANISM: Campylobacter jejuni

<400> SEQUENCE: 87

Met Arg Phe Asp Phe Phe Val Ser Lys Arg Leu Asn Ile Ser Arg Asn
1               5                   10                  15

Lys Ala Leu Glu Leu Ile Glu Asn Glu Glu Ile Leu Leu Asn Gly Lys
            20                  25                  30

Ser Phe Lys Ala Ser Phe Asp Val Lys Asn Phe Leu Glu Asn Leu Lys
        35                  40                  45

Lys Thr Gln Asp Leu Asn Pro Glu Asp Ile Leu Leu Ala Asn Glu Leu
    50                  55                  60

```
Lys Leu Asp Leu Leu Ser Glu Ile Tyr Val Ser Arg Ala Ala Leu Lys
 65                  70                  75                  80

Leu Lys Lys Phe Leu Glu Glu Asn Asp Ile Glu Ile Lys His Lys Asn
             85                   90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
            115                 120                 125

Leu His Pro Ser Leu Arg Ala Asn Glu Lys Ile Ile Leu His Glu Asn
            130                 135                 140

Thr Asp Leu Arg Ala Phe Lys Ser Glu Glu Lys Phe Glu Leu Val Thr
145                 150                 155                 160

Cys Asp Val Ser Phe Ile Ser Leu Ile Asn Leu Leu Tyr Tyr Val Asp
            165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
            195                 200                 205

Lys Ala Ile Leu Lys Ala Arg Met Asp Phe Glu Lys Glu Cys Ala Lys
210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Phe Lys Asn
            245                 250

<210> SEQ ID NO 88
<211> LENGTH: 253
<212> TYPE: PRT
<213> ORGANISM: Campylobacter jejuni

<400> SEQUENCE: 88

Met Arg Phe Asp Phe Phe Val Ser Lys Arg Leu Asn Ile Ser Arg Asn
 1               5                  10                  15

Lys Ala Leu Glu Leu Ile Glu Asn Glu Glu Ile Leu Leu Asn Gly Lys
             20                  25                  30

Ser Phe Lys Ala Ser Phe Asp Val Lys Asn Phe Leu Glu Asn Leu Lys
         35                  40                  45

Lys Thr Gln Asp Leu Asn Pro Glu Asp Ile Leu Leu Ala Asn Glu Leu
 50                  55                  60

Lys Leu Asp Leu Leu Ser Glu Ile Tyr Val Ser Arg Ala Ala Leu Lys
 65                  70                  75                  80

Leu Lys Lys Phe Leu Glu Glu Asn Asp Ile Glu Ile Lys His Lys Asn
             85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
            115                 120                 125

Leu His Pro Ser Leu Arg Ala Asn Glu Lys Ile Ile Leu His Glu Asn
            130                 135                 140

Thr Asp Leu Arg Ala Phe Lys Ser Glu Glu Lys Phe Glu Leu Val Thr
145                 150                 155                 160

Cys Asp Val Ser Phe Ile Ser Leu Ile Asn Leu Leu Tyr Tyr Val Asp
            165                 170                 175

Asn Leu Ala Leu Lys Glu Ile Ile Leu Leu Phe Lys Pro Gln Phe Glu
            180                 185                 190
```

```
Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Glu Cys Ala Lys
    210                 215                 220

Leu Ser Trp Leu Leu Lys Asn Thr Gln Lys Ser Ser Ile Lys Gly Lys
225                 230                 235                 240

Glu Gly Asn Val Glu Tyr Phe Tyr Tyr Ile Lys Asn
                245                 250
```

<210> SEQ ID NO 89
<211> LENGTH: 253
<212> TYPE: PRT
<213> ORGANISM: Campylobacter jejuni

<400> SEQUENCE: 89

```
Met Arg Phe Asp Phe Phe Val Ser Lys Arg Leu Asn Ile Ser Arg Asn
1               5                   10                  15

Lys Ala Leu Glu Leu Ile Glu Asn Glu Ile Leu Leu Asn Gly Lys
            20                  25                  30

Ser Phe Lys Ala Ser Phe Asp Val Lys Asn Phe Leu Glu Asn Leu Lys
        35                  40                  45

Lys Thr Gln Asp Leu Asn Pro Glu Asp Ile Leu Leu Ala Asn Glu Leu
    50                  55                  60

Lys Leu Asp Leu Leu Ser Glu Ile Tyr Val Ser Arg Ala Ala Leu Lys
65                  70                  75                  80

Leu Lys Asn Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
        115                 120                 125

Leu His Ser Ser Leu Arg Val Asn Glu Lys Ile Ile Leu Tyr Glu Asn
    130                 135                 140

Thr Asp Leu Arg Thr Phe Lys Ser Glu Glu Lys Phe Glu Leu Val Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Ala Cys Ala Lys
    210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Ile Lys Asn
                245                 250
```

<210> SEQ ID NO 90
<211> LENGTH: 253
<212> TYPE: PRT
<213> ORGANISM: Campylobacter jejuni

<400> SEQUENCE: 90

```
Met Arg Phe Asp Phe Phe Val Ser Lys Arg Leu Asn Ile Ser Arg Asn
1               5                   10                  15
```

```
Lys Ala Leu Glu Leu Ile Glu Asn Glu Glu Ile Leu Leu Asn Gly Lys
            20                  25                  30

Ser Phe Lys Ala Ser Phe Asp Val Lys Asn Phe Leu Glu Asn Leu Lys
            35                  40                  45

Lys Thr Gln Asp Leu Asn Leu Glu Asp Ile Leu Leu Ala Asn Glu Leu
 50                  55                  60

Lys Leu Asp Leu Leu Ser Glu Ile Tyr Val Ser Arg Ala Ala Leu Lys
 65                  70                  75                  80

Leu Lys Asn Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
            115                 120                 125

Leu His Ser Ser Leu Arg Val Asn Glu Lys Ile Ile Leu His Glu Asn
130                 135                 140

Thr Asp Leu Arg Ala Phe Lys Ser Glu Glu Lys Phe Glu Leu Val Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
            195                 200                 205

Lys Ala Ile Leu Lys Ala Arg Met Asp Phe Glu Lys Ala Cys Ala Lys
            210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Ile Lys Asn
                245                 250

<210> SEQ ID NO 91
<211> LENGTH: 253
<212> TYPE: PRT
<213> ORGANISM: Campylobacter jejuni

<400> SEQUENCE: 91

Met Arg Phe Asp Phe Phe Val Ser Lys Arg Leu Asn Ile Ser Arg Asn
 1               5                  10                  15

Lys Ala Leu Glu Leu Ile Glu Asn Glu Glu Val Leu Leu Asn Gly Lys
            20                  25                  30

Ser Phe Lys Ala Ser Phe Asp Val Lys Asn Phe Leu Glu Asn Leu Lys
            35                  40                  45

Lys Thr Gln Asp Leu Asn Pro Glu Asp Ile Leu Leu Ala Asp Glu Leu
 50                  55                  60

Lys Leu Asp Leu Leu Ser Glu Ile Tyr Val Ser Arg Ala Ala Leu Lys
 65                  70                  75                  80

Leu Lys Asn Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
            115                 120                 125

Leu His Pro Ser Leu Arg Ala Asn Glu Lys Ile Ile Leu His Glu Asn
```

```
            130                 135                 140
Ile Asp Leu Arg Ala Phe Lys Ser Glu Glu Lys Phe Glu Leu Val Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Gly Val Leu Lys Asp Asp
            195                 200                 205

Lys Ala Ile Leu Lys Ala Arg Met Asp Phe Glu Lys Glu Cys Ala Lys
            210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
            245                 250

<210> SEQ ID NO 92
<211> LENGTH: 253
<212> TYPE: PRT
<213> ORGANISM: Campylobacter jejuni

<400> SEQUENCE: 92

Met Arg Phe Asp Phe Val Ser Lys Arg Leu Asn Ile Ser Arg Asn
1               5                   10                  15

Lys Ala Leu Glu Leu Ile Glu Asn Glu Glu Ile Leu Leu Asn Gly Lys
            20                  25                  30

Ser Phe Lys Ala Ser Phe Asp Val Lys Asn Phe Leu Glu Asn Leu Lys
        35                  40                  45

Lys Thr Gln Asp Leu Asn Leu Glu Asp Ile Leu Leu Ala Asn Glu Leu
    50                  55                  60

Lys Leu Asp Leu Leu Ser Glu Ile Tyr Val Ser Arg Ala Ala Leu Lys
65                  70                  75                  80

Leu Lys Asn Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
        115                 120                 125

Leu His Ser Ser Leu Arg Val Asn Glu Lys Ile Ile Leu His Glu Asn
    130                 135                 140

Thr Asp Leu Arg Thr Phe Lys Ser Glu Glu Lys Phe Glu Leu Val Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Ala Cys Ala Lys
    210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
            245                 250
```

<210> SEQ ID NO 93
<211> LENGTH: 253
<212> TYPE: PRT
<213> ORGANISM: Campylobacter jejuni

<400> SEQUENCE: 93

Met Arg Phe Asp Phe Phe Val Ser Lys Arg Leu Asn Ile Ser Arg Asn
1               5                   10                  15

Lys Ala Leu Glu Leu Ile Glu Asn Glu Val Leu Leu Asn Gly Lys
            20                  25                  30

Ser Phe Lys Ala Ser Phe Asp Val Lys Asn Phe Leu Glu Asn Leu Lys
            35                  40                  45

Lys Thr Gln Asp Leu Asn Pro Glu Asp Ile Leu Leu Ala Asn Glu Leu
        50                  55                  60

Lys Leu Asp Leu Leu Arg Glu Ile Tyr Val Ser Arg Ala Ala Leu Lys
65                  70                  75                  80

Leu Lys Asn Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
        115                 120                 125

Leu His Pro Ser Leu Arg Ala Asn Glu Lys Ile Ile Leu His Glu Asn
    130                 135                 140

Thr Asp Leu Arg Ala Phe Lys Ser Glu Glu Lys Phe Glu Phe Ile Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Gly
        195                 200                 205

Lys Ala Ile Leu Lys Ala Arg Met Asp Phe Glu Lys Ala Cys Ala Lys
    210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Ile Lys Asn
                245                 250

<210> SEQ ID NO 94
<211> LENGTH: 253
<212> TYPE: PRT
<213> ORGANISM: Campylobacter jejuni

<400> SEQUENCE: 94

Met Arg Phe Asp Phe Phe Val Ser Lys Arg Leu Asp Ile Ser Arg Asn
1               5                   10                  15

Lys Ala Leu Glu Leu Ile Glu Asn Glu Val Leu Leu Asn Gly Lys
            20                  25                  30

Ser Phe Lys Ala Ser Phe Asp Val Lys Asn Phe Leu Glu Asn Leu Lys
            35                  40                  45

Lys Thr Gln Asp Leu Asn Pro Glu Asp Ile Leu Leu Ala Asp Glu Leu
        50                  55                  60

Lys Leu Asp Leu Leu Ser Glu Ile Tyr Val Ser Arg Ala Ala Leu Lys
65                  70                  75                  80

```
Leu Lys Asn Phe Leu Glu Glu Asn Asp Ile Glu Ile Lys His Lys Asn
                 85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
            115                 120                 125

Leu His Pro Ser Leu Arg Ala Asn Glu Lys Ile Ile Leu His Glu Asn
            130                 135                 140

Ile Asp Leu Arg Ala Phe Lys Ser Glu Glu Lys Phe Glu Leu Val Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
            195                 200                 205

Lys Ala Ile Leu Lys Ala Arg Met Asp Phe Glu Lys Glu Cys Ala Lys
210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Ile Lys Asn
            245                 250

<210> SEQ ID NO 95
<211> LENGTH: 253
<212> TYPE: PRT
<213> ORGANISM: Campylobacter jejuni

<400> SEQUENCE: 95

Met Arg Phe Asp Phe Phe Val Ser Lys Arg Leu Asn Ile Ser Arg Asn
1               5                   10                  15

Lys Ala Leu Glu Leu Ile Glu Asn Glu Glu Ile Leu Leu Asn Gly Lys
            20                  25                  30

Ser Phe Lys Ala Ser Phe Asp Val Lys Asn Phe Leu Glu Asn Leu Lys
        35                  40                  45

Lys Thr Gln Asp Leu Asn Leu Glu Asp Ile Leu Leu Ala Asn Glu Leu
    50                  55                  60

Lys Leu Asp Leu Leu Ser Glu Ile Tyr Val Ser Arg Ala Ala Leu Lys
65                  70                  75                  80

Leu Lys Asn Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Thr Leu Asp Val Gly Ser Asn Gln
            115                 120                 125

Leu His Pro Ser Leu Arg Ala Asn Glu Ile Ile Leu His Glu Asn
            130                 135                 140

Thr Asp Leu Arg Ala Phe Lys Ser Glu Glu Lys Phe Glu Leu Val Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
            195                 200                 205
```

Lys Ala Ile Leu Lys Ala Arg Met Asp Phe Glu Lys Ala Cys Ala Lys
        210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
                245                 250

<210> SEQ ID NO 96
<211> LENGTH: 251
<212> TYPE: PRT
<213> ORGANISM: Campylobacter jejuni

<400> SEQUENCE: 96

Met Ile Phe Phe Val Ser Lys Arg Leu Asn Ile Ser Arg Asn Lys Ala
1               5                   10                  15

Leu Glu Leu Ile Glu Asn Glu Glu Ile Leu Leu Asn Gly Lys Ser Phe
            20                  25                  30

Lys Ala Ser Phe Asp Val Lys Asn Phe Leu Glu Asn Leu Lys Lys Thr
        35                  40                  45

Gln Asp Leu Asn Pro Glu Asp Ile Leu Leu Ala Asn Glu Leu Lys Leu
    50                  55                  60

Asp Leu Leu Ser Glu Ile Tyr Val Ser Arg Ala Ala Leu Lys Leu Lys
65                  70                  75                  80

Lys Phe Leu Glu Glu Asn Asp Ile Glu Ile Lys His Lys Asn Cys Leu
                85                  90                  95

Asp Ile Gly Ser Ser Thr Gly Gly Phe Val Gln Ile Leu Leu Glu Asn
            100                 105                 110

Gln Ala Leu Lys Ile Thr Ala Leu Asp Val Gly Ser Asn Gln Leu His
        115                 120                 125

Pro Ser Leu Arg Ala Asn Glu Lys Ile Ile Leu His Glu Asn Thr Asp
    130                 135                 140

Leu Arg Ala Phe Lys Ser Glu Glu Lys Phe Glu Leu Val Thr Cys Asp
145                 150                 155                 160

Val Ser Phe Ile Ser Leu Ile Asn Leu Leu Tyr Tyr Val Asp Asn Leu
                165                 170                 175

Ala Leu Lys Glu Ile Ile Leu Leu Phe Lys Pro Gln Phe Glu Val Gly
            180                 185                 190

Lys Asn Ile Lys Arg Asp Lys Lys Gly Val Leu Lys Asp Asp Lys Ala
        195                 200                 205

Ile Leu Lys Ala Arg Met Asp Phe Glu Lys Glu Cys Ala Lys Leu Gly
    210                 215                 220

Trp Leu Leu Lys Asn Thr Gln Lys Ser Ser Ile Lys Gly Lys Glu Gly
225                 230                 235                 240

Asn Val Glu Tyr Phe Tyr Tyr Tyr Ile Lys Asn
                245                 250

<210> SEQ ID NO 97
<211> LENGTH: 253
<212> TYPE: PRT
<213> ORGANISM: Campylobacter jejuni

<400> SEQUENCE: 97

Met Arg Phe Asp Phe Phe Val Ser Lys Arg Leu Asn Ile Ser Arg Asn
1               5                   10                  15

Lys Ala Leu Glu Leu Ile Glu Asn Glu Glu Ile Leu Leu Asn Gly Lys
            20                  25                  30

-continued

Ser Phe Lys Ala Ser Phe Asp Val Lys Asn Phe Leu Glu Asn Leu Lys
        35                  40                  45

Lys Thr Gln Asp Leu Asn Leu Glu Asp Ile Leu Leu Ala Asn Glu Leu
    50                  55                  60

Lys Leu Asp Leu Leu Ser Glu Ile Tyr Val Ser Arg Ala Ala Leu Lys
65                  70                  75                  80

Leu Lys Asn Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
                100                 105                 110

Glu Asn Gln Ala Leu Lys Ile Thr Ala Leu Asp Val Gly Ser Asn Gln
                115                 120                 125

Leu His Ser Ser Leu Arg Val Asn Glu Lys Ile Ile Leu Tyr Glu Asn
    130                 135                 140

Thr Asp Leu Arg Thr Phe Lys Ser Glu Glu Lys Phe Glu Leu Val Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
                180                 185                 190

Val Gly Lys Asn Ile Lys Arg Asp Lys Lys Gly Val Leu Lys Asp Asp
            195                 200                 205

Lys Ala Ile Leu Lys Ala Arg Met Asp Phe Glu Lys Ala Cys Ala Lys
    210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
                245                 250

<210> SEQ ID NO 98
<211> LENGTH: 253
<212> TYPE: PRT
<213> ORGANISM: Campylobacter jejuni

<400> SEQUENCE: 98

Met Arg Phe Asp Phe Phe Val Ser Lys Arg Leu Asn Ile Ser Arg Asn
1               5                   10                  15

Lys Ala Leu Glu Leu Ile Glu Asn Glu Glu Val Leu Leu Asn Gly Lys
                20                  25                  30

Ser Phe Lys Ala Ser Phe Asp Val Lys Asn Phe Leu Glu Asn Leu Lys
        35                  40                  45

Lys Ala Gln Asp Leu Asn Pro Glu Asp Val Leu Leu Thr Asp Glu Leu
    50                  55                  60

Lys Leu Asp Leu Leu Ser Glu Ile Tyr Val Ser Arg Ala Ala Leu Lys
65                  70                  75                  80

Leu Lys Asn Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
                100                 105                 110

Glu Asn Gln Ala Leu Lys Ile Thr Ala Leu Asp Val Gly Asn Asn Gln
                115                 120                 125

Leu His Pro Ser Leu Arg Thr Asn Glu Lys Ile Ile Leu His Glu Asn
    130                 135                 140

Thr Asp Leu Arg Ala Phe Lys Ser Glu Glu Lys Phe Glu Leu Ile Thr

```
                145                 150                 155                 160
Cys Asp Val Ser Phe Ile Ser Leu Ile Asn Leu Leu Tyr Tyr Ile Asp
                    165                 170                 175

Asn Leu Ala Leu Lys Glu Ile Ile Leu Leu Phe Lys Pro Gln Phe Glu
                180                 185                 190

Val Gly Lys Asn Ile Lys Arg Asp Lys Lys Gly Val Leu Lys Asp Asp
                195                 200                 205

Lys Ala Ile Leu Lys Ala Arg Met Asp Phe Glu Lys Glu Cys Ala Lys
210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
                245                 250

<210> SEQ ID NO 99
<211> LENGTH: 251
<212> TYPE: PRT
<213> ORGANISM: Campylobacter jejuni

<400> SEQUENCE: 99

Met Ile Phe Phe Val Ser Lys Arg Leu Asn Ile Ser Arg Asn Lys Ala
1               5                   10                  15

Leu Glu Leu Ile Glu Asn Glu Glu Ile Leu Leu Asn Gly Lys Ser Phe
                20                  25                  30

Lys Ala Ser Phe Asp Val Lys Asn Phe Leu Glu Asn Leu Lys Lys Thr
            35                  40                  45

Gln Asp Leu Asn Pro Glu Asp Ile Leu Leu Ala Asn Glu Leu Lys Leu
        50                  55                  60

Asp Leu Leu Ser Glu Ile Tyr Val Ser Arg Ala Ala Leu Lys Leu Lys
65                  70                  75                  80

Lys Phe Leu Glu Glu Asn Asp Ile Glu Ile Lys His Lys Asn Cys Leu
                85                  90                  95

Asp Ile Gly Ser Ser Thr Gly Gly Phe Val Gln Ile Leu Leu Glu Asn
                100                 105                 110

Gln Ala Leu Lys Ile Thr Ala Leu Asp Val Gly Ser Asn Gln Leu His
            115                 120                 125

Pro Ser Leu Arg Ala Asn Glu Lys Ile Ile Leu His Glu Asn Thr Asp
        130                 135                 140

Leu Arg Ala Phe Lys Ser Glu Lys Phe Glu Leu Val Thr Cys Asp
145                 150                 155                 160

Val Ser Phe Ile Ser Leu Ile Asn Leu Leu Tyr Tyr Val Asp Asn Leu
                165                 170                 175

Ala Leu Lys Glu Ile Ile Leu Leu Phe Lys Pro Gln Phe Glu Val Gly
                180                 185                 190

Lys Asn Ile Lys Arg Asp Lys Lys Gly Val Leu Lys Asp Asp Arg Ala
            195                 200                 205

Ile Leu Lys Ala Arg Met Asp Phe Glu Lys Glu Cys Ala Lys Leu Gly
        210                 215                 220

Trp Phe Leu Lys Asn Thr Gln Lys Ser Ser Ile Lys Gly Lys Glu Gly
225                 230                 235                 240

Asn Val Glu Tyr Phe Tyr Tyr Tyr Ile Lys Asn
                245                 250

<210> SEQ ID NO 100
<211> LENGTH: 253
```

```
<212> TYPE: PRT
<213> ORGANISM: Campylobacter jejuni

<400> SEQUENCE: 100

Met Arg Phe Asp Phe Val Ser Lys Arg Leu Asn Ile Ser Arg Asn
1               5                   10                  15

Lys Ala Leu Glu Leu Ile Glu Ser Glu Val Leu Leu Asn Gly Lys
                20                  25                  30

Ser Phe Lys Ala Ser Phe Asp Val Lys Asn Phe Leu Glu Asn Leu Lys
            35                  40                  45

Lys Thr Gln Asp Leu Asn Pro Glu Asp Ile Leu Leu Ala Asn Glu Leu
        50                  55                  60

Lys Leu Asn Leu Leu Ser Glu Ile Tyr Val Ser Arg Ala Ala Leu Lys
65                  70                  75                  80

Leu Lys Asn Phe Leu Glu Glu Asn Asp Ile Glu Ile Lys Gln Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
        115                 120                 125

Leu His Ser Asn Leu Arg Thr Asn Glu Lys Val Ile Leu His Glu Asn
130                 135                 140

Thr Asp Leu Arg Ala Phe Lys Ser Glu Glu Lys Phe Glu Phe Ile Thr
145                 150                 155                 160

Cys Asp Val Ser Phe Ile Ser Leu Ile Asn Leu Leu Tyr Tyr Ile Asp
            165                 170                 175

Asn Leu Ala Leu Lys Glu Ile Ile Leu Leu Phe Lys Pro Gln Phe Glu
        180                 185                 190

Val Gly Lys Asn Ile Lys Arg Asp Lys Lys Gly Val Leu Lys Asp Asp
            195                 200                 205

Lys Ala Ile Leu Lys Ala Arg Met Asp Phe Glu Lys Ala Cys Ala Lys
210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
            245                 250

<210> SEQ ID NO 101
<211> LENGTH: 253
<212> TYPE: PRT
<213> ORGANISM: Campylobacter jejuni

<400> SEQUENCE: 101

Met Arg Phe Asp Phe Val Ser Lys Arg Leu Asn Ile Ser Arg Asn
1               5                   10                  15

Lys Ala Leu Glu Leu Ile Glu Asn Glu Val Leu Leu Asn Gly Lys
                20                  25                  30

Ser Phe Lys Ala Ser Phe Asp Val Lys Asn Phe Leu Glu Asn Leu Lys
            35                  40                  45

Lys Thr Gln Asp Leu Asn Pro Glu Asp Ile Leu Leu Thr Asp Gly Leu
        50                  55                  60

Lys Leu Asp Leu Leu Ser Glu Ile Tyr Val Ser Arg Ala Ala Leu Lys
65                  70                  75                  80

Leu Lys Asn Phe Leu Glu Glu Asn Asp Ile Glu Ile Lys His Lys Asn
                85                  90                  95
```

```
Cys Leu Asp Ile Gly Ser Ser Thr Gly Gly Phe Val Gln Ile Leu Leu
                100                 105                 110

Glu Asn Gln Ala Leu Lys Ile Thr Ala Leu Asp Val Gly Asn Asn Gln
            115                 120                 125

Leu His Leu Ser Leu Arg Thr Asn Glu Lys Ile Ile Leu His Glu Asn
        130                 135                 140

Thr Asp Leu Arg Ala Phe Lys Ser Glu Glu Lys Phe Glu Leu Ile Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Glu Cys Ala Lys
210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Ile Lys Asn
                245                 250

<210> SEQ ID NO 102
<211> LENGTH: 253
<212> TYPE: PRT
<213> ORGANISM: Campylobacter jejuni

<400> SEQUENCE: 102

Met Arg Phe Asp Phe Phe Ile Ser Lys Arg Leu Asn Ile Ser Arg Asn
1               5                   10                  15

Lys Ala Leu Glu Leu Ile Glu Asn Glu Val Leu Leu Asn Gly Lys
            20                  25                  30

Asn Phe Lys Ala Ser Cys Asp Val Lys Asn Phe Leu Glu Asn Leu Lys
        35                  40                  45

Lys Ala Gln Asp Leu Asn Pro Glu Asp Val Leu Leu Ala Asp Glu Leu
    50                  55                  60

Lys Leu Asp Leu Leu Ser Glu Ile Tyr Val Ser Arg Ala Ala Leu Lys
65                  70                  75                  80

Leu Lys Asn Phe Leu Glu Glu Asn Asp Ile Glu Val Lys His Lys Asn
                85                  90                  95

Cys Leu Asp Ile Gly Ser Ser Thr Gly Gly Phe Val Gln Ile Leu Leu
                100                 105                 110

Glu Asn Lys Ala Leu Lys Ile Thr Ala Leu Asp Val Gly Ser Asn Gln
            115                 120                 125

Leu His Pro Ser Leu Arg Thr Asn Glu Lys Val Ile Leu His Glu Asn
        130                 135                 140

Thr Asp Leu Arg Ala Phe Lys Ser Glu Glu Lys Phe Glu Leu Ile Thr
145                 150                 155                 160

Cys Asp Val Ser Phe Ile Ser Leu Val Asn Leu Leu Tyr Tyr Ile Asn
                165                 170                 175

Asn Leu Ala Leu Lys Glu Met Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Ala Cys Ala Lys
210                 215                 220
```

```
Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
                245                 250
```

<210> SEQ ID NO 103
<211> LENGTH: 253
<212> TYPE: PRT
<213> ORGANISM: Campylobacter jejuni

<400> SEQUENCE: 103

```
Met Arg Phe Asp Phe Val Ser Lys Arg Leu Asn Ile Ser Arg Asn
1               5                   10                  15

Lys Ala Leu Glu Leu Ile Glu Asn Glu Glu Val Leu Leu Asn Gly Lys
                20                  25                  30

Ser Phe Lys Ala Ser Phe Asp Val Lys Asn Phe Leu Glu Asn Leu Lys
            35                  40                  45

Lys Thr Gln Asp Leu Asn Pro Glu Asp Ile Leu Leu Thr Asp Gly Leu
50                  55                  60

Lys Leu Asp Leu Leu Ser Glu Ile Tyr Val Ser Arg Ala Ala Leu Lys
65                  70                  75                  80

Leu Lys Asn Phe Leu Glu Glu Asn Gly Ile Glu Ile Lys His Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Asn Asn Gln
        115                 120                 125

Leu His Leu Ser Leu Arg Thr Asn Glu Lys Ile Ile Leu His Glu Asn
130                 135                 140

Thr Asp Leu Arg Thr Phe Lys Ser Glu Glu Lys Phe Glu Leu Ile Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Ala Cys Ala Lys
210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Tyr Ile Lys Asn
                245                 250
```

<210> SEQ ID NO 104
<211> LENGTH: 253
<212> TYPE: PRT
<213> ORGANISM: Campylobacter jejuni

<400> SEQUENCE: 104

```
Met Arg Phe Asp Phe Val Ser Lys Arg Leu Asn Ile Ser Arg Asn
1               5                   10                  15

Lys Ala Leu Glu Leu Ile Glu Asn Glu Glu Val Leu Leu Asn Gly Lys
                20                  25                  30

Ser Phe Lys Ala Ser Phe Asp Val Lys Asn Leu Leu Glu Asn Leu Leu
            35                  40                  45
```

Lys Lys Gln Asp Leu Asn Ser Glu Glu Ile Tyr Leu Ser Lys Glu Leu
            50                  55                  60

Asn Leu Glu Leu Leu Ser Glu Ile Tyr Ile Ser Arg Ala Ala Leu Lys
 65                  70                  75                  80

Leu Lys Asn Phe Leu Glu Glu Asn Asn Ile Glu Val Asn Asn Lys Asn
                 85                  90                  95

Cys Leu Asp Ile Gly Ser Ser Thr Gly Gly Phe Val Gln Ile Leu Leu
                100                 105                 110

Glu Asn Lys Ala Leu Lys Ile Thr Ala Leu Asp Val Gly Ser Asn Gln
            115                 120                 125

Leu His Ser Ser Leu Arg Thr Asn Glu Lys Ile Ile Leu Tyr Glu Asn
130                 135                 140

Thr Asp Leu Arg Val Phe Lys Ser Glu Glu Lys Phe Glu Phe Ile Thr
145                 150                 155                 160

Cys Asp Val Ser Phe Ile Ser Leu Val Asn Leu Leu Tyr Tyr Ile Asn
                165                 170                 175

Asn Leu Ala Leu Arg Glu Ile Ile Leu Leu Phe Lys Pro Gln Phe Glu
                180                 185                 190

Val Gly Lys Asn Val Lys Arg Asp Lys Gly Val Leu Lys Asp Asp
            195                 200                 205

Lys Val Ile Leu Lys Ala Lys Met Asp Phe Glu Lys Glu Cys Ala Lys
210                 215                 220

Leu Gly Trp Ile Leu Lys Asn Thr Gln Lys Ser Cys Ile Lys Gly Lys
225                 230                 235                 240

Glu Gly Asn Val Glu Tyr Phe Tyr Tyr Tyr Ile Lys Asn
                245                 250

<210> SEQ ID NO 105
<211> LENGTH: 188
<212> TYPE: PRT
<213> ORGANISM: Campylobacter jejuni

<400> SEQUENCE: 105

Met Asp Leu Leu Ser Glu Ile Tyr Val Ser Arg Ala Ala Leu Lys Leu
 1               5                  10                  15

Lys Lys Phe Leu Glu Glu Asn Asp Ile Glu Ile Lys His Lys Asn Cys
                20                  25                  30

Leu Asp Ile Gly Ser Ser Thr Gly Gly Phe Val Gln Ile Leu Leu Glu
                35                  40                  45

Asn Gln Ala Leu Lys Ile Thr Ala Leu Asp Val Gly Ser Asn Gln Leu
 50                  55                  60

His Pro Ser Leu Arg Val Asn Glu Lys Ile Ile Leu His Glu Asn Thr
 65                  70                  75                  80

Asp Leu Arg Ala Phe Lys Ser Glu Glu Lys Phe Glu Leu Val Thr Cys
                 85                  90                  95

Asp Val Ser Phe Ile Ser Leu Ile Asn Leu Leu Tyr Tyr Ile Asp Asn
                100                 105                 110

Leu Ala Leu Lys Glu Ile Ile Leu Leu Phe Lys Pro Gln Phe Glu Val
            115                 120                 125

Gly Lys Asn Ile Lys Arg Asp Lys Lys Gly Val Leu Lys Asp Asp Lys
130                 135                 140

Ala Ile Leu Lys Ala Arg Met Asp Phe Glu Lys Ala Cys Ala Lys Leu
145                 150                 155                 160

Gly Trp Leu Leu Lys Asn Thr Gln Lys Ser Ser Ile Lys Gly Lys Glu

```
              165                 170                 175
Gly Asn Val Glu Tyr Phe Tyr Tyr Tyr Ile Lys Asn
            180                 185

<210> SEQ ID NO 106
<211> LENGTH: 52
<212> TYPE: PRT
<213> ORGANISM: Campylobacter jejuni

<400> SEQUENCE: 106

Met Arg Phe Asp Phe Phe Val Ser Lys Arg Leu Asn Ile Ser Arg Asn
1               5                   10                  15

Lys Ala Leu Glu Leu Ile Glu Asn Glu Glu Ile Leu Leu Asn Gly Lys
            20                  25                  30

Ser Phe Lys Ala Ser Phe Asp Val Lys Asn Phe Leu Glu Asn Leu Lys
        35                  40                  45

Lys Arg Lys Ile
        50

<210> SEQ ID NO 107
<211> LENGTH: 183
<212> TYPE: DNA
<213> ORGANISM: Campylobacter jejuni

<400> SEQUENCE: 107
atggtttcag atgtttctat gggtaatgtt aatttaatga ctgctgttaa tacttcagtt    60
ttgaaaaaat ctatggacac aaacgaggca ttgatgaatg aactcatcga aggtatggaa   120
ggtgtctctc aagcctccgc tccacaagct tctagctcta gtggtttgga tatttacgct   180
taa                                                                 183

<210> SEQ ID NO 108
<211> LENGTH: 60
<212> TYPE: PRT
<213> ORGANISM: Campylobacter jejuni

<400> SEQUENCE: 108

Met Val Ser Asp Val Ser Met Gly Asn Val Asn Leu Met Thr Ala Val
1               5                   10                  15

Asn Thr Ser Val Leu Lys Lys Ser Met Asp Thr Asn Glu Ala Leu Met
            20                  25                  30

Asn Glu Leu Ile Glu Gly Met Glu Gly Val Ser Gln Ala Ser Ala Pro
        35                  40                  45

Gln Ala Ser Ser Ser Ser Gly Leu Asp Ile Tyr Ala
    50                  55                  60

<210> SEQ ID NO 109
<211> LENGTH: 384
<212> TYPE: DNA
<213> ORGANISM: Campylobacter jejuni

<400> SEQUENCE: 109
atgcaggtaa attatagaac gattagctcg tatgaatacg atgctattag tggtcagtat    60
aaacaggtgg ataaacagat tgaagattat tcttcatctg gagattctga ttttatggat   120
atgttaaata aggcggatga aagtcaagc ggagatgctt taaattctag cagtagtttt   180
caaagcaatg cgcaaaactc aaattcaaat ttaagtaatt atgctcaaat gtcaaatgtt   240
tacgcttatc gttttagaca aaatgaaggc gagctgtcta tgagagctca aagtgctagc   300
```

```
gttcataatg atcttacaca acaaggtgca aatgaacaaa gtaagaataa tactttgtta      360
aatgatttat tgaacgcaat ttaa                                            384
```

<210> SEQ ID NO 110
<211> LENGTH: 127
<212> TYPE: PRT
<213> ORGANISM: Campylobacter jejuni

<400> SEQUENCE: 110

```
Met Gln Val Asn Tyr Arg Thr Ile Ser Ser Tyr Glu Tyr Asp Ala Ile
1               5                   10                  15

Ser Gly Gln Tyr Lys Gln Val Asp Lys Gln Ile Glu Asp Tyr Ser Ser
            20                  25                  30

Ser Gly Asp Ser Asp Phe Met Asp Met Leu Asn Lys Ala Asp Glu Lys
        35                  40                  45

Ser Ser Gly Asp Ala Leu Asn Ser Ser Ser Phe Gln Ser Asn Ala
    50                  55                  60

Gln Asn Ser Asn Ser Asn Leu Ser Asn Tyr Ala Gln Met Ser Asn Val
65                  70                  75                  80

Tyr Ala Tyr Arg Phe Arg Gln Asn Glu Gly Glu Leu Ser Met Arg Ala
                85                  90                  95

Gln Ser Ala Ser Val His Asn Asp Leu Thr Gln Gln Gly Ala Asn Glu
            100                 105                 110

Gln Ser Lys Asn Asn Thr Leu Leu Asn Asp Leu Leu Asn Ala Ile
        115                 120                 125
```

<210> SEQ ID NO 111
<211> LENGTH: 168
<212> TYPE: DNA
<213> ORGANISM: Campylobacter jejuni

<400> SEQUENCE: 111

```
atgaaaaaag ttgtactaat ctcagcatta ctaggtgctt tcgcagctaa tgttttttgca     60 gctaatactc caagcgatgt aaatcaaaca catacaaaag ctaaagctga taaaaaacat    120
gaagctaaaa ctcacaaaaa aacaaaagag caaacaccag ctcaataa                 168
```

<210> SEQ ID NO 112
<211> LENGTH: 55
<212> TYPE: PRT
<213> ORGANISM: Campylobacter jejuni

<400> SEQUENCE: 112

```
Met Lys Lys Val Val Leu Ile Ser Ala Leu Leu Gly Ala Phe Ala Ala
1               5                   10                  15

Asn Val Phe Ala Ala Asn Thr Pro Ser Asp Val Asn Gln Thr His Thr
            20                  25                  30

Lys Ala Lys Ala Asp Lys Lys His Glu Ala Lys Thr His Lys Lys Thr
        35                  40                  45

Lys Glu Gln Thr Pro Ala Gln
    50                  55
```

<210> SEQ ID NO 113
<211> LENGTH: 336
<212> TYPE: DNA
<213> ORGANISM: Campylobacter jejuni

<400> SEQUENCE: 113

```
atgatggcta aatttagaat tcaatacagc gcaggttttg ggcactatac gcaaaatcac      60
```

```
aagggttttg gacctacgat ttatatagaa gaggtcgtag agtttgataa tggcaaggat    120
tattttgact atatagattt ttataaaact tattcaaaga gcgatgatac ttattttcat    180
atcagttttt tagaagatag acctctaagc gataaagaaa tcaccattcg caatgaatac    240
cgcaaaatgc gtgatgaaaa ctgtaaaaaa gccaaggagg aatttatagc caacaatgag    300
cttgatgtgg agcatttgcc tactcaccat gattaa                              336
```

<210> SEQ ID NO 114
<211> LENGTH: 111
<212> TYPE: PRT
<213> ORGANISM: Campylobacter jejuni

<400> SEQUENCE: 114

```
Met Met Ala Lys Phe Arg Ile Gln Tyr Ser Ala Gly Phe Gly His Tyr
1               5                   10                  15

Thr Gln Asn His Lys Gly Phe Gly Pro Thr Ile Tyr Ile Glu Glu Val
            20                  25                  30

Val Glu Phe Asp Asn Gly Lys Asp Tyr Phe Asp Tyr Ile Asp Phe Tyr
        35                  40                  45

Lys Thr Tyr Ser Lys Ser Asp Asp Thr Tyr Phe His Ile Ser Phe Leu
    50                  55                  60

Glu Asp Arg Pro Leu Ser Asp Lys Glu Ile Thr Ile Arg Asn Glu Tyr
65                  70                  75                  80

Arg Lys Met Arg Asp Glu Asn Cys Lys Lys Ala Lys Glu Glu Phe Ile
                85                  90                  95

Ala Asn Asn Glu Leu Asp Val Glu His Leu Pro Thr His His Asp
            100                 105                 110
```

<210> SEQ ID NO 115
<211> LENGTH: 498
<212> TYPE: DNA
<213> ORGANISM: Campylobacter jejuni

<400> SEQUENCE: 115

```
atgaaaaaaa tcttttttac ttcaatcgca gctcttgcag ttgttattag tggttgtagc     60
acaaaaagca ctagcgtaag cggtgatagt agtgttgatt caaatcgtgg ttcaggtgga    120
agtgatggtt gggatattga ttcaaaaatt tctcaactta atgatacttt aaataaagta    180
tattttgatt ttgataaatt caacattcgt cctgatatgc aaaatgttgt aagcacaaat    240
gctaatattt taacactga agtaagcggt gtaagtatta ctgttgaagg aaactgcgat    300
gagtggggaa ccgatgaata taaccaagct ctaggtttaa aaagagcaaa agctgtaaaa    360
gaagctttaa tcgctaaagg tgtaaatgct gatagaattg ctgttaaaag ctatggagaa    420
acaaatcctg tgtgcactga aaaaactaaa gcttgcgatg cgcaaaatag acgtgctgaa    480
tttaaattat caagataa                                                  498
```

<210> SEQ ID NO 116
<211> LENGTH: 165
<212> TYPE: PRT
<213> ORGANISM: Campylobacter jejuni

<400> SEQUENCE: 116

```
Met Lys Lys Ile Leu Phe Thr Ser Ile Ala Ala Leu Ala Val Val Ile
1               5                   10                  15

Ser Gly Cys Ser Thr Lys Ser Thr Ser Val Ser Gly Asp Ser Ser Val
            20                  25                  30
```

Asp Ser Asn Arg Gly Ser Gly Ser Asp Gly Trp Asp Ile Asp Ser
            35                  40                  45

Lys Ile Ser Gln Leu Asn Asp Thr Leu Asn Lys Val Tyr Phe Asp Phe
        50                  55                  60

Asp Lys Phe Asn Ile Arg Pro Asp Met Gln Asn Val Val Ser Thr Asn
65                  70                  75                  80

Ala Asn Ile Phe Asn Thr Glu Val Ser Gly Val Ser Ile Thr Val Glu
                85                  90                  95

Gly Asn Cys Asp Glu Trp Gly Thr Asp Glu Tyr Asn Gln Ala Leu Gly
            100                 105                 110

Leu Lys Arg Ala Lys Ala Val Lys Glu Ala Leu Ile Ala Lys Gly Val
        115                 120                 125

Asn Ala Asp Arg Ile Ala Val Lys Ser Tyr Gly Glu Thr Asn Pro Val
130                 135                 140

Cys Thr Glu Lys Thr Lys Ala Cys Asp Ala Gln Asn Arg Arg Ala Glu
145                 150                 155                 160

Phe Lys Leu Ser Arg
                165

<210> SEQ ID NO 117
<211> LENGTH: 840
<212> TYPE: DNA
<213> ORGANISM: Campylobacter jejuni

<400> SEQUENCE: 117
atgaaaaaaa tacttctaag tgttttaacg gcctttgttg cagtagtatt ggctgcttgt      60
ggaggaaatt ctgactctaa aactttaaat tctcttgata agatcaagca aaatggagtt    120
gttaggattg gggtatttgg cgataaacca ccttttggtt atgtggatga aaaggaaac     180 aatcaaggct atgatatagc tttagctaaa cgcatagcaa agaactttt tggcgatgaa     240 aataaggtgc aatttgttct tgttgaagct gcaaataggg ttgagttttt aaaatcaaat    300
aaagtagata ttattttggc taattttact caaactccgc aaagggcaga gcaggttgat    360
ttttgctcgc cttatatgaa ggtagcttta ggcgtagctg taccaaagga tagtaatata    420
actagcgtag aagatttaaa agataaaacc ttgcttttaa acaaaggcac aacagcagat    480
gcttatttta cgcaaaatta tcctaatatt aaaacttaa aatatgatca aaataccgaa     540
acctttgccg cttttgatgga taaaagaggc gatgctttaa gtcatgataa taccttactt    600
tttgcttggg tgaaagatca tcctgatttt aaaatgggta ttaaagagtt aggtaacaaa    660
gatgttatcg caccagcggt taaaaaggc gataagaac ttaagaatt tatcgataat      720 ttgatcatca aactaggcca agagcagttt tttcacaagg cttatgatga aacttttaaaa    780 gctcattttg gagatgatgt taaggccgat gatgtagtga ttgaaggtgg aaaaatttaa    840

<210> SEQ ID NO 118
<211> LENGTH: 279
<212> TYPE: PRT
<213> ORGANISM: Campylobacter jejuni

<400> SEQUENCE: 118

Met Lys Lys Ile Leu Leu Ser Val Leu Thr Ala Phe Val Ala Val Val
1               5                   10                  15

Leu Ala Ala Cys Gly Gly Asn Ser Asp Ser Lys Thr Leu Asn Ser Leu
            20                  25                  30

Asp Lys Ile Lys Gln Asn Gly Val Val Arg Ile Gly Val Phe Gly Asp

|  |  |  |  | 35 |  |  |  | 40 |  |  |  | 45 |  |  |
|---|---|---|---|---|---|---|---|---|---|---|---|---|---|---|

Lys Pro Pro Phe Gly Tyr Val Asp Glu Lys Gly Asn Asn Gln Gly Tyr
 50                  55                  60

Asp Ile Ala Leu Ala Lys Arg Ile Ala Lys Glu Leu Phe Gly Asp Glu
 65                  70                  75                  80

Asn Lys Val Gln Phe Val Leu Val Glu Ala Asn Arg Val Glu Phe
                 85                  90                  95

Leu Lys Ser Asn Lys Val Asp Ile Ile Leu Ala Asn Phe Thr Gln Thr
                100                 105                 110

Pro Gln Arg Ala Glu Gln Val Asp Phe Cys Ser Pro Tyr Met Lys Val
            115                 120                 125

Ala Leu Gly Val Ala Val Pro Lys Asp Ser Asn Ile Thr Ser Val Glu
        130                 135                 140

Asp Leu Lys Asp Lys Thr Leu Leu Leu Asn Lys Gly Thr Thr Ala Asp
145                 150                 155                 160

Ala Tyr Phe Thr Gln Asn Tyr Pro Asn Ile Lys Thr Leu Lys Tyr Asp
                165                 170                 175

Gln Asn Thr Glu Thr Phe Ala Ala Leu Met Asp Lys Arg Gly Asp Ala
            180                 185                 190

Leu Ser His Asp Asn Thr Leu Leu Phe Ala Trp Val Lys Asp His Pro
        195                 200                 205

Asp Phe Lys Met Gly Ile Lys Glu Leu Gly Asn Lys Asp Val Ile Ala
210                 215                 220

Pro Ala Val Lys Lys Gly Asp Lys Glu Leu Lys Glu Phe Ile Asp Asn
225                 230                 235                 240

Leu Ile Ile Lys Leu Gly Gln Glu Gln Phe Phe His Lys Ala Tyr Asp
                245                 250                 255

Glu Thr Leu Lys Ala His Phe Gly Asp Asp Val Lys Ala Asp Val
            260                 265                 270

Val Ile Glu Gly Gly Lys Ile
        275

<210> SEQ ID NO 119
<211> LENGTH: 780
<212> TYPE: DNA
<213> ORGANISM: Campylobacter jejuni

<400> SEQUENCE: 119
atggttttta gaaatctttt gttaaagttg gcagttttg ctctaggtgc ttgtgttgca      60
tttagcaatg ctaatgcagc agaaggtaaa cttgagtcta ttaaatctaa aggacaatta     120
atagttggtg ttaaaaatga tgttccgcat tatgctttac ttgatcaagc aacaggtgaa     180
attaaaggtt tcgaagtaga tgttgccaaa ttgctagcta aagtatatt gggtgatgat      240 aaaaaaataa aactagttgc agttaatgct aaaacaagag gcccctttgct tgataatggt    300 agtgtagatg cggtgatagc aacttttact attactccag agagaaaaag aatttataat    360
ttctcagagc cttattatca agatgctata gggcttttgg ttttaaaaga aaaaaaatat    420
aaatctttag ctgatatgaa aggtgcaaat attggagtgg ctcaagctgc aactacaaaa    480
aaagctatag gtgaagctgc taaaaaaatt ggcattgatg ttaaatttag tgaatttcct    540
gattatccaa gtaaaaagc tgctttagat gctaaaagag ttgatgcgtt ttctgtagac    600
aaatcaatat tgttaggtta tgtggatgat aaaagtgaaa tttgccaga tagttttgaa    660 ccacaaagtt atggtattgt aaccaaaaaa gatgatccag cttttgcaaa atatgttgat    720

-continued gattttgtaa aagaacataa aaatgaaatt gatgctttag cgaaaaaatg gggtttataa    780

<210> SEQ ID NO 120
<211> LENGTH: 259
<212> TYPE: PRT
<213> ORGANISM: Campylobacter jejuni

<400> SEQUENCE: 120

Met Val Phe Arg Lys Ser Leu Leu Lys Leu Ala Val Phe Ala Leu Gly
1               5                   10                  15

Ala Cys Val Ala Phe Ser Asn Ala Asn Ala Ala Glu Gly Lys Leu Glu
            20                  25                  30

Ser Ile Lys Ser Lys Gly Gln Leu Ile Val Gly Val Lys Asn Asp Val
        35                  40                  45

Pro His Tyr Ala Leu Leu Asp Gln Ala Thr Gly Glu Ile Lys Gly Phe
    50                  55                  60

Glu Val Asp Val Ala Lys Leu Leu Ala Lys Ser Ile Leu Gly Asp Asp
65                  70                  75                  80

Lys Lys Ile Lys Leu Val Ala Val Asn Ala Lys Thr Arg Gly Pro Leu
                85                  90                  95

Leu Asp Asn Gly Ser Val Asp Ala Val Ile Ala Thr Phe Thr Ile Thr
            100                 105                 110

Pro Glu Arg Lys Arg Ile Tyr Asn Phe Ser Glu Pro Tyr Tyr Gln Asp
        115                 120                 125

Ala Ile Gly Leu Leu Val Leu Lys Glu Lys Tyr Lys Ser Leu Ala
    130                 135                 140

Asp Met Lys Gly Ala Asn Ile Gly Val Ala Gln Ala Thr Thr Lys
145                 150                 155                 160

Lys Ala Ile Gly Glu Ala Ala Lys Lys Ile Gly Ile Asp Val Lys Phe
                165                 170                 175

Ser Glu Phe Pro Asp Tyr Pro Ser Ile Lys Ala Ala Leu Asp Ala Lys
            180                 185                 190

Arg Val Asp Ala Phe Ser Val Asp Lys Ser Ile Leu Leu Gly Tyr Val
        195                 200                 205

Asp Asp Lys Ser Glu Ile Leu Pro Asp Ser Phe Glu Pro Gln Ser Tyr
    210                 215                 220

Gly Ile Val Thr Lys Lys Asp Asp Pro Ala Phe Ala Lys Tyr Val Asp
225                 230                 235                 240

Asp Phe Val Lys Glu His Lys Asn Glu Ile Asp Ala Leu Ala Lys Lys
                245                 250                 255

Trp Gly Leu

<210> SEQ ID NO 121
<211> LENGTH: 1275
<212> TYPE: DNA
<213> ORGANISM: Campylobacter jejuni

<400> SEQUENCE: 121
atgaaactag ttaaacttag tttagttgca gctcttgctg caggtgcttt ttcagcagct    60
aacgctactc cacttgaaga agcgatcaaa gatgttgatg tatcaggtgt attaagatac    120
agatacgata caggtaattt tgataaaaat ttcgttaaca actcaaattt aaacaacagc    180
aaacaagatc acaaatatag agcacaagtt aacttcagtg ctgctatagc tgataacttc    240
aaagcttttg ttcaatttga ctataatgct gctgatggtg ttatggtgc taatggaata    300 aaaaatgatc aaaaaggact ttttgttcgt caattatact taacttatac aaatgaagat    360

-continued

```
gttgctacaa gtgtaatcgc tggtaaacaa caattaaacc ttatctggac ggataacgct       420
attgatggtt tagttggcac aggtgttaaa gtagtaaata acagcatcga tggtttaact       480
ctagctgctt ttgctgtaga tagcttcatg gctgcagagc aaggtgcaga tttattagaa       540
catagtaata tttcaacaac atcaaatcaa gctccttta aagtagattc agtaggaaat        600
ctttacggtg ctgctgctgt aggttcttat gatcttgctg gtggacaatt caacccacaa       660
ttatggttag cttattggga tcaagtagca ttcttctatg ctgtagatgc agcttatagt       720
acaactatct ttgatggaat caactggaca cttgaaggtg cttacttagg aaatagcctt       780
gatagcgaac ttgatgataa acacacgct aatggcaatt tatttgcttt aaaaggtagc        840
attgaagtaa atggttggga tgctagcctt ggtggtttat actacggtga taagaaaaa        900 gcttctacag ttgtaatcga agatcaaggt aatcttggtt cttacttgc aggtgaggaa        960 atttctata ctactggttc aagactaaat ggtgatactg gtagaaatat cttcggttat       1020
gtaactggtg atatacttt caacgaaaca gttcgcgttg gtgctgactt cgtatatggt       1080
ggaacaaaaa cagaagctgc taatcattta ggtggtggta aaaaacttga agctgttgca      1140
agagtagatt acaaatactc tccaaaactt aacttctcag cattctattc ttatgtgaac      1200
ctagatcaag gtgtaaacac taatgaaagt gctgatcata gcactgtaag acttcaagct      1260
ctttacaaat tctaa                                                      1275
```

<210> SEQ ID NO 122
<211> LENGTH: 424
<212> TYPE: PRT
<213> ORGANISM: Campylobacter jejuni

<400> SEQUENCE: 122

```
Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
            20                  25                  30

Asp Val Ser Gly Val Leu Arg Tyr Arg Tyr Asp Thr Gly Asn Phe Asp
        35                  40                  45

Lys Asn Phe Val Asn Asn Ser Asn Leu Asn Asn Asn Lys Gln Asp His
    50                  55                  60

Lys Tyr Arg Ala Gln Val Asn Phe Ser Ala Ala Ile Ala Asp Asn Phe
65                  70                  75                  80

Lys Ala Phe Ile Gln Phe Asp Tyr Asn Ala Val Asp Gly Gly Thr Gly
                85                  90                  95

Val Asp Asn Val Thr Asn Ala Glu Lys Gly Leu Phe Val Arg Gln Leu
            100                 105                 110

Tyr Leu Thr Tyr Thr Asn Glu Asp Val Ala Thr Ser Val Ile Ala Gly
        115                 120                 125

Lys Gln Gln Leu Asn Leu Ile Trp Thr Asp Asn Ala Ile Asp Gly Leu
    130                 135                 140

Val Gly Thr Gly Ile Lys Val Val Asn Asn Ser Ile Asp Gly Leu Thr
145                 150                 155                 160

Leu Ala Ala Phe Ala Val Asp Ser Phe Met Ala Glu Glu Gln Gly Ala
                165                 170                 175

Asp Leu Leu Gly Gln Ser Thr Ile Ser Thr Thr Gln Lys Ala Ala Pro
            180                 185                 190

Phe Lys Val Asp Ser Val Gly Asn Leu Tyr Gly Ala Ala Ala Val Gly
        195                 200                 205
```

```
Ser Tyr Asp Leu Ala Gly Gly Gln Phe Asn Pro Gln Leu Trp Leu Ala
    210                 215                 220

Tyr Trp Asp Gln Val Ala Phe Phe Tyr Ala Val Asp Ala Ala Tyr Ser
225                 230                 235                 240

Thr Thr Ile Phe Asp Gly Ile Asn Trp Thr Leu Glu Gly Ala Tyr Leu
                245                 250                 255

Gly Asn Ser Leu Asp Ser Glu Leu Asp Asp Lys Thr His Ala Asn Gly
            260                 265                 270

Asn Leu Phe Ala Leu Lys Gly Ser Ile Glu Val Asn Gly Trp Asp Ala
        275                 280                 285

Ser Leu Gly Gly Leu Tyr Tyr Gly Asp Lys Glu Lys Ala Ser Thr Val
    290                 295                 300

Val Ile Glu Asp Gln Gly Asn Leu Gly Ser Leu Leu Ala Gly Glu Glu
305                 310                 315                 320

Ile Phe Tyr Thr Thr Gly Ser Arg Leu Asn Gly Asp Thr Gly Arg Asn
                325                 330                 335

Ile Phe Gly Tyr Val Thr Gly Tyr Thr Phe Asn Glu Thr Val Arg
            340                 345                 350

Val Gly Ala Asp Phe Val Tyr Gly Gly Thr Lys Thr Glu Asp Thr Ala
        355                 360                 365

His Val Gly Gly Lys Lys Leu Glu Ala Val Ala Arg Val Asp Tyr
    370                 375                 380

Lys Tyr Ser Pro Lys Leu Asn Phe Ser Ala Phe Tyr Ser Tyr Val Asn
385                 390                 395                 400

Leu Asp Gln Gly Val Asn Thr Asn Glu Ser Ala Asp His Ser Thr Val
                405                 410                 415

Arg Leu Gln Ala Leu Tyr Lys Phe
            420

<210> SEQ ID NO 123
<211> LENGTH: 1719
<212> TYPE: DNA
<213> ORGANISM: Campylobacter jejuni

<400> SEQUENCE: 123
atgggatttc gtattaacac caatgttgca gctttaaatg caaaagcaaa cgctgattta      60
aatagtaaaa gtttagatgc ttctttaagc agacttagtt caggtcttag aatcaactcc     120
gcagcagatg atgcttcagg gatggcgata gcagatagtt taagatctca agctaatact     180
ttaggtcaag ctatatctaa tggtaatgat gctttaggta tcttacaaac tgctgataag     240
gctatggatg agcaacttaa atcttagat acaatcaaaa ctaaggcaac tcaagcggct     300
caagatggac aaagtttaaa acaagaacc atgcttcaag cagatatcaa ccgtttaatg     360
gaagaacttg acaatattgc aaatactact tcatttaacg gtaaacaact tttaagtggg     420
aattttatca atcaagaatt tcaaatcggt gcaagttcaa atcaaactgt aaaagctact     480
ataggagcaa ctcaatcttc taagataggt ttaacacgct tgaaacagg aggaagaatt     540 tcaactagtg gcgaagtaca atttactctt aaaaattaca atggtataga tgattttcag     600
tttcaaaaag ttgtgatttc aacttcagtt ggaacaggac ttggagcttt agcagatgag     660
atcaataaaa atgctgataa aacaggtgtt agagctactt ttacagtaga aactagaggt     720
atagctgcag ttagagcagg agctacttca gatactttg ctatcaatgg ggtaaaaatc     780
ggtaaagtag attacaaaga tggtgatgct aatggagcct tagttgctgc aatcaattcg     840
```

```
gttaaagata ccactggagt tgaagcttcg atcgatgcta atggacaact tttacttact    900
tcaagagaag gtagagggat taaaatcgat ggtaatatag gtggaggtgc ctttatcaat    960
gctgatatga agaaaaacta tggccgcttg tctttagtta aaaatgatgg taaagatatt   1020
ttaatcagcg gtagcaatct ttcttctgca ggttttggtg caactcaatt tatctctcaa   1080
gcttctgttt ctttaagaga gtcaaaagga caaattgatg ctaatatcgc tgatgctatg   1140
ggatttggtt ctgcaaacaa aggagttgtg ttaggtggtt attcttctgt tagtgcctat   1200
atgagtagcg caggaagtgg attttcttca ggttcaggtt attctgtagg tagcggtaaa   1260
aattattcca caggttttgc aaacgctata gctatttcag ctgcttcgca actttctacg   1320
gtatataatg tttctgcagg ctcaggtttt tcaagtggtt caacactttc tcagtttgca   1380
actatgaaaa caactgcttt tggagtaaaa gatgaaacag caggtgttac cacacttaaa   1440
ggcgctatgg ctgtgatgga tatagctgaa acagctataa caaatcttga tcaaatcaga   1500
gccgacattg gttcggtaca aaatcaagtt acatcaacta taaacaacat caccgtaact   1560
caagtaaacg ttaaagcagc agaatcgcaa atccgtgatg tagactttgc agccgagagt   1620
gcaaactact ctaaagcaaa tatcttagct caaagcggct cttatgccat ggcacaggct   1680
aattctgttc aacaaaatgt tttaagatta ctacagtag                          1719
```

<210> SEQ ID NO 124
<211> LENGTH: 572
<212> TYPE: PRT
<213> ORGANISM: Campylobacter jejuni

<400> SEQUENCE: 124

```
Met Gly Phe Arg Ile Asn Thr Asn Val Ala Ala Leu Asn Ala Lys Ala
1               5                   10                  15

Asn Ala Asp Leu Asn Ser Lys Ser Leu Asp Ala Ser Leu Ser Arg Leu
            20                  25                  30

Ser Ser Gly Leu Arg Ile Asn Ser Ala Ala Asp Asp Ala Ser Gly Met
        35                  40                  45

Ala Ile Ala Asp Ser Leu Arg Ser Gln Ala Asn Thr Leu Gly Gln Ala
    50                  55                  60

Ile Ser Asn Gly Asn Asp Ala Leu Gly Ile Leu Gln Thr Ala Asp Lys
65                  70                  75                  80

Ala Met Asp Glu Gln Leu Lys Ile Leu Asp Thr Ile Lys Thr Lys Ala
                85                  90                  95

Thr Gln Ala Ala Gln Asp Gly Gln Ser Leu Lys Thr Arg Thr Met Leu
            100                 105                 110

Gln Ala Asp Ile Asn Arg Leu Met Glu Glu Leu Asp Asn Ile Ala Asn
        115                 120                 125

Thr Thr Ser Phe Asn Gly Lys Gln Leu Leu Ser Gly Asn Phe Ile Asn
    130                 135                 140

Gln Glu Phe Gln Ile Gly Ala Ser Ser Asn Gln Thr Val Lys Ala Thr
145                 150                 155                 160

Ile Gly Ala Thr Gln Ser Ser Lys Ile Gly Leu Thr Arg Phe Glu Thr
                165                 170                 175

Gly Gly Arg Ile Ser Thr Ser Gly Glu Val Gln Phe Thr Leu Lys Asn
            180                 185                 190

Tyr Asn Gly Ile Asp Asp Phe Gln Phe Gln Lys Val Val Ile Ser Thr
        195                 200                 205

Ser Val Gly Thr Gly Leu Gly Ala Leu Ala Asp Glu Ile Asn Lys Asn
    210                 215                 220
```

Ala Asp Lys Thr Gly Val Arg Ala Thr Phe Thr Val Glu Thr Arg Gly
225                 230                 235                 240

Ile Ala Ala Val Arg Ala Gly Ala Thr Ser Asp Thr Phe Ala Ile Asn
            245                 250                 255

Gly Val Lys Ile Gly Lys Val Asp Tyr Lys Asp Gly Asp Ala Asn Gly
        260                 265                 270

Ala Leu Val Ala Ala Ile Asn Ser Val Lys Asp Thr Thr Gly Val Glu
    275                 280                 285

Ala Ser Ile Asp Ala Asn Gly Gln Leu Leu Thr Ser Arg Glu Gly
290                 295                 300

Arg Gly Ile Lys Ile Asp Gly Asn Ile Gly Gly Ala Phe Ile Asn
305                 310                 315                 320

Ala Asp Met Lys Glu Asn Tyr Gly Arg Leu Ser Leu Val Lys Asn Asp
            325                 330                 335

Gly Lys Asp Ile Leu Ile Ser Gly Ser Asn Leu Ser Ser Ala Gly Phe
        340                 345                 350

Gly Ala Thr Gln Phe Ile Ser Gln Ala Ser Val Ser Leu Arg Glu Ser
    355                 360                 365

Lys Gly Gln Ile Asp Ala Asn Ile Ala Asp Ala Met Gly Phe Gly Ser
370                 375                 380

Ala Asn Lys Gly Val Val Leu Gly Gly Tyr Ser Ser Val Ser Ala Tyr
385                 390                 395                 400

Met Ser Ser Ala Gly Ser Gly Phe Ser Gly Ser Gly Tyr Ser Val
            405                 410                 415

Gly Ser Gly Lys Asn Tyr Ser Thr Gly Phe Ala Asn Ala Ile Ala Ile
        420                 425                 430

Ser Ala Ala Ser Gln Leu Ser Thr Val Tyr Asn Val Ser Ala Gly Ser
    435                 440                 445

Gly Phe Ser Ser Gly Ser Thr Leu Ser Gln Phe Ala Thr Met Lys Thr
450                 455                 460

Thr Ala Phe Gly Val Lys Asp Glu Thr Ala Gly Val Thr Thr Leu Lys
465                 470                 475                 480

Gly Ala Met Ala Val Met Asp Ile Ala Glu Thr Ala Ile Thr Asn Leu
            485                 490                 495

Asp Gln Ile Arg Ala Asp Ile Gly Ser Val Gln Asn Gln Val Thr Ser
        500                 505                 510

Thr Ile Asn Asn Ile Thr Val Thr Gln Val Asn Val Lys Ala Ala Glu
    515                 520                 525

Ser Gln Ile Arg Asp Val Asp Phe Ala Ala Glu Ser Ala Asn Tyr Ser
530                 535                 540

Lys Ala Asn Ile Leu Ala Gln Ser Gly Ser Tyr Ala Met Ala Gln Ala
545                 550                 555                 560

Asn Ser Val Gln Gln Asn Val Leu Arg Leu Leu Gln
            565                 570

<210> SEQ ID NO 125
<211> LENGTH: 702
<212> TYPE: DNA
<213> ORGANISM: Campylobacter jejuni

<400> SEQUENCE: 125
atgaaaacaa ataatatctt tatggcttta gccatagttt tggcaagttt gattctagct    60
tttggattta caaggctttt aagtgatttt aaaacacttg aaagaagtgt aagtgtaaag   120

```
ggtttaagtc aaaaagaagt cgaagcggat actttgatac ttcctataaa attcacaaga    180
tcaaacaaca atcttacaaa tttatacgaa gaactagaac aagataaaga aaatatcatc    240
aaatttttag aaaaacaagg cataaaagaa gatgagatca gctacaactc gccaaatatc    300
atagatcgtt taagcgatcc ttatagcaac gacactcaag ctgcataccg atacataggc    360
actgcgaatt tactcatcta tactcaaaat gtaaagcttg gaaaaagcat actagaaaac    420
atttcaagtc ttgcaaaatt tggtatagta acaaaaatcg atgattatga tatagaatac    480
ctttacacca agctaaatga tataaaacca caaatgatag aagaagcaac gctcaatgct    540
agaaatgcag cgataaaatt cgcacaagac tcaaacagcc atctaggcaa gataaaaaag    600
gcttctcaag gacaatttag cattagcaac agagataaaa acaccccctta tatcaaaacc    660 ataagagtgg tttctactat agaatactac ttaaaagact ga                      702
```

<210> SEQ ID NO 126
<211> LENGTH: 233
<212> TYPE: PRT
<213> ORGANISM: Campylobacter jejuni

<400> SEQUENCE: 126

```
Met Lys Thr Asn Asn Ile Phe Met Ala Leu Ala Ile Val Leu Ala Ser
1               5                   10                  15

Leu Ile Leu Ala Phe Gly Phe Asn Lys Ala Leu Ser Asp Phe Lys Thr
            20                  25                  30

Leu Glu Arg Ser Val Ser Val Lys Gly Leu Ser Gln Lys Glu Val Glu
        35                  40                  45

Ala Asp Thr Leu Ile Leu Pro Ile Lys Phe Thr Arg Ser Asn Asn Asn
    50                  55                  60

Leu Thr Asn Leu Tyr Glu Glu Leu Glu Gln Asp Lys Glu Asn Ile Ile
65                  70                  75                  80

Lys Phe Leu Glu Lys Gln Gly Ile Lys Glu Asp Glu Ile Ser Tyr Asn
                85                  90                  95

Ser Pro Asn Ile Ile Asp Arg Leu Ser Asp Pro Tyr Ser Asn Asp Thr
            100                 105                 110

Gln Ala Ala Tyr Arg Tyr Ile Gly Thr Ala Asn Leu Leu Ile Tyr Thr
        115                 120                 125

Gln Asn Val Lys Leu Gly Lys Ser Ile Leu Glu Asn Ile Ser Ser Leu
    130                 135                 140

Ala Lys Phe Gly Ile Val Thr Lys Ile Asp Asp Tyr Asp Ile Glu Tyr
145                 150                 155                 160

Leu Tyr Thr Lys Leu Asn Asp Ile Lys Pro Gln Met Ile Glu Glu Ala
                165                 170                 175

Thr Leu Asn Ala Arg Asn Ala Ala Ile Lys Phe Ala Gln Asp Ser Asn
            180                 185                 190

Ser His Leu Gly Lys Ile Lys Lys Ala Ser Gln Gly Gln Phe Ser Ile
        195                 200                 205

Ser Asn Arg Asp Lys Asn Thr Pro Tyr Ile Lys Thr Ile Arg Val Val
    210                 215                 220

Ser Thr Ile Glu Tyr Tyr Leu Lys Asp
225                 230
```

<210> SEQ ID NO 127
<211> LENGTH: 837
<212> TYPE: DNA
<213> ORGANISM: Campylobacter jejuni

<400> SEQUENCE: 127

```
atggaaaatc aaaaaaatga atttgatgat attattttag aaaaaagtaa taaaagtgaa      60
aaagtaaaaa aaattctttt acgagttatt gctttagtta ttttgttttt agctatcatg     120
atagttatga agcttattaa tggtagtggt gatgaaaata cgcaaaatca aagtgtattg     180
ccaagtgaac ctatagcaac tcaagacaat aacaatgata cttcttttga agtatgcca      240
attacagata atacttcagc agaagatcaa tttgaggcat taagaaaaca atttcaagat     300
gaacaaaata caactcaaaa tacaacaacc tctagttcaa ataacaatga tactacaaat     360
tttgctatgc ctgatcaaga agttccagca gaaccaacag caactacttc agcaaatacc     420
actccacaag caagtactcc taaacaagaa gtaacacaaa ctgcaaaatc taagaagaa      480
gcaaaaaaac aaacagctgt aaaaaaagaa aagaaagtg caaacaaac ccctaaaaaa       540
gaacaaaatg caaatgattt atttaaaaat gttgatgcta aacctgtaca tccaagtggt     600
ttagcatcgg gtatttatgt gcaaattttc tcagtaagta atttggatca aaaatcaaaa     660
gaacttgctt ctgtaaagca aaaaggttat gattataaac tttataaaac tacagttgga     720
agtaaagaaa ttaccaaggt tttaatagga ccatttgaaa aggcagatat tgcagcagaa     780
cttgctaaaa tccgtaagga tattgcaaaa gatgcttttt cttttacttt aaaatga       837
```

<210> SEQ ID NO 128
<211> LENGTH: 278
<212> TYPE: PRT
<213> ORGANISM: Campylobacter jejuni

<400> SEQUENCE: 128

```
Met Glu Asn Gln Lys Asn Glu Phe Asp Asp Ile Ile Leu Glu Lys Ser
1               5                   10                  15

Asn Lys Ser Glu Lys Val Lys Lys Ile Leu Leu Arg Val Ile Ala Leu
            20                  25                  30

Val Ile Leu Phe Leu Ala Ile Met Ile Val Met Lys Leu Ile Asn Gly
        35                  40                  45

Ser Gly Asp Glu Asn Thr Gln Asn Gln Ser Val Leu Pro Ser Glu Pro
    50                  55                  60

Ile Ala Thr Gln Asp Asn Asn Asn Asp Thr Ser Phe Glu Ser Met Pro
65                  70                  75                  80

Ile Thr Asp Asn Thr Ser Ala Glu Asp Gln Phe Glu Ala Leu Arg Lys
                85                  90                  95

Gln Phe Gln Asp Glu Gln Asn Thr Thr Gln Asn Thr Thr Thr Ser Ser
            100                 105                 110

Ser Asn Asn Asn Asp Thr Thr Asn Phe Ala Met Pro Asp Gln Glu Val
        115                 120                 125

Pro Ala Glu Pro Thr Ala Thr Thr Ser Ala Asn Thr Thr Pro Gln Ala
    130                 135                 140

Ser Thr Pro Lys Gln Glu Val Thr Gln Thr Ala Lys Ser Lys Glu Glu
145                 150                 155                 160

Ala Lys Lys Gln Thr Ala Val Lys Lys Glu Lys Glu Ser Ala Lys Gln
                165                 170                 175

Thr Pro Lys Lys Glu Gln Asn Ala Asn Asp Leu Phe Lys Asn Val Asp
            180                 185                 190

Ala Lys Pro Val His Pro Ser Gly Leu Ala Ser Gly Ile Tyr Val Gln
        195                 200                 205

Ile Phe Ser Val Ser Asn Leu Asp Gln Lys Ser Lys Glu Leu Ala Ser
    210                 215                 220
```

Val Lys Gln Lys Gly Tyr Asp Tyr Lys Leu Tyr Lys Thr Thr Val Gly
225                 230                 235                 240

Ser Lys Glu Ile Thr Lys Val Leu Ile Gly Pro Phe Glu Lys Ala Asp
            245                 250                 255

Ile Ala Ala Glu Leu Ala Lys Ile Arg Lys Asp Ile Ala Lys Asp Ala
        260                 265                 270

Phe Ser Phe Thr Leu Lys
        275

<210> SEQ ID NO 129
<211> LENGTH: 1479
<212> TYPE: DNA
<213> ORGANISM: Campylobacter jejuni

<400> SEQUENCE: 129

```
atgaataaaa taatttcaat tagtgctata gcaagtttta ctcttttgat ttcagcttgc    60
tctttaagtc caaatttaaa tattcccgaa gcaaactata gcattgataa taagcttgga   120
gccttatctt gggaaaaaga aaacaatagc tctatcacaa aaaattggtg aaagactttt   180
gatgatgaaa atttaaataa agtggttgat ttagcactta aaaataataa tgatttaaaa   240
cttgctttca tacacatgga acaagctgct gctcaattag gtatagattt tagcagtttg   300
ttgccaaaat ttgatggtag cgcaagcgga agtcgtgcaa aaacagctat aaatgctcca   360
agcaatcgaa ctggggaagt aagttacggt aatgatttta aaatgggact taatttaagc   420
tatgaaatcg atctttgggg aaaatatcgc gatacatatc gcgcctcaaa atcaggcttt   480
aaagcaagtg agtatgatta tgaagctgca agactttctg ttatttcaaa tacagttcaa   540
acttattta atcttgtaaa tgcttatgaa atgaaaatg ctcttaaaga agcctataaa    600
tctgcaaaag aaatttatag gattaatgat gaaaaattc aagttggtgc tgtaggtgaa   660
tatgaacttg ctcaagcaag agccaactta gaaagtatgg ctttgcaata taatgaagca   720
aagttaaata agaaaaatta ccttaaagct ttaaaaattt taacttcaaa tgatttaaat   780
gacatacttt acaaaaatca aagctatcaa gtttttaatc ttaaagaatt tgacattcca   840
actggaattt caagtaccat cttgcttcaa cgtccagata ttggctcttc tttagaaaaa   900
ttaactcagc aaaattatct tgttggagta gctcgcacgg ctttcttacc tagcctttct   960
ttaacaggat tattgggatt tgaaagcggg gatttagata ccttggttaa aggaggttct  1020
aagacttgga atataggtgg aaactttact ctgcctattt ttcattgggg tgaaatttac  1080
caaaatgtaa atttagccaa gcttaataaa gatgaagctt tgtaaaatta tcaaaatact  1140
ttgattactg cttttggaga aattcgctat gctttagtag ctagaaaaac tatacgctta  1200
caatacgata atgcacaagc aagcgaacaa tcttacaaaa gaatctatga aattgctaaa  1260
gaacgctatg atataggaga atgtctttg caagattatt tagaggcacg tcaaaattgg  1320
cttaatgctg cggttgcttt taataatatt aaatattctt atgccaattc catagtagat  1380
gtaatcaaag catttggtgg aggatttgag caaagtgaag atacgagtaa aaatataaaa  1440
gaagaatcaa aaaatttaga tatgtctttt agagaatag                          1479
```

<210> SEQ ID NO 130
<211> LENGTH: 492
<212> TYPE: PRT
<213> ORGANISM: Campylobacter jejuni

<400> SEQUENCE: 130

-continued

```
Met Asn Lys Ile Ile Ser Ile Ser Ala Ile Ala Ser Phe Thr Leu Leu
1               5                   10                  15

Ile Ser Ala Cys Ser Leu Ser Pro Asn Leu Asn Ile Pro Glu Ala Asn
            20                  25                  30

Tyr Ser Ile Asp Asn Lys Leu Gly Ala Leu Ser Trp Glu Lys Glu Asn
        35                  40                  45

Asn Ser Ser Ile Thr Lys Asn Trp Trp Lys Asp Phe Asp Asp Glu Asn
    50                  55                  60

Leu Asn Lys Val Val Asp Leu Ala Leu Lys Asn Asn Asn Asp Leu Lys
65                  70                  75                  80

Leu Ala Phe Ile His Met Glu Gln Ala Ala Gln Leu Gly Ile Asp
                85                  90                  95

Phe Ser Ser Leu Leu Pro Lys Phe Asp Gly Ser Ala Ser Gly Ser Arg
                100                 105                 110

Ala Lys Thr Ala Ile Asn Ala Pro Ser Asn Arg Thr Gly Glu Val Ser
            115                 120                 125

Tyr Gly Asn Asp Phe Lys Met Gly Leu Asn Leu Ser Tyr Glu Ile Asp
    130                 135                 140

Leu Trp Gly Lys Tyr Arg Asp Thr Tyr Arg Ala Ser Lys Ser Gly Phe
145                 150                 155                 160

Lys Ala Ser Glu Tyr Asp Tyr Glu Ala Ala Arg Leu Ser Val Ile Ser
                165                 170                 175

Asn Thr Val Gln Thr Tyr Phe Asn Leu Val Asn Ala Tyr Glu Asn Glu
            180                 185                 190

Asn Ala Leu Lys Glu Ala Tyr Lys Ser Ala Lys Glu Ile Tyr Arg Ile
        195                 200                 205

Asn Asp Glu Lys Phe Gln Val Gly Ala Val Gly Glu Tyr Glu Leu Ala
    210                 215                 220

Gln Ala Arg Ala Asn Leu Glu Ser Met Ala Leu Gln Tyr Asn Glu Ala
225                 230                 235                 240

Lys Leu Asn Lys Glu Asn Tyr Leu Lys Ala Leu Lys Ile Leu Thr Ser
                245                 250                 255

Asn Asp Leu Asn Asp Ile Leu Tyr Lys Asn Gln Ser Tyr Gln Val Phe
            260                 265                 270

Asn Leu Lys Glu Phe Asp Ile Pro Thr Gly Ile Ser Ser Thr Ile Leu
        275                 280                 285

Leu Gln Arg Pro Asp Ile Gly Ser Ser Leu Glu Lys Leu Thr Gln Gln
    290                 295                 300

Asn Tyr Leu Val Gly Val Ala Arg Thr Ala Phe Leu Pro Ser Leu Ser
305                 310                 315                 320

Leu Thr Gly Leu Leu Gly Phe Glu Ser Gly Asp Leu Asp Thr Leu Val
                325                 330                 335

Lys Gly Gly Ser Lys Thr Trp Asn Ile Gly Asn Phe Thr Leu Pro
            340                 345                 350

Ile Phe His Trp Gly Glu Ile Tyr Gln Asn Val Asn Leu Ala Lys Leu
    355                 360                 365

Asn Lys Asp Glu Ala Phe Val Asn Tyr Gln Asn Thr Leu Ile Thr Ala
        370                 375                 380

Phe Gly Glu Ile Arg Tyr Ala Leu Val Ala Arg Lys Thr Ile Arg Leu
385                 390                 395                 400

Gln Tyr Asp Asn Ala Gln Ala Ser Glu Gln Ser Tyr Lys Arg Ile Tyr
                405                 410                 415

Glu Ile Ala Lys Glu Arg Tyr Asp Ile Gly Glu Met Ser Leu Gln Asp
```

```
                420                 425                 430
Tyr Leu Glu Ala Arg Gln Asn Trp Leu Asn Ala Ala Val Ala Phe Asn
            435                 440                 445

Asn Ile Lys Tyr Ser Tyr Ala Asn Ser Ile Val Asp Val Ile Lys Ala
        450                 455                 460

Phe Gly Gly Gly Phe Glu Gln Ser Glu Asp Thr Ser Lys Asn Ile Lys
465                 470                 475                 480

Glu Glu Ser Lys Asn Leu Asp Met Ser Phe Arg Glu
            485                 490
```

<210> SEQ ID NO 131
<211> LENGTH: 2091
<212> TYPE: DNA
<213> ORGANISM: Campylobacter jejuni

<400> SEQUENCE: 131

| | | | | | |
|---|---|---|---|---|---|
| atgaaaaaaa | tatgtctatc | agtttgcgcc | attggtctct | taagctccaa | tgccatatcg | 60 |
| caaaatgtag | aactagatag | ctcaatcgtt | agtgcttctg | gctttaccca | agatattaaa | 120 |
| gaagctcctg | ctactatcaa | tgttatcact | aaaaaagaat | tacaaagtaa | gccttataga | 180 |
| gatgttgcag | aggctatcgc | agatatccca | ggcgttgatt | tatatgctag | caagggaaaa | 240 |
| acaggttctt | ataatatcac | tatgagggt | attactggat | atactttggt | tttgattgat | 300 |
| gggcgtcgtc | agggtattgg | cggagaggtg | ggccctaatg | gttttaatga | aatttcaaat | 360 |
| tctttcttac | ctccgatttc | tagtatagaa | aggatagaag | ttataaaagg | tcctatgagt | 420 |
| actttatatg | gctctgaagc | tttaggcggg | gtggtaaata | tcattaccaa | aaaagtaagt | 480 |
| gataaatggg | aaacttctgt | aagtttggat | gctcttttaa | atgaaaataa | agattggggt | 540 |
| aatacttatg | gaacaagtat | ttattctagt | ggtcctttga | tgaatgacaa | attgggtcta | 600 |
| acacttcgat | ttagagaatt | ttacagacag | caatctaatg | ttgaatttac | aaatggaagt | 660 |
| ggacaaagag | ttcaaggaga | tcaagctcaa | agtcctacaa | aggcaaataa | ttttaacata | 720 |
| ggaacaagaa | ttagttattt | ggctaatgat | tataataccct | ttatatttga | tatagatttt | 780 |
| tcaagaaatc | attatgataa | taaacaaggt | caattaggaa | ccatcacaag | tccaggtaga | 840 |
| acaccaggta | gcttaacggg | tggttatgca | gatattatgg | aagttgataa | atttgtgact | 900 |
| tatttaagtc | atgagggtgt | ttatgaaaat | ttttctatca | cttctggttt | gcaatatat | 960 |
| agagtgagca | atgatggccg | cgaagtcgta | gggcaatcta | cacagccgtt | tttgggagaa | 1020 |
| aatagagata | tagtcgcaga | agatattatc | ttagatacta | agtctgttat | tcctctagga | 1080 |
| caaagtcata | tttttaagcgt | aggcggtgaa | ataggcttg | aaaaaatgca | agataaaata | 1140 |
| gctagtccta | ctaattttga | tcagtattta | ttggcaattt | ttgcagagga | tgagtatagt | 1200 |
| ataaaagatg | atttaagact | tacttttgga | gcaagatata | atcatcatga | aattttgga | 1260 |
| aacaatgttt | cgccaagagc | ttatgtggtt | tataatccta | ctaatgagct | tactttaaaa | 1320 |
| ggcggtgtat | ctacaggctt | tagaacccct | tatgcaaacc | gttgataaa | tggaacttac | 1380 |
| agttatagtg | gccaaggcag | atttcctaca | tatggaaatc | ctgatttaaa | agaagagaca | 1440 |
| tctttaaact | atgaaatagc | agctatttac | aataatgatt | tattttatgt | ttcagcaaca | 1500 |
| ggttttttaa | cgaattttaa | agataaaatt | tcaagtcaaa | gttataataa | tagcgaacca | 1560 |
| atcccaggta | ttggcacttg | tgatgctgat | agatgttcta | gagcaatcaa | tcatggcaag | 1620 |
| gttgaataca | aaggtgtaga | acttggagca | gggataagcc | ctcttgataa | tttaaatgta | 1680 |
| aattttgctt | atacttatct | tgatactgaa | gttaaagaag | cacaagatag | aagtgtgata | 1740 |

```
ggtaaacctg aacaagatag tttaaaacac aatatcatgt taaaaaccga atacagcttc    1800
tataataaaa ttaccccttg gataaaaggc gagtggcaaa tagatcgcta tatgggtgat    1860
actaatatca atagagaata ttacaaggat atctttttag cttccatggg tgtgcgttat    1920
gatatcaaca aacaatggag tatcaatgca gctatttata atcttttga caaaagcttt     1980 acaaatggct gggaatctta tgcaagtggg agtggtagca cttgggtaaa tacctataac    2040
cgtatagaag aaggaagaag aatgtatatt tctatcaatg gtaacttta a              2091
```

<210> SEQ ID NO 132
<211> LENGTH: 696
<212> TYPE: PRT
<213> ORGANISM: Campylobacter jejuni

<400> SEQUENCE: 132

```
Met Lys Lys Ile Cys Leu Ser Val Cys Ala Ile Gly Leu Leu Ser Ser
1               5                   10                  15

Asn Ala Ile Ser Gln Asn Val Glu Leu Asp Ser Ser Ile Val Ser Ala
            20                  25                  30

Ser Gly Phe Thr Gln Asp Ile Lys Glu Ala Pro Ala Thr Ile Asn Val
        35                  40                  45

Ile Thr Lys Lys Glu Leu Gln Ser Lys Pro Tyr Arg Asp Val Ala Glu
    50                  55                  60

Ala Ile Ala Asp Ile Pro Gly Val Asp Leu Tyr Ala Ser Lys Gly Lys
65                  70                  75                  80

Thr Gly Ser Tyr Asn Ile Thr Met Arg Gly Ile Thr Gly Tyr Thr Leu
                85                  90                  95

Val Leu Ile Asp Gly Arg Arg Gln Gly Ile Gly Gly Glu Val Gly Pro
            100                 105                 110

Asn Gly Phe Asn Glu Ile Ser Asn Ser Phe Leu Pro Pro Ile Ser Ser
        115                 120                 125

Ile Glu Arg Ile Glu Val Ile Lys Gly Pro Met Ser Thr Leu Tyr Gly
    130                 135                 140

Ser Glu Ala Leu Gly Gly Val Val Asn Ile Ile Thr Lys Lys Val Ser
145                 150                 155                 160

Asp Lys Trp Glu Thr Ser Val Ser Leu Asp Ala Leu Leu Asn Glu Asn
                165                 170                 175

Lys Asp Trp Gly Asn Thr Tyr Gly Thr Ser Ile Tyr Ser Ser Gly Pro
            180                 185                 190

Leu Met Asn Asp Lys Leu Gly Leu Thr Leu Arg Phe Arg Glu Phe Tyr
        195                 200                 205

Arg Gln Gln Ser Asn Val Glu Phe Thr Asn Gly Ser Gly Gln Arg Val
    210                 215                 220

Gln Gly Asp Gln Ala Gln Ser Pro Thr Lys Ala Asn Asn Phe Asn Ile
225                 230                 235                 240

Gly Thr Arg Ile Ser Tyr Leu Ala Asn Asp Tyr Asn Thr Phe Ile Phe
                245                 250                 255

Asp Ile Asp Phe Ser Arg Asn His Tyr Asp Asn Lys Gln Gly Gln Leu
            260                 265                 270

Gly Thr Ile Thr Ser Pro Gly Arg Thr Pro Gly Ser Leu Thr Gly Gly
        275                 280                 285

Tyr Ala Asp Ile Met Glu Val Asp Lys Phe Val Thr Tyr Leu Ser His
    290                 295                 300

Glu Gly Val Tyr Glu Asn Phe Ser Ile Thr Ser Gly Leu Gln Tyr Asn
```

| | | | | 305 | | | | | 310 | | | | | 315 | | | | | 320 |

Arg Val Ser Asn Asp Gly Arg Glu Val Gly Gln Ser Thr Gln Pro
                325                     330                     335

Phe Leu Gly Glu Asn Arg Asp Ile Val Ala Glu Asp Ile Ile Leu Asp
                340                     345                     350

Thr Lys Ser Val Ile Pro Leu Gly Gln Ser His Ile Leu Ser Val Gly
                355                     360                     365

Gly Glu Tyr Arg Leu Glu Lys Met Gln Asp Lys Ile Ala Ser Pro Thr
370                     375                     380

Asn Phe Asp Gln Tyr Leu Leu Ala Ile Phe Ala Glu Asp Glu Tyr Ser
385                     390                     395                     400

Ile Lys Asp Asp Leu Arg Leu Thr Phe Gly Ala Arg Tyr Asn His His
                405                     410                     415

Glu Ile Phe Gly Asn Asn Val Ser Pro Arg Ala Tyr Val Val Tyr Asn
                420                     425                     430

Pro Thr Asn Glu Leu Thr Leu Lys Gly Gly Val Ser Thr Gly Phe Arg
                435                     440                     445

Thr Pro Tyr Ala Asn Arg Leu Ile Asn Gly Thr Tyr Ser Tyr Ser Gly
450                     455                     460

Gln Gly Arg Phe Pro Thr Tyr Gly Asn Pro Asp Leu Lys Glu Glu Thr
465                     470                     475                     480

Ser Leu Asn Tyr Glu Ile Ala Ala Ile Tyr Asn Asn Asp Leu Phe Tyr
                485                     490                     495

Val Ser Ala Thr Gly Phe Leu Thr Asn Phe Lys Asp Lys Ile Ser Ser
                500                     505                     510

Gln Ser Tyr Asn Asn Ser Glu Pro Ile Pro Gly Ile Gly Thr Cys Asp
                515                     520                     525

Ala Asp Arg Cys Ser Arg Ala Ile Asn His Gly Lys Val Glu Tyr Lys
                530                     535                     540

Gly Val Glu Leu Gly Ala Gly Ile Ser Pro Leu Asp Asn Leu Asn Val
545                     550                     555                     560

Asn Phe Ala Tyr Thr Tyr Leu Asp Thr Glu Val Lys Glu Ala Gln Asp
                565                     570                     575

Arg Ser Val Ile Gly Lys Pro Glu Gln Asp Ser Leu Lys His Asn Ile
                580                     585                     590

Met Leu Lys Thr Glu Tyr Ser Phe Tyr Asn Lys Ile Thr Pro Trp Ile
                595                     600                     605

Lys Gly Glu Trp Gln Ile Asp Arg Tyr Met Gly Asp Thr Asn Ile Asn
610                     615                     620

Arg Glu Tyr Tyr Lys Asp Ile Phe Leu Ala Ser Met Gly Val Arg Tyr
625                     630                     635                     640

Asp Ile Asn Lys Gln Trp Ser Ile Asn Ala Ala Ile Tyr Asn Leu Phe
                645                     650                     655

Asp Lys Ser Phe Thr Asn Gly Trp Glu Ser Tyr Ala Ser Gly Ser Gly
                660                     665                     670

Ser Thr Trp Val Asn Thr Tyr Asn Arg Ile Glu Glu Gly Arg Arg Met
                675                     680                     685

Tyr Ile Ser Ile Asn Gly Asn Phe
                690                     695

<210> SEQ ID NO 133
<211> LENGTH: 573
<212> TYPE: DNA
<213> ORGANISM: Campylobacter jejuni

<400> SEQUENCE: 133

```
atgaaaaaag tttattgag ttcattggtt gcggtgtctt tgttaagcac aggtttgttt    60
gctaaagaat atactttaga taaagcacat acagatgtag gttttaaaat caaacattta   120
caaattagca atgtaaaagg aaatttcaaa gattattctg cggtgattga ttttgatcct   180
gcgagtgctg aatttaaaaa gcttgatgta actataaaaa tcgcatctgt aaatacagaa   240
aatcaaacaa gagataatca cttacaacaa gatgattttt tcaaagcaaa aaatatcct   300
gatatgactt ttacaatgaa aaatatgaa aaatcgata atgaaaaagg caaatgaca    360
ggaactttaa ctatagctgg agtttctaaa gatatcgttt tagatgctga aatcggcggt   420
gtagctaaag gcaaagatgg aaaagaaaaa ataggatttt ctttaaatgg aaaaatcaaa   480
cgctctgatt ttaaatttgc aacaagtact tcaactatta ctttaagtga tgatattaat   540
ttaaatatcg aagttgaagc gaacgaaaaa taa                                573
```

<210> SEQ ID NO 134
<211> LENGTH: 190
<212> TYPE: PRT
<213> ORGANISM: Campylobacter jejuni

<400> SEQUENCE: 134

```
Met Lys Lys Val Leu Leu Ser Ser Leu Val Ala Val Ser Leu Leu Ser
1               5                   10                  15
Thr Gly Leu Phe Ala Lys Glu Tyr Thr Leu Asp Lys Ala His Thr Asp
            20                  25                  30
Val Gly Phe Lys Ile Lys His Leu Gln Ile Ser Asn Val Lys Gly Asn
        35                  40                  45
Phe Lys Asp Tyr Ser Ala Val Ile Asp Phe Asp Pro Ala Ser Ala Glu
    50                  55                  60
Phe Lys Lys Leu Asp Val Thr Ile Lys Ile Ala Ser Val Asn Thr Glu
65                  70                  75                  80
Asn Gln Thr Arg Asp Asn His Leu Gln Gln Asp Asp Phe Phe Lys Ala
                85                  90                  95
Lys Lys Tyr Pro Asp Met Thr Phe Thr Met Lys Lys Tyr Glu Lys Ile
            100                 105                 110
Asp Asn Glu Lys Gly Lys Met Thr Gly Thr Leu Thr Ile Ala Gly Val
        115                 120                 125
Ser Lys Asp Ile Val Leu Asp Ala Glu Ile Gly Gly Val Ala Lys Gly
    130                 135                 140
Lys Asp Gly Lys Glu Lys Ile Gly Phe Ser Leu Asn Gly Lys Ile Lys
145                 150                 155                 160
Arg Ser Asp Phe Lys Phe Ala Thr Ser Thr Ser Thr Ile Thr Leu Ser
                165                 170                 175
Asp Asp Ile Asn Leu Asn Ile Glu Val Glu Ala Asn Glu Lys
            180                 185                 190
```

<210> SEQ ID NO 135
<211> LENGTH: 8
<212> TYPE: PRT
<213> ORGANISM: Artificial Sequence
<220> FEATURE:
<223> OTHER INFORMATION: Synthetic

<400> SEQUENCE: 135

```
Asn Lys Gly Val Ile Ser Ala Lys
1               5
```

```
<210> SEQ ID NO 136
<211> LENGTH: 65
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is R or I
<220> FEATURE:
<221> NAME/KEY: MISC_FEATURE
<222> LOCATION: (3)..(3)
<223> OTHER INFORMATION: X is F or absent
<220> FEATURE:
<221> NAME/KEY: MISC_FEATURE
<222> LOCATION: (4)..(4)
<223> OTHER INFORMATION: X is D or absent
<220> FEATURE:
<221> NAME/KEY: MISC_FEATURE
<222> LOCATION: (7)..(7)
<223> OTHER INFORMATION: X is V or I
<220> FEATURE:
<221> NAME/KEY: MISC_FEATURE
<222> LOCATION: (12)..(12)
<223> OTHER INFORMATION: X is N or D
<220> FEATURE:
<221> NAME/KEY: MISC_FEATURE
<222> LOCATION: (24)..(24)
<223> OTHER INFORMATION: X is N or S
<220> FEATURE:
<221> NAME/KEY: MISC_FEATURE
<222> LOCATION: (27)..(27)
<223> OTHER INFORMATION: X is I or V
<220> FEATURE:
<221> NAME/KEY: MISC_FEATURE
<222> LOCATION: (33)..(33)
<223> OTHER INFORMATION: X is S or N
<220> FEATURE:
<221> NAME/KEY: MISC_FEATURE
<222> LOCATION: (38)..(38)
<223> OTHER INFORMATION: X is F or C
<220> FEATURE:
<221> NAME/KEY: MISC_FEATURE
<222> LOCATION: (43)..(43)
<223> OTHER INFORMATION: X is F or L
<220> FEATURE:
<221> NAME/KEY: MISC_FEATURE
<222> LOCATION: (50)..(50)
<223> OTHER INFORMATION: X is T, A or K
<220> FEATURE:
<221> NAME/KEY: MISC_FEATURE
<222> LOCATION: (55)..(55)
<223> OTHER INFORMATION: X is P, L or S
<220> FEATURE:
<221> NAME/KEY: MISC_FEATURE
<222> LOCATION: (57)..(57)
<223> OTHER INFORMATION: X is D or E
<220> FEATURE:
<221> NAME/KEY: MISC_FEATURE
<222> LOCATION: (58)..(58)
<223> OTHER INFORMATION: X is I or V
<220> FEATURE:
<221> NAME/KEY: MISC_FEATURE
<222> LOCATION: (59)..(59)
<223> OTHER INFORMATION: X is L or Y
<220> FEATURE:
<221> NAME/KEY: MISC_FEATURE
<222> LOCATION: (61)..(61)
<223> OTHER INFORMATION: X is A, T or S
<220> FEATURE:
<221> NAME/KEY: MISC_FEATURE
<222> LOCATION: (62)..(62)
<223> OTHER INFORMATION: X is N, D or K
<220> FEATURE:
<221> NAME/KEY: MISC_FEATURE
<222> LOCATION: (63)..(63)
```

<223> OTHER INFORMATION: X is E or G
<220> FEATURE:
<221> NAME/KEY: MISC_FEATURE
<222> LOCATION: (65)..(65)
<223> OTHER INFORMATION: X is K or N

<400> SEQUENCE: 136

Met Xaa Xaa Xaa Phe Phe Xaa Ser Lys Arg Leu Xaa Ile Ser Arg Asn
1               5                   10                  15

Lys Ala Leu Glu Leu Ile Glu Xaa Glu Glu Xaa Leu Leu Asn Gly Lys
            20                  25                  30

Xaa Phe Lys Ala Ser Xaa Asp Val Lys Asn Xaa Leu Glu Asn Leu Lys
        35                  40                  45

Lys Xaa Gln Asp Leu Asn Xaa Glu Xaa Xaa Xaa Leu Xaa Xaa Xaa Leu
    50                  55                  60

Xaa
65

<210> SEQ ID NO 137
<211> LENGTH: 125
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is D or E
<220> FEATURE:
<221> NAME/KEY: MISC_FEATURE
<222> LOCATION: (3)..(3)
<223> OTHER INFORMATION: X is D or E
<220> FEATURE:
<221> NAME/KEY: MISC_FEATURE
<222> LOCATION: (6)..(6)
<223> OTHER INFORMATION: X is A or T
<220> FEATURE:
<221> NAME/KEY: MISC_FEATURE
<222> LOCATION: (10)..(10)
<223> OTHER INFORMATION: X is E, K or absent
<220> FEATURE:
<221> NAME/KEY: MISC_FEATURE
<222> LOCATION: (11)..(11)
<223> OTHER INFORMATION: X is T or absent
<220> FEATURE:
<221> NAME/KEY: MISC_FEATURE
<222> LOCATION: (13)..(13)
<223> OTHER INFORMATION: X is N, S or I
<220> FEATURE:
<221> NAME/KEY: MISC_FEATURE
<222> LOCATION: (16)..(16)
<223> OTHER INFORMATION: X is L or I
<220> FEATURE:
<221> NAME/KEY: MISC_FEATURE
<222> LOCATION: (37)..(37)
<223> OTHER INFORMATION: X is H or Y
<220> FEATURE:
<221> NAME/KEY: MISC_FEATURE
<222> LOCATION: (44)..(44)
<223> OTHER INFORMATION: X is V or I
<220> FEATURE:
<221> NAME/KEY: MISC_FEATURE
<222> LOCATION: (53)..(53)
<223> OTHER INFORMATION: X is R or H
<220> FEATURE:
<221> NAME/KEY: MISC_FEATURE
<222> LOCATION: (61)..(61)
<223> OTHER INFORMATION: X is K or E
<220> FEATURE:
<221> NAME/KEY: MISC_FEATURE
<222> LOCATION: (77)..(77)
<223> OTHER INFORMATION: X is A or T
<220> FEATURE:

```
<221> NAME/KEY: MISC_FEATURE
<222> LOCATION: (87)..(87)
<223> OTHER INFORMATION: X is A, V or T
<220> FEATURE:
<221> NAME/KEY: MISC_FEATURE
<222> LOCATION: (95)..(95)
<223> OTHER INFORMATION: X is K or E
<220> FEATURE:
<221> NAME/KEY: MISC_FEATURE
<222> LOCATION: (99)..(125)
<223> OTHER INFORMATION: Amino Acids are optionally absent
<220> FEATURE:
<221> NAME/KEY: MISC_FEATURE
<222> LOCATION: (107)..(107)
<223> OTHER INFORMATION: X is N or D
<220> FEATURE:
<221> NAME/KEY: MISC_FEATURE
<222> LOCATION: (115)..(115)
<223> OTHER INFORMATION: X is N or S
<220> FEATURE:
<221> NAME/KEY: MISC_FEATURE
<222> LOCATION: (122)..(122)
<223> OTHER INFORMATION: X is N or D
<220> FEATURE:
<221> NAME/KEY: MISC_FEATURE
<222> LOCATION: (123)..(123)
<223> OTHER INFORMATION: X is K or E

<400> SEQUENCE: 137

Xaa Lys Xaa Phe Leu Xaa Phe Leu Asn Xaa Xaa Lys Xaa Glu Asn Xaa
1               5                   10                  15

Ala Leu Ala Glu Asn Glu Phe Leu Gly Val Asp His Ile Ser Phe Leu
            20                  25                  30

Gly Phe Leu Leu Xaa Arg Trp Asn Phe Asp Asp Xaa Leu Ile Glu Ser
        35                  40                  45

Ile Cys Phe Val Xaa Thr Pro His Ala Ala Arg Glu Xaa Val Lys Lys
50                  55                  60

Ser Ala Tyr Ala Leu Ala Ile Thr Asp His Leu Phe Xaa Pro His Asp
65                  70                  75                  80

Gly Ser Ser Pro Phe Asn Xaa Lys Ala Ala Val Ala Leu Leu Xaa Glu
                85                  90                  95

Ala Lys Thr Gln Gly Ile Asn Phe Asp Leu Xaa Asn Leu Leu Ser Lys
            100                 105                 110

Leu Pro Xaa Lys Ala Lys Glu Asn Leu Xaa Xaa Glu Asp
        115                 120                 125

<210> SEQ ID NO 138
<211> LENGTH: 102
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is D or E
<220> FEATURE:
<221> NAME/KEY: MISC_FEATURE
<222> LOCATION: (3)..(3)
<223> OTHER INFORMATION: X is D or E
<220> FEATURE:
<221> NAME/KEY: MISC_FEATURE
<222> LOCATION: (6)..(6)
<223> OTHER INFORMATION: X is A or T
<220> FEATURE:
<221> NAME/KEY: MISC_FEATURE
<222> LOCATION: (10)..(10)
<223> OTHER INFORMATION: X is E, K or absent
<220> FEATURE:
<221> NAME/KEY: MISC_FEATURE
```

```
<222> LOCATION: (11)..(11)
<223> OTHER INFORMATION: X is T or absent
<220> FEATURE:
<221> NAME/KEY: MISC_FEATURE
<222> LOCATION: (13)..(13)
<223> OTHER INFORMATION: X is N, S, or I
<220> FEATURE:
<221> NAME/KEY: MISC_FEATURE
<222> LOCATION: (16)..(16)
<223> OTHER INFORMATION: X is L or I
<220> FEATURE:
<221> NAME/KEY: MISC_FEATURE
<222> LOCATION: (37)..(37)
<223> OTHER INFORMATION: X is H or Y
<220> FEATURE:
<221> NAME/KEY: MISC_FEATURE
<222> LOCATION: (44)..(44)
<223> OTHER INFORMATION: X is V or I
<220> FEATURE:
<221> NAME/KEY: MISC_FEATURE
<222> LOCATION: (53)..(53)
<223> OTHER INFORMATION: X is R or H
<220> FEATURE:
<221> NAME/KEY: MISC_FEATURE
<222> LOCATION: (61)..(61)
<223> OTHER INFORMATION: X is K or E
<220> FEATURE:
<221> NAME/KEY: MISC_FEATURE
<222> LOCATION: (77)..(77)
<223> OTHER INFORMATION: X is A or T
<220> FEATURE:
<221> NAME/KEY: MISC_FEATURE
<222> LOCATION: (87)..(87)
<223> OTHER INFORMATION: X is A, V or T
<220> FEATURE:
<221> NAME/KEY: MISC_FEATURE
<222> LOCATION: (95)..(95)
<223> OTHER INFORMATION: X is K or E
<220> FEATURE:
<221> NAME/KEY: MISC_FEATURE
<222> LOCATION: (99)..(102)
<223> OTHER INFORMATION: Amino Acids are optionally absent

<400> SEQUENCE: 138

Xaa Lys Xaa Phe Leu Xaa Phe Leu Asn Xaa Xaa Lys Xaa Glu Asn Xaa
1               5                   10                  15

Ala Leu Ala Glu Asn Glu Phe Leu Gly Val Asp His Ile Ser Phe Leu
            20                  25                  30

Gly Phe Leu Leu Xaa Arg Trp Asn Phe Asp Asp Xaa Leu Ile Glu Ser
        35                  40                  45

Ile Cys Phe Val Xaa Thr Pro His Ala Ala Arg Glu Xaa Val Lys Lys
    50                  55                  60

Ser Ala Tyr Ala Leu Ala Ile Thr Asp His Leu Phe Xaa Pro His Asp
65                  70                  75                  80

Gly Ser Ser Pro Phe Asn Xaa Lys Ala Ala Val Ala Leu Leu Xaa Glu
                85                  90                  95

Ala Lys Asn Ser Arg Asn
            100

<210> SEQ ID NO 139
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: X is N or D
<220> FEATURE:
<221> NAME/KEY: MISC_FEATURE
```

<222> LOCATION: (17)..(17)
<223> OTHER INFORMATION: X is N or S
<220> FEATURE:
<221> NAME/KEY: MISC_FEATURE
<222> LOCATION: (24)..(24)
<223> OTHER INFORMATION: X is N or D
<220> FEATURE:
<221> NAME/KEY: MISC_FEATURE
<222> LOCATION: (25)..(25)
<223> OTHER INFORMATION: X is K or E

<400> SEQUENCE: 139

Thr Gln Gly Ile Asn Phe Asp Leu Xaa Asn Leu Leu Ser Lys Leu Pro
1               5                   10                  15

Xaa Lys Ala Lys Glu Asn Leu Xaa Xaa Glu Asp
            20                  25

<210> SEQ ID NO 140
<211> LENGTH: 4
<212> TYPE: PRT
<213> ORGANISM: Artificial Sequence
<220> FEATURE:
<223> OTHER INFORMATION: Synthetic

<400> SEQUENCE: 140

Asn Ser Arg Asn
1

<210> SEQ ID NO 141
<211> LENGTH: 450
<212> TYPE: DNA
<213> ORGANISM: Campylobacter jejuni

<400> SEQUENCE: 141
atgtcagtta caaaacaatt attacaaatg caagcagatg ctcatcattt atgggttaaa      60
tttcataatt atcactggaa tgtaaaaggt ttgcaatttt tttctataca cgagtacaca     120
gaaaaagctt atgaagaaat ggcagaactt tttgatagtt gtgctgaaag agttttacaa     180
cttggcgaaa aagctatcac ttgccaaaaa gttttaatgg aaaatgcaaa aagtccaaaa     240
gttgcaaaag attgctttac tccgcttgaa gtcatagaac tgatcaaaca agattatgaa     300
tatcttttag cagaatttaa aaaactcaat gaagcagcag aaaaagaaag tgatactaca     360
acagctgctt tgcacaaga aaatatcgca aaatatgaaa aagtctttg gatgataggc       420
gctactttac aaggtgcttg caaaatgtaa                                     450

<210> SEQ ID NO 142
<211> LENGTH: 149
<212> TYPE: PRT
<213> ORGANISM: Campylobacter jejuni

<400> SEQUENCE: 142

Met Ser Val Thr Lys Gln Leu Leu Gln Met Gln Ala Asp Ala His His
1               5                   10                  15

Leu Trp Val Lys Phe His Asn Tyr His Trp Asn Val Lys Gly Leu Gln
            20                  25                  30

Phe Phe Ser Ile His Glu Tyr Thr Glu Lys Ala Tyr Glu Glu Met Ala
        35                  40                  45

Glu Leu Phe Asp Ser Cys Ala Glu Arg Val Leu Gln Leu Gly Glu Lys
    50                  55                  60

Ala Ile Thr Cys Gln Lys Val Leu Met Glu Asn Ala Lys Ser Pro Lys
65                  70                  75                  80

-continued

```
Val Ala Lys Asp Cys Phe Thr Pro Leu Glu Val Ile Glu Leu Ile Lys
                 85                  90                  95

Gln Asp Tyr Glu Tyr Leu Leu Ala Glu Phe Lys Lys Leu Asn Glu Ala
            100                 105                 110

Ala Glu Lys Glu Ser Asp Thr Thr Ala Ala Phe Ala Gln Glu Asn
        115                 120                 125

Ile Ala Lys Tyr Glu Lys Ser Leu Trp Met Ile Gly Ala Thr Leu Gln
    130                 135                 140

Gly Ala Cys Lys Met
145
```